(12) United States Patent
Bell et al.

(10) Patent No.: US 7,569,572 B2
(45) Date of Patent: Aug. 4, 2009

(54) PYRAZOLO[4,3-D]PYRIMIDINES

(75) Inventors: Andrew Simon Bell, Sandwich (GB); David Graham Brown, Sandwich (GB); David Nathan Abraham Fox, Sandwich (GB); Ian Roger Marsh, Sandwich (GB); Andrew Ian Morrell, Sandwich (GB); Dafydd Rhys Owen, Sandwich (GB); Michael John Palmer, Sandwich (GB); Carol Ann Winslow, Sandwich (GB); Hwang Fun Lu, Ballwin, MO (US); Thomas Edward Rogers, Ballwin, MO (US)

(73) Assignee: Pfizer Inc, New York, NY (US)

( * ) Notice: Subject to any disclaimer, the term of this patent is extended or adjusted under 35 U.S.C. 154(b) by 370 days.

(21) Appl. No.: 10/599,702

(22) PCT Filed: Mar. 30, 2005

(86) PCT No.: PCT/IB2005/000891

§ 371 (c)(1),
(2), (4) Date: Dec. 19, 2006

(87) PCT Pub. No.: WO2005/097799

PCT Pub. Date: Oct. 20, 2005

(65) Prior Publication Data

US 2008/0293697 A1 Nov. 27, 2008

Related U.S. Application Data

(60) Provisional application No. 60/572,049, filed on May 18, 2004, provisional application No. 60/572,024, filed on May 18, 2004.

(30) Foreign Application Priority Data

Apr. 7, 2004 (GB) ................................. 0407927.3
Apr. 7, 2004 (GB) ................................. 0407946.3

(51) Int. Cl.
*C07D 487/04* (2006.01)
*A61K 31/519* (2006.01)
*A61P 9/12* (2006.01)

(52) U.S. Cl. ................................. 514/262.1; 544/262
(58) Field of Classification Search ................ 544/262; 514/262.1
See application file for complete search history.

(56) References Cited

U.S. PATENT DOCUMENTS

| | | | |
|---|---|---|---|
| 3,951,980 A | 4/1976 | Henry et al. ................. 451/2 |
| 4,282,631 A | 8/1981 | Uehara et al. ................ 13/2 |
| 5,091,431 A | 2/1992 | Tulshian et al. ............ 514/262 |
| 5,442,044 A | 8/1995 | Hoover et al. .................. 5/6 |
| 6,001,830 A | 12/1999 | Lee et al. ..................... 31/50 |
| 6,106,864 A | 8/2000 | Dolan et al. .................. 9/14 |
| 6,130,223 A | 10/2000 | Jonas et al. ................. 514/258 |
| 6,184,338 B1 | 2/2001 | Schwindeman et al. ...... 528/392 |
| 6,288,078 B1 | 9/2001 | Walsh et al. ................. 514/300 |
| 6,432,957 B1 | 8/2002 | Kodoma et al. ............... 31/496 |
| 6,465,486 B1 | 10/2002 | Baxter et al. ................... 31/47 |
| 6,566,360 B1 | 5/2003 | Niewohner et al. .......... 514/243 |
| 6,777,419 B1 | 8/2004 | Jonas et al. ............... 514/262.1 |
| 2001/0047013 A1 | 11/2001 | Lang et al. ..................... 213/2 |
| 2002/0058668 A1 | 5/2002 | Yuan ........................ 514/258 |
| 2002/0127593 A1 | 9/2002 | Reich et al. .................. 435/6 |
| 2003/0187261 A1 | 10/2003 | Havlicek et al. ............ 514/276 |
| 2004/0002990 A1 | 1/2004 | Sander et al. .................. 17/30 |
| 2004/0023990 A1 | 2/2004 | Eggenweiler et al. .... 514/262.1 |
| 2004/0029900 A1 | 2/2004 | Jonas et al. ............... 514/262.1 |
| 2004/0063730 A1 | 4/2004 | Eggenweiler et al. .... 514/262.1 |
| 2004/0077664 A1 | 4/2004 | Eggenweiler et al. .... 514/262.1 |

FOREIGN PATENT DOCUMENTS

| | | | |
|---|---|---|---|
| EP | 0296811 | 6/1987 | ................... 125/67 |
| EP | 0297858 | 7/1987 | ..................... 471/8 |
| EP | 0349239 | 7/1988 | ..................... 487/4 |
| EP | 319479 | 6/1989 | ...................... 9/30 |
| EP | 400661 | 5/1990 | ..................... 403/4 |
| EP | 0937459 | 8/1999 | ..................... 31/40 |
| EP | 1072595 | 1/2001 | ................... 211/22 |
| EP | 0579496 | 11/2001 | ..................... 401/4 |
| EP | 1176142 | 1/2002 | ................... 231/14 |
| EP | 1176147 | 1/2002 | .................... 487/4 |
| EP | 1241170 | 9/2002 | ................... 487/14 |
| EP | 1348707 | 10/2003 | .................... 487/4 |
| FR | 2638745 | 11/1988 | ..................... 281/2 |
| JP | 03142277 | 10/1989 | |
| JP | 2002255932 | 9/2002 | ..................... 205/4 |
| WO | WO 8605518 | 9/1986 | ...................... 1/68 |

(Continued)

OTHER PUBLICATIONS

Vippagunta et. al. (Advanced Drug Delivery Reviews, 2001, 48, 3-26).*

(Continued)

*Primary Examiner*—Brenda L Coleman
*Assistant Examiner*—Susanna Moore
(74) *Attorney, Agent, or Firm*—Gregg C. Benson; Robert T. Ronau

(57) ABSTRACT

This invention relates to compounds of formula (I).

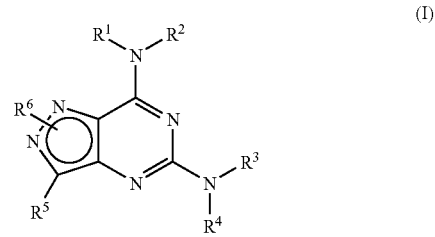

18 Claims, No Drawings

FOREIGN PATENT DOCUMENTS

| | | | |
|---|---|---|---|
| WO | WO 8605519 | 9/1986 | ............ 1/68 |
| WO | WO 9301181 | 1/1993 | ............ 401/12 |
| WO | WO 93/06104 | 4/1993 | ............ 487/4 |
| WO | WO 93/07149 | 4/1993 | ............ 487/4 |
| WO | WO 93/12095 | 6/1993 | ............ 239/91 |
| WO | WO 94/00453 | 1/1994 | ............ 473/30 |
| WO | WO 94/05661 | 3/1994 | ............ 471/4 |
| WO | WO 95/19978 | 7/1995 | ............ 471/14 |
| WO | WO 9616657 | 6/1996 | ............ 31/505 |
| WO | WO 9817668 | 4/1998 | ............ 495/4 |
| WO | WO 98/49166 | 11/1998 | ............ 487/4 |
| WO | WO 9928325 | 6/1999 | ............ 495/4 |
| WO | WO 99/45006 | 9/1999 | ............ 413/14 |
| WO | WO 9954333 | 10/1999 | ............ 487/4 |
| WO | WO 00/24745 | 5/2000 | ............ 487/4 |
| WO | WO 01/27112 | 4/2001 | ............ 487/4 |
| WO | WO 01/27113 | 4/2001 | ............ 487/4 |
| WO | WO 0123389 | 4/2001 | ............ 487/4 |
| WO | WO 01/32646 | 5/2001 | |
| WO | WO 01/47901 | 7/2001 | ............ 271/6 |
| WO | WO 0147495 | 7/2001 | ............ 9/14 |
| WO | WO 02/10171 | 2/2002 | ............ 487/4 |
| WO | WO 0213798 | 2/2002 | |
| WO | WO 02/42292 | 5/2002 | ............ 401/6 |
| WO | WO 02066481 | 8/2002 | ............ 487/4 |
| WO | WO 02102314 | 12/2002 | |
| WO | WO 2004006867 | 1/2004 | |
| WO | WO 2004096810 | 11/2004 | ............ 487/4 |

OTHER PUBLICATIONS

Thayer, A.M. (Chem. & Eng. News, 2007, 85(25), 31-34).*
Organic Reactions, vol. 41 and vol. 42, p. 42, 1992.
Chambers et al. Journal Organic Chemistry, *Selective Sequential Demasking of the Ester Functions of 1-Methyl-3,4,5-tris(methoxycarbonyl)pyrazole*, 50, 4736-4738, 1985.
Zeitschrift fur Chemie 28; 2; 59-60, 1988.
Webber, R., et.al., Journal Med. Chem., *Substituted 2-Iminopiperidines as Inhibitors of Human Nitric Oxide Synthase Isoforms*, 41 (1); 96-101, 1998.
Singh, B., et. al., J Het. Chem., *Three Convenient and Novel Syntheses of 4-Amino-2-arylpyrimidines*, 14; 1413; 1977.
Hara, H., et. al., J. Het. Chem., *On the Amination of Azaheterocycles. A New Procedure for the Introduction of an Amino Group* (1), 19; 1285; 1982.
Orozco, M., et. al., J. Pharmaceutical Science, *Quantum Chemical Study of the Electronic and Conformational Characteristics of Adenosine and 8-Substituted Derivatives: Functional Implications in the Mechanism of Reaction of Adenosine Deaminase*, 79(2), 133-137, 1990.
Orozco, M., et. a., Quantitative Struct.-Act. Relat., *Theoretical Approximation to the Reaction Mechanism of Adenosine Deaminase*, 8: 109-114, 1989.
Orozco, M., et. al., Molecular Pharmacology, *Theoretical Study of the Protonation and Tautomerization of Adenosine, Formycin, and Their 2-$NH_2$ and 2-F Derivatives: Functional Implications in the Mechanism of Reaction of Adenosine Deaminase*, 35(2): 257-264, 1988.
Upadhya, K., et. al., Nucleic Acids Research, *Synthesis of 5-chloroformycin A, 5-chloro-2'-deoxyformycin A and certain related 5,7-disubstituted 3-β-D-ribofuranosylpyrazolo[4,3-d]pyrimidines from formycin A*, 14(4): 1747-1764, 1986.
Secrist III, J., et. al., Journal Med. Chem., *2-Fluoroformycin and 2-Aminoformycin. Synthesis and Biological Activity*, 28(11): 1740-1742, 1985.
Diederich, F., *Metal-Catalysed Cross-Coupling Reactions*, Wiley-VCH, 1998.
Norris, T., et. al., J. Chem. Soc. Perkin Trans. 1, *Synthesis of trovafloxacin using various (1α, 5α, 6α)-3-azabicyclo[3.1.0]hexane derivatives*, 1615-1622, 2000.
Bochis, R., et. al., J. Med. Chem., *Substituted Imidazo[1,2-α]pyridine-2-carbamate Anthelmintics*, 24(12) 1518-1521, 1981.
Yakovlev, M., et. a., Chemistry of. Heterocyclic Compound, *Synthesis of Substituted 2,5-Diazabicyclo[2.2.1]Heptanes*, 36(4): 429-431, 2000.
Smith, S., et. al., Tetrahedron Letters, *Tandem cyclisation and [2,3]-Stevens rearrangement to 2-substituted pyrrolidines*, 43, 899-902, 2002.
Barlocco, D., et. al., J. Med. Chem., *Mono- and Disubstituted-3,8-diazabicyclo[3.2.1]octane Derivatives as Analgesics Structurally Related to Epibatidine: Synthesis, Activity, and Modeling*, 41, 674-681, 1998.
Baraldi, P., et. al., IL Farmaco, *Synthesis, Antibacterial Activity and Structure-Activity Relationships of N-Substituted 4-Diazo-Pyrazole-5-Carboxamides*, 46 (11), 1337-1350, 1991.
Brown, H., et. al., J. Org. Chem., *Hydroboration. 71. Hydroboration of Representative Heterocyclic Olefins with Borane-Methyl Sulfide, 9-Borabicyclo[3.3.1]nonane, Dicyclohexylborane, and Disiamylborane. Synthesis of Heterocyclic Alcohols*, 50, 1582-1589, 1985.
H.C.Van Der Plas, Rec.1. Trav. Chim. Pays-Bas., *Syntheses of Amino and Bromo Derivatives of 4-methyl-,4-t-butyl-and 4-phenyl-pyrimidine*, 84, 1101-1106, 1965.
Dumaitre, B., et. al., Journal of Medicinal Chemistry, American Chemical Society, *Synthesis and Cyclic GMP Phosphodiesterase Inhibitory Activity of a Series of 6-Phenylpyrazolou3,4-Dpyrimidones*, 39(8), 1635-1644, 1996.
Czarniecki, M., et. al., Annu. Rep. Med. Chem., *Inhibitors of Types I and V Phosphodiesterase: Elevation of cGMP as a Therapeutic Strategy*, 31, 61-70, 1996.

* cited by examiner

PYRAZOLO[4,3-D]PYRIMIDINES

This application claims priority under 35 U.S.C. §371 of International Application No. PCT/IB2005/000891, filed Mar. 30, 2005, designating the United States, which claims the benefit from United Kingdom Application No. 0407946.3 and Application No. 0407927.3 filed on Apr. 7, 2004, and claims the benefit from U.S. Application No. 60/572,049 and Application No. 60/572,024 filed on May 18, 2004.

The present invention relates to a series of novel 5,7-diaminopyrazolo[4,3-d]pyrimidines, which are cyclic guanylate monophosphate (cGMP)-specific phosphodiesterase type 5 inhibitors (hereinafter referred to as PDE-5 inhibitors) that are useful in the treatment of hypertension and other disorders, to processes for their preparation, intermediates used in their preparation, to compositions containing them and the uses of said compounds and compositions.

i) Hypertension

The prevalence of hypertension in developed countries is about 20% of the adult population, rising to about 60-70% of those aged 60 or more. Hypertension is associated with an increased risk of stroke, myocardial infarction, atrial fibrillation, heart failure, peripheral vascular disease and renal impairment. Despite the large number of drugs available in various pharmacological categories, the need for an effective treatment of hypertension is still not satisfied.

ii) PDE5 Inhibitors

Vascular endothelial cells secrete nitric oxide (NO). This acts on vascular smooth muscle cells and leads to the activation of guanylate cyclase and the accumulation of cyclic guanosine monophosphate (cGMP). The accumulation of cGMP causes the muscles to relax and the blood vessels to dilate, leading to a reduction in blood pressure. The cGMP is inactivated by hydrolysis to guanosine 5'-monophosphate (GMP) by a cGMP-specific phosphodiesterase. One important cGMP-phosphodiesterase has been identified as Phosphodiesterase type 5 (PDE5). Inhibitors of PDE5 decrease the rate of hydrolysis of cGMP and so potentiate the actions of nitric oxide.

Inhibitors of PDE5 have been reported in several chemical classes, including: pyrazolo[4,3-d]pyrimidin-7-ones (e.g. published international patent applications WO 93/06104, WO 98/49166, WO 99/54333, WO 00/24745, WO 01/27112 and WO 01/27113); pyrazolo[3,4-d]pyrimidin-4-ones (e.g. published international patent application WO 93/07149); pyrazolo[4,3-d]pyrimidines (e.g. published international patent application WO 01/18004); quinazolin-4-ones (e.g. published international patent application WO 93/12095); pyrido[3,2-d]pyrimidin-4-ones (e.g. published international patent application WO 94/05661); purin-6-ones (e.g. published international patent application WO 94/00453); hexahydropyrazino[2',1':6,1]pyrido[3,4-b]indole-1,4-diones (e.g. published international application WO 95/19978) and imidazo[5,1-f][1,2,4]triazin-ones (e.g. published international application WO 99/24433).

WO 02/00660 discloses pyrazolo[4,3-d]pyrimidines with a PDE-5 inhibiting effect, which can be used for treating disorders of the cardiovascular system.

WO 01/18004 discloses pyrazolo[4,3-d]pyrimidines with a PDE-5 inhibiting effect.

There remains a demand for new PDE5 inhibitors, particularly with improved pharmacokinetic and pharmacodynamic properties. The compounds provided herein are potent inhibitors of PDE5 that have improved selectivity in vitro and/or an extended half-life in vivo.

According to a first aspect, the present invention provides compounds of formula (I)

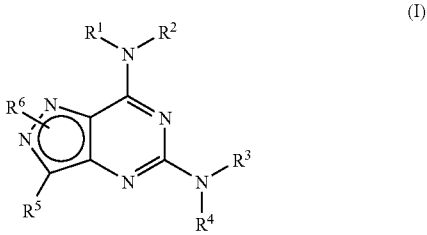

wherein $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ groups, or $R^E$, which is optionally substituted with one or more $R^9$ groups, or hydrogen;

or —$NR^3R^4$ forms $R^F$, which is optionally substituted with one or more $R^{10}$ groups;

$R^5$ is —Y—$NR^{15}R^{16}$;

$R^6$, which may be attached at $N^1$ or $N^2$, is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, ($C_3$-$C_6$ cycloalkyl) methoxy, $C_1$-$C_6$ haloalkoxy or a cyclic group selected from $R^J$, $R^K$, $R^L$ and $R^M$, or $R^6$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy, or $R^6$ is hydrogen;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or $CN$;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, $CN$, $C_3$-$C_6$ cycloalkyl, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{21}R^{13}$, $CN$, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is selected from $R^{17}$, $R^{17}C(O)$ and $R^{18}SO_2$, and $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups, or —$NR^{15}R^{16}$ constitutes a 3- to 8-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;

$R^{19}$ is selected from $R^{21}$, —$NR^{23}R^{24}$, $CO_2R^{25}$, —$CONR^{26}R^{27}$, $R^{28}$ and phenyl optionally substituted by $R^{29}$;

$R^{20}$ is selected from $R^{21}$, $R^{22}$ and oxo;

$R^{21}$ is oxo, hydroxy, $C_1$-$C_6$ alkoxy, $C_1$-$C_6$ (haloalkyl)oxy or $C_3$-$C_7$ cycloalkyloxy;

$R^{22}$ is $C_1$-$C_6$ alkyl or $C_1$-$C_6$ haloalkyl;

$R^{23}$ and $R^{24}$ are each independently selected from hydrogen and $C_1$-$C_6$ alkyl;

or —$NR^{23}R^{24}$ constitutes an azetidine, pyrrolidine, piperidine or morpholine ring;

$R^{25}$ is hydrogen or $C_1$-$C_6$ alkyl;

$R^{26}$ and $R^{27}$ are each independently selected from hydrogen and $C_1$-$C_6$ alkyl;

or —$NR^{26}R^{27}$ constitutes an azetidine, pyrrolidine, piperidine or morpholine ring;

$R^{28}$ is a saturated, unsaturated or aromatic heterocycle with up to 10 ring atoms, at least one of which is selected from nitrogen, oxygen and sulphur;

$R^{29}$ is selected from halo, $R^{21}$ and $R^{22}$, $R^A$ and $R^J$ are each independently a $C_3$-$C_{10}$ cycloalkyl or $C_3$-$C_{10}$ cycloalkenyl group, each of which may be either monocyclic or, when there are an appropriate number of ring atoms, polycyclic and which may be fused to either
  (a) a monocyclic aromatic ring selected from a benzene ring and a 5- or 6-membered heteroaromatic ring containing up to three heteroatoms selected from nitrogen, oxygen and sulphur, or
  (b) a 5-, 6- or 7-membered heteroalicyclic ring containing up to three heteroatoms selected from nitrogen, oxygen and sulphur;

$R^B$ and $R^K$ are each independently a phenyl or naphthyl group, each of which may be fused to
  (a) a $C_5$-$C_7$ cycloalkyl or $C_5$-$C_7$ cycloalkenyl ring,
  (b) a 5-, 6- or 7-membered heteroalicyclic ring containing up to three heteroatoms selected from nitrogen, oxygen and sulphur, or
  (c) a 5- or 6-membered heteroaromatic ring containing up to three heteroatoms selected from nitrogen, oxygen and sulphur;

$R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^D$ and $R^M$ are each independently a 5- or 6-membered heteroaromatic ring containing up to three heteroatoms independently selected from nitrogen, oxygen and sulphur, which ring may further be fused to
  (a) a second 5- or 6-membered heteroaromatic ring containing up to three heteroatoms selected from nitrogen, oxygen and sulphur;
  (b) $C_5$-$C_7$ cycloalkyl or $C_5$-$C_7$ cycloalkenyl ring;
  (c) a 5-, 6- or 7-membered heteroalicyclic ring containing up to three heteroatoms selected from nitrogen, oxygen and sulphur; or
  (d) a benzene ring;

$R^E$, $R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur; and Y is a covalent bond, $C_1$-$C_6$ alkylenyl or $C_3$-$C_7$ cycloalkylenyl;

a tautomer thereof or a pharmaceutically acceptable salt, solvate or polymorph of said compound or tautomer.

As used herein, alkylenyl indicates an alkyl-m,n-diyl unit where m and n are the same or different, such as methylene (—$CH_2$—), ethylene (—$CH_2CH_2$—) and propane-1,2-diyl (—$CH(CH_3)CH_2$—).

As used herein, cycloalkylenyl indicates a cycloalkyl-m,n-diyl unit where m and n are the same or different, such as cyclopropane-1,1-diyl and cyclohexane-1,4-diyl.

Unless otherwise indicated, an alkyl or alkoxy group may be straight or branched and contain 1 to 8 carbon atoms, preferably 1 to 6 and particularly 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Unless otherwise indicated, an alkenyl or alkynyl group may be straight or branched and contain 2 to 8 carbon atoms, preferably 2 to 6 and particularly 2 to 4 carbon atoms and may contain up to 3 double or triple bonds which may be conjugated. Examples of alkenyl and alkynyl include vinyl, allyl, butadienyl and propargyl.

Unless otherwise indicated, a cycloalkyl or cycloalkoxy group may contain 3 to 10 ring-atoms, may be either monocyclic or, when there are an appropriate number of ring atoms, polycyclic. Examples of cycloalkyl groups are cyclopropyl, cyclopentyl, cyclohexyl and adamantyl.

Unless otherwise indicated, a cycloalkenyl group may contain 3 to 10 ring-atoms, may be either monocyclic or, when there are an appropriate number of ring atoms, polycyclic and may contain up to 3 double bonds. Examples of cycloalkenyl groups are cyclopentenyl and cyclohexenyl.

Aryl includes phenyl, naphthyl, anthracenyl and phenanthrenyl.

Unless otherwise indicated, a heteroalicyclyl group contains 3 to 10 ring-atoms up to 4 of which may be hetero-atoms such as nitrogen, oxygen and sulfur, and may be saturated or partially unsaturated. Examples of heteroalicyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Unless otherwise indicated, a heteroaryl group contains 3 to 10 ring-atoms up to 4 of which may be hetero-atoms such as nitrogen, oxygen and sulfur. Examples of heteroaryl groups are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, tetrazolyl, triazinyl. In addition, the term heteroaryl includes fused heteroaryl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, benzothiazolyl, phthalimido, benzofuranyl, benzodiazepinyl, indolyl and isoindolyl.

Halo means fluoro, chloro, bromo or iodo.

Haloalkyl includes monohaloalkyl, polyhaloalkyl and perhaloalkyl, such as 2-bromoethyl, 2,2,2-trifluoroethyl, chlorodifluoromethyl and trichloromethyl.

Haloalkoxy includes monohaloalkoxy, polyhaloalkoxy and perhaloalkoxy, such as 2-bromoethoxy, 2,2,2-trifluoroethoxy, chlorodifluoromethoxy and trichloromethoxy. Halocycloalkyl includes monohalocycloalkyl, polyhalocycloalkyl and perhalocycloalkyl.

Unless otherwise indicated, the term substituted means substituted by one or more defined groups. In the case where groups may be selected from a number of alternative groups, the selected groups may be the same or different.

In some embodiments, $R^{21}$ is hydroxy, $C_1$-$C_6$ alkoxy, $C_1$-$C_6$ (haloalkyl)oxy or $C_3$-$C_7$ cycloalkyloxy.

In one preferred embodiment, $R^1$ is $R^A$, which is optionally substituted with one or more $R^7$ groups; and $R^A$ is a $C_3$-$C_{10}$ cycloalkyl group, which may be either monocyclic or, when there are an appropriate number of ring atoms, polycyclic, which may be fused to either (a) a monocyclic aromatic ring selected from a benzene ring and a 5- or 6-membered heteroaromatic ring containing up to three heteroatoms selected from nitrogen, oxygen and sulphur, or (b) a 5-, 6- or 7-membered heteroalicyclic ring containing up to three heteroatoms selected from nitrogen, oxygen and sulphur.

Preferably, $R^A$ is a monocyclic $C_3$-$C_8$ cycloalkyl group.

More preferably, $R^A$ is a monocyclic $C_5$-$C_7$ cycloalkyl group.

Most preferably, $R^A$ is cyclopentyl or cyclohexyl.

In another preferred embodiment, $R^1$ is $R^B$, which is optionally substituted with one or more $R^7$ groups.

Preferably, $R^B$ is phenyl.

In another preferred embodiment, $R^1$ is $R^C$, which is optionally substituted with one or more $R^7$ groups.

Preferably, $R^C$ is a monocyclic saturated or partly unsaturated ring system containing between 3 and 8 ring atoms, of which at least one is a heteroatom selected from nitrogen, oxygen and sulphur.

More preferably, $R^C$ is a monocyclic saturated or partly unsaturated ring system containing between 5 and 7 ring atoms, of which at least one is a heteroatom selected from nitrogen, oxygen and sulphur.

Most preferably, $R^C$ is a monocyclic saturated ring system containing between 5 and 7 ring atoms, of which at least one is a heteroatom selected from nitrogen, oxygen and sulphur.

In another preferred embodiment, $R^1$ is $R^D$, which is optionally substituted with one or more $R^7$ groups.

Preferably, $R^D$ is a 5- or 6-membered heteroaromatic ring containing up to three heteroatoms independently selected from nitrogen, oxygen and sulphur.

More preferably, $R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms.

More preferably $R^D$ is furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl or pyrazinyl.

Most preferably, $R^D$ is pyrazolyl, imidazolyl, isoxazolyl, oxazolyl, oxadiazolyl, pyridyl, pyridazinyl, pyrimidyl or pyrazinyl.

Preferably, $R^7$ is halo, $C_1$-$C_6$ alkyl, $C_1$-$C_6$ haloalkyl, $OR^{12}$ or $CONR^{12}R^{13}$.

More preferably, $R^7$ is halo, $C_1$-$C_3$ alkyl, $C_1$-$C_3$ alkoxy, hydroxy or $CONH(C_1$-$C_3$ alkyl).

Most preferably, $R^7$ is fluoro, methyl, ethyl, hydroxy, methoxy, propoxy or CONHMe.

Preferably, $R^2$ is hydrogen or methyl.

More preferably, $R^2$ is hydrogen.

Preferably, $R^3$ is hydrogen, $C_1$-$C_6$ alkyl, which is optionally substituted with one or more $R^8$ groups, or $R^E$, which is optionally substituted with one or more $R^9$ groups; and wherein $R^E$ is a monocyclic or, when there are an appropriate number of ring atoms, polycyclic saturated ring system containing between 3 and 7 ring atoms, of which at least one is a heteroatom selected from nitrogen, oxygen and sulphur.

More preferably, $R^3$ is hydrogen, $C_1$-$C_4$ alkyl, which is optionally substituted with one or more $R^8$ groups, or $R^E$, which is optionally substituted with one or more $R^9$ groups; and wherein $R^E$ is a monocyclic saturated ring system containing between 3 and 7 ring atoms, of which at least one is a heteroatom selected from nitrogen, oxygen and sulphur.

In one preferred embodiment, $R^3$ is $R^E$, which is optionally substituted with one or more $R^9$ groups and wherein $R^E$ is a monocyclic saturated ring system containing between 3 and 7 ring atoms containing one nitrogen atom.

More preferably, $R^E$ is azetidinyl, pyrrolidinyl or piperidinyl.

In another preferred embodiment, $R^3$ is $C_1$-$C_4$ alkyl, which is optionally substituted with one or more $R^8$ groups and wherein $R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups.

More preferably, $R^8$ is hydroxy, methoxy, methoxyphenyl, $NH_2$, NHMe, $NMe_2$, $NHCO_2{}^tBu$, $NMeCO_2{}^tBu$, $CO_2H$, CONHMe, $R^G$ or $R^H$, the last two of which are optionally substituted with one or more $R^9$ groups.

In one preferred embodiment, $R^8$ is $R^G$, which is optionally substituted with one or more $R^9$ groups and wherein $R^G$ is a monocyclic saturated ring system containing between 3 and 7 ring atoms, of which at least one is a heteroatom selected from nitrogen, oxygen and sulphur.

More preferably, $R^G$ is a monocyclic saturated ring system containing between 3 and 7 ring atoms containing one nitrogen atom and optionally one oxygen atom.

Most preferably, $R^G$ is pyrrolidinyl, piperidinyl or morpholinyl.

In another preferred embodiment, $R^8$ is $R^H$, which is optionally substituted with one or more $R^9$ groups and wherein $R^H$ is a 5- or 6-membered heteroaromatic ring containing up to two nitrogen atoms.

More preferably, $R^H$ is pyrazolyl.

Preferably, $R^9$ is methyl or $CO_2{}^tBu$.

In another preferred embodiment, $R^3$ is hydrogen or $C_1$-$C_4$ alkyl, which is optionally substituted with one or more $R^8$ groups, or $R^3$ is azetidinyl, pyrrolidinyl or piperidinyl, each of which is optionally substituted with one or more $R^9$ groups, wherein $R^8$ is hydroxy, methoxy, methoxyphenyl, $NH_2$, NHMe, $NMe_2$, $NHCO_2{}^tBu$, $NMeCO_2{}^tBu$, $CO_2H$, CONHMe, pyrrolidinyl, piperidinyl, morpholinyl or pyrazolyl, the last four of which are optionally substituted with one or more $R^9$ groups and wherein $R^9$ is methyl or $CO_2{}^tBu$.

In one preferred embodiment, $R^4$ is hydrogen, $C_1$-$C_6$ alkyl, $C_1$-$C_6$ haloalkyl, $C_2$-$C_6$ alkenyl or $C_2$-$C_6$ alkynyl.

More preferably, $R^4$ is hydrogen, $C_1$-$C_6$ alkyl or $C_1$-$C_6$ haloalkyl.

Most preferably, $R^4$ is hydrogen, methyl or ethyl.

In another preferred embodiment, —$NR^3R^4$ forms $R^F$, which is optionally substituted with one or more $R^{10}$ groups and wherein RF is a monocyclic or, when there are an appropriate number of ring atoms, polycyclic saturated ring system containing between 3 and 10 ring atoms containing at least one nitrogen atom and optionally one other atom selected from oxygen and sulphur.

More preferably, $R^F$ is a monocyclic or, when there are an appropriate number of ring atoms, polycyclic saturated ring system containing between 3 and 10 ring atoms containing one or two nitrogen atoms and optionally one other atom selected from oxygen and sulphur.

Most preferably, $R^F$ is selected from azetidinyl, pyrrolidinyl, piperidinyl, piperazinyl, morpholinyl, 3-azabicyclo[3.1.0]hex-3-yl, homopiperazinyl, 2,5-diazabicyclo[4.3.0]non-2-yl, 3,8-diazabicyclo[3.2.1]oct-3-yl, 3,8-diazabicyclo[3.2.1]oct-8-yl, 2,5-diazabicyclo[2.2.1]hept-2-yl, 1,4-diazabicyclo[4.3.0]non-4-yl and 1,4-diazabicyclo[3.2.2]non-4-yl.

Preferably $R^{10}$ is halo, $OR^{12}$, $NR^{12}R^{13}$, $NR^{12}CO_2R^{14}$, $CO_2R^{13}$, oxo, $C_1$-$C_8$ alkyl or $C_1$-$C_6$ haloalkyl, the last two of which are optionally substituted by $R^{11}$.

More preferably, $R^{10}$ is halo, methyl, ethyl, isopropyl, hydroxy, methoxy, $NH_2$, NHMe, $NMe_2$, $NHCO_2{}^tBu$, $CO_2H$, $CO_2{}^tBu$, oxo, benzyl, —$CH_2NH_2$, —$CH_2NHMe$, $CH_2NMe_2$ or —$CH_2NMeCO_2{}^tBu$.

In one preferred embodiment, $R^5$ is —Y—$NR^{15}R^{16}$ and Y is $C_1$-$C_6$ alkylenyl. More preferably, Y is methylene (—$CH_2$—).

In another preferred embodiment, $R^5$ is —Y—$NR^{15}R^{16}$, $R^{15}$ is $R^{17}C(O)$ or $R^{18}SO_2$—, and $R^{16}$ is hydrogen or $C_1$-$C_6$ alkyl.

In another preferred embodiment, $R^5$ is —Y—$NR^{15}R^{16}$, $R^{15}$ is $R^{17}$, and $R^{16}$ is hydrogen or $C_1$-$C_6$ alkyl.

In another preferred embodiment, $R^{17}$ is $R^{18}$ and $R^{18}$ is $C_1$-$C_6$ alkyl optionally substituted with one $R^{19}$ group.

In another preferred embodiment, $R^5$ is —Y—$NR^{15}R^{16}$ wherein —$NR^{15}R^{16}$ constitutes a 3- to 8-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl. More preferably, —$NR^{15}R^{16}$ constitutes a 5- or 6-membered saturated ring which may optionally include one further nitrogen atom, and which may optionally be substituted with a group selected from $R^{21}$, $R^{22}$ and ($C_1$-$C_6$ alkoxy)$C_1$-$C_6$ alkyl. Preferably $R^{21}$ is $C_1$-$C_6$ alkoxy and $R^{22}$ is $C_1$-$C_6$ alkyl.

Preferably, $R^6$ is positioned on $N^1$ to give the compound of formula ($I^A$):

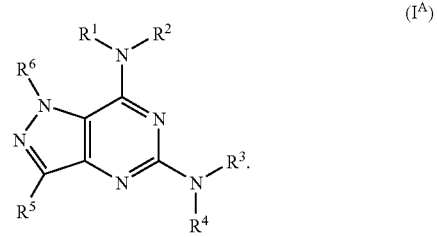

In an alternative embodiment of the present invention, $R^6$ may be positioned on $N^2$ to give the compound of formula ($I^B$):

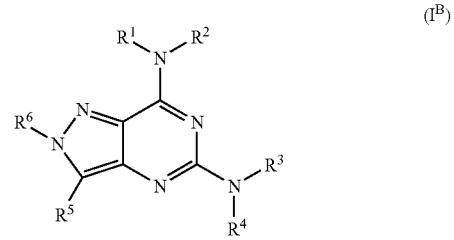

Preferably, $R^6$ is $C_1$-$C_6$ alkyl or $C_1$-$C_6$ haloalkyl, each of which is optionally substituted by $C_1$-$C_6$ alkoxy, $C_1$-$C_6$ haloalkoxy or a cyclic group selected from $R^J$, $R^L$ and $R^M$, or $R^6$ is $R^N$ or hydrogen;

$R^J$ is a $C_3$-$C_7$ monocyclic cycloalkyl group;

$R^L$ and $R^N$ are each independently a monocyclic, saturated or partly unsaturated ring system containing between 4 and 7 ring atoms, of which at least one is a heteroatom selected from nitrogen, oxygen and sulphur; and $R^M$ is a 5- or 6-membered heteroaromatic ring containing up to three heteroatoms independently selected from nitrogen, oxygen and sulphur.

More preferably, $R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur; and $R^M$ is a 5- or 6-membered heteroaromatic ring containing a heteroatom selected from nitrogen, oxygen and sulphur.

More preferably, $R^6$ is $C_1$-$C_4$ alkyl or $C_1$-$C_4$ haloalkyl, each of which is optionally substituted by $C_1$-$C_4$ alkoxy or a cyclic group selected from $R^J$, $R^L$ and $R^M$, or $R^6$ is $R^N$ or hydrogen;

$R^J$ is cyclopropyl or cyclobutyl;

$R^L$ and $R^N$ are each independently a monocyclic saturated ring system containing either 5 or 6 ring atoms containing one heteroatom selected from nitrogen, oxygen and sulphur; and $R^M$ is a 5- or 6-membered heteroaromatic ring containing one nitrogen atom.

More preferably, $R^6$ is $C_1$-$C_4$ alkyl or $C_1$-$C_4$ haloalkyl, each of which is optionally substituted by $C_1$-$C_4$ alkoxy, cyclopropyl, cyclobutyl, tetrahydrofuranyl, tetrahydropyranyl or pyridinyl, or $R^6$ is hydrogen or tetrahydropyranyl.

Most preferably, $R^6$ is hydrogen, methyl, ethyl, isopropyl, isobutyl, methoxyethyl, methoxypropyl, ethoxyethyl, ethoxypropyl, propoxyethyl, 2,2,2-trifluoroethyl, tetrahydrofuranylmethyl, tetrahydropyranylmethyl, tetrahydropyranyl or pyridinylmethyl.

Preferred embodiments of compounds of formula (I) are those that incorporate two or more of the foregoing preferences.

In some embodiments, the compounds of formula (I) are as follows:

$R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$NR^{15}R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{13}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $C_3$-$C_6$ cycloalkyl, $R^G$ or $R^H$, the last two of which are optionally substituted with one or more $R^{19}$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is selected from $R^{17}$, $R^{17}C(O)$ and $R^{18}SO_2$, and $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups, or —$NR^{15}R^{16}$ constitutes a 3- to 8-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;

$R^{19}$ is selected from $R^{21}$, —$NR^{23}R^{24}$, —$CO_2R^{25}$, —$CONR^{26}R^{27}$, $R^{28}$ and phenyl optionally substituted by $R^{29}$;

$R^{20}$ is selected from $R^{21}$, $R^{22}$ and oxo;

$R^{21}$ is hydroxy, $C_1$-$C_6$ alkoxy, $C_1$-$C_6$ (haloalkyl)oxy or $C_3$-$C_7$ cycloalkyloxy;

$R^{22}$ is $C_1$-$C_6$ alkyl or $C_1$-$C_6$ haloalkyl;

$R^{23}$ and $R^{24}$ are each independently selected from hydrogen and $C_1$-$C_6$ alkyl;

or —$NR^{23}R^{24}$ constitutes an azetidine, pyrrolidine, piperidine or morpholine ring;

$R^{25}$ is hydrogen or $C_1$-$C_6$ alkyl;

$R^{26}$ and $R^{27}$ are each independently selected from hydrogen and $C_1$-$C_6$ alkyl;

or —$NR^{26}R^{27}$ constitutes an azetidine, pyrrolidine, piperidine or morpholine ring;

$R^{28}$ is a saturated, unsaturated or aromatic heterocycle with up to 10 ring atoms, at least one of which is selected from nitrogen, oxygen and sulphur;

$R^{29}$ is selected from halo, $R^{21}$ and $R^{22}$, $R^A$ is a monocyclic $C_3$-$C_8$ cycloalkyl group;

$R^B$ is phenyl;

$R^C$ is a monocyclic saturated or partly unsaturated ring system containing between 3 and 8 ring atoms, of which at least one is a heteroatom selected from nitrogen, oxygen and sulphur;

$R^D$ is a 5- or 6-membered heteroaromatic ring containing up to three heteroatoms independently selected from nitrogen, oxygen and sulphur;

$R^E$ is a monocyclic saturated ring system containing between 3 and 7 ring atoms, of which at least one is a heteroatom selected from nitrogen, oxygen and sulphur;

$R^F$ is a monocyclic or, when there are an appropriate number of ring atoms, polycyclic saturated ring system containing between 3 and 10 ring atoms, of which at least one is a heteroatom selected from nitrogen, oxygen and sulphur;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

$R^K$ is a phenyl or naphthyl group, each of which may be fused to (a) a $C_5$-$C_7$ cycloalkyl or $C_5$-$C_7$ cycloalkenyl ring, (b) a 5-, 6- or 7-membered heteroalicyclic ring containing up to three heteroatoms selected from nitrogen, oxygen and sulphur, or (c) a 5- or 6-membered heteroaromatic ring containing up to three heteroatoms selected from nitrogen, oxygen and sulphur;

$R^G$ is a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur;

$R^M$ is a 5- or 6-membered heteroaromatic ring containing a heteroatom selected from nitrogen, oxygen and sulphur; and Y is $C_1$-$C_6$ alkylenyl.

In other embodiments, the compounds of formula (I) are as follows:

$R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$NR^{15}R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is selected from $R^{17}$, $R^{17}C(O)$ and $R^{18}SO_2$, and $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups, or —$NR^{15}R^{16}$ constitutes a 3- to 8-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;

$R^{19}$ is selected from $R^{21}$, —$NR^{23}R^{24}$, —$CO_2R^{25}$, —$CONR^{26}R^{27}$, $R^{28}$ and phenyl optionally substituted by $R^{29}$;

$R^{20}$ is selected from $R^{21}$, $R^{22}$ and oxo;

$R^{21}$ is hydroxy, $C_1$-$C_6$ alkoxy, $C_1$-$C_6$ (haloalkyl)oxy or $C_3$-$C_7$ cycloalkyloxy;

$R^{22}$ is $C_1$-$C_6$ alkyl or $C_1$-$C_6$ haloalkyl;

$R^{23}$ and $R^{24}$ are each independently selected from hydrogen and $C_1$-$C_6$ alkyl;

or —$NR^{23}R^{24}$ constitutes an azetidine, pyrrolidine, piperidine or morpholine ring;

$R^{25}$ is hydrogen or $C_1$-$C_6$ alkyl;

$R^{26}$ and $R^{27}$ are each independently selected from hydrogen and $C_1$-$C_6$ alkyl;

or —$NR^{26}R^{27}$ constitutes an azetidine, pyrrolidine, piperidine or morpholine ring;

$R^{28}$ is a saturated, unsaturated or aromatic heterocycle with up to 10 ring atoms, at least one of which is selected from nitrogen, oxygen and sulphur;

$R^{29}$ is selected from halo, $R^{21}$ and $R^{22}$ $R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

$R^K$ is a phenyl or naphthyl group, each of which may be fused to
  (a) a $C_5$-$C_7$ cycloalkyl or $C_5$-$C_7$ cycloalkenyl ring,
  (b) a 5-, 6- or 7-membered heteroalicyclic ring containing up to three heteroatoms selected from nitrogen, oxygen and sulphur, or
  (c) a 5- or 6-membered heteroaromatic ring containing up to three heteroatoms selected from nitrogen, oxygen and sulphur;

$R^M$ is a 5- or 6-membered heteroaromatic ring containing a heteroatom selected from nitrogen, oxygen and sulphur; and Y is —$CH_2$—.

Preferably $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$NR^{15}R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}NR^{12}C(O)R^{13}$, $NR^{12}CO_2R^{14}$, $C(O)R^{12}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{13}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is hydrogen or $C_1$-$C_3$ alkyl:

$R^{16}$ is tetrazol-5-yl, 5-trifluoromethyl-1,2,4-triazol-3-yl or 2,5-dihydro-5-oxo-1,2,4-oxadiazol-3-yl;

$R^A$ is a monocyclic $C_3$-$C_8$ cycloalkyl group;

$R^B$ is phenyl;

$R^C$ is a monocyclic saturated or partly unsaturated ring system containing between 3 and 8 ring atoms, of which at least one is a heteroatom selected from nitrogen, oxygen and sulphur;

$R^D$ is a 5- or 6-membered heteroaromatic ring containing up to three heteroatoms independently selected from nitrogen, oxygen and sulphur;

$R^E$ is a monocyclic saturated ring system containing between 3 and 7 ring atoms, of which at least one is a heteroatom selected from nitrogen, oxygen and sulphur;

$R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is $C_1$-$C_6$ alkylenyl.

More preferably, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$NR^{15}R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is hydrogen;

$R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is methylene.

In some embodiments, $R^2$ in compounds of formula ($I^A$) is hydrogen, and the compounds correspond in structure to formula ($I^A$-1):

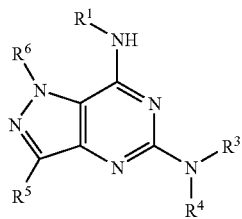

(I^A-1)

wherein $R^1$ is cyclic group selected from $R^B$ and $R^D$, each of which is optionally substituted with one or more $R^7$ groups;

$R^B$ is phenyl;

$R^D$ is a 6-membered heteroaromatic ring including 1, 2, or 3 nitrogen atoms;

$R^7$ is halo, $C_1$-$C_3$ alkyl, $C_1$-$C_3$ alkoxy, hydroxy or CONH($C_1$-$C_3$ alkyl);

$R^3$ is hydrogen, $C_1$-$C_4$ alkyl, which is optionally substituted with one or more $R^8$ groups, or $R^3$ is azetidinyl, pyrrolidinyl or piperidinyl, each of which is optionally substituted with one or more $R^9$ groups; and $R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^8$ is hydroxy, methoxy, methoxyphenyl, $NH_2$, NHMe, $NMe_2$, $NHCO_2{}^tBu$, $NMeCO_2{}^tBu$, $CO_2H$, CONHMe, pyrrolidinyl, piperidinyl, morpholinyl or pyrazolyl, the last four of which are optionally substituted with one or more $R^9$ groups;

$R^9$ is methyl or $CO_2{}^tBu$;

$R^F$ is a monocyclic or, when there are an appropriate number of ring atoms, polycyclic saturated ring system containing between 3 and 10 ring atoms containing one or two nitrogen atoms and optionally one other atom selected from oxygen and sulphur;

$R^{10}$ is halo, methyl, ethyl, isopropyl, hydroxy, methoxy, $NH_2$, NHMe, $NMe_2$, $NHCO_2{}^tBu$, $CO_2H$, $CO_2{}^tBu$, oxo, benzyl, —$CH_2NH_2$, —$CH_2NHMe$, $CH_2NMe_2$ or —$CH_2NMeCO_2{}^tBu$;

$R^5$ is —Y—$NR^{15}R^{16}$;

Y is $C_1$-$C_6$ alkylenyl;

$R^{15}$ is selected from $R^{17}$, $R^{17}C(O)$ and $R^{18}SO_2$, and $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups, or —$NR^{15}R^{16}$ constitutes a 3- to 8-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;

$R^{19}$ is selected from $R^{21}$, —$NR^{23}R^{24}$, —$CO_2R^{21}$, $CONR^{26}R^{27}$, $R^{28}$ and phenyl optionally substituted by $R^{29}$;

$R^{20}$ is selected from $R^{21}$, $R^{22}$ and oxo;

$R^{21}$ is oxo, hydroxy, $C_1$-$C_6$ alkoxy, $C_1$-$C_6$ (haloalkyl)oxy or $C_3$-$C_7$ cycloalkyloxy;

$R^{22}$ is $C_1$-$C_6$ alkyl or $C_1$-$C_6$ haloalkyl;

$R^{23}$ and $R^{24}$ are each independently selected from hydrogen and $C_1$-$C_6$ alkyl;

or —$NR^{23}R^{24}$ constitutes an azetidine, pyrrolidine, piperidine or morpholine ring;

$R^{25}$ is hydrogen or $C_1$-$C_6$ alkyl;

$R^{26}$ and $R^{27}$ are each independently selected from hydrogen and $C_1$-$C_6$ alkyl;

or —$NR^{26}R^{27}$ constitutes an azetidine, pyrrolidine, piperidine or morpholine ring;

$R^{28}$ is a saturated, unsaturated or aromatic heterocycle with up to 10 ring atoms, at least one of which is selected from nitrogen, oxygen and sulphur;

$R^{29}$ is selected from halo, $R^{21}$ and $R^{22}$, $R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur; and $R^M$ is a 5- or 6-membered heteroaromatic ring containing a heteroatom selected from nitrogen, oxygen and sulphur.

In some embodiments, the compounds of formula (I$^A$-1) correspond in structure to formulas (I$^A$-2) and (I$^A$-3):

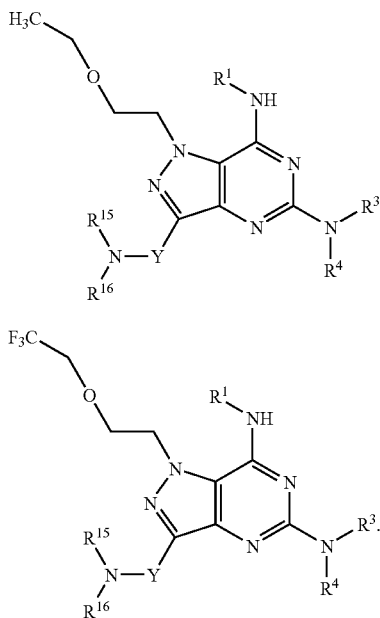

In some embodiments, the compounds of formula (I$^A$-2) and (I$^A$-3) are as follows:

$R^1$ is phenyl, pyridinyl, or pyrimidinyl, each optionally substituted with one or more $R^7$ groups;

$R^7$ is halo or $C_1$-$C_3$ alkyl;

$R^3$ is hydrogen or alkyl substituted with one or more $R^8$ groups, and $R^4$ is hydrogen or $C_1$-$C_6$ alkyl, or —NR$^3$R$^4$ forms piperazinyl optionally substituted with one or more $R^{10}$ groups;

$R^8$ is hydroxy or methoxy;

$R^{10}$ is methyl;

Y is methylene;

$R^{15}$ is selected from $R^{17}$, $R^{17}$C(O) and $R^{18}$SO$_2$, and $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups, or —NR$^{15}$R$^{16}$ constitutes a 5- to 7-membered saturated ring which may optionally include one or more further heteroatoms selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;

$R^{19}$ is selected from $R^{21}$ and —NR$^{23}$R$^{24}$;

$R^{20}$ is selected from $R^{21}$, $R^{22}$ and oxo;

$R^{21}$ is oxo, hydroxy, and $C_1$-$C_6$ alkoxy;

$R^{22}$ is $C_1$-$C_6$ alkyl or $C_1$-$C_6$ haloalkyl; and $R^{23}$ and $R^{24}$ are each independently selected from hydrogen and $C_1$-$C_6$ alkyl.

In some embodiments, the compounds of formula (I$^A$-2) and (I$^A$-3) are as follows:

$R^1$ is phenyl, pyridinyl, or pyrimidinyl, each optionally substituted with one or more $R^7$ groups;

$R^7$ is halo or $C_1$-$C_3$ alkyl;

$R^3$ is hydrogen or alkyl substituted with one or more $R^8$ groups, and $R^4$ is hydrogen or $C_1$-$C_6$ alkyl, or —NR$^3$R$^4$ forms piperazinyl optionally substituted with one or more $R^{10}$ groups;

$R^8$ is hydroxy or methoxy;

$R^{10}$ is methyl;

Y is methylene;

$R^{15}$ is selected from $R^{17}$, $R^{17}$C(O) and $R^{18}$SO$_2$, and $R^{16}$ is selected from hydrogen, $C_1$-$C_6$ alkyl, $C_1$-$C_6$ haloalkyl and $C_3$-$C_{10}$ cycloalkyl optionally substituted with one or more hydroxy groups, or —NR$^{15}$R$^{16}$ constitutes a 5- to 7-membered saturated ring which may optionally include one or more further heteroatoms selected from nitrogen, oxygen and sulphur, and which may optionally be substituted with one or more groups selected from $C_1$-$C_6$ alkyl, oxo, hydroxy and ($C_1$-$C_6$ alkoxy) $C_1$-$C_6$ alkyl;

$R^{17}$ is hydrogen or $R^{18}$;

$R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more hydroxy groups;

$R^{19}$ is selected from hydroxy, $C_1$-$C_3$ alkoxy and —NR$^{23}$R$^{24}$; and $R^{23}$ and $R^{24}$ are each independently selected from hydrogen and $C_1$-$C_6$ alkyl.

In some embodiments, the compounds of formula (I$^A$-1) correspond in structure to one of the formulas below:

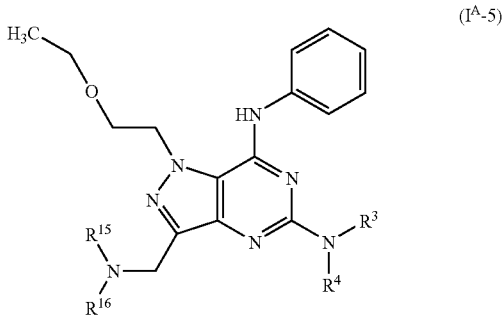

-continued
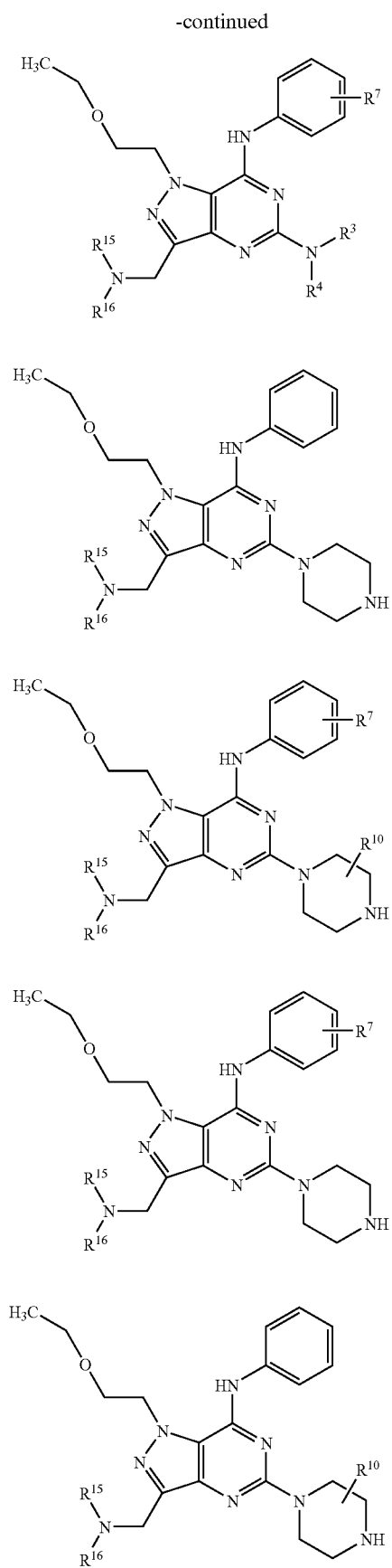
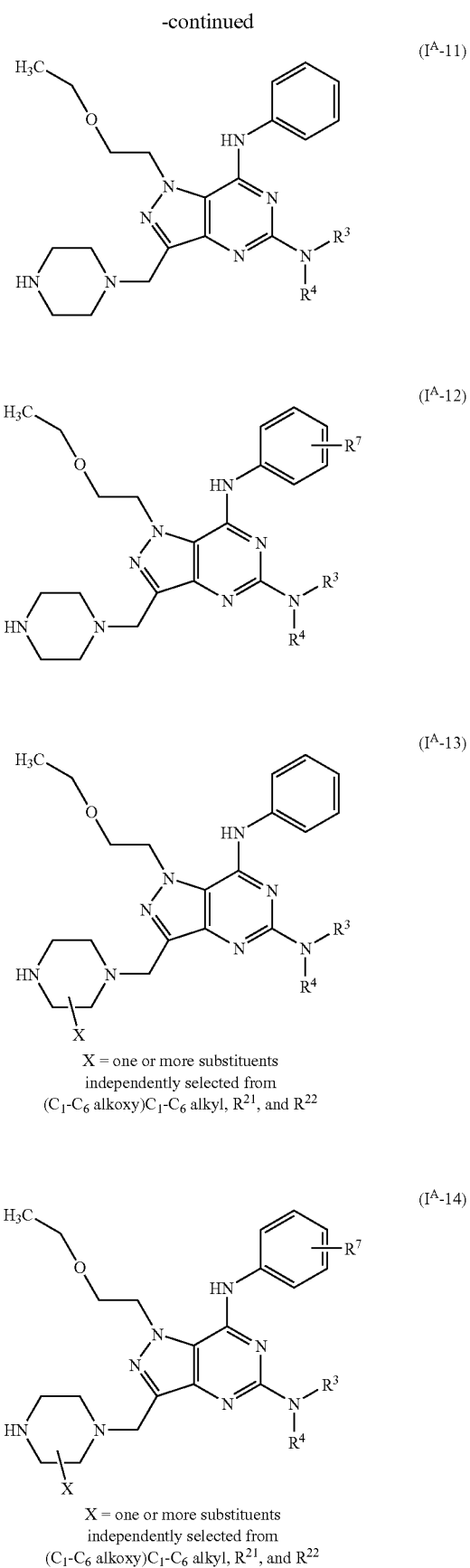

-continued

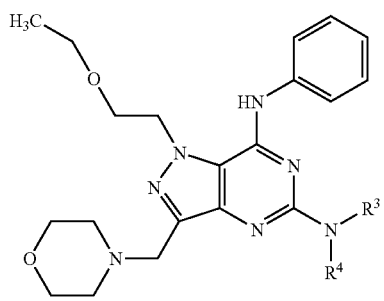
(I^A-15)

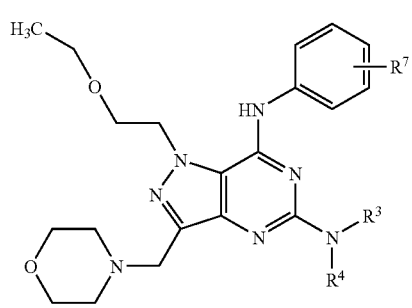
(I^A-16)

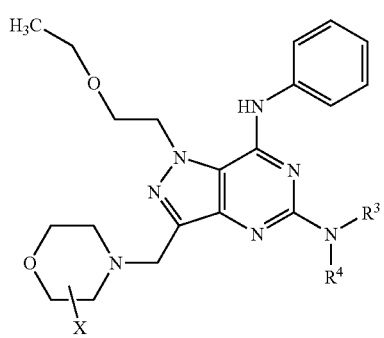
(I^A-17)

X = one or more substituents
independently selected from
($C_1$-$C_6$ alkoxy)$C_1$-$C_6$ alkyl, $R^{21}$, and $R^{22}$

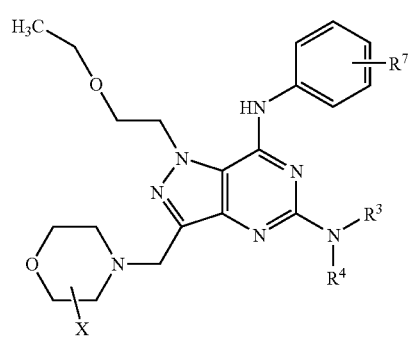
(I^A-18)

X = one or more substituents
independently selected from
($C_1$-$C_6$ alkoxy)$C_1$-$C_6$ alkyl, $R^{21}$, and $R^{22}$ -continued

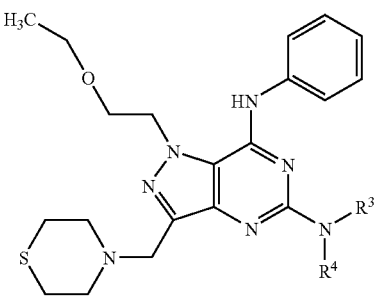
(I^A-19)

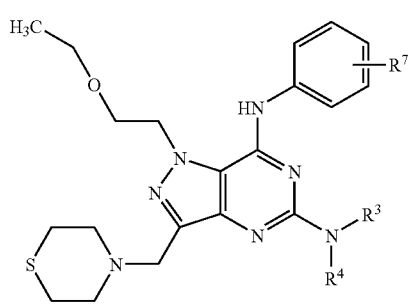
(I^A-20)

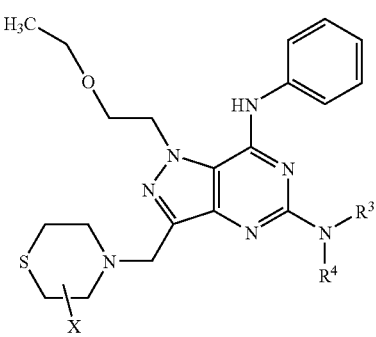
(I^A-21)

X = one or more substituents
independently selected from
($C_1$-$C_6$ alkoxy)$C_1$-$C_6$ alkyl, $R^{21}$, and $R^{22}$

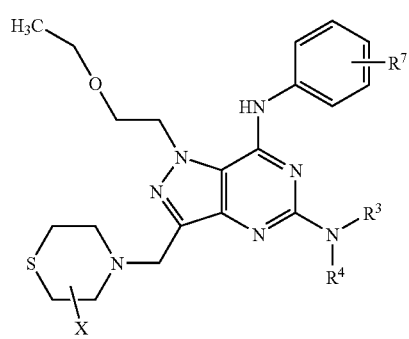
(I^A-22)

X = one or more substituents
independently selected from
($C_1$-$C_6$ alkoxy)$C_1$-$C_6$ alkyl, $R^{21}$, and $R^{22}$

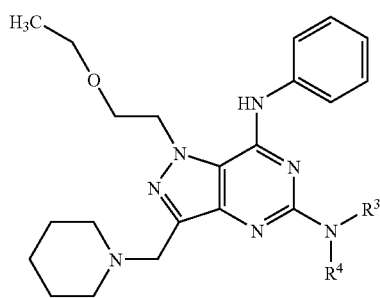
(I^A-23)
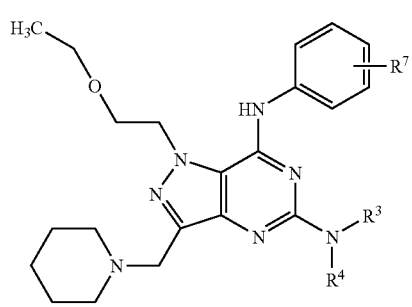
(I^A-24)
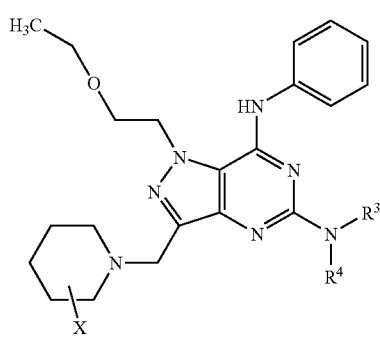
(I^A-25)
X = one or more substituents independently selected from ($C_1$-$C_6$ alkoxy)$C_1$-$C_6$ alkyl, $R^{21}$, and $R^{22}$
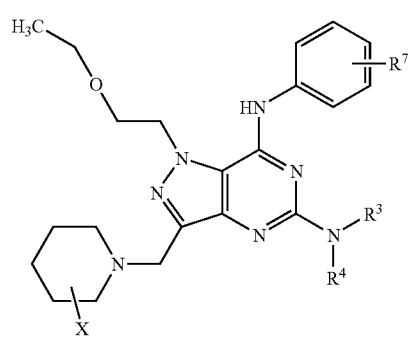
(I^A-26)
X = one or more substituents independently selected from ($C_1$-$C_6$ alkoxy)$C_1$-$C_6$ alkyl, $R^{21}$, and $R^{22}$
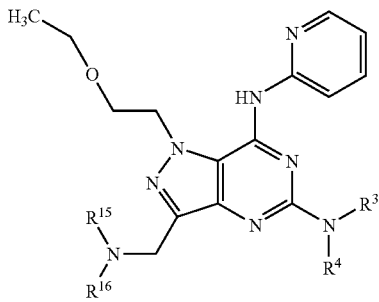
(I^A-27)
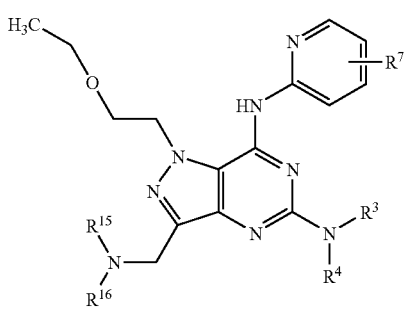
(I^A-28)
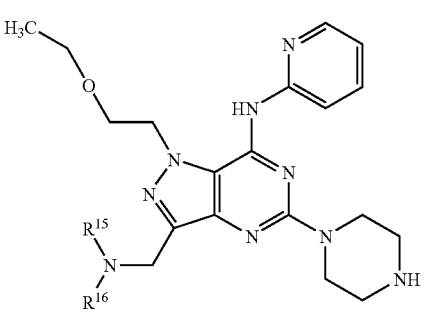
(I^A-29)
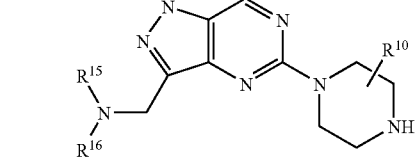
(I^A-30)
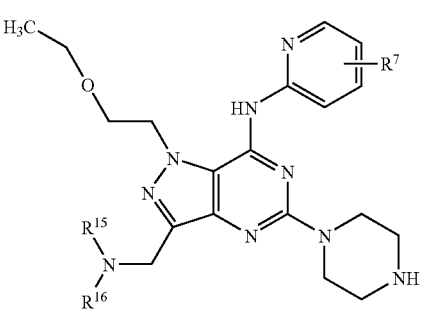
(I^A-31)

-continued
(I^A-32)
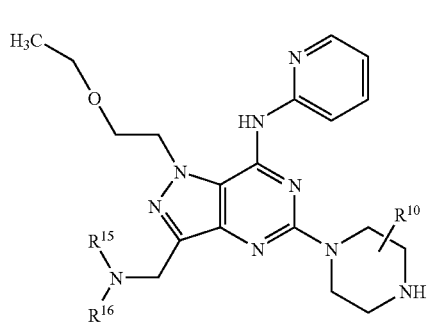
(I^A-33)
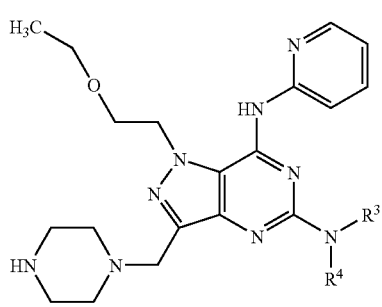
(I^A-34)
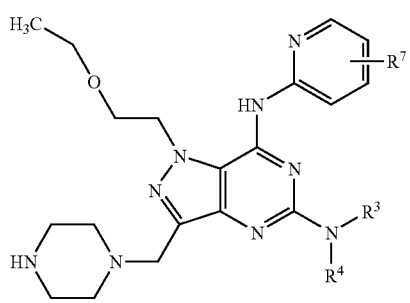
(I^A-35)
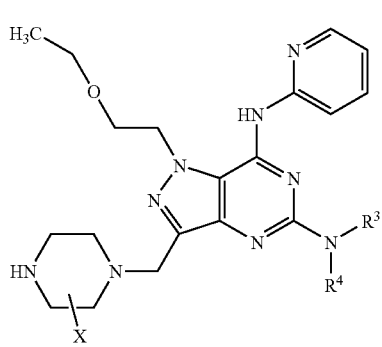
X = one or more substituents independently selected from $(C_1-C_6 \text{ alkoxy})C_1-C_6$ alkyl, $R^{21}$, and $R^{22}$
-continued
(I^A-36)
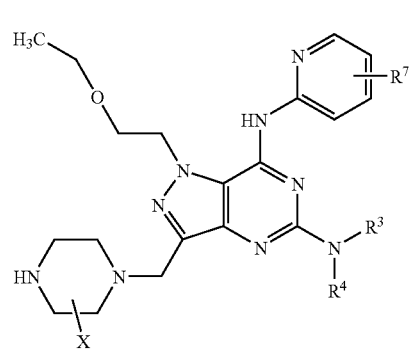
X = one or more substituents independently selected from $(C_1-C_6 \text{ alkoxy})C_1-C_6$ alkyl, $R^{21}$, and $R^{22}$
(I^A-37)
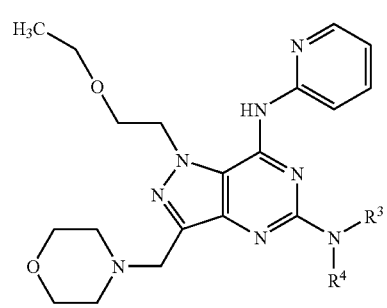
(I^A-38)
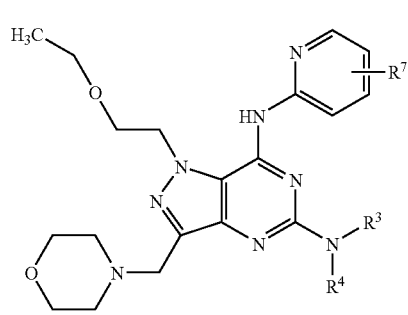
(I^A-39)
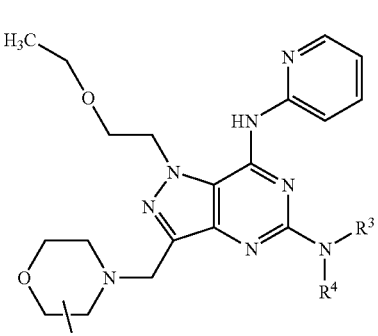
X = one or more substituents independently selected from $(C_1-C_6 \text{ alkoxy})C_1-C_6$ alkyl, $R^{21}$, and $R^{22}$

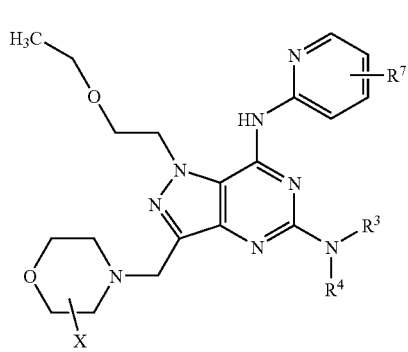

(I^A-40)

X = one or more substituents independently selected from (C$_1$-C$_6$ alkoxy)C$_1$-C$_6$ alkyl, R$^{21}$, and R$^{22}$

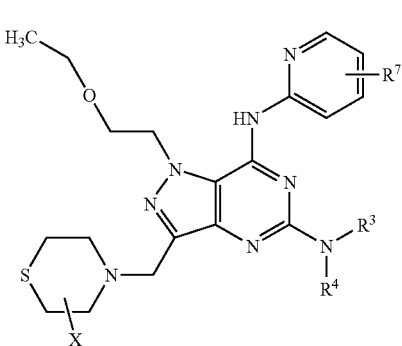

(I^A-44)

X = one or more substituents independently selected from (C$_1$-C$_6$ alkoxy)C$_1$-C$_6$ alkyl, R$^{21}$, and R$^{22}$ (I^A-41)

(I^A-45)

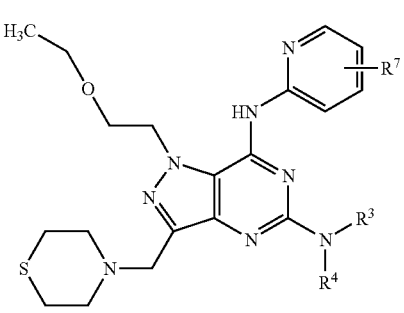

(I^A-42)

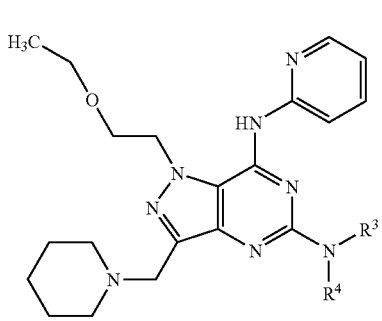

(I^A-46)

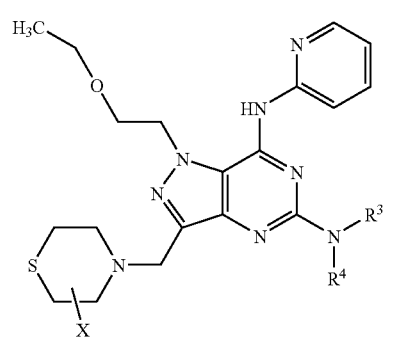

(I^A-43)

X = one or more substituents independently selected from (C$_1$-C$_6$ alkoxy)C$_1$-C$_6$ alkyl, R$^{21}$, and R$^{22}$

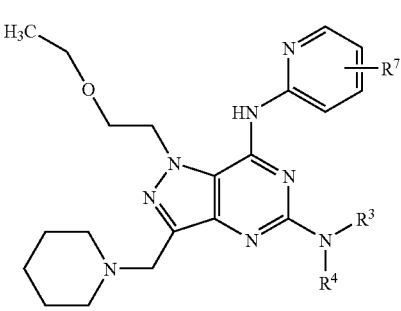

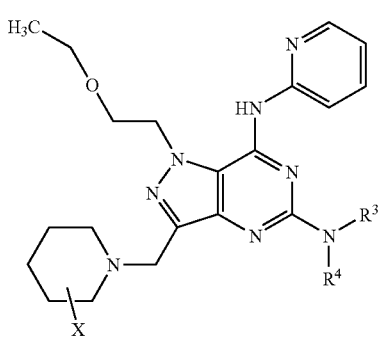

(I^A-47)

X = one or more substituents independently selected from (C$_1$-C$_6$ alkoxy)C$_1$-C$_6$ alkyl, R$^{21}$, and R$^{22}$

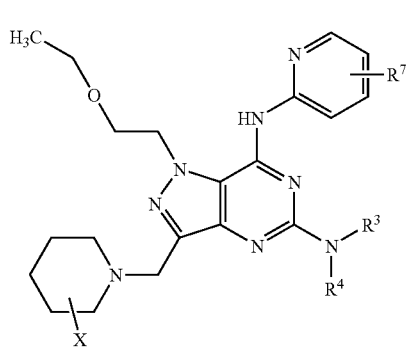
(I^A-48)
X = one or more substituents independently selected from (C$_1$-C$_6$ alkoxy)C$_1$-C$_6$ alkyl, R$^{21}$, and R$^{22}$
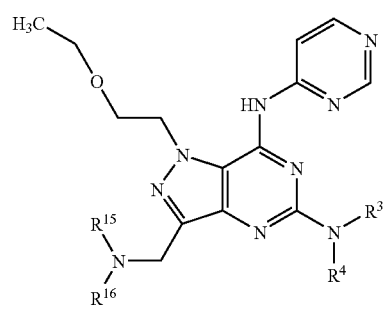
(I^A-49)
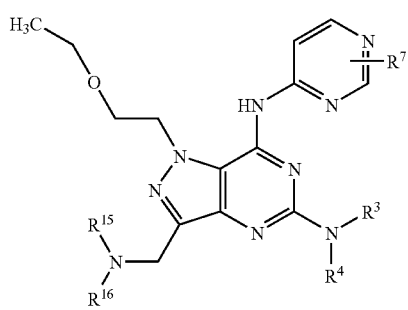
(I^A-50)
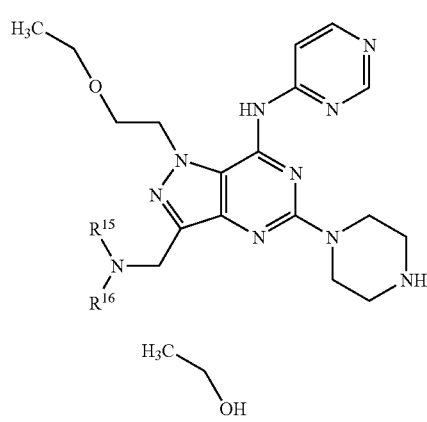
(I^A-51)
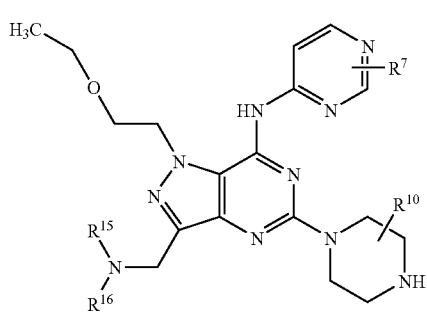
(I^A-52)
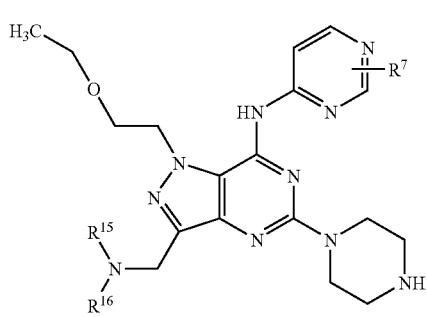
(I^A-53)
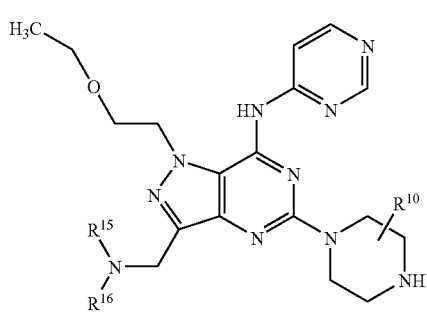
(I^A-54)
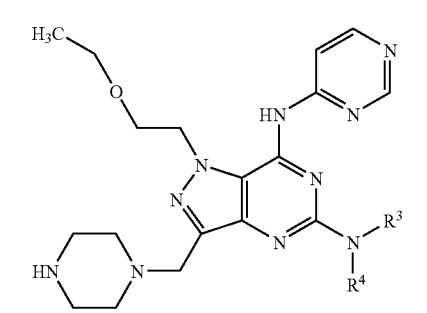
(I^A-55)
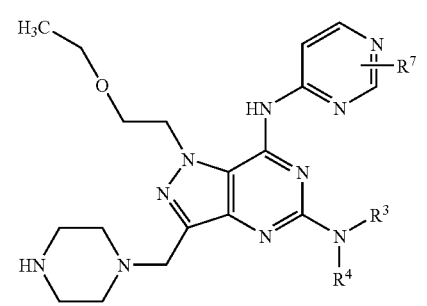
(I^A-56)

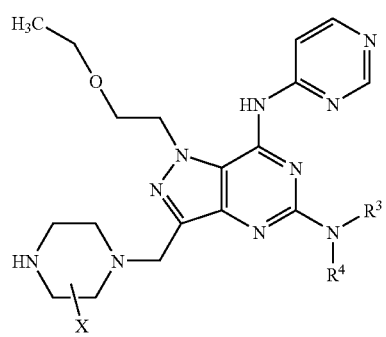

(I^A-57)

X = one or more substituents independently selected from ($C_1$-$C_6$ alkoxy)$C_1$-$C_6$ alkyl, $R^{21}$, and $R^{22}$

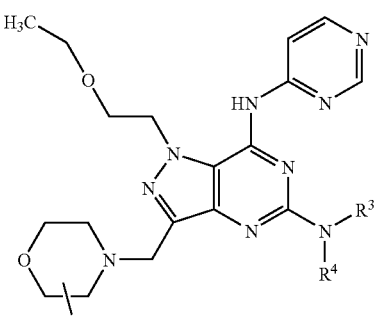

(I^A-61)

X = one or more substituents independently selected from ($C_1$-$C_6$ alkoxy)$C_1$-$C_6$ alkyl, $R^{21}$, and $R^{22}$

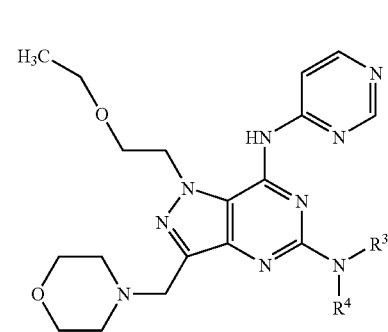

(I^A-58)

X = one or more substituents independently selected from ($C_1$-$C_6$ alkoxy)$C_1$-$C_6$ alkyl, $R^{21}$, and $R^{22}$

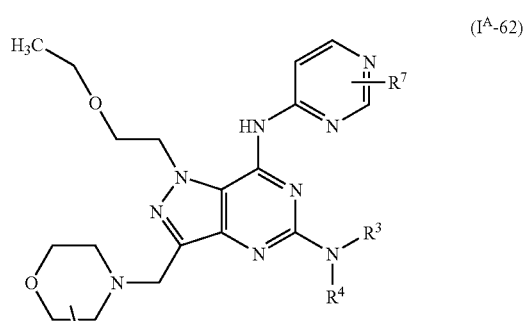

(I^A-62)

X = one or more substituents independently selected from ($C_1$-$C_6$ alkoxy)$C_1$-$C_6$ alkyl, $R^{21}$, and $R^{22}$

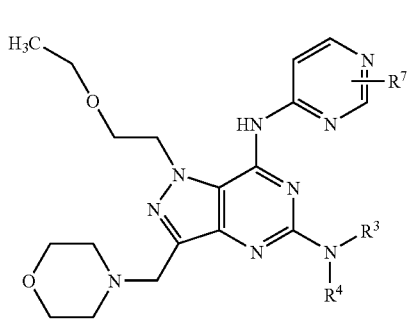

(I^A-59)

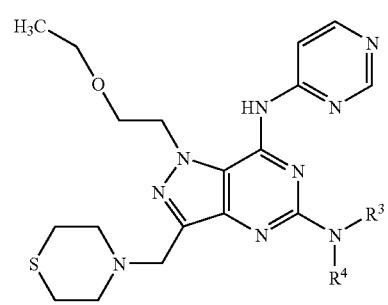

(I^A-63)

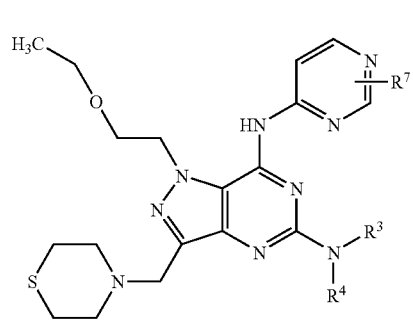

(I^A-60)

(I^A-64)

-continued

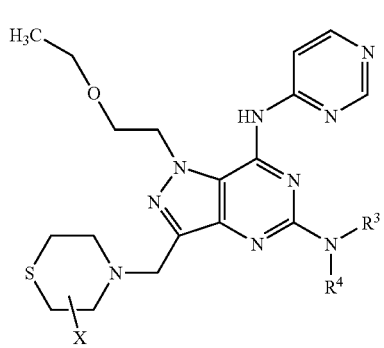

(I^A-65)

X = one or more substituents
independently selected from
$(C_1-C_6$ alkoxy$)C_1-C_6$ alkyl, $R^{21}$, and $R^{22}$ (I^A-66)

X = one or more substituents
independently selected from
$(C_1-C_6$ alkoxy$)C_1-C_6$ alkyl, $R^{21}$, and $R^{22}$

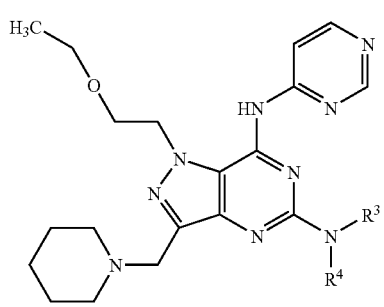

(I^A-67)

(I^A-68)

-continued

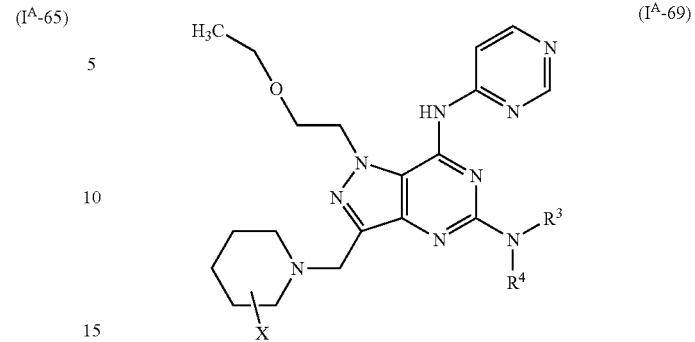

(I^A-69)

X = one or more substituents
independently selected from
$(C_1-C_6$ alkoxy$)C_1-C_6$ alkyl, $R^{21}$, and $R^{22}$ (I^A-70)

X = one or more substituents
independently selected from
$(C_1-C_6$ alkoxy$)C_1-C_6$ alkyl, $R^{21}$, and $R^{22}$

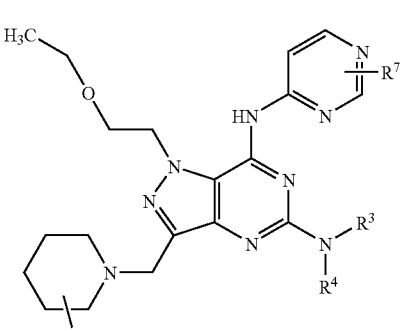

(I^A-71)

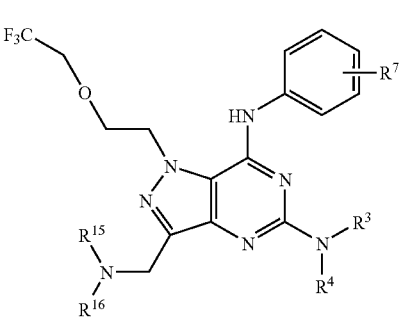

(I^A-72)

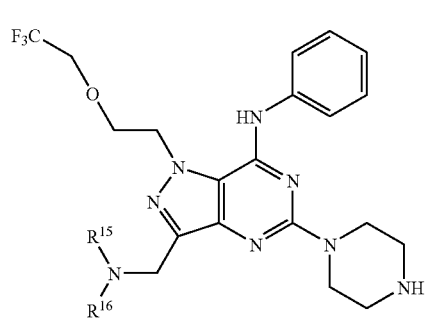
(I^A-73)
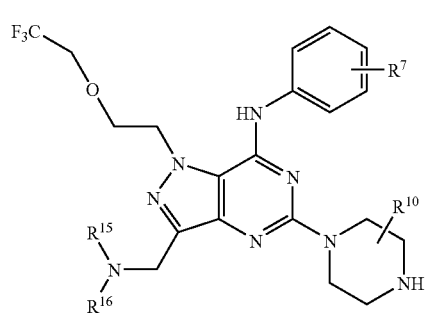
(I^A-74)
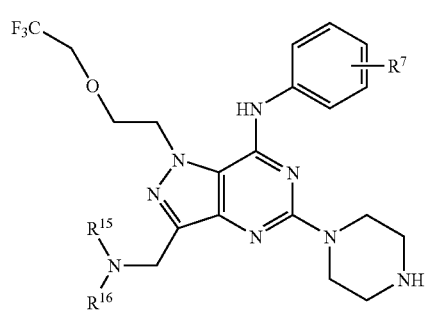
(I^A-75)
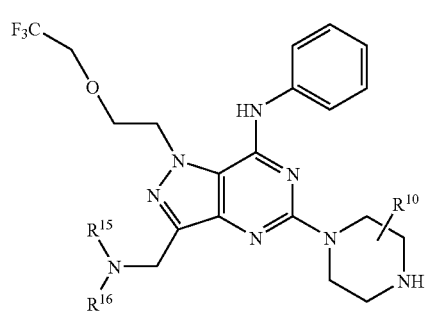
(I^A-76)
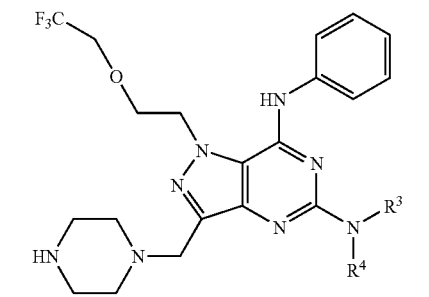
(I^A-77)
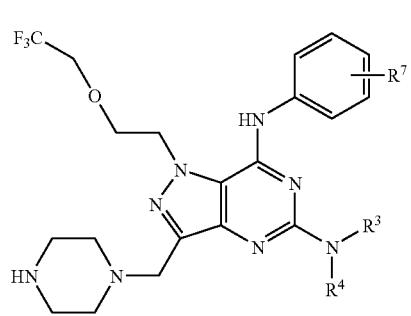
(I^A-78)
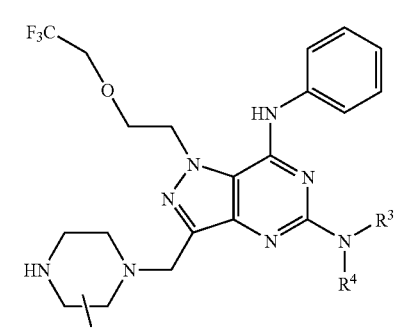
(I^A-79)
X = one or more substituents independently selected from $(C_1-C_6 \text{ alkoxy})C_1-C_6$ alkyl, $R^{21}$, and $R^{22}$
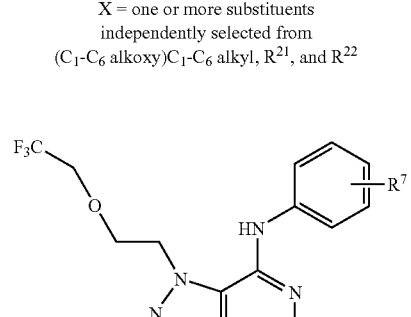
(I^A-80)
X = one or more substituents independently selected from $(C_1-C_6 \text{ alkoxy})C_1-C_6$ alkyl, $R^{21}$, and $R^{22}$
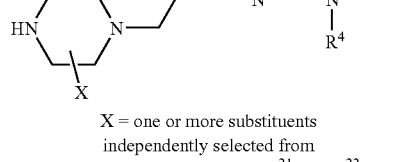
(I^A-81)
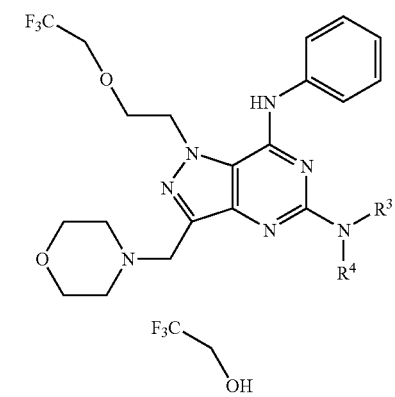

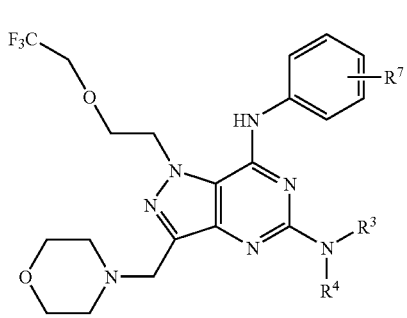

(I^A-82)

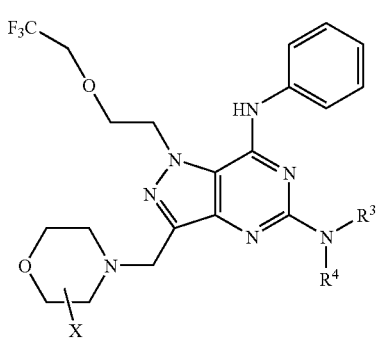

(I^A-83)

X = one or more substituents
independently selected from
($C_1$-$C_6$ alkoxy)$C_1$-$C_6$ alkyl, $R^{21}$, and $R^{22}$

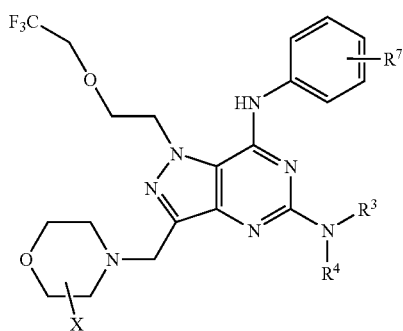

(I^A-84)

X = one or more substituents
independently selected from
($C_1$-$C_6$ alkoxy)$C_1$-$C_6$ alkyl, $R^{21}$, and $R^{22}$

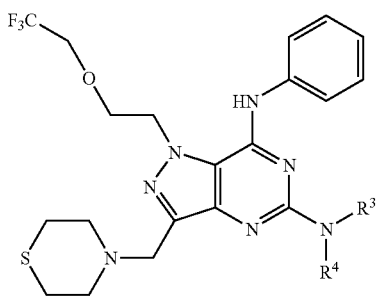

(I^A-85)

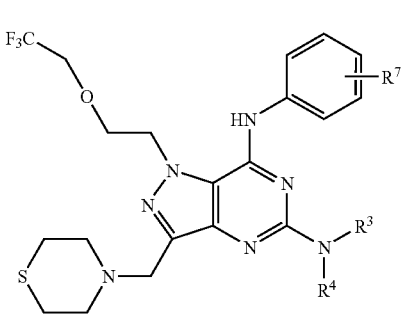

(I^A-86)

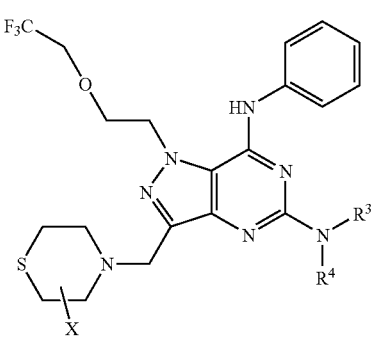

(I^A-87)

X = one or more substituents
independently selected from
($C_1$-$C_6$ alkoxy)$C_1$-$C_6$ alkyl, $R^{21}$, and $R^{22}$

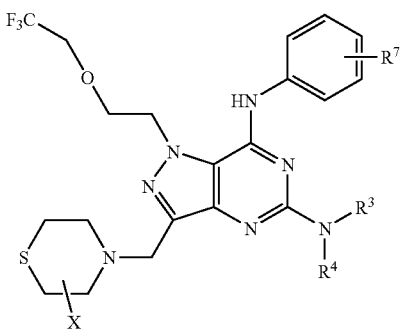

(I^A-88)

X = one or more substituents
independently selected from
($C_1$-$C_6$ alkoxy)$C_1$-$C_6$ alkyl, $R^{21}$, and $R^{22}$

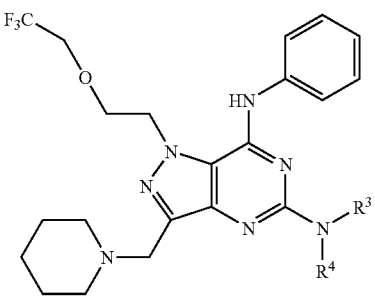

(I^A-89)

-continued
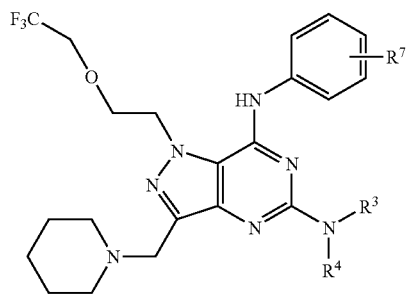
(I^A-90)
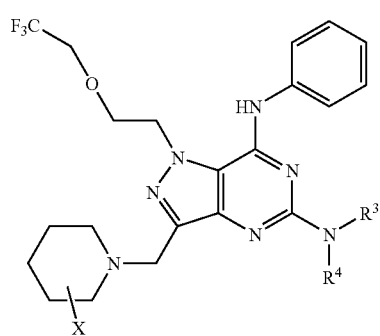
(I^A-91)
X = one or more substituents independently selected from (C_1-C_6 alkoxy)C_1-C_6 alkyl, R^21, and R^22
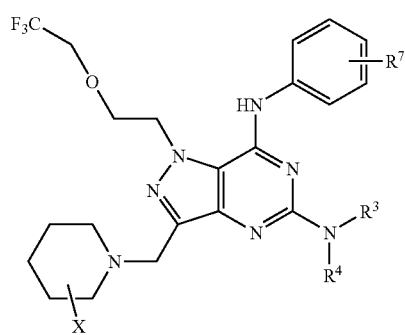
(I^A-92)
X = one or more substituents independently selected from (C_1-C_6 alkoxy)C_1-C_6 alkyl, R^21, and R^22
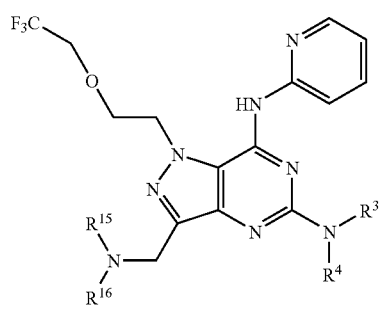
(I^A-93)
-continued
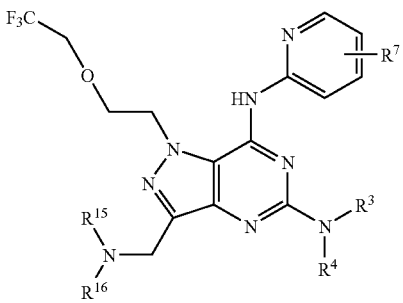
(I^A-94)
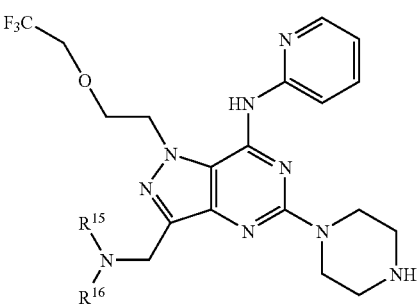
(I^A-95)
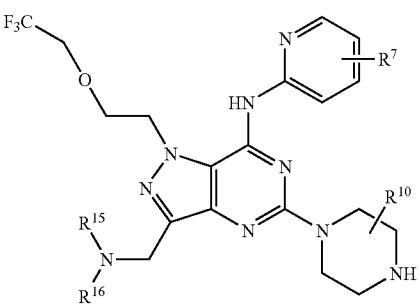
(I^A-96)
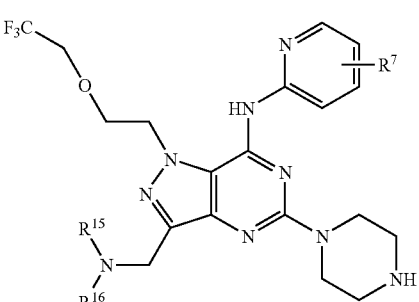
(I^A-97)
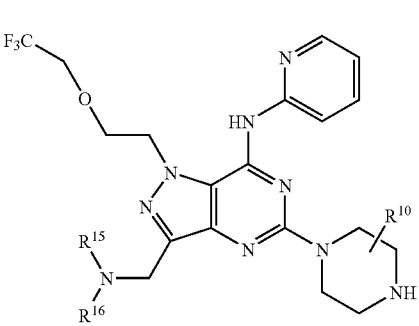
(I^A-98)

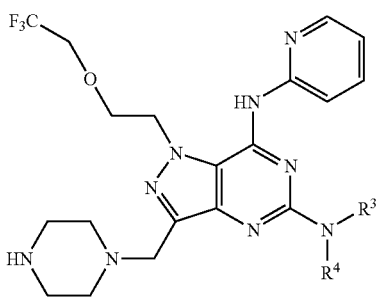
(I^A-99)

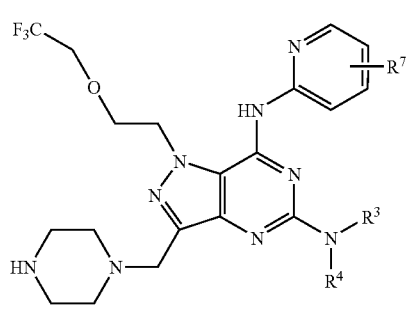
(I^A-100)

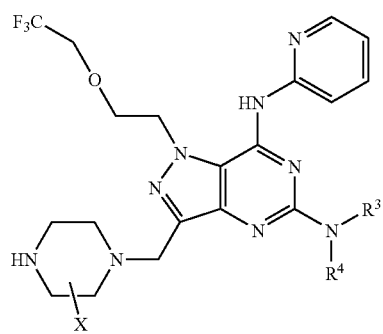
(I^A-101)

X = one or more substituents independently selected from (C₁-C₆ alkoxy)C₁-C₆ alkyl, R²¹, and R²²

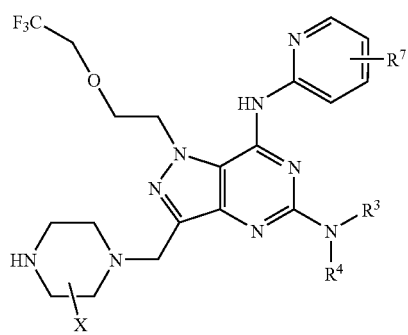
(I^A-102)

X = one or more substituents independently selected from (C₁-C₆ alkoxy)C₁-C₆ alkyl, R²¹, and R²²

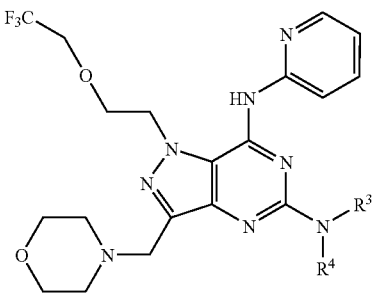
(I^A-103)

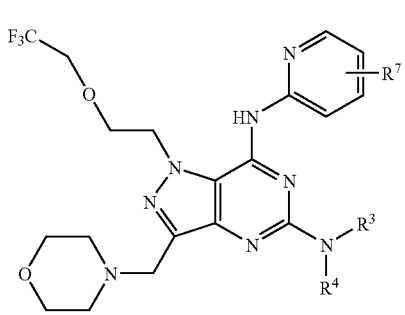
(I^A-104)

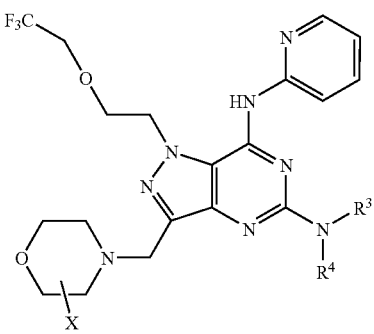
(I^A-105)

X = one or more substituents independently selected from (C₁-C₆ alkoxy)C₁-C₆ alkyl, R²¹, and R²²

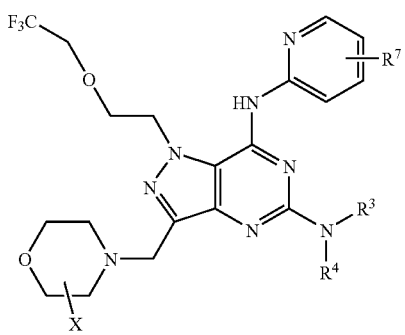
(I^A-106)

X = one or more substituents independently selected from (C₁-C₆ alkoxy)C₁-C₆ alkyl, R²¹, and R²²

-continued

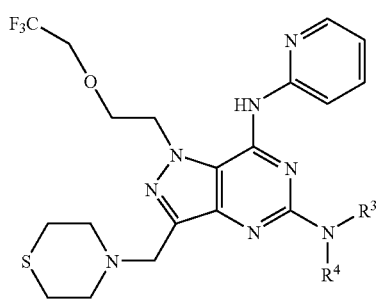
(I^A-107)

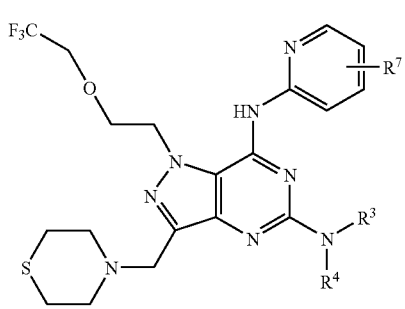
(I^A-108)

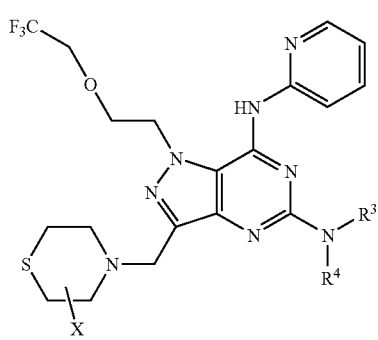
(I^A-109)

X = one or more substituents independently selected from (C₁-C₆ alkoxy)C₁-C₆ alkyl, R²¹, and R²²

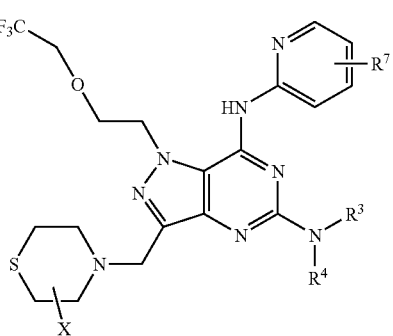
(I^A-110)

X = one or more substituents independently selected from (C₁-C₆ alkoxy)C₁-C₆ alkyl, R²¹, and R²²

-continued

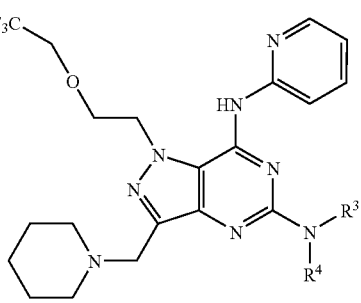
(I^A-111)

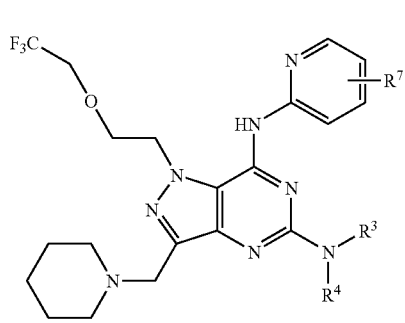
(I^A-112)

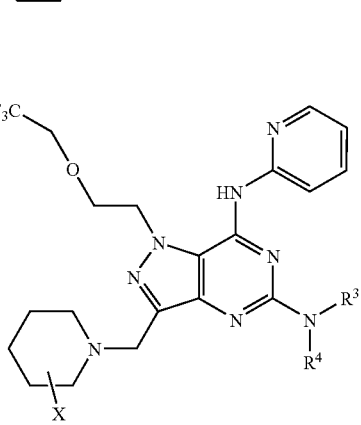
(I^A-113)

X = one or more substituents independently selected from (C₁-C₆ alkoxy)C₁-C₆ alkyl, R²¹, and R²²

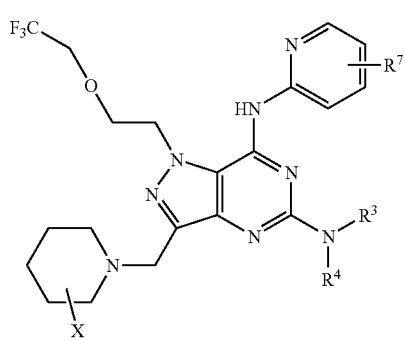
(I^A-114)

X = one or more substituents independently selected from (C₁-C₆ alkoxy)C₁-C₆ alkyl, R²¹, and R²²

-continued
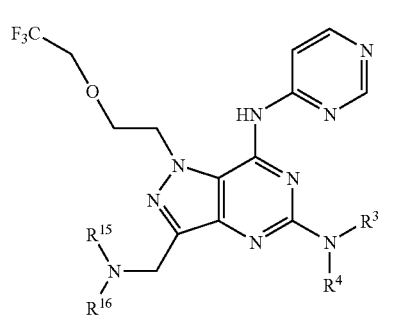
(I^A-115)
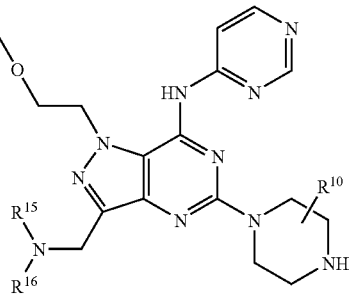
(I^A-120)
(I^A-116)
(I^A-121)
(I^A-117)
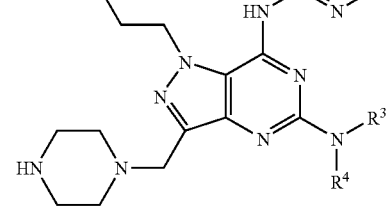
(I^A-122)
(I^A-118)
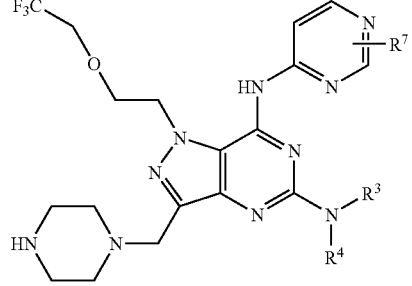
(I^A-123)
(I^A-119)
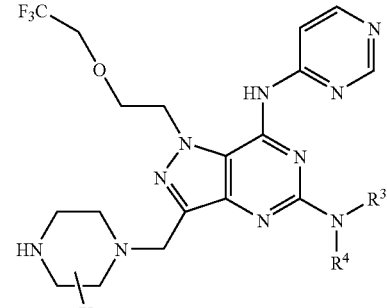
X = one or more substituents independently selected from (C₁-C₆ alkoxy)C₁-C₆ alkyl, R²¹, and R²²

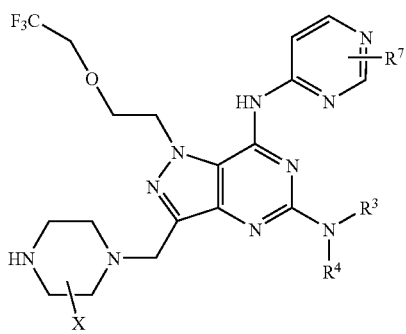

(I^A-124)

X = one or more substituents independently selected from $(C_1-C_6 \text{ alkoxy})C_1-C_6 \text{ alkyl}$, $R^{21}$, and $R^{22}$

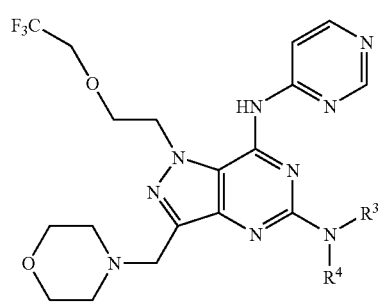

(I^A-125)

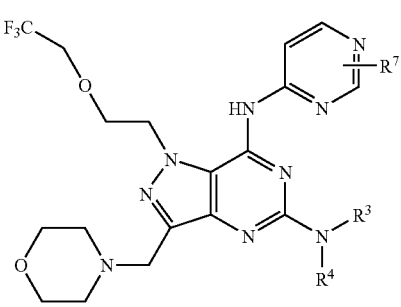

(I^A-126)

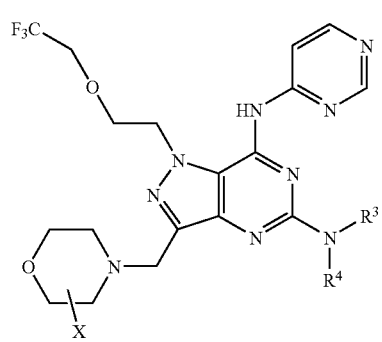

(I^A-127)

X = one or more substituents independently selected from $(C_1-C_6 \text{ alkoxy})C_1-C_6 \text{ alkyl}$, $R^{21}$, and $R^{22}$

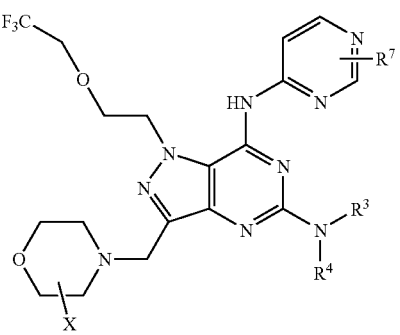

(I^A-128)

X = one or more substituents independently selected from $(C_1-C_6 \text{ alkoxy})C_1-C_6 \text{ alkyl}$, $R^{21}$, and $R^{22}$

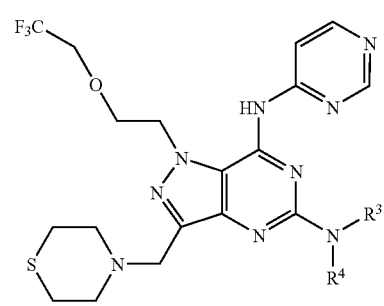

(I^A-129)

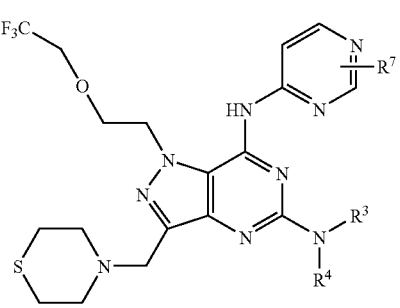

(I^A-130)

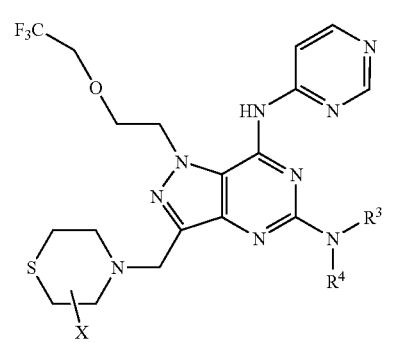

(I^A-131)

X = one or more substituents independently selected from $(C_1-C_6 \text{ alkoxy})C_1-C_6 \text{ alkyl}$, $R^{21}$, and $R^{22}$ -continued

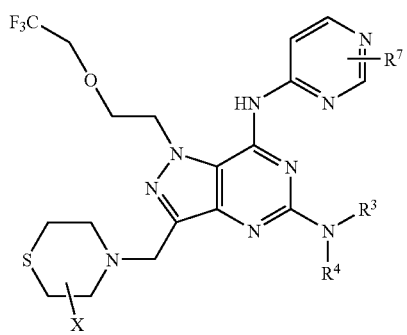
(I^A-132)

X = one or more substituents independently selected from (C$_1$-C$_6$ alkoxy)C$_1$-C$_6$ alkyl, R$^{21}$, and R$^{22}$

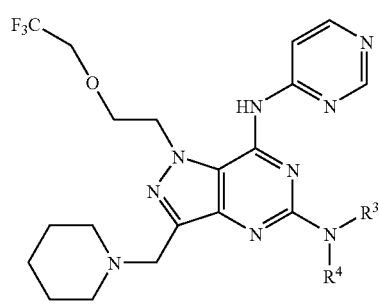
(I^A-133)

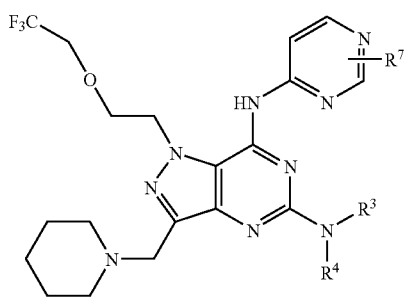
(I^A-134)

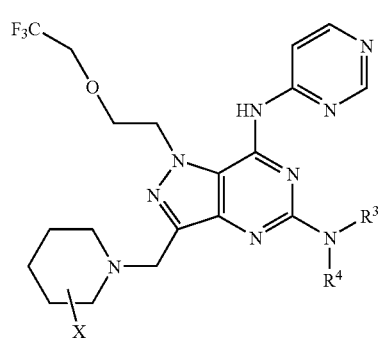
(I^A-135)

X = one or more substituents independently selected from (C$_1$-C$_6$ alkoxy)C$_1$-C$_6$ alkyl, R$^{21}$, and R$^{22}$ -continued

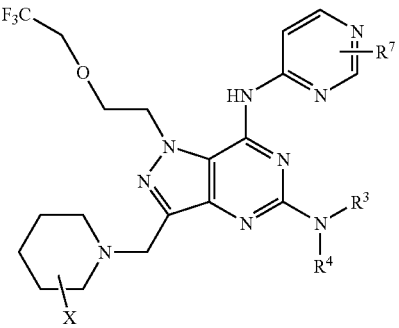
(I^A-136)

X = one or more substituents independently selected from (C$_1$-C$_6$ alkoxy)C$_1$-C$_6$ alkyl, R$^{21}$, and R$^{22}$ In formulas (I$^A$-5) through (I$^A$-136) above, R$^7$ and R$^{10}$ represent one or more R$^7$ or R$^{10}$ substituents, respectively.

In some embodiments, in the compounds of formula (I$^A$-2) correspond in structure to formula (I$^A$-4)

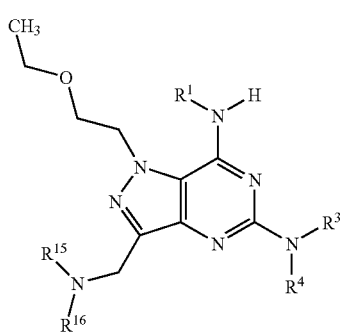
(I^A-4)

wherein

R$^1$ is a cyclic group R$^D$ which is optionally substituted with one or more C$_1$-C$_3$ alkyl groups;

R$^3$ and R$^4$ are each independently hydrogen or C$_1$-C$_3$ alkyl optionally substituted with a group selected from OH and OCH$_3$;

R$^{15}$ is selected from R$^{17}$, R$^{17}$C(O) and R$^{18}$SO$_2$, and

R$^{16}$ is selected from hydrogen and C$_1$-C$_3$ alkyl, or —NR$^{15}$R$^{16}$ constitutes a 5- or 6-membered saturated ring which may optionally include one further heteroatom selected from nitrogen and oxygen, and which may optionally be substituted with a group selected from methyl, methoxy and methoxymethyl;

R$^{17}$ is selected from C$_1$-C$_3$ alkyl optionally substituted a group selected from hydroxy, methoxy and dimethylamino;

R$^{18}$ is selected from C$_1$-C$_3$ alkyl optionally substituted a group selected from hydroxy, methoxy and dimethylamino; and R$^D$ is a 6-membered heteroaromatic ring containing one or two nitrogen atoms;

a tautomer thereof or a pharmaceutically acceptable salt, solvate or polymorph of said compound or tautomer.

In the compounds of formula ($I^4$-4):

$R^1$ is preferably a cyclic group $R^A$, which is optionally substituted with a methyl group.

$R^A$ is preferably a pyridyl, pyrimidinyl or pyrazinyl group.

Preferably, $R^3$ is $C_1$-$C_3$ alkyl optionally substituted with a group selected from OH and $OCH_3$ and $R^4$ hydrogen or $C_1$-$C_3$ alkyl.

$R^3$ is more preferably methyl or ethyl optionally substituted at the 2-position with a group selected from OH and $OCH_3$.

$R^4$ is more preferably hydrogen or methyl.

In one preferred embodiment, $R^{15}$ is selected from $R^{17}$, $R^{17}C(O)$ and $R^{18}SO_2$ and $R^{16}$ is selected from hydrogen and $C_1$-$C_3$ alkyl.

In one more preferred embodiment, $R^{15}$ is $R^{17}$ and $R^{17}$ is $C_1$-$C_3$ alkyl or 2-methoxyethyl.

In another more preferred embodiment $R^{15}$ is $R^{17}C(O)$ and $R^{17}$ is selected from methyl, ethyl, hydroxymethyl and dimethylaminomethyl.

In another more preferred embodiment $R^{15}$ is $R^{18}SO_2$ and $R^{18}$ is methyl.

In another preferred embodiment —$NR^{15}R^{16}$ constitutes a 5- or 6-membered saturated ring which may optionally include one further heteroatom selected from nitrogen and oxygen, and which may optionally be substituted with a group selected from methyl, methoxy and methoxymethyl.

More preferably —$NR^{15}R^{16}$ constitutes a pyrrolidine, morpholine or piperazine ring optionally be substituted with a group selected from methyl, methoxy and methoxymethyl.

In one embodiment, preferred compounds are the compounds from Examples 1-107.

In another embodiment, preferred compounds are:

2-dimethylamino-N-[5-dimethylamino-1-(2-ethoxyethyl)-7-(4-methylpyridin-2-ylamino)-1H-pyrazolo[4,3-d]pyrimidin-3-ylmethyl]acetamide, N-[5-dimethylamino-1-(2-ethoxyethyl)-7-(4-methylpyridin-2-ylamino)-1H-pyrazolo[4,3-d]pyrimidin-3-ylmethyl]methanesulfonamide, N-[5-dimethylamino-1-(2-ethoxyethyl)-7-(4-methylpyridin-2-ylamino)-1H-pyrazolo[4,3-d]pyrimidin-3-ylmethyl]-2-hydroxyacetamide, N-[5-dimethylamino-1-(2-ethoxyethyl)-7-(4-methylpyridin-2-ylamino)-1H-pyrazolo[4,3-d]pyrimidin-3-ylmethyl]acetamide, N-[1-(2-ethoxyethyl)-5-ethylamino-7-(4-methylpyridin-2-ylamino)-1H-pyrazolo[4,3-d]pyrimidin-3-ylmethyl]acetamide, N-[5-dimethylamino-1-(2-ethoxyethyl)-7-(4-methylpyridin-2-ylamino)-1H-pyrazolo[4,3-d]pyrimidin-3-ylmethyl]propionamide, N-[1-(2-ethoxyethyl)-5-ethylamino-7-(4-methylpyridin-2-ylamino)-1H-pyrazolo[4,3-d]pyrimidin-3-ylmethyl]propionamide, N-[1-(2-ethoxyethyl)-5-ethylamino-7-(4-methylpyridin-2-ylamino)-1H-pyrazolo[4,3-d]pyrimidin-3-ylmethyl]-N-methylacetamide, 1-(2-ethoxyethyl)-$N^5$,$N^5$-dimethyl-3-[(4-methylpiperazin-1-yl)methyl]-$N^7$-(4-methylpyridin-2-yl)-1H-pyrazolo[4,3-d]pyrimidine-5,7-diamine, 1-(2-ethoxyethyl)-$N^5$,$N^5$-dimethyl-3-[(4-morpholino)methyl]-$N^7$-(4-methylpyridin-2-yl)-1H-pyrazolo[4,3-d]pyrimidine-5,7-diamine, and 1-(2-ethoxyethyl)-3-(ethylaminomethyl)-$N^5$,$N^5$-dimethyl-$N^7$-(4-methylpyridin-2-yl)-1H-pyrazolo[4,3-d]pyrimidine-5,7-diamine and tautomers thereof and pharmaceutically acceptable salts, solvates and polymorphs of said compounds or tautomers.

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with ($C_1$-$C_8$)alkyl;

(ii) where the compound of formula (I) contains an alcohol functionality (—OH), an ether thereof, for example, replacement of the hydrogen with ($C_1$-$C_6$)alkanoyloxymethyl; and (iii) where the compound of formula (I) contains a primary or secondary amino functionality (—$NH_2$ or —NHR where R≠H), an amide thereof, for example, replacement of one or both hydrogens with ($C_1$-$C_{10}$)alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The present invention provides for pharmaceutical compositions comprising compounds of formula (I), or pharmaceutically acceptable salts, solvates or polymorphs thereof, and a pharmaceutically acceptable diluent or carrier.

The present invention also provides for pharmaceutical compositions comprising compounds of formula (I), or pharmaceutically acceptable salts, solvates or polymorphs thereof, and a second pharmaceutically active agent selected from aspirin, angiotensin II receptor antagonists (such as losartan, candesartan, telmisartan, valsartan, irbesartan and eprosartan), calcium channel blockers (such as amlodipine), beta-blockers (i.e. beta-adrenergic receptor antagonists such as sotalol, propranolol, timolol, atenolol, carvedilol and metoprolol), CI1027, CCR5 receptor antagonists, imidazolines, sGCa's (soluble guanylate cyclase activators) antihypertensive agents, diuretics (such as hydrochlorothiazide, torsemide, chlorothiazide, chlorthalidone and amiloride), alpha adrenergic antagonists (such as doxazosin), ACE (angiotensin converting enzyme) inhibitors (such as quinapril, enalapril, ramipril and lisinopril), aldosterone receptor antagonists (such as eplerenone and spironolactone), neutral endopeptidase inhibitors, antidiabetic agents (such as insulin, sulfonylureas (such as glyburide, glipizide and glimepiride), glitazones (such as rosiglitazone and pioglitazone) and meformin), cholesterol lowering agents (such as atorvastatin, pravastatin, lovastatin, simvastatin, clofibrate and rosuvastatin), and alpha-2-delta ligands (such as gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)-(3-amino-methyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid, and (3S,5R)-3-amino-5-methyl-octanoic acid).

The compounds of formula (I) are inhibitors of PDE5. Accordingly, in a further aspect the present invention provides for the use of a compound of formula (I), or a tautomer, salt or solvate thereof, as a pharmaceutical agent, and particularly as a therapeutic agent for the treatment of a condition where inhibition of PDE5 is known, or can be shown, to produce a beneficial effect.

The term "treatment" includes palliative, curative and prophylactic treatment.

Conditions suitable for treatment with the compounds of the invention include hypertension (including essential hypertension, pulmonary hypertension, secondary hypertension, isolated systolic hypertension, hypertension associated with diabetes, hypertension associated with atherosclerosis, and renovascular hypertension), congestive heart failure, angina (including stable, unstable and variant (Prinzmetal) angina), stroke, coronary artery disease, congestive heart failure, conditions of reduced blood vessel patency (such as post-percutaneous coronary angioplasty), peripheral vascular disease, atherosclerosis, nitrate-induced tolerance, nitrate tolerance, diabetes, impaired glucose tolerance, metabolic syndrome, obesity, sexual dysfunction (including male erectile disorder, impotence, female sexual arousal disorder, clitoral dysfunction, female hypoactive sexual desire disorder, female sexual pain disorder, female sexual orgasmic dysfunction and sexual dysfunction due to spinal cord injury), premature labour, pre-eclampsia, dysmenorrhea, polycystic ovary syndrome, benign prostatic hyperplasia, bladder outlet obstruction, incontinence, chronic obstructive pulmonary disease, acute respiratory failure, bronchitis, chronic asthma, allergic asthma, allergic rhinitis, gut motility disorders (including irritable bowel syndrome), Kawasaki's syndrome, multiple sclerosis, Alzheimer's disease, psoriasis, skin necrosis, scarring, fibrosis, pain (particularly neuropathic pain), cancer, metastasis, baldness, nutcracker oesophagus, anal fissure and haemorrhoids.

The present invention provides for methods of treatment of a disorder or condition where inhibition of PDE5 is known, or can be shown, to produce a beneficial effect, in a mammal by administering to said mammal a therapeutically effective amount of a compound of formula (I), or a pharmaceutically acceptable salt, solvate or polymorph thereof.

The present invention also provides for methods of treatment of the conditions enumerated above in a mammal by administering to said mammal a therapeutically effective amount of a compound of formula (I), or a pharmaceutically acceptable salt, solvate or polymorph thereof.

In some embodiments, the present invention provides for methods of treatment of essential hypertension, pulmonary hypertension, secondary hypertension, isolated systolic hypertension, hypertension associated with diabetes, hypertension associated with atherosclerosis, and renovascular hypertension in a mammal by administering to said mammal a therapeutically effective amount of a compound of formula (I), or a pharmaceutically acceptable salt, solvate or polymorph thereof.

In some embodiments, the present invention provides for methods of treatment of diabetes in a mammal by administering to said mammal a therapeutically effective amount of a compound of formula (I), or a pharmaceutically acceptable salt, solvate or polymorph thereof.

The present invention also provides for methods of treatment of the conditions enumerated above in a mammal by administering to said mammal a therapeutically effective amount of a compound of formula (I), or a pharmaceutically acceptable salt, solvate or polymorph thereof and a second pharmaceutically active agent selected from aspirin, angiotensin II receptor antagonists (such as losartan, candesartan, telmisartan, valsartan, irbesartan and eprosartan), calcium channel blockers (such as amlodipine), beta-blockers (i.e. beta-adrenergic receptor antagonists such as sotalol, propranolol, timolol, atenolol, carvedilol and metoprolol), CI1027, CCR5 receptor antagonists, imidazolines, sGCa (soluble guanylate cyclase activators) antihypertensive agents, diuretics (such as hydrochlorothiazide, torsemide, chlorothiazide, chlorthalidone and amiloride), alpha adrenergic antagonists (such as doxazosin), ACE (angiotensin converting enzyme) inhibitors (such as quinapril, enalapril, ramipril and lisinopril), aldosterone receptor antagonists (such as eplerenone and spironolactone), neutral endopeptidase inhibitors, antidiabetic agents (such as insulin, sulfonylureas (such as glyburide, glipizide and glimepiride), glitazones (such as rosiglitazone and pioglitazone) and metformin), cholesterol lowering agents (such as atorvastatin, pravastatin, lovastatin, simvastatin, clofibrate and rosuvastatin), and alpha-2-delta ligands (such as gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S, 4S)-(1-aminomethyl-3,4-dimethyl-cyclopentyl)-acetic acid, (1α,3α,5α)-(3-amino-methyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid, and (3S,5R)-3-amino-5-methyl-octanoic acid).

The present invention provides for uses of compounds of formula (I) or pharmaceutically acceptable salts, solvates or polymorphs thereof, in the preparation of a medicament for the treatment of a disorder or condition where inhibition of PDE5 is known, or can be shown, to produce a beneficial effect.

In a further aspect, the present invention provides for the use of a compound of formula (I), or a tautomer, salt or solvate thereof, for the manufacture of a medicament for the treatment of hypertension (including essential hypertension, pulmonary hypertension, secondary hypertension, isolated systolic hypertension, hypertension associated with diabetes, hypertension associated with atherosclerosis, and renovascular hypertension), congestive heart failure, angina (including stable, unstable and variant (Prinzmetal) angina), stroke, coronary artery disease, congestive heart failure, conditions of reduced blood vessel patency (such as post-percutaneous coronary angioplasty), peripheral vascular disease, atherosclerosis, nitrate-induced tolerance, nitrate tolerance, diabetes, impaired glucose tolerance, metabolic syndrome, obesity, sexual dysfunction (including male erectile disorder, impotence, female sexual arousal disorder, clitoral dysfunction, female hypoactive sexual desire disorder, female sexual pain disorder, female sexual orgasmic dysfunction and sexual dysfunction due to spinal cord injury), premature labour, pre-eclampsia, dysmenorrhea, polycystic ovary syndrome, benign prostatic hyperplasia, bladder outlet obstruction, incontinence, chronic obstructive pulmonary disease, acute respiratory failure, bronchitis, chronic asthma, allergic asthma, allergic rhinitis, gut motility disorders (including irritable bowel syndrome), Kawasaki's syndrome, multiple sclerosis, Alzheimer's disease, psoriasis, skin necrosis, scarring, fibrosis, pain (particularly neuropathic pain), cancer, metastasis, baldness, nutcracker oesophagus, anal fissure and haemorrhoids.

In some embodiments, the present invention provides for uses of compounds of formula (I) or pharmaceutically acceptable salts, solvates or polymorphs thereof, in the preparation of a medicament for the treatment of essential hypertension, pulmonary hypertension, secondary hypertension, isolated systolic hypertension, hypertension associated with diabetes, hypertension associated with atherosclerosis, and renovascular hypertension.

In some embodiments, the present invention provides for uses of compounds of formula (I) or pharmaceutically acceptable salts, solvates or polymorphs thereof, in the preparation of a medicament for the treatment of diabetes.

The compounds of the present invention may be used alone or in combination with other therapeutic agents. When used in combination with another therapeutic agent the administration of the two agents may be simultaneous or sequential. Simultaneous administration includes the administration of a single dosage form that comprises both agents and the administration of the two agents in separate dosage forms at substantially the same time. Sequential administration includes the administration of the two agents according to different schedules provided that there is an overlap in the periods during which the treatment is provided. Suitable agents with which the compounds of formula (I) can be co-administered include aspirin, angiotensin II receptor antagonists (such as losartan, candesartan, telmisartan, valsartan, irbesartan and eprosartan), calcium channel blockers (such as amlodipine), beta-blockers (i.e. beta-adrenergic receptor antagonists such as sotalol, propranolol, timolol, atenolol, carvedilol and metoprolol), CI1027, CCR5 receptor antagonists, imidazolines, sGCa's (soluble guanylate cyclase activators) antihypertensive agents, diuretics (such as hydrochlorothiazide, torsemide, chlorothiazide, chlorthalidone and amiloride), alpha adrenergic antagonists (such as doxazosin), ACE (angiotensin converting enzyme) inhibitors (such as quinapril, enalapril, ramipril and lisinopril), aldosterone receptor antagonists (such as eplerenone and spironolactone), neutral endopeptidase inhibitors, antidiabetic agents (such as insulin, sulfonylureas (such as glyburide, glipizide and glimepiride), glitazones (such as rosiglitazone and pioglitazone) and metformin), cholesterol lowering agents (such as atorvastatin, pravastatin, lovastatin, simvastatin, clofibrate and rosuvastatin), and alpha-2-delta ligands (such as gabapentin, pregabalin, [(1R,5R,6S)-6-(aminomethyl)bicyclo[3.2.0]hept-6-yl] acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)-(3-aminomethyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid).

The compounds of formula (I) may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 20 mg of the compound of formula (I). The overall daily dose will typically be in the range 1 µg to 80 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula . . . in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.1 mg to 500 mg depending, of course, on the mode of administration. For example, oral administration may require a total daily dose of from 0.1 mg to 500 mg, while an intravenous dose may only require from 0.01 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

Compounds of the invention may be prepared, in known manner in a variety of ways. In the following reaction schemes and hereafter, unless otherwise stated $R^1$ to $R^{18}$ are as defined in the first aspect.

These processes form further aspects of the invention.

a) Compounds of formula ($I^C$), i.e. compounds of formula (I) wherein $R^{15}$ is $R^{17}C(O)$ can be prepared by acylation of the corresponding compounds of formula ($I^D$), i.e. compounds of formula (I) wherein $R^{15}$ is hydrogen, as illustrated in Scheme 1.

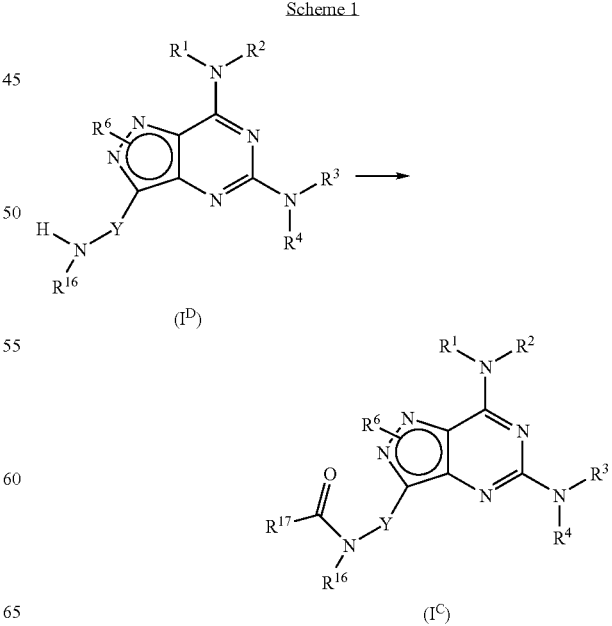

The compound of formula (I$^D$) is treated with 1-2 equivalents of an acylating agent such as an acyl chloride R$^{17}$C(O)Cl or an anhydride (R$^{17}$C(O))$_2$O in a suitable solvent in the presence of a tertiary amine base such as triethylamine, N-ethyldiisopropylamine or pyridine. Suitable solvents include dichloromethane and dimethylformamide. Preferably, the compound of formula (I$^D$) is treated with about 1.3 equivalents of acyl chloride and about 1.3 equivalents of triethylamine in dichloromethane for 18 hours.

Alternatively, a mixture of the compound of formula (I$^D$) and an acid R$^{17}$COOH in a suitable solvent is treated with a condensing agent, optionally in the presence of 1-hydroxybenzotriazole (HOBT) (or 1-hydroxy-7-azabenzotriazole (HOAT)) and a tertiary amine base such as triethylamine, N-ethyldiisopropylamine or 4-(dimethylamino)pyridine, at a temperature of between 0° C. and the boiling point of the solvent. Suitable solvents include acetonitrile, dichloromethane, dimethylformamide, ethyl acetate, N-methylpyrrolidinone, tetrahydrofuran and mixtures thereof. Suitable condensing agents include: 1,1'-carbonyldiimidazole, carbodiimides such as dicyclohexylcarbodiimide (DCC) and 1-(3-dimethylaminopropyl)-1-ethylcarbodiimide (WSCDI); uronium salts such as O-(benzotriazol-1-yl)-1,1,3,3-tetramethyluronium hexafluorophosphate (HBTU) and O-(7-azabenzotriazol-1-yl)-1,1,3,3-tetramethyluronium hexafluorophosphate (HATU); phosphonium salts such as 1-benzotriazolyloxy-tris(dimethylamino)phosphonium hexafluorophosphate (BOP) and 1-benzotriazolyloxytris(pyrrolidino)-phosphonium hexafluorophosphate (PyBOP); diphenylphosphinic chloride (Dpp-Cl) and bis(2-oxo-3-oxazolidinyl)phosphinic chloride (BOP-Cl). Preferably, an equimolar solution of the compound of formula (ID) and the acid in dichloromethane is treated with about 1.1 equivalents of HATU and about 1.5 equivalents of N-ethyldiisopropylamine at room temperature for 18 hours.

It will be appreciated that any functional groups in R$^1$, R$^3$, R$^4$, R$^{16}$ and R$^{17}$, and particularly any primary or secondary amine groups, may need to be protected in order to allow this reaction to proceed successfully. In such a case a subsequent deprotection step will be necessary.

b) Compounds of formula (I$^E$), i.e. compounds of formula (I) wherein R$^{15}$ is R$^{18}$SO$_2$ can be prepared by sulfonylation of the corresponding compounds of formula (I$^D$), as illustrated in Scheme 2.

Scheme 2

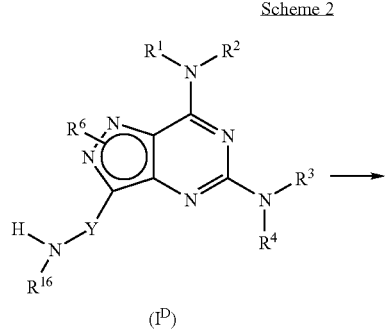

(I$^D$)

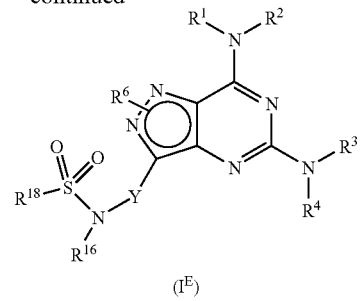

(I$^E$)

The compound of formula (I$^D$) is treated with 1-2 equivalents of a sulfonyl chloride R$^{18}$SO$_2$Cl in a suitable solvent in the presence of a tertiary amine base such as triethylamine, N-ethyldiisopropylamine or pyridine. Suitable solvents include dichloromethane and dimethylformamide. Preferably, the compound of formula (I$^D$) is treated with about 1.1 equivalents of sulfonyl chloride and about 1.5 equivalents of N-ethyldiisopropylamine in dichloromethane for 18 hours.

Again, any functional groups in R$^1$, R$^3$, R$^4$, R$^{16}$ and R$^{17}$, and particularly any primary or secondary amine groups, may need to be protected.

c) Compounds of formula (I$^F$), i.e. compounds of formula (I) wherein R$^{15}$ is R$^{17}$, may be prepared by elaboration of the C$^3$-substituent R$^{5A}$ of a precursor of formula (II) as illustrated in Scheme 3.

Scheme 3

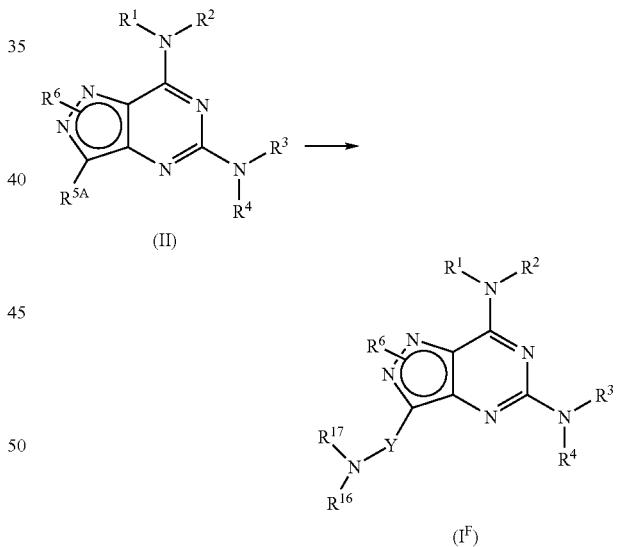

Where at least one of R$^{16}$ and R$^{17}$ is hydrogen, such that the amine function of R$^5$ is a primary or secondary amine, the group R$^{5A}$ may be the same as R$^5$ with the amine protected by protecting group such as a tert-butyloxycarbonyl (BOC), fluorenylmethyloxycarbonyl (Fmoc) or benzyloxycarbonyl (Z, sometimes referred to as Cbz) group. In such cases the transformation of Scheme 1 is a deprotection step appropriate for the protecting group used, such as treatment with acid (e.g. HCl in dioxan or trifluoroacetic acid in dichloromethane) for the removal of a BOC group, treatment with a base (such as piperidine) for the removal of an Fmoc group, or catalytic hydrogenolysis for the removal of a Z group. Other protected functional groups may be deprotected in the same step or, if orthogonal protecting groups are chosen, deprotection may be stepwise.

Where neither of $R^{16}$ and $R^{17}$ is hydrogen, such that the amine function of $R^5$ is a tertiary amine, no protecting group can be used.

Scheme 3 also provides for the elaboration of the amine group of $R^5$ in one or more steps from a functional group that is more amenable to the reaction conditions needed for the preparation of the compounds of formula (II). Examples of such reactions, which include substitution reactions, imine reduction reactions and rearrangement reactions, are illustrated in Schemes 3A to 3J, in which $R^a$, $R^b$, $R^c$ and $R^d$ are hydrogen, alkyl, cycloalkyl or aryl groups.

Substitution Reactions

Primary, secondary and tertiary amines may be prepared by the reaction of an alkylating agent with ammonia, a primary or a secondary amine respectively, as illustrated in scheme 3A, wherein LG is a halogen atom such as a chlorine, bromine or iodine atom, or a sulphonate group such as a methanesulphonate, toluenesulphonate to trifluoromethanesulphonate group.

Scheme 3A

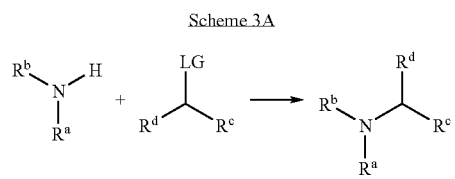

A variation of this reaction is illustrated in Scheme 3B. In this case the alkylating agent is an epoxide.

Scheme 3B

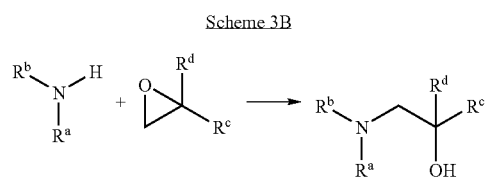

The utility of these reactions is sometimes limited by the propensity of the product amine to react with the alkylating agent, resulting in a complex mixture. This problem can be overcome by the use of an amine equivalent that gives a product that is incapable of further reaction. Scheme 3C illustrates the use of an alkali metal azide or phthalimide as an amine equivalent.

Scheme 3C

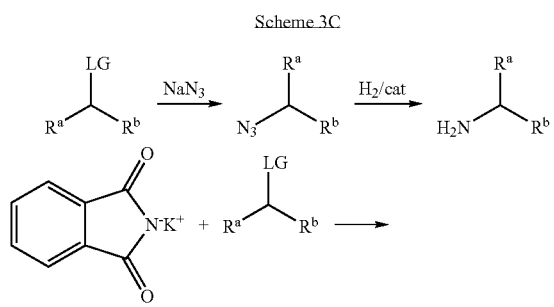

-continued

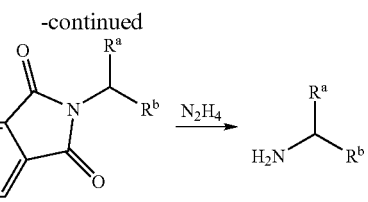

Imine Reduction Reactions

Compounds containing a carbon-nitrogen double bond are susceptible to reduction to give the corresponding amine. Scheme 3D illustrates the reductive amination of an aldehyde or ketone, in which an iminium species is generated as a reactive intermediate.

Scheme 3D

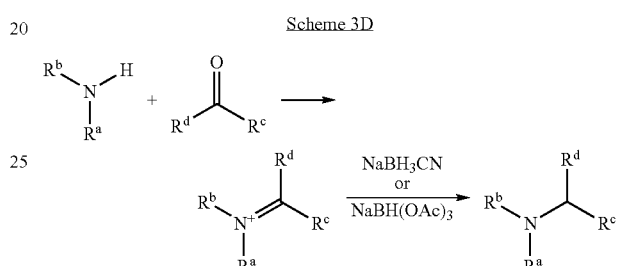

This method is generally applicable to the synthesis of secondary and tertiary amines. It is less well suited to the synthesis of primary amines (i.e. when $R^a$ and $R^b$ are both hydrogen). In this case the use of hydroxylamine provides a more practicable route, as illustrated in scheme 3E.

Scheme 3E

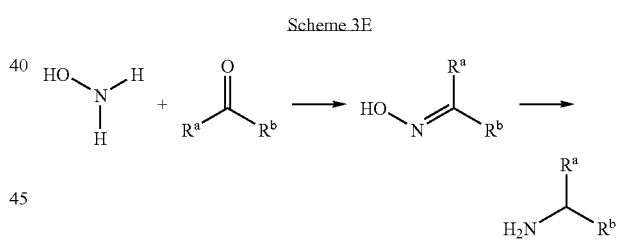

The carbon-nitrogen triple bond of nitrites is also amenable to reduction to provide primary amines, as illustrated in scheme 3F. The nitrile may be obtained by the reaction of an alkali meal cyanide with an appropriate alkylating agent.

Scheme 3F

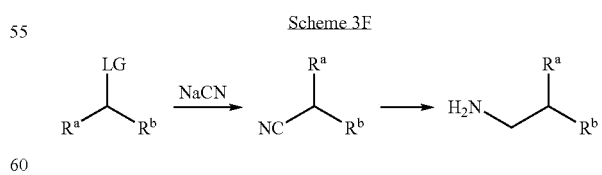

Amide Reduction Reactions

Compounds containing an amide functional group can be reduced to the corresponding amines using reagents such as lithium aluminiumhydride, as illustrated in scheme 3G. The amides can generally be prepared from the corresponding acids and amines.

Scheme 3G

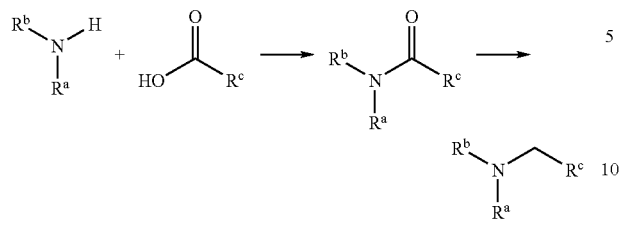

Carbamate esters are reduced in an analogous manner to the corresponding N-methyl amines.

Rearrangement Reactions

A number of well known reactions involving rearrangement reactions are useful for the preparation of amines. One example, illustrated in Scheme 3H, is the Curtius reaction, in which a carboxylic acid is converted to the corresponding acyl azide and then to an acyl nitrene that rearranges to an isocyanate. Hydrolysis gives the amine.

Scheme 3H

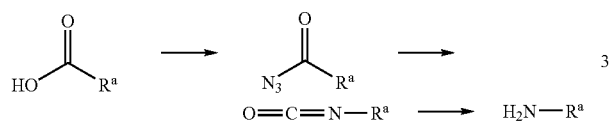

The Lossen rearrangement provides an equivalent process in which the acyl nitrene is generated from a hydroxamic acid. The Schmidt reaction and the Hofmann reaction are other equivalent processes.

The Beckmann rearrangement, illustrated in Scheme 3J, provides secondary amines from oximes.

Scheme 3J

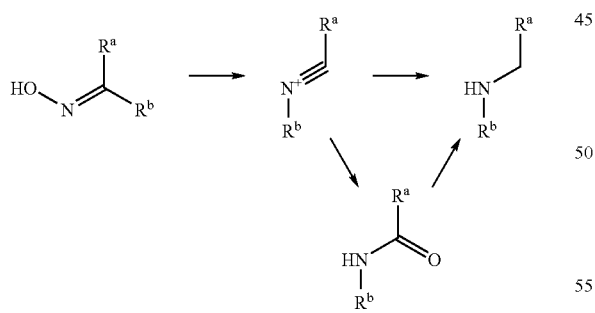

The intermediate nitrilium ion can be reduced in situ to provide the amine directly, or quenched with water to provide an amide that can be reduced to the amine in a separate step.

Preferred methods of introducing the group —NR$^{16}$R$^{17}$ are the displacement reaction of Scheme 3A and the reductive amination of Scheme 3D. The particularly preferred variants are illustrated in Schemes 3K and 3L (where —W— is a covalent bond or an alkylenyl group such that —W—CH$_2$— forms —Y—).

Scheme 3K

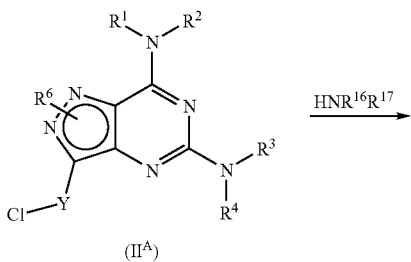

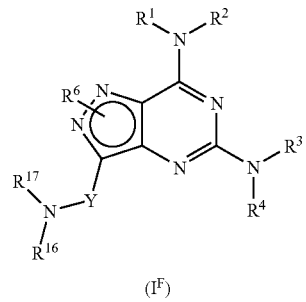

Scheme 3L

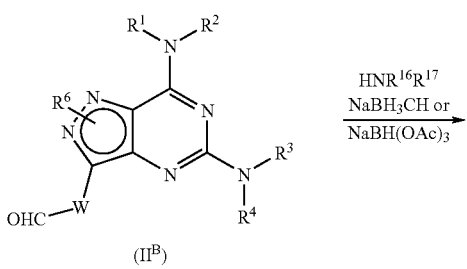

In the light of the foregoing discussion, it will be appreciated that R$^{5A}$ may be, for example, —W—CO$_2$H, —Y—CO$_2$H, —W—CO$_2$R$^A$, —Y—CO$_2$R$^A$, —W—CHO, —W—CN, —Y—OH, —Y-LG or —Y—NHPG, where —W— is a covalent bond or an alkylenyl group such that —W—CH$_2$— forms —Y—, R$^A$ is a methyl, ethyl, tert-butyl or benzyl group, LG is a leaving group as defined above, PG is an amine protecting group and Y is as defined for general formula (I). Of these, the less reactive groups such as —W—CO$_2$R$^A$, —Y—CO$_2$R$^A$, —W—CN, —Y—OH and —Y—NHPG are more likely to be compatible with the conditions required in the overall synthetic sequence. The groups —Y-Cl and —W—CHO present in the compounds of formulae (II$^A$) and (II$^B$) are unlikely to be compatible with the conditions required to elaborate the compounds. Both groups are, however, readily prepared from the more robust groups such as —W—CO$_2$R$^A$. These transformations are described in more detail in parts o) to z) below.

It will further be appreciated that the elaboration of the amine group of R$^5$ does not necessarily need to be the last step of the synthetic route, but may be carried out at any point during the route provided that the amine (optionally in protected form) is compatible with the subsequent chemical transformations. In particular, it has been found that it can be advantageous to elaborate R$^5$ before introducing the —NR$^3$R$^4$ group as described in part d) below. When the amine group of R$^5$ is elaborated early in the synthesis it may be necessary to use a suitable protecting group in order to carry it through the subsequent manipulations.

d) Compounds of formula (II) can be prepared from the corresponding monochlorides of formula (III) by reaction with HNR$^3$R$^4$ as illustrated in Scheme 4.

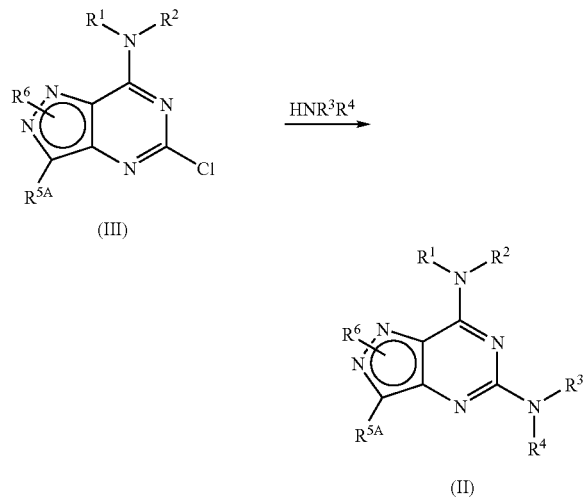

A solution of the monochloride (III) and the amine HNR$^3$R$^4$ in a suitable dipolar aprotic solvent are stirred at elevated temperature for between 1 and 24 hours. Suitable solvents include dimethylsulfoxide, dimethylformamide and N-methylpyrrolidinone. An excess of a tertiary amine such as N-ethyldiisopropylamine, N-methylmorpholine or triethylamine may optionally be included. It is sometimes necessary to perform the reaction at elevated pressure in a closed vessel, particularly when the amine HNR$^3$R$^4$ or the solvent is volatile.

Preferably, the monochloride is treated with 1-5 equivalents of the amine HNR$^3$R$^4$ and optionally 3-5 equivalents of N-ethyldiisopropylamine in dimethylsulfoxide or N-methylpyrrolidinone at 100-125° C. for 12-18 hours, in a sealed vessel.

It will be appreciated that any functional groups in HNR$^3$R$^4$, and particularly any primary or secondary amine groups, may need to be protected in order to allow this reaction to proceed successfully. In such a case a subsequent deprotection step such as is described in part c) will be necessary. The protecting group can be selected such that it can be removed at the same as the protecting group of the amine in R$^5$ (where such a protecting group is present). Alternatively it may be preferable to provide for sequential removal of the protecting groups.

e) Compounds of formula (III) can be prepared from the corresponding dichlorides of formula (IV) by reaction with HNR$^1$R$^2$ as illustrated in Scheme 5.

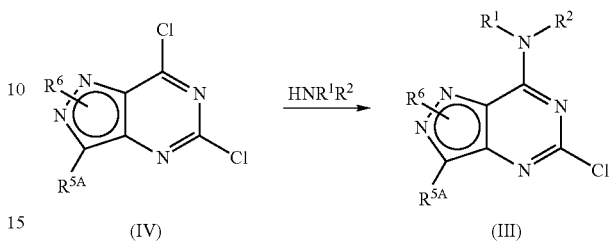

A solution of the dichloride (IV), the amine HNR$^1$R$^2$ and an excess of a tertiary amine such as N-ethyldiisopropylamine, N-methylmorpholine or triethylamine in a suitable dipolar aprotic solvent are stirred at ambient or elevated temperature for between 1 and 24 hours. Suitable solvents include dimethylsulfoxide, dimethylformamide and N-methylpyrrolidinone. It will be appreciated that any functional groups in HNR$^1$R$^2$, and particularly any primary or secondary amine groups, may need to be protected in order to allow this reaction to proceed successfully. Preferably, the monochloride is treated with 2-5 equivalents of the amine HNR$^1$R$^2$ and optionally 2-5 equivalents of N-ethyldiisopropylamine in dimethylsulfoxide or a mixture of dimethylsulfoxide and N-methylpyrrolidinone at 30-90° C. for 1-18 hours.

Alternatively, a solution of the amine HNR$^1$R$^2$ in a suitable solvent is treated with butyllithium or sodium hexamethyldisilazide at low temperature, and the dichloride is added to the resulting solution. Suitable solvents include tetrahydrofuran and dioxan.

As discussed in part d), reactive functional groups in HNR$^1$R$^2$ may need to be protected for this reaction to give a satisfactory result.

When R$^{5A}$ is an ester group such as —CO$_2$CH$_3$ directly attached to the pyrazolopyrimidine nucleus, the reaction of compounds of formula (IV) with less reactive amines HNR$^1$R$^2$ can be low-yielding. In such cases it is sometimes advantageous to use an alternative strategy, as discussed in part z) below.

f) Compounds of formula (IV) can be prepared from the corresponding pyrazolopyrimidinediones formula (V) as illustrated in Scheme 6.

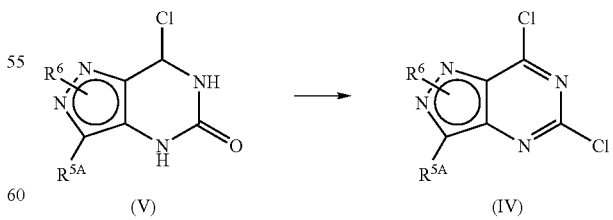

The dione is treated with a large excess of a suitable chlorinating reagent such as phosphorus oxychloride (POCl$_3$) or phenylphosphonyl dichloride (PhP(O)Cl$_2$) in the presence of a tertiary amine such as N-ethyldiisopropylamine, N-methylmorpholine, triethylamine or N,N-dimethylaniline or tetraethylammonium chloride at elevated temperature for 8-48 hours. Dimethylformamide can optionally be added as a catalyst. The reaction may be performed in the absence of a solvent. When a solvent is used then suitable solvents include acetonitrile and propionitrile. Preferably, the dione is treated with 10-30 equivalents of $POCl_3$ and 3 equivalents of N-ethyldiisopropylamine or 3-5 equivalents of tetraethylammonium chloride in acetonitrile or propionitrile at reflux for 18 hours.

g) Compounds of formula (V) can be prepared from the corresponding aminoamides of formula (VI) as illustrated in Scheme 7.

Scheme 7

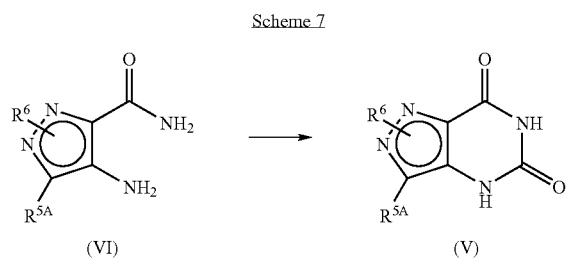

(VI)    (V)

A solution of the pyrazolecarboxamide (VI) and phosgene or an equivalent thereof, such as carbonyl diimidazole, trichloromethyl chloroformate or bis(trichloromethyl) carbonate, in a dipolar aprotic solvent is stirred at a temperature of between ambient temperature and the boiling point of the solvent, optionally at elevated pressure, for between 2 and 18 hours. Preferably, a solution of the dione and 1-2 equivalent of carbonyl diimidazole in dimethylformamide is stirred at 70° C. to 90° C. for 18 hours.

h) Compounds of formula (VI) can be prepared from the corresponding nitroamides of formula (VII) as illustrated in Scheme 8.

Scheme 8

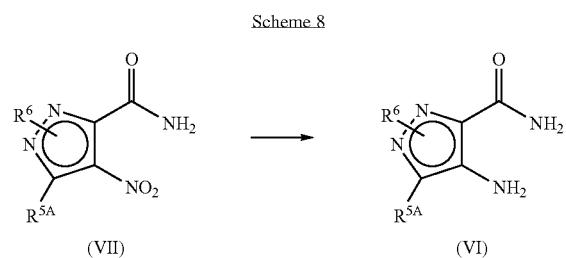

(VII)    (VI)

Reduction of the nitro group can be achieved by, for example, transfer or catalytic hydrogenation, or by a dissolving metal reduction.

For transfer hydrogenation, the nitro compound is reacted with a suitable hydrogen donor, such as ammonium formate or cyclohexene, in a polar solvent, such as tetrahydrofuran, methanol or ethanol, in the presence of a transition metal or transition metal salt catalyst, such as palladium or palladium (II) hydroxide, optionally at elevated temperature and pressure.

For catalytic hydrogenation, a solution of the nitro compound in a polar solvent, such as tetrahydrofuran, methanol or ethanol, is stirred under a hydrogen atmosphere in the presence of a transition metal or transition metal salt catalyst, such as palladium or palladium(II) hydroxide, optionally at elevated pressure. The catalyst may be in solution (homogeneous catalysis) or in suspension (heterogeneous catalysis).

For dissolving metal reduction, the nitro compound is treated with a suitable reactive metal, such as zinc or tin, in the presence of an acid such as acetic acid or hydrochloric acid. Other reducing agents, such as tin(II) chloride, may also be used.

i) Compounds of formula (VII) can be prepared from the corresponding nitroacids of formula (VIII) as illustrated in Scheme 9.

Scheme 9

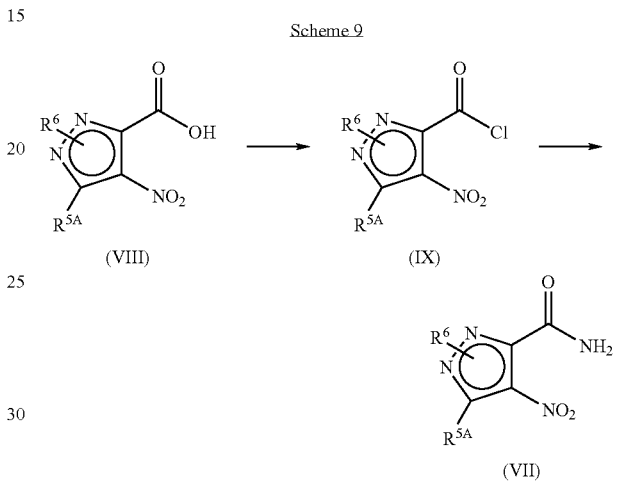

(VIII)    (IX)

(VII)

The acid (VIII) is converted to the corresponding acid chloride (IX) by treatment with oxalyl chloride and dimethylformamide in a suitable solvent such as dichloromethane, or with thionyl chloride. A solution of the acid chloride in a suitable solvent such as dichloromethane, tetrahydrofuran or dioxan is then treated with gaseous ammonia or aqueous ammonia to provide the amide of formula (VII).

j) Compounds of formula (VIII) can be prepared from the corresponding acids of formula (X) as illustrated in Scheme 10.

Scheme 10

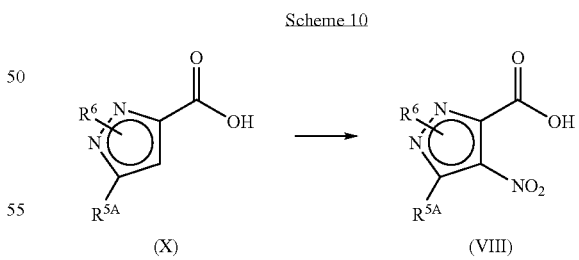

(X)    (VIII)

The nitration of pyrazoles is well known. The compounds of formula (X) are treated with nitric acid or a mixture of nitric acid and sulphuric acid to provide the compounds of formula (VIII).

k) Certain compounds of formula (X) are commercially available. Compounds of formula (X) that are not items of commerce can be prepared via the corresponding methyl esters (XI) as illustrated in Schemes 11 to 13.

Scheme 11

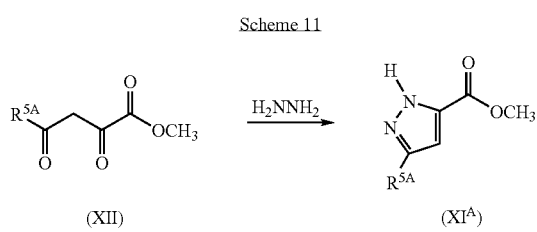

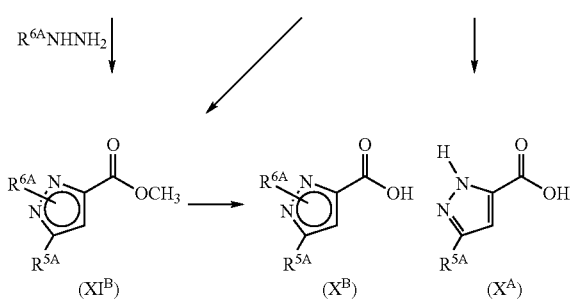

The method illustrated in Scheme 9 is the Knorr pyrazole synthesis. A 1,3-diketone of formula (XII) is reacted with hydrazine to give a pyrazole of formula (XI$^A$), or with a substituted hydrazine R$^{6A}$—NHNH$_2$, wherein R$^{6A}$ is any group according to R$^6$ except hydrogen, to give a pyrazole of formula (XI$^B$).

Pyrazoles of formula (XI$^B$) may also be obtained by N-alkylation of the corresponding pyrazoles of formula (XI$^A$). The pyrazole of formula (XI$^A$) is treated with a base such as an alkaline metal carbonate or bicarbonate, for example potassium carbonate or caesium carbonate, or a tertiary amine, for example triethylamine, diisopropylethylamine or pyridine, and the appropriate chloride (R$^{6A}$—Cl), bromide (R$^{6A}$—Br), iodide (R$^{6A}$—I), mesylate (R$^{6A}$—OSO$_2$CH$_3$) or tosylate (R$^{6A}$—OSO$_2$Tol) in a suitable solvent at a temperature of between −70° C. and 100° C. Suitable solvents include alcohols such as methanol, ethanol, isopropanol and butanol, ethers such as tetrahydrofuran and dioxan, dimethylformamide and acetonitrile. When the reaction gives a mixture of the N$^1$- and N$^2$-alkylated products, these can be separated using standard techniques.

The methyl esters of formula (XI$^A$) and (XI$^B$) are hydrolysed to provide the corresponding acids of formula (X$^A$) and (X$^B$) by treatment with an alkali metal hydroxide, such as lithium hydroxide, sodium hydroxide or potassium hydroxide, in a suitable solvent. Suitable solvents include lower alcohols, such as methanol and ethanol, and mixtures of water and dioxan or tetrahydrofuran.

Compounds of formula (XII) can be prepared from the corresponding methyl ketones of formula (XIII) using a crossed Claisen condensation as illustrated in Scheme 12.

Scheme 12

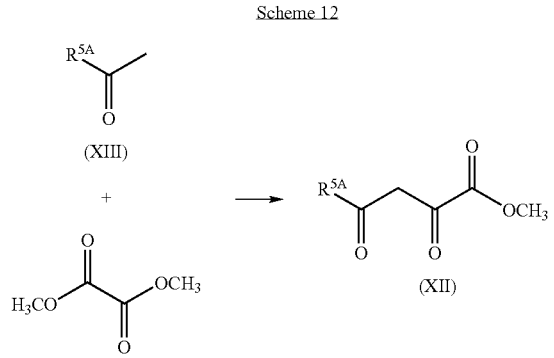

A methyl ketone of formula (XIII) is reacted with dimethyl oxalate in a suitable solvent in the presence of a suitable base. Suitable solvents include ethers, such as tetrahydrofuran. Suitable bases include sodium hydride, potassium t-butoxide and lithium diisopropylamide. Alternatively, unless R$^{5A}$ includes a reactive functional group, sodium methoxide may be used as the base and methanol as the solvent.

Scheme 13

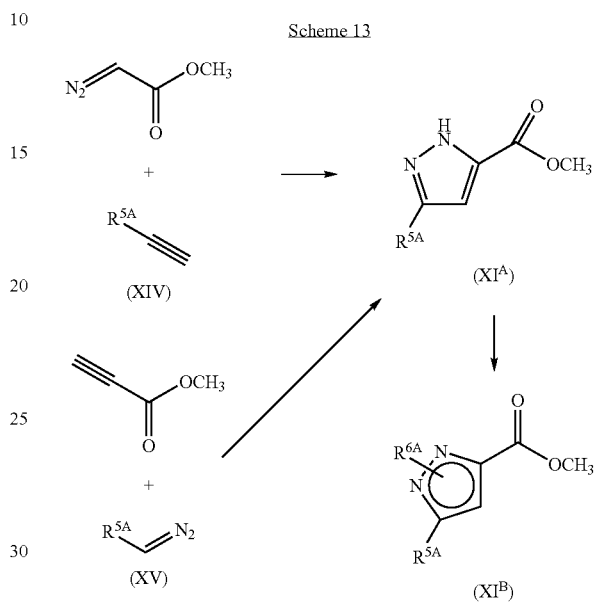

The method illustrated in Scheme 13 is the Pechmann pyrazole synthesis. A diazo compound and an acetylene are combined to produce a pyrazole of formula (XI$^A$). When R$^{5A}$ is other than —COOCH$_3$ two variants of the method can be considered. An acetylene of formula (XIV) can be combined with methyl diazoacetate, or a diazo compound of formula (XV) can be combined with methyl propiolate. The initial reaction product (XI$^A$) may be N-alkylated as described above to give the pyrazoles of formula (XI$^B$).

1) A particularly useful series of compounds are those wherein R$^{5A}$ is —CO$_2$CH$_3$. Their elaboration is illustrated in Scheme 14.

Scheme 14

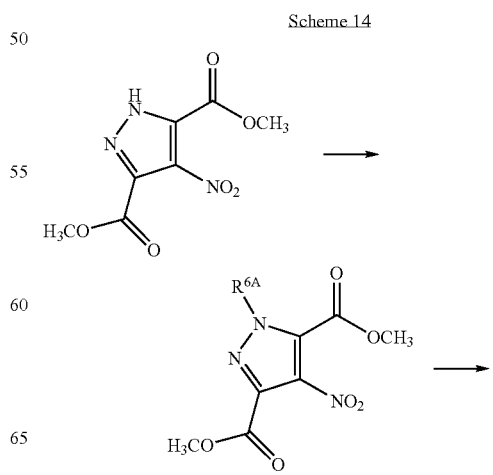

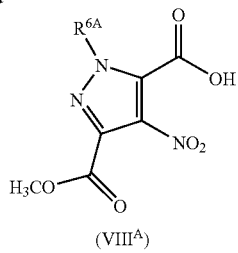

(VIII^A)

Dimethyl 4-nitropyrazole-3,5-dicarboxylate is readily prepared according to the method described in published international patent application WO00/24745 (see preparation 2, page 48), and can be N-alkylated according to the methods described in part k) above. Because the two nitrogen atoms of the pyrazole are equivalent, a single alkylation product is obtained. Selective hydrolysis of the diester with one equivalent of alkali metal hydroxide according to the method of Chambers et al. (J. Org. Chem. 50, 4736-4738,1985) cleaves the ester adjacent to the substituted nitrogen, providing the monoacids of formula (VIII^A), i.e. compounds of formula (VIII) wherein $R^{5A}$ is —CO$_2$CH$_3$ and $R^{6A}$ is attached at the nitrogen atom adjacent to the free carboxylic acid group.

m) In some embodiments of the compounds of formula (I), the group $R^6$ may not be compatible with the synthetic methods described above. An alternative in these circumstances is to introduce the $R^6$ group at a late stage, as illustrated in Scheme 15.

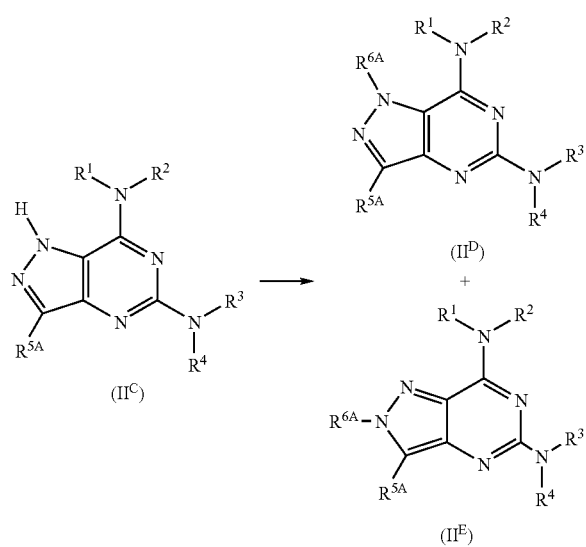

A compound of formula (II^C), i.e. a compound of formula (II) wherein $R^6$ is hydrogen, can be alkylated using the methods described in part k) above. The reaction will generally give a mixture of the $N^1$-alkylated compound (II^D) and the $N^2$-isomer (II^E). These can be separated and purified by conventional methods. The use of more reactive alkylating agents tends to promote alkylation at the $N^2$ position.

It will be appreciated that the alkylation reaction to introduce $R^{6A}$ might also be carried out at other stages in the synthetic sequence.

n) Compounds of formula (I^F) wherein Y is a covalent bond can be prepared by the methods described in parts c) to f) above, starting from compounds of formula (V^A), i.e. compounds of formula (V) wherein $R^{5A}$ is —NR$^{16}$R$^{17}$, provided that any incompatible functional groups are suitably protected. The requisite compounds of formula (V^A) can be prepared from the corresponding compounds of formula (V^B), i.e. compounds of formula (V) wherein $R^{5A}$ is hydrogen, following the method illustrated in Scheme 16.

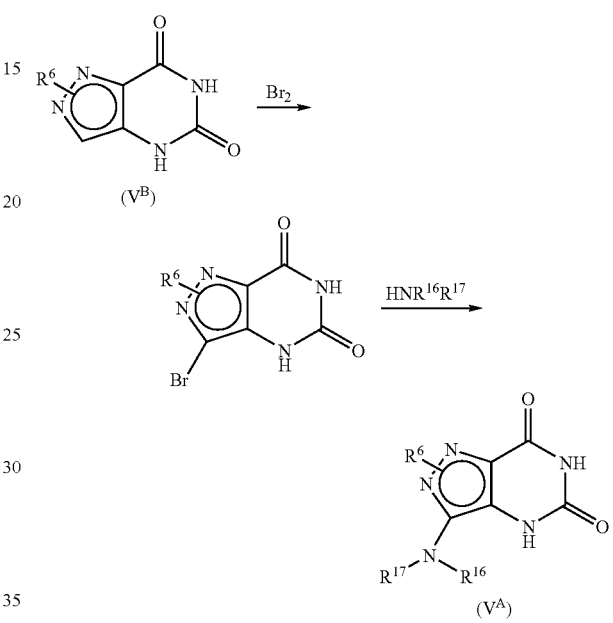

The pyrazolopyrimidinedione of formula (V^B) can be brominated by treatment with bromine. Treatment with an amine HNR$^{15}$R$^{16}$ leads to the introduction of the amino group at the C$^3$-position. The compound of formula (V^B) may be treated with chlorine to give the 3-chloropyrazolopyrimidinedione which reacts in an analogous manner to provide the compound of formula (V^A).

The compounds of formula (V^B) can be prepared from methylpyrazole-3-carboxylate by N-alkylation (when $R^6$ is other than hydrogen) as described in part k) above, followed by elaboration as described in parts j), i), h) and g).

As previously noted in part c), compounds of formula (II) and (III) in which $R^{5A}$ is —W—CO$_2$H, —Y—CO$_2$H, —W—CO$_2$R$^4$, —Y—CO$_2$R$^4$, —W—CHO, —W—CN, —Y—OH or —Y-LG are particularly useful precursors to compounds wherein the amine group in $R^5$ has been elaborated. It may be necessary or convenient to introduce some of these groups by manipulating a more accessible starting material. Interconversions of these common functional groups are well known in the art. Some representative manipulations are described below. It will be appreciated that the synthetic transformations discussed may also be used in the elaboration of precursor compounds such as the pyrazoles of formula (XI).

o) Esters of formula (III^A), in which —V— represents either —W— or —Y—, i.e. compounds of formula (III) wherein $R^{5A}$ is —V—CO$_2$R$^4$, and the corresponding acids of formula (III^B), i.e. compounds of formula (III) wherein $R^{5A}$ is —V—CO$_2$H, may be interconverted as illustrated in Schemes *17A and *17B.

Scheme 17A

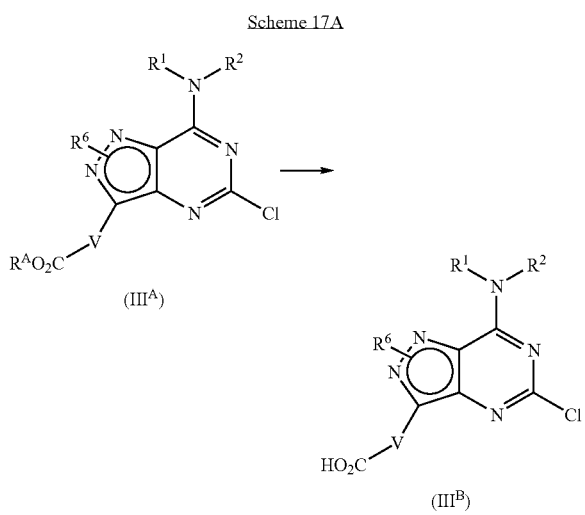

When $R^A$ is methyl or ethyl the conversion may conveniently be accomplished by treating the compound of formula (III$^A$) with an alkaline metal hydroxide such as lithium hydroxide, sodium hydroxide or potassium hydroxide in a suitable solvent at a temperature of between about 10° C. and the boiling point of the solvent. Suitable solvents include water, methanol, ethanol and mixtures of water with methanol, ethanol, tetrahydrofuran and dioxan. When $R^A$ is tert-butyl the conversion may be accomplished by treating the compound of formula (III$^A$) with an acid such as hydrogen chloride or trifluoroacetic acid in a suitable solvent at a temperature of between 0° C. and ambient temperature. Suitable solvents include dioxan and dichloromethane. When $R^A$ is benzyl the conversion may conveniently be accomplished by treating the compound of formula (III$^A$) with an alkaline metal hydroxide as discussed above, or by hydrogenolysis using molecular hydrogen or a suitable hydrogen donor such as ammonium formate in the presence of a transition metal or transition metal salt catalyst such as palladium-on-carbon, in a suitable solvent, such as methanol.

Scheme 17B

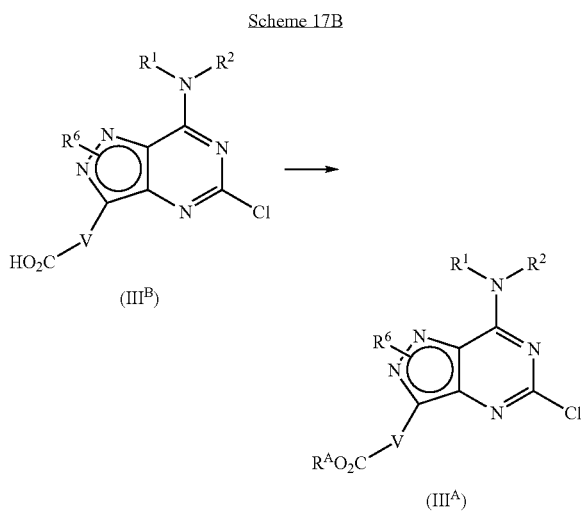

The conversion may conveniently be accomplished by treating a mixture of the acid of formula (III$^B$) and an alcohol $R^A$—OH in a suitable solvent with a condensing agent such as a carbodiimide, e.g. dicyclohexylcarbodiimide or N-(3-dimethylaminopropyl)-N'-ethylcarbodiimide, optionally in the presence of 4-dimethylaminopyridine, at a temperature of between 0° C. and the boiling point of the solvent. Suitable solvents include dichloromethane and dimethylformamide. Alternatively, the acid of formula (III$^B$) may be converted to the corresponding acid chloride using thionyl chloride or oxalyl chloride and then treated with the alcohol $R^A$—OH.

p) Compounds of formula (III$^C$), i.e. compounds of formula (III$^A$) wherein V is CH$_2$, may be prepared from the corresponding compounds of formula (III$^D$), i.e. compounds of formula (III$^B$) wherein V is a covalent bond, by a one-carbon homologation method such as the Arndt-Eistert reaction illustrated in Scheme 18.

Scheme 18

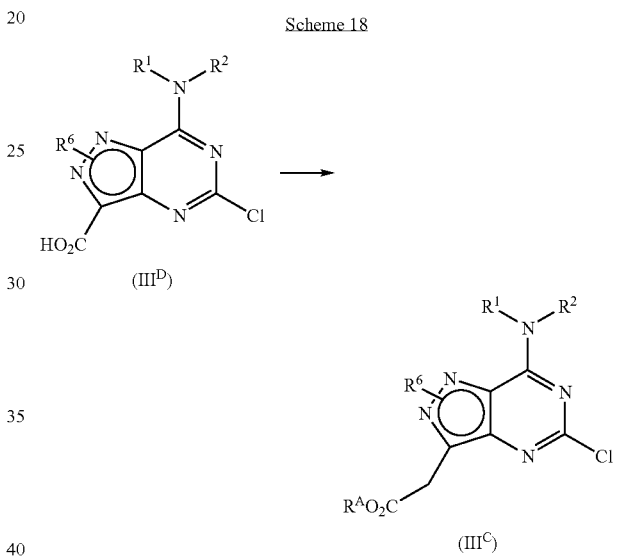

The carboxylic acid is converted to a reactive intermediate such as the acid chloride (by reaction with oxalyl chloride) or a mixed anhydride (by reaction with isobutyl chloroformate). The intermediate is reacted with diazomethane to provide an α-diazoketone. This is treated with silver oxide in the presence of $R^A$—OH to give the homologated ester of formula (III$^C$).

q) Compounds of formula (III$^E$), i.e. compounds of formula (III$^B$) wherein V is CH$_2$, may be prepared from the corresponding nitriles of formula III$^F$ by the method illustrated in Scheme 19.

Scheme 19

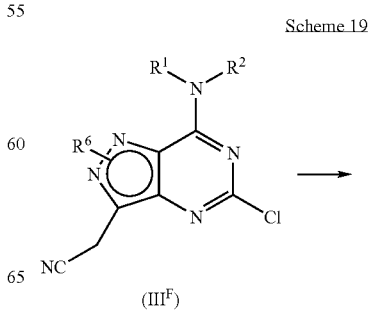

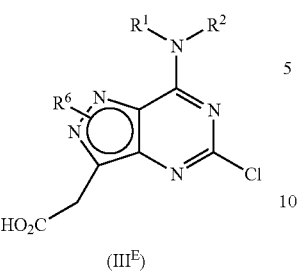

(III^E)

The nitrile group can be hydrolysed, e.g. by treatment with aqueous mineral acids, such as hydrochloric acid.

r) Compounds of formula (III^F) can be prepared from the corresponding chlorides of formula (III^G) by the method illustrated in Scheme 20.

Scheme 20

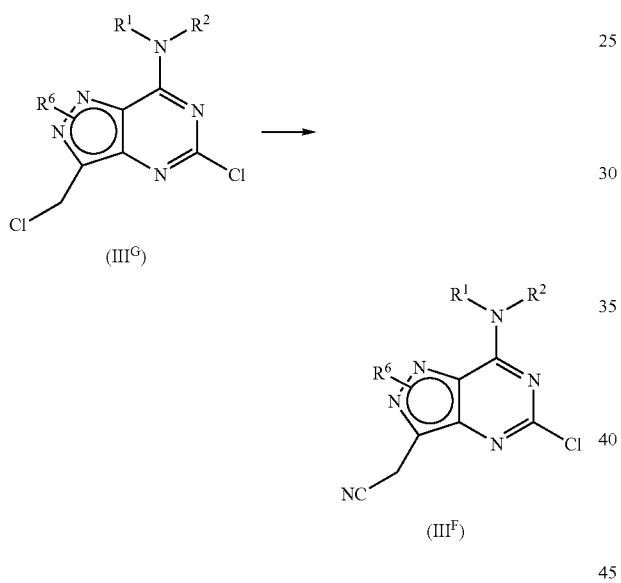

(III^G)

(III^F)

The chloride is treated with a metal cyanide, such as sodium cyanide or potassium cyanide in a suitable solvent, such as dimethylsulfoxide, dimethylformamide or ethanol.

s) Compounds of formula (III^G) can be prepared from the corresponding alcohols of formula (III^H) by the method illustrated in Scheme 21.

Scheme 21

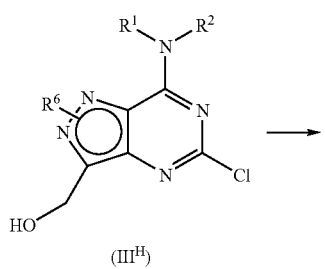

(III^H)

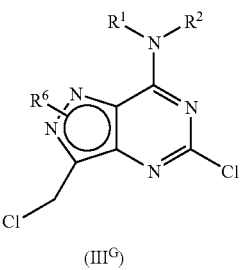

(III^G)

The alcohol is treated with a mixture of triphenylphosphine and N-chlorosuccinimide or tetrachloromethane, or with thionyl chloride.

t) Compounds of formula (III^H) can be prepared from the corresponding esters of formula (III^J), i.e. compounds according to formula (III^4) wherein V is a covalent bond, or from the corresponding acids of formula (III^D) by the method illustrated in Scheme 22.

Scheme 22

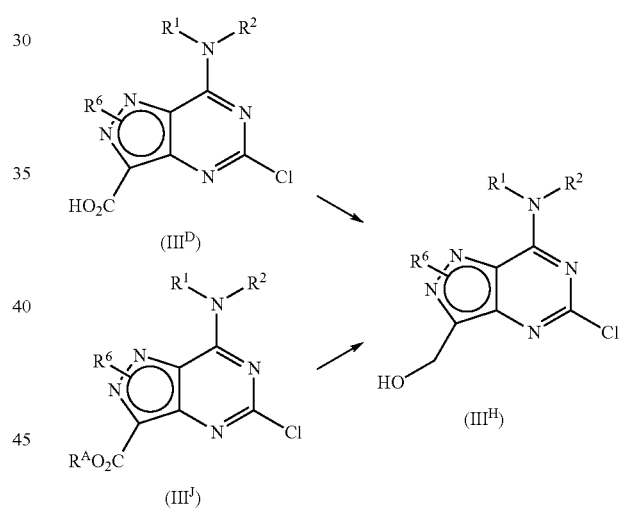

(III^D)

(III^J)

(III^H)

The acids of formula (III^D) and the esters of formula (III^J) can be reduced to the alcohols of formula (III^H) by treatment with lithium aluminium hydride in a suitable solvent at a temperature of between 0° and the boiling point of the solvent. Suitable solvents include ethers such as tetrahydrofuran. The acids can also be reduced by treatment with isobutyl chloroformate and a tertiary amine base to provide a mixed anhydride, followed by reaction with sodium borohydride. The esters can also be reduced by treatment with diisobutylaluminum hydride or lithium borohydride.

u) Compounds of formula (III^K), i.e. compounds of formula (III^4) wherein V is $CH_2CH_2$ can be prepared from the corresponding acrylate ester of formula (III^L) by the method illustrated in Scheme 23.

Scheme 23

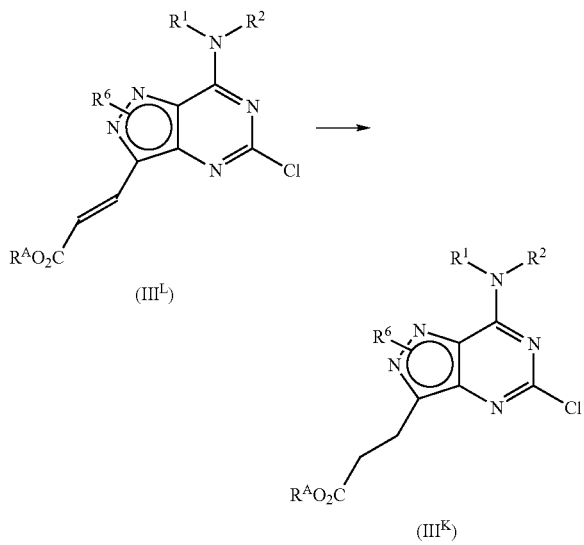

The reduction of the carbon-carbon double bond of (III$^L$) to give the compounds of formula (III$^K$) can be accomplished by catalytic hydrogenation using molecular hydrogen in the presence of a transition metal catalyst such as palladium, platinum or nickel. When R$^A$ is benzyl the conditions can be chosen such that only the double bond is reduced or reduction is accompanied by hydrogenolytic cleavage of the ester to give the carboxylic acid.

The acrylates of formula (III$^L$) can also be treated with alkylcopper reagents to give analogues of the compounds of formula (III$^K$) in which an alkyl substituent is introduced on the carbon atom adjacent to the pyrazolopyrimidine ring system, or with a sulphonium ylid or a carbene equivalent to give a 2-(pyrazolopyrimidinyl)-cyclopropane-1-carboxylate derivative.

v) Compounds of formula (III$^L$) can be prepared from the corresponding aldehydes of formula (III$^M$) by the method illustrated in Scheme 24.

Scheme 24

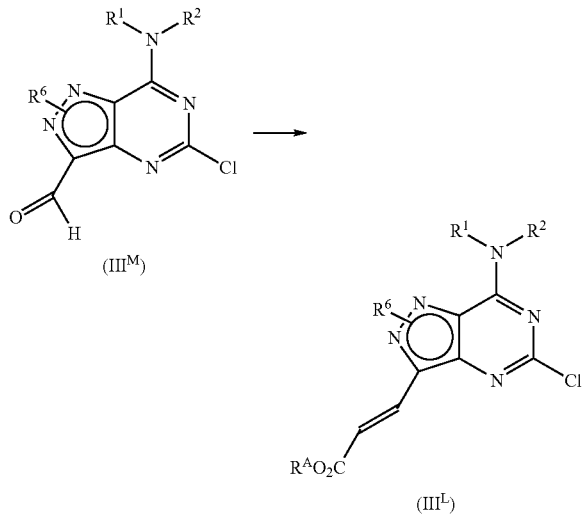

The aldehyde of formula (III$^M$) can be converted to the acrylate ester of formula (III$^L$) by reaction with a phosphorus reagent following the protocols of the Wittig, Horner or Wadsworth-Horner-Emmons reactions. The reagent is prepared by treating a triphenylphosphonium salt Ph$_3$P$^+$CH$_2$CO$_2$R$^A$.X$^-$ (Wittig), a phosphine oxide Ph$_2$P(O)CH$_2$CO$_2$R$^A$ (Horner), or a phosphonate (EtO)$_2$P(O)CH$_2$CO$_2$R$^A$ (Wadsworth-Horner-Emmons), with a base such as butyllithium, a lithium dialkylamide or an alkaline metal alkoxide, in a suitable solvent such as tetrahydrofuran.

The method is not limited to the preparation of α-unsubstituted acrylate esters. The use of an alkyl-substituted phosphorus reagent such as Ph$_3$P$^+$CH(R)CO$_2$R$^A$.X$^-$ or the equivalent phosphine oxide or phosphonate, wherein R is alkyl, gives access to the corresponding α-alkyl acrylate derivative.

The conversion of the aldehydes of formula (III$^M$) to acrylate esters of formula (III$^L$) can also be achieved by reaction with a malonate derivative following the method of the Knoevenagel condensation.

w) Compounds of formula (III$^M$) can be prepared from the esters of formula (III$^J$) or more preferably from the corresponding alcohols of formula (III$^H$) by the methods illustrated in Scheme 25.

Scheme 25

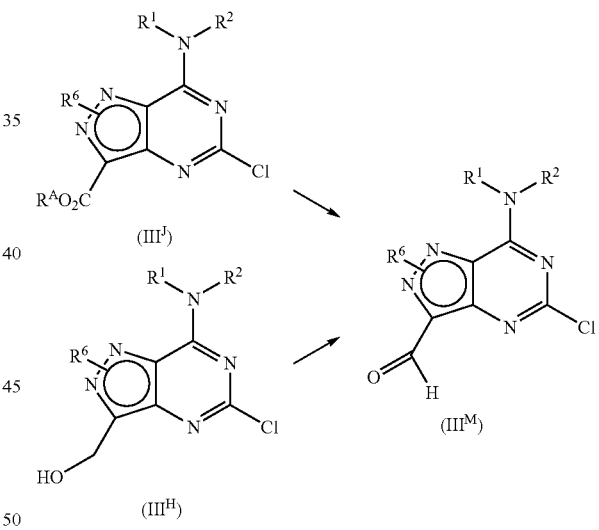

The reduction of the esters of formula (III$^J$) can be achieved using diisobutylaluminium hydride (DIBAL) in a suitable solvent at a temperature of less than 0° C., preferably less than −60° C. Suitable solvents include hydrocarbons such as pentane, hexane and toluene, ethers such as tetrahydrofuran, and mixtures thereof.

The oxidation of the alcohols of formula (III$^H$) can be achieved using a chromium(VI) reagent such as pyridinium chlorochromate, a hypervalent iodine reagent such as the Dess-Martin periodinane, or a combination of tetra-n-propylammonium perruthenate and N-methylmorpholine-N-oxide in a suitable solvent at a temperature of between 0° C. and ambient temperature. Suitable solvents include dichloromethane.

x) The aldehydes of formula (III$^M$) may be converted to esters of formula (III$^C$) as illustrated in Scheme 26

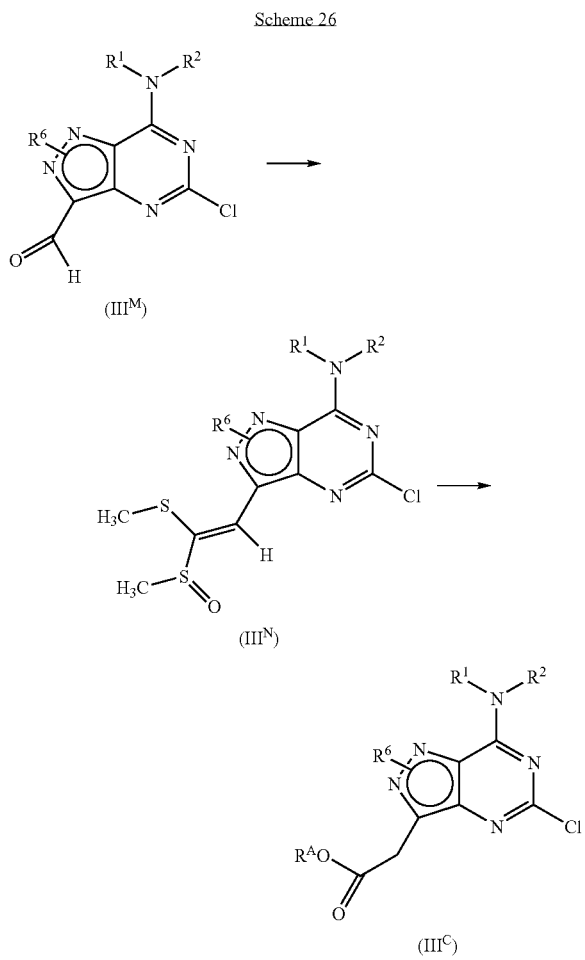

The aldehyde is treated with methyl methylmercaptomethyl sulfoxide (CH$_3$SCH$_2$S(O)CH$_3$) and triton B in tetrahydrofuran to give intermediate (III$^N$) which is treated with the appropriate alcohol R$^4$OH and acetyl chloride to provide the ester of formula (III$^C$). This method is particularly useful when R$^4$ is methyl.

y) Compounds of formula (III$^K$) can also be prepared from the corresponding chlorides of formula (III$^G$) by the method illustrated in Scheme 27.

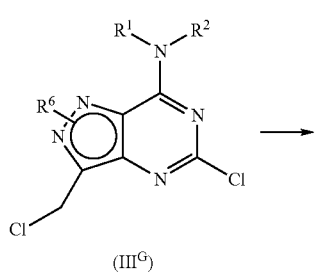

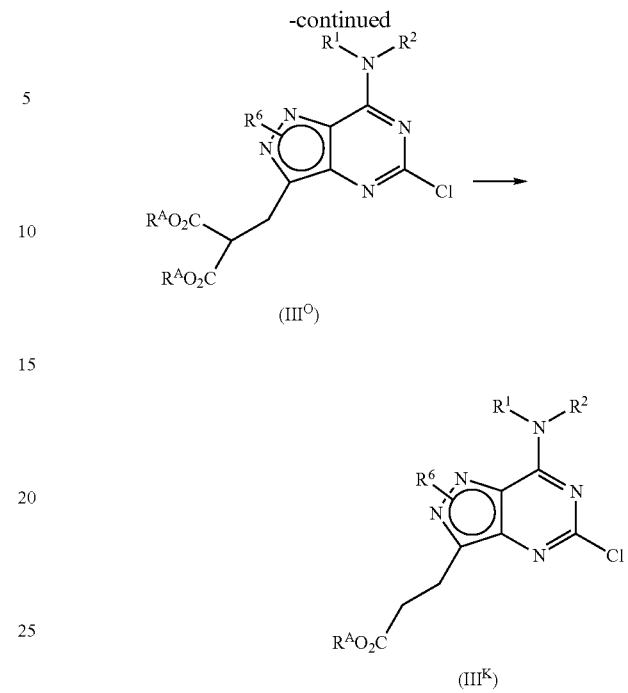

The chloride of formula (III$^G$) is reacted with a dialkyl malonate (R$^4$O$_2$C)$_2$CH$_2$ and a base in a suitable solvent. Typically, the base is an alkaline metal alkoxide such as sodium ethoxide or potassium tert-butoxide, and the solvent is an alcohol such as ethanol or an ether such as tetrahydrofuran. Preferably the base and the solvent are chosen such as to minimise transesterification with the malonate reagent and the intermediate (III$^O$). For example, when the reagent is diethyl malonate the base is preferably sodium ethoxide and the solvent is ethanol. The intermediate (III$^O$) is then decarboxylated to give the product (III$^K$). This can be achieved by selective hydrolysis using one equivalent of an alkaline metal hydroxide, such as sodium hydroxide, followed by acidification, or by any other method known in the art.

The method is not limited to symmetrical malonates. For example, the use of tert-butyl methyl malonate would give an intermediate (III$^O$) in which one R$^4$ is methyl and the other is tert-butyl. By choosing the appropriate conditions, decarboxylation could then be controlled to give a product (III$^K$) in which R$^4$ was either tert-butyl or methyl.

The method can be extended to substituted malonates (R$^4$O$_2$C)$_2$CHR, where R is an alkyl group. This gives access to compounds analogous to (III$^K$) in which the group R is a substituent on the carbon atom adjacent to the R$^4$O$_2$C group. These compounds can also be prepared by alkylating the intermediate (III$^O$) with R—Br or R—I in the presence of an alkaline metal alkoxide base.

z) As mentioned in part e) above, the reaction of compounds of formula (IV$^A$), i.e. compounds of formula (IV) wherein R$^{5A}$ is —CO$_2$R$^4$, with weakly nucleophilic amines HNR$^1$R$^2$ is sometimes not high yielding. An alternative route is illustrated in Schemes 28A and 28B.

Scheme 28A

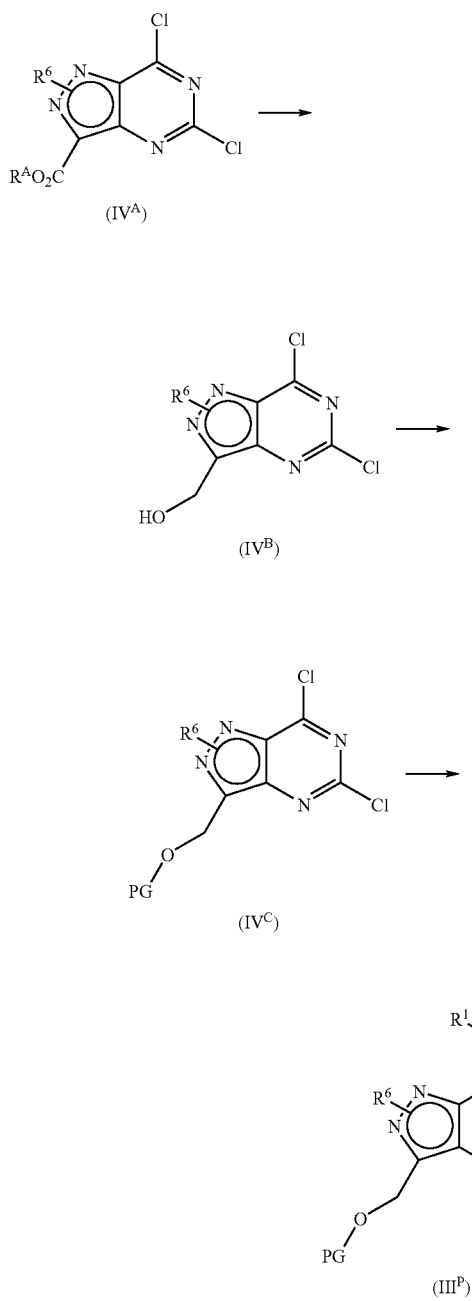

Scheme 28B

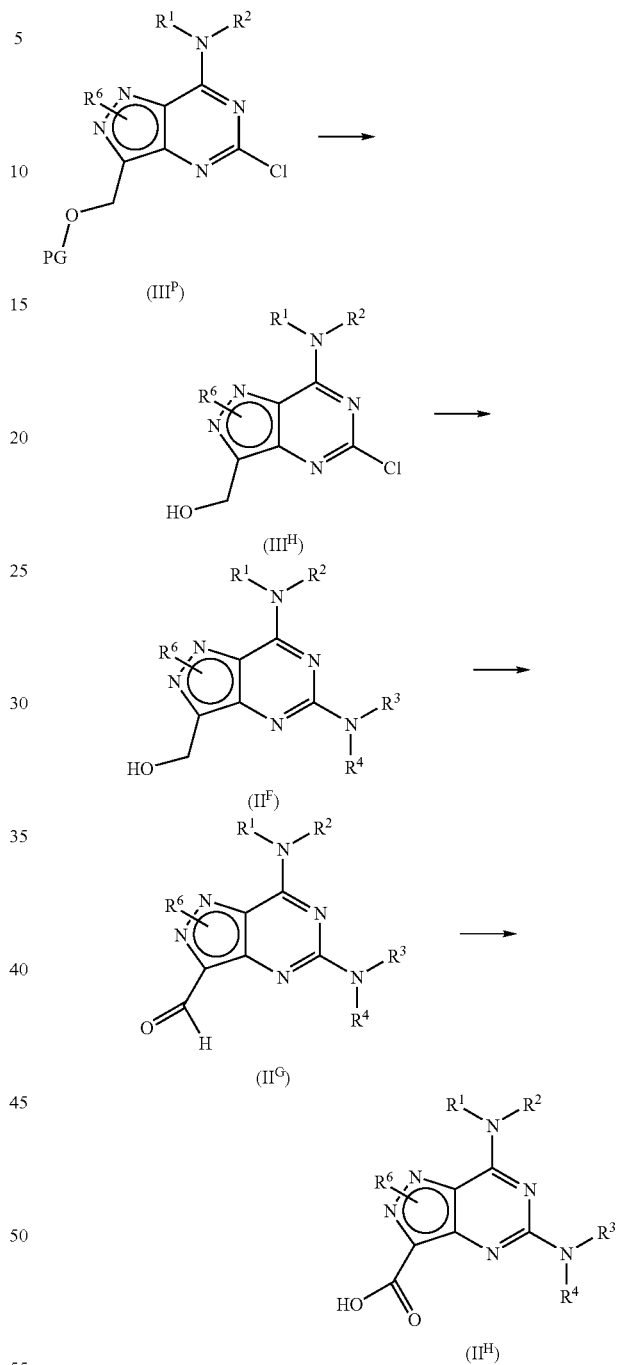

The esters of formula (IV$^A$) can be reduced to the alcohols of formula (IV$^B$) according to the methods described in part t) above. A preferred method is reduction with diisobutylaluminium hydride at a temperature of between −20° C. and 0° C. The primary alcohol is then protected to give compounds of formula (IV$^C$), wherein PG is an alcohol protecting group. A preferred protecting group is a trialkylsilyl group, particularly a tert-butyldimethylsilyl group. The compounds of formula (IV$^C$) are then reacted with an amine HNR$^1$R$^2$ according to the methods described in part e) above to give compounds of formula (III$^P$).

The compounds of formula (III$^P$) are deprotected to provide the primary alcohols of formula (III$^H$) using appropriate conditions. When PG is a trialkylsilyl group it may be removed by treatment with a fluoride salt, such as tetrabutylammonium fluoride, or with hydrochloric acid. The alcohols of formula (III$^H$) may then be further modified as discussed above. For example, the —NR$^3$R$^4$ group may be introduced according to the methods described in part d) above to provide compounds of formula (II$^F$). The primary alcohol may then be oxidised as described in part w) above to provide the aldehydes of formula (II$^G$). A preferred oxidising agent is the Dess-Martin periodinane. Finally, if the carboxylic acids are desired, the aldehydes of formula (II$^G$) may be oxidised to provide the acids of formula (II$^H$). Suitable oxidising agents include potassium permanganate, Jones' reagent and sodium chlorite. A preferred method is to treat the aldehydes with sodium chlorite, sodium dihydrogenphosphate and 2-methyl-2-butene in tert-butanol at room temperature for about 1 hour.

Compounds of formula (I$^A$-4) can also be prepared by following Schemes 29-41:

aa) Compounds of formula (I$^A$), i.e. compounds of formula (I$^A$-4) wherein R$^{15}$ is R$^{17}$C(O) can be prepared by acylation of the corresponding compounds of formula (II), as illustrated in Scheme 29.

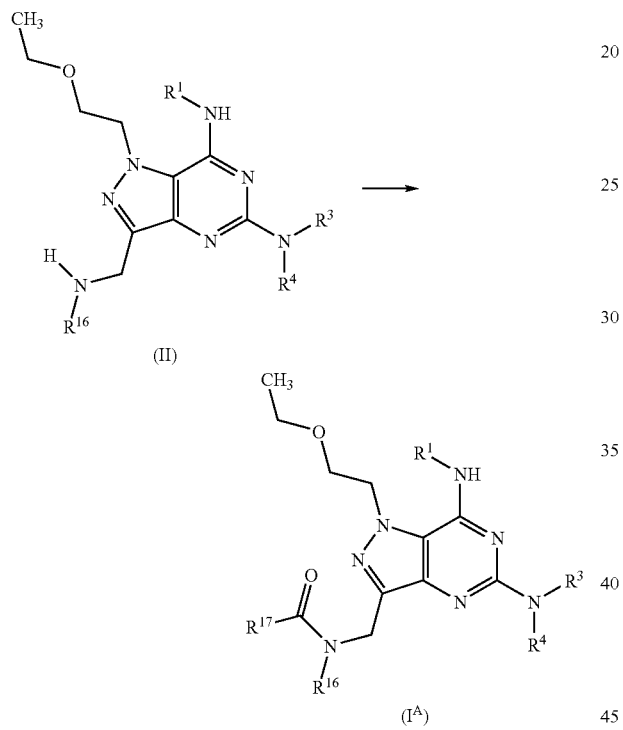

The compound of formula (II) is treated with 1-2 equivalents of an acylating agent such as an acyl chloride R$^{17}$C(O)Cl or an anhydride (R$^{17}$C(O))$_2$O in a suitable solvent in the presence of a tertiary amine base such as triethylamine, N-ethyldiisopropylamine or pyridine. Suitable solvents include dichloromethane and dimethylformamide. Preferably, the compound of formula (II) is treated with about 1.3 equivalents of acyl chloride and about 1.3 equivalents of triethylamine in dichloromethane for 18 hours.

Alternatively, a mixture of the compound of formula (II) and an acid R$^{17}$COOH in a suitable solvent is treated with a condensing agent, optionally in the presence of 1-hydroxybenzotriazole (HOBT) (or 1-hydroxy-7-azabenzotriazole (HOAT)) and a tertiary amine base such as triethylamine, N-ethyldiisopropylamine or 4-(dimethylamino)pyridine, at a temperature of between 0° C. and the boiling point of the solvent. Suitable solvents include acetonitrile, dichloromethane, dimethylformamide, ethyl acetate, N-methylpyrrolidinone, tetrahydrofuran and mixtures thereof. Suitable condensing agents include: 1,1'-carbonyldiimidazole, carbo-diimides such as dicyclohexylcarbodiimide (DCC) and 1-(3-dimethylaminopropyl)-1-ethylcarbodiimide (WSCDI); uranium salts such as O-(benzotriazol-1-yl)-1,1,3,3-tetramethyluronium hexafluorophosphate (HBTU) and O-(7-azabenzotriazol-1-yl)-1,1,3,3-tetramethyluronium hexafluorophosphate (HATU); phosphonium salts such as 1-benzotriazolyloxy-tris(dimethylamino)phosphonium hexafluorophosphate (BOP) and 1-benzotriazolyloxytris (pyrrolidino)-phosphonium hexafluorophosphate (PyBOP); diphenylphosphinic chloride (Dpp-Cl) and bis(2-oxo-3-oxazolidinyl)phosphinic chloride (BOP-Cl). Preferably, an equimolar solution of the compound of formula (ID) and the acid in dichloromethane is treated with about 1.1 equivalents of HATU and about 1.5 equivalents of N-ethyldiisopropylamine at room temperature for 18 hours.

bb) Compounds of formula (I$^B$), i.e. compounds of formula (I$^A$-4) wherein R$^{15}$ is R$^{18}$SO$_2$ can be prepared by sulfonylation of the corresponding compounds of formula (II), as illustrated in Scheme 30.

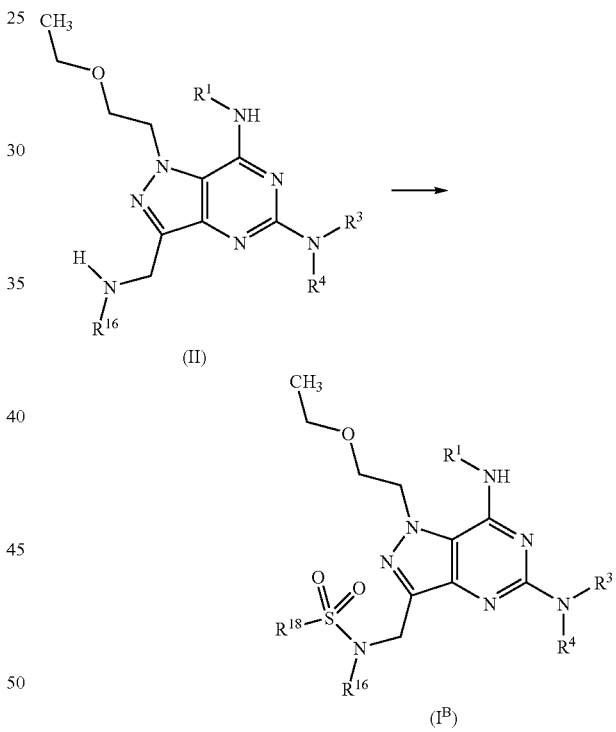

The compound of formula (II) is treated with 1-2 equivalents of a sulfonyl chloride R$^{18}$SO$_2$Cl in a suitable solvent in the presence of a tertiary amine base such as triethylamine, N-ethyldiisopropylamine or pyridine. Suitable solvents include dichloromethane and dimethylformamide. Preferably, the compound of formula (II) is treated with about 1.1 equivalents of sulfonyl chloride and about 1.5 equivalents of N-ethyldiisopropylamine in dichloromethane for 18 hours.

cc) Compounds of formula (I$^C$), i.e. compounds of formula (I$^A$-4) wherein R$^{15}$ is R$^{17}$, and compounds of formula (II) may be prepared by reductive amination of an aldehyde of formula (III) with an amine HNR$^{16}$R$^{17}$ or R$^{16}$NH$_2$ respectively, as illustrated in Scheme 31.

Scheme 31

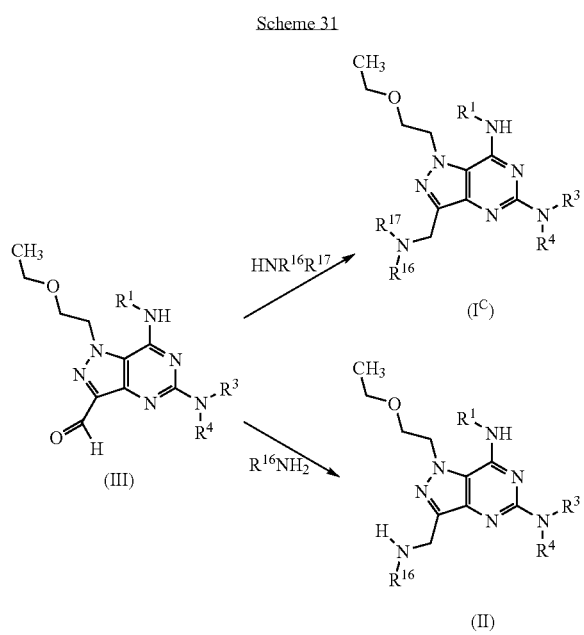

A solution of the amine and the aldehyde in a suitable solvent is treated with a reducing agent such as sodium cyanoborohydride (NaBH$_3$CN) or sodium tri(acetoxy)borohydride (Na(AcO$_3$)BH), optionally in the presence of acetic acid, at a temperature of between 0° C. and the boiling point of the solvent, for 1 hour to 24 hours. Suitable solvents include alcohols, particularly methanol and ethanol.

This method is also suitable for the preparation of compounds of formula (I) wherein —NR$^{15}$R$^{16}$ constitutes a saturated ring. The appropriate amine HNR$^{15}$R$^{16}$ is used in place of the amine HNR$^{16}$R$^{17}$.

dd) Compounds of formula (I$^C$) and compounds of formula (II) may also be prepared by reaction of a chloride or bromide of formula (IV), wherein X is a leaving group such as Cl, Br or CH$_3$SO$_2$O—, with an amine HNR$^{16}$R$^{17}$ or R$^{16}$NH$_2$ respectively, as illustrated in Scheme 32.

Scheme 32

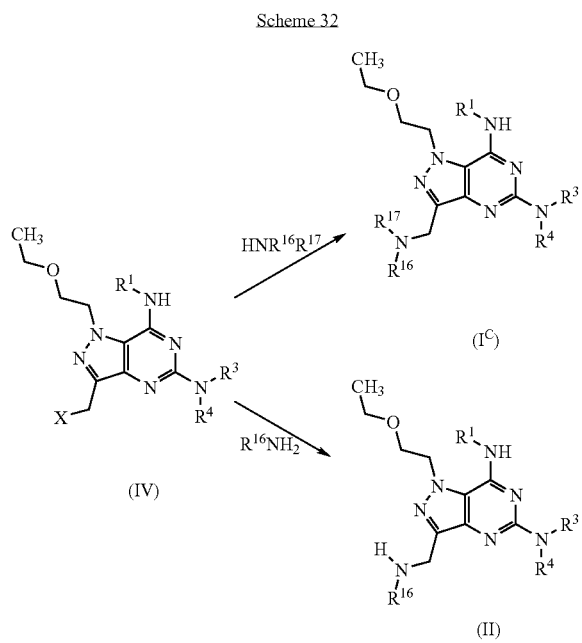

A solution of the amine and the compound of formula (IV) in a suitable solvent, optionally in the presence of a base such as a tertiary amine (for example N-ethyldiisopropylamine) or an alkali metal carbonate (for example potassium carbonate), is stirred at a temperature of between 0° C. and the boiling point of the solvent, for 1 hour to 24 hours. Suitable solvents include tetrahydrofuran, dimethylformamide and dimethylsulfoxide. Preferably the leaving group X is Br or Cl, and more preferably it is Cl.

This method is also suitable for the preparation of compounds of formula (I) wherein —NR$^{15}$R$^{16}$ constitutes a saturated ring. The appropriate amine HNR$^{15}$R$^{16}$ is used in place of the amine ee) Compounds of formula (III) can be prepared from the esters of formula (V) either directly or, more preferably, via the corresponding alcohols of formula (VI) by the methods illustrated in Scheme 33.

Scheme 33

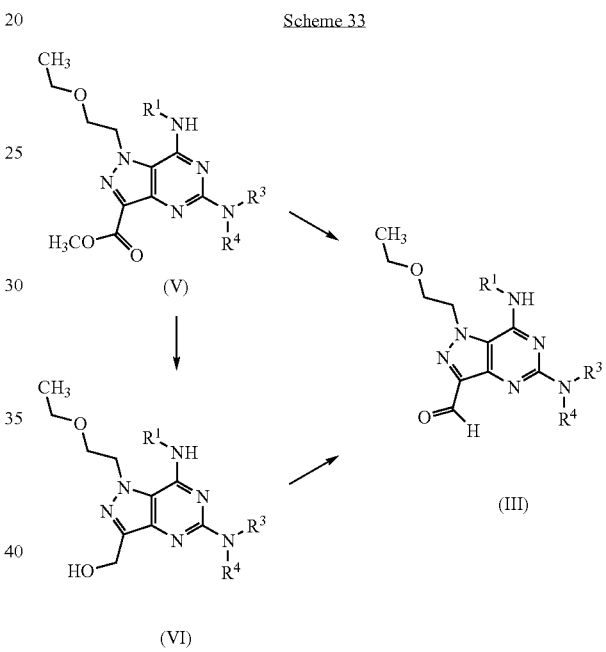

The reduction of the esters of formula (V) to give the aldehydes of formula (III) may be achieved using diisobutylaluminium hydride (DIBAL) in a suitable solvent at a temperature of less than 0° C., preferably less than −60° C. Suitable solvents include hydrocarbons such as pentane, hexane and toluene, ethers such as tetrahydrofuran, and mixtures thereof. The use of excess DIBAL or higher temperatures generally results in the production of the alcohols of formula (VI). These alcohols may also be produced using other reducing agents such as lithium aluminiumhydride or lithium borohydride.

The oxidation of the alcohols of formula (VI) can be achieved using a chromium(VI) reagent such as pyridinium chlorochromate, a hypervalent iodine reagent such as the Dess-Martin periodinane, or a combination of tetra-n-propylammonium perruthenate and N-methylmorpholine-N-oxide in a suitable solvent at a temperature of between 0° C. and ambient temperature. Suitable solvents include dichloromethane. The use of Dess-Martin periodinane is preferred.

ff) Compounds of formula (IV) can be prepared from the corresponding alcohols of formula (VI) by the method illustrated in Scheme 34.

Scheme 34

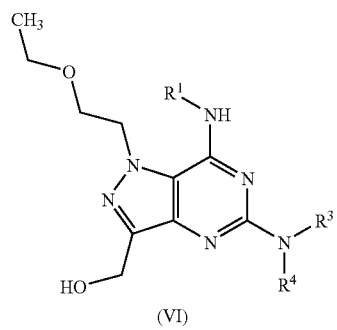
(VI)

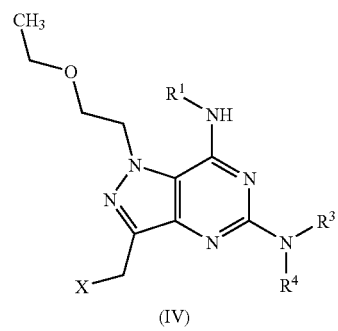
(IV)

Compounds of formula (IV) wherein X is Cl may be prepared by treating the alcohol of formula (VI) with a mixture of triphenylphosphine and N-chlorosuccinimide or tetrachloromethane, or with thionyl chloride. Suitable solvents include dichloromethane and tetrahydrofuran. The analogous compounds wherein X is Br may be prepared by reaction with a mixture of triphenylphosphine and N-bromosuccinimide, bromine, or tetrabromomethane.

Compounds of formula (IV) wherein X is an alkylsulfonate, such as $CH_3SO_2O—$, may be prepared by treating the alcohol with the corresponding alkylsulfonyl chloride in the presence of a tertiary amine base.

gg) Compounds of formula (V) can be prepared from the corresponding monochlorides of formula (VII) by reaction with $HNR^2R^3$ as illustrated in Scheme 35.

Scheme 35

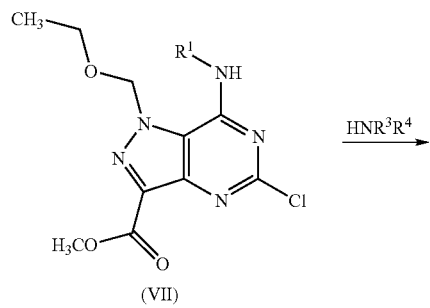
(VII)

-continued

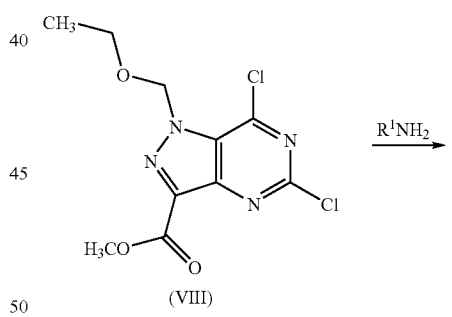
(V)

A solution of the monochloride (VII) and the amine $HNR^3R^4$ in a suitable dipolar aprotic solvent are stirred at elevated temperature for between 1 and 24 hours. Suitable solvents include dimethylsulfoxide, dimethylformamide and N-methylpyrrolidinone. An excess of a tertiary amine such as N-ethyldiisopropylamine, N-methylmorpholine or triethylamine may optionally be included. It is sometimes necessary to perform the reaction at elevated pressure in a closed vessel, particularly when the amine $HNR^3R^4$ or the solvent is volatile.

Preferably, the monochloride is treated with 1-5 equivalents of the amine $HNR^3R^4$ and optionally 3-5 equivalents of N-ethyldiisopropylamine in dimethylsulfoxide or N-methylpyrrolidinone at 100-125° C. for 12-18 hours, in a sealed vessel.

hh) Compounds of formula (VII) can be prepared from the dichloride of formula (VIII) by reaction with $R^1NH_2$ as illustrated in Scheme 36.

Scheme 36

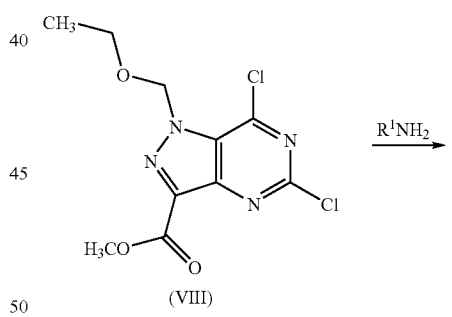
(VIII)

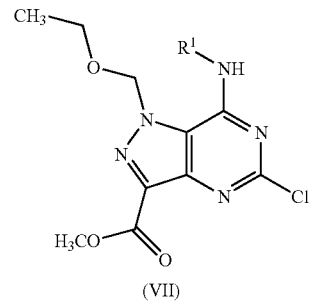
(VII)

A solution of the dichloride (VIII), the amine $R^1NH_2$ and an excess of a tertiary amine such as N-ethyldiisopropylamine, N-methylmorpholine or triethylamine in a suitable dipolar aprotic solvent are stirred at ambient or elevated temperature for between 1 and 24 hours. Suitable solvents include dimethylsulfoxide, dimethylformamide and N-methylpyrrolidinone. Preferably, the monochloride is treated with 2-5 equivalents of the amine $R^1NH_2$ and optionally 2-5 equivalents of N-ethyldiisopropylamine in dimethylsulfoxide or a mixture of dimethylsulfoxide and N-methylpyrrolidinone at 30-90° C. for 1-18 hours.

Alternatively, a solution of the amine $R^1NH_2$ in a suitable solvent is treated with butyllithium or sodium hexamethyldisilazide at low temperature, and the dichloride is added to the resulting solution. Suitable solvents include tetrahydrofuran and dioxan.

With less reactive amines $R^1NH_2$ this reaction can be low-yielding. In such cases it is sometimes advantageous to use an alternative strategy, as discussed in part I) below.

The preparation of the dichloride of formula (VIII) is described in detail in the Examples.

ii) In a variation of the foregoing strategy, the compounds of formulae (I) and (II) may be prepared from monochlorides of formulae ($IX^A$) and ($IX^B$) respectively, as illustrated in Scheme 37.

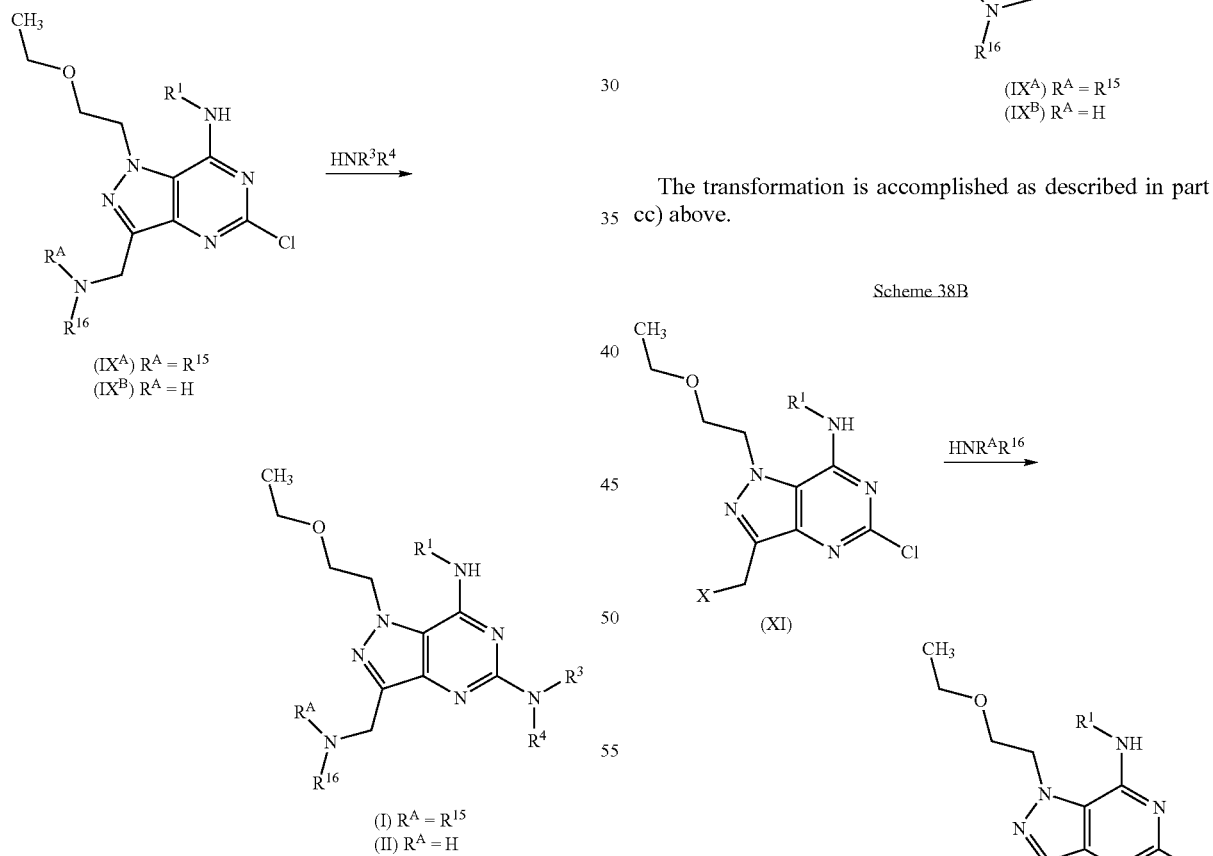

The transformation is accomplished as described in part gg) above.

jj) The compounds of formulae ($IX^A$) and ($IX^B$) may be prepared from the corresponding aldehydes of formula (X) or the alkylating agents of formula (XI) by the methods illustrated in Schemes 38A and 38B (wherein X has the same meaning as defined in part dd) above) respectively.

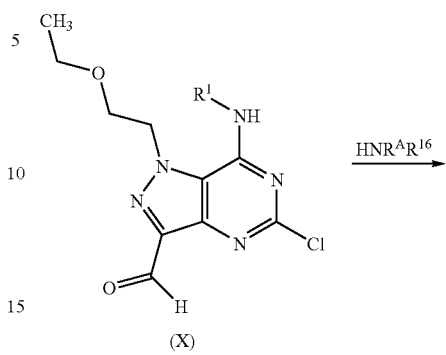

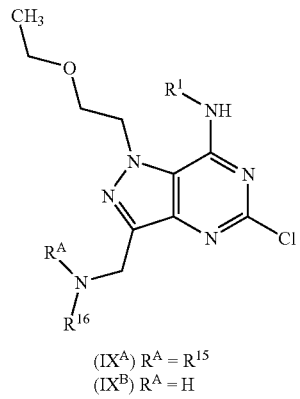

The transformation is accomplished as described in part cc) above.

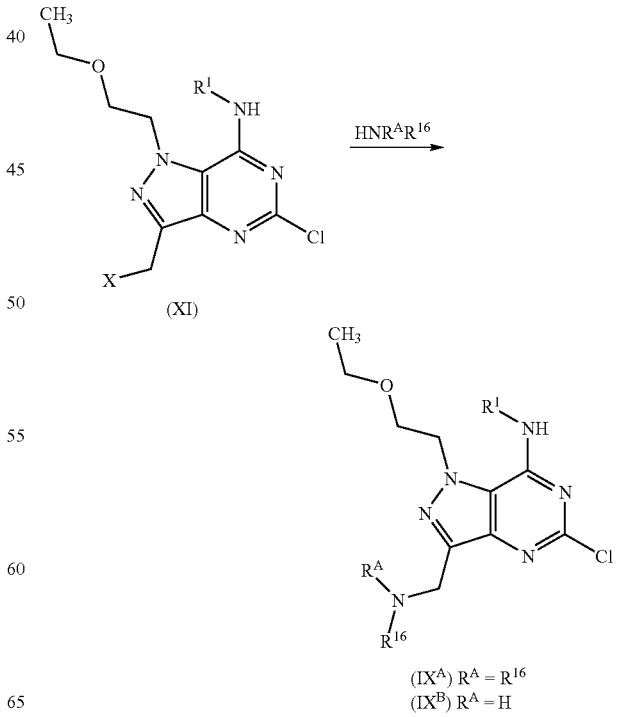

The transformation is accomplished as described in part dd) above.

kk) The compounds of formula (X) and (XI) can be prepared from the esters of formula (VII) as illustrated in Scheme 39.

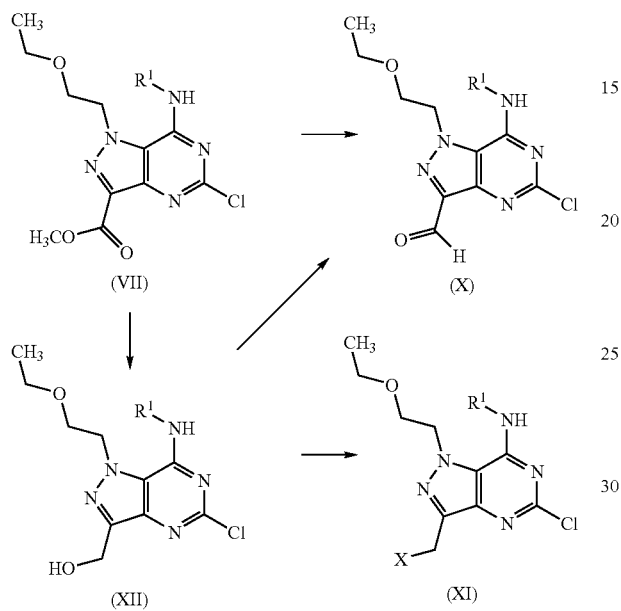

The aldehydes of formula (X) may be prepared by limited reduction of the ester group or indirectly via the alcohols of formula (XII) using the methods described in part ee) above. The compounds of formula (XI) can be prepared from the alcohols of formula (XII) using the methods described in part ff) above.

ll) As mentioned in part hh) above, the reaction of compounds of formula (VIII) with weakly nucleophilic amines $R^1NH_2$ is sometimes not high yielding. An alternative route is illustrated in Scheme 40.

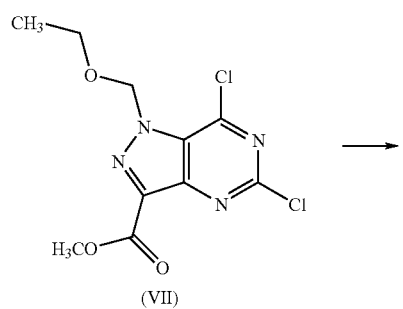

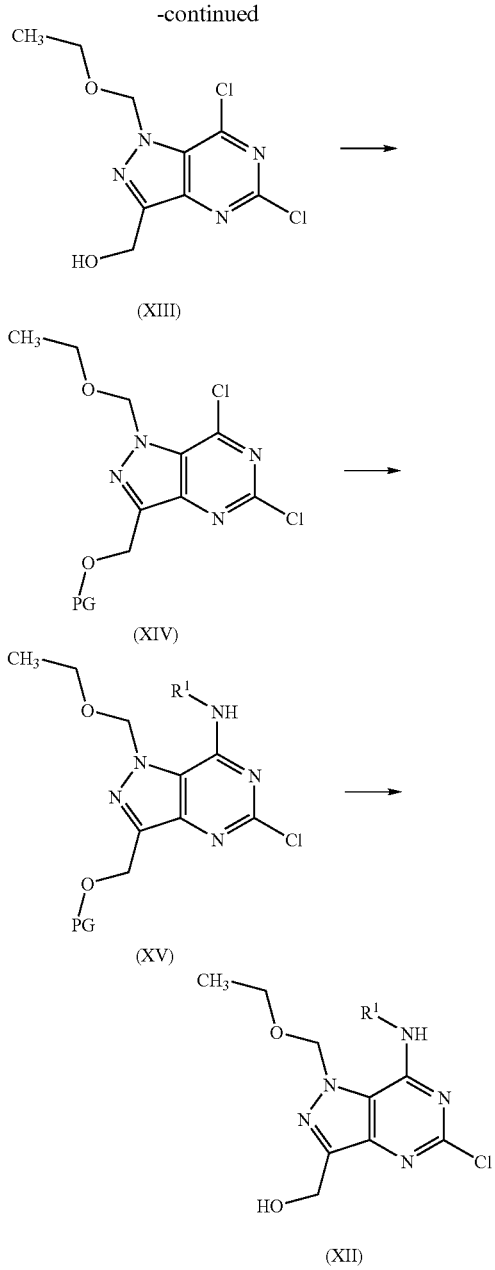

The reduction of the ester of formula (VII) is described in detail in the Examples. The primary alcohol (XIII) is then protected to give compounds of formula (XIV), wherein PG is an alcohol protecting group. A preferred protecting group is a trialkylsilyl group, particularly a tert-butyldimethylsilyl group. The compounds of formula (XIV) are then reacted with an amine $R^1NH_2$ according to the method described in part hh) above to give compounds of formula (XV). Finally, the compounds of formula (XV) are deprotected to provide the primary alcohols of formula (XII) using appropriate conditions. When PG is a trialkylsilyl group it may be removed by treatment with a fluoride salt, such as tetrabutylammonium fluoride, or with hydrochloric acid. The alcohols of formula (XII) may then be further elaborated as described in parts kk), jj) and ii) above.

mm) In a further variation, the alcohols of formula (XII) may be elaborated following the route illustrated in Scheme 41.

Scheme 41

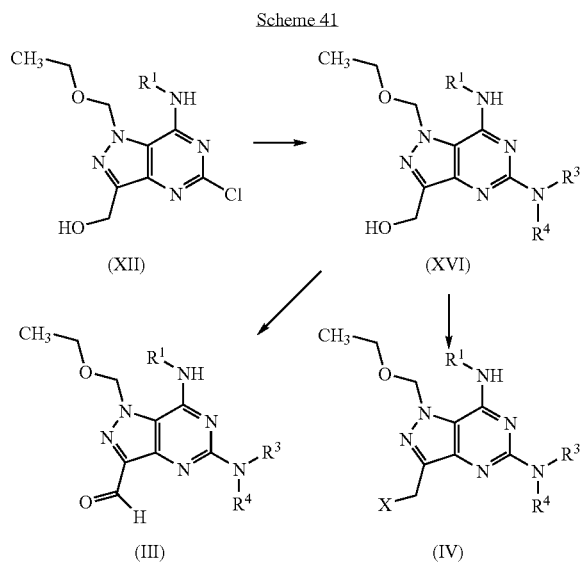

The —NR³R⁴ group may be introduced according to the methods described in part gg) above to provide compounds of formula (XVI). The primary alcohol group may then be oxidised as described in part ee) above to provide the aldehydes of formula (III), or derivatised as described in part ff) above to provide the compounds of formula (IV).

The following compounds form further aspects of the present invention:

A compound of formula (II$^A$)

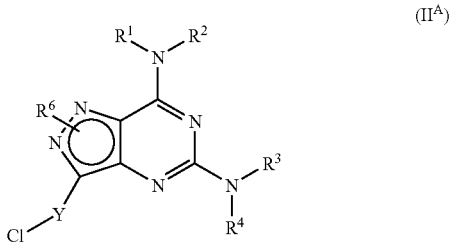

wherein $R^1$, $R^2$, $R^3$, $R^4$, $R^6$ and Y are as defined above in the discussion about compounds of formula (I). Preferably, $R^6$ is attached at $N^1$. Preferably, Y is —CH₂—.

A compound of formula (II$^B$)

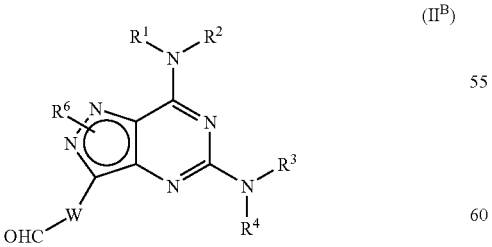

wherein $R^1$, $R^2$, $R^3$, $R^4$, and $R^6$ are as defined above in the discussion about compounds of formula (I), and W is as defined above in, for example, Schemes 3J and 3L and the discussion accompanying those schemes. Preferably, $R^6$ is attached at $N^1$. Preferably, W is a covalent bond.

A compound of formula (XVI)

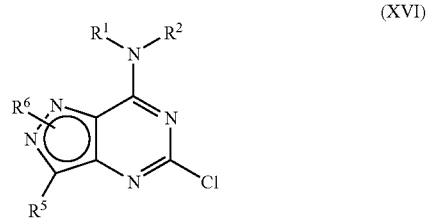

wherein $R^1$, $R^2$, $R^5$ and $R^6$ are as defined above in the discussion about compounds of formula (I). Preferably, $R^6$ is attached at $N^1$.

A compound of formula (III)

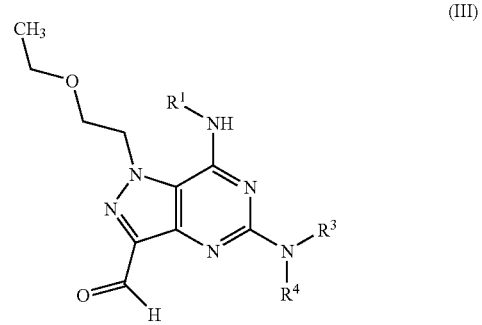

wherein $R^1$, $R^3$ and $R^4$ are as defined above in the discussion about compounds of formula (I$^4$-4).

A compound of formula (IV)

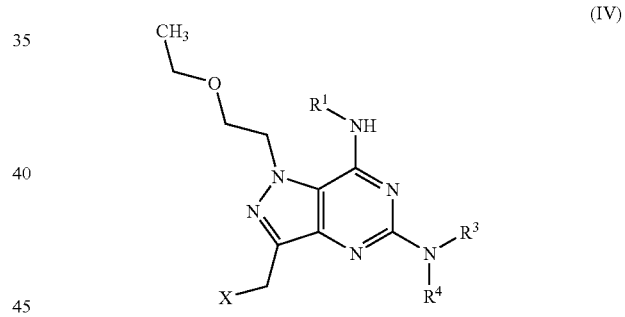

wherein $R^1$, $R^3$ and $R^4$ are as defined above in the discussion about compounds of formula (I$^4$-4) and X is Cl, Br or CH₃SO₂O—.

A compound of formula (XI$^A$)

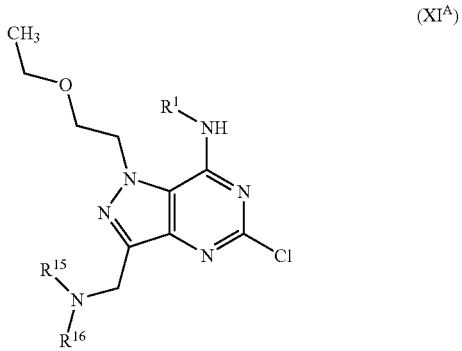

wherein $R^1$, $R^{15}$ and $R^{16}$ are as defined above in the discussion about compounds of formula (I$^4$-4).

A compound of formula (XI$^B$)

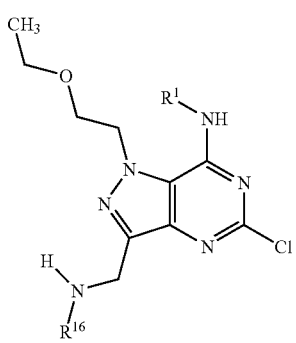

(XI$^B$)

wherein $R^1$ and $R^{16}$ are as defined above in the discussion about compounds of formula (I$^A$-4).

The invention is further illustrated by the following, non-limiting examples.

Melting points were determined on a Gallenkamp melting point apparatus using glass capillary tubes and are uncorrected. Unless otherwise indicated all reactions were carried out under a nitrogen atmosphere, using commercially available anhydrous solvents. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40-63 □m silica gel (Merck silica gel 60). Ion exchange chromatography was performed using with the specified ion exchange resin which had been pre-washed with deionised water. Proton NMR spectra were measured on a Varian Inova 300, Varian Inova 400, or Varian Mercury 400 spectrometer in the solvents specified. In the NMR spectra, only non-exchangeable protons which appeared distinct from the solvent peaks are reported. Low resolution mass spectra were recorded on either a Fisons Trio 1000, using thermospray positive ionisation, or a Finnigan Navigator, using electrospray positive or negative ionisation. High resolution mass spectra were recorded on a Bruker Apex II FT-MS using electrospray positive ionisation. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in a suitable solvent.

Abbreviations, Definitions and Glossary
AcOH acetic acid
Amberlyst® 15 Ion exchange resin, available from Aldrich Chemical Company
APCI Atmospheric Pressure Chemical Ionisation
Arbocel™ Filtration agent, from J. Rettenmaier & Sohne, Germany
atm Pressure in atmospheres (1 atm=760 Torr=101.3 kPa)
Biotage™ Chromatography performed using Flash 75 silica gel cartridge, from Biotage, UK
BOC tert-butoxycarbonyl
br Broad
c Concentration used for optical rotation measurements in g per 100 ml (1 mg/ml is c 0.10)
cat Catalytic
CBz benzyloxycarbonyl
CDI N,N'-carbonyldiimidazole
d Doublet
DCC N,N'-dicyclohexylcarbodiimide
DCM dichloromethane
dd Doublet of doublets
DEAD diethyl azodicarboxylate
Degussa® 101 10 wt % palladium on activated carbon, Degussa type E101 available from Aldrich Chemical Company
Dess-Martin 1,1,1-triacetoxy-1,1-dihydro-1,2-benziodoxol-3(1H)-one period inane
Develosil Combi—Supplied by Phenomenex—manufactured by Nomura Chemical Co.
RP C$_{30}$ hplc Composed of spherical silica particles (size 3 μm or 5 μm) which have a
column chemically bonded surface of C30 chains. These particles are packed into stainless steel columns of dimensions 2 cm internal diameter and 25 cm long.
DIAD diisopropyl azodicarboxylate
DIBAL diisobutylaluminium hydride
DMAP 4-dimethylaminopyridine
DMF N,N-dimethylformamide
DMSO dimethyl sulphoxide
Dowex® Ion exchange resin, from Aldrich Chemical Company
ee Enantiomeric excess
Et$_3$N triethylamine
EtOAc ethyl acetate
EtOH ethanol
HOAT 1-hydroxy-7-azabenzotriazole
HOBT 1-hydroxybenzotriazole hydrate
HRMS High Resolution Mass Spectrocopy (electrospray ionisation positive scan)
Hünig's base N-ethyldiisopropylamine
Hyflo™ Hyflo Supercel®, from Aldrich Chemical Company
KHMDS potassium bis(trimethylsilyl)amide
liq Liquid
LRMS Low Resolution Mass Spectroscopy (electrospray or thermospray ionisation positive scan)
LRMS (ES$^-$) Low Resolution Mass Spectroscopy (electrospray ionisation negative scan)
m Multiplet
m/z Mass spectrum peak
MCI™ gel High porous polymer, CHP20P 75-150 μm, from Mitsubishi Chemical Corporation
MeOH methanol
Mukaiyama's 2-chloro-1-methylpyridinium iodide reagent
NaHMDS sodium bis(trimethylsilyl)amide
NMM N-methylmorpholine
NMO 4-methylmorpholine N-oxide
NMP 1-methyl-2-pyrrolidinone
Phenomenex Luna Supplied by Phenomenex. Composed of spherical silica particles (size 5 μm or C18 hplc column 10 μm) which have a chemically bonded surface of C18 chains. These particles are packed into a stainless steel column of dimensions 2.1 cm internal diameter and 25 cm long.
psi Pounds per square inch (1 psi=6.9 kPa)
PyBOP® Benzotriazol-1-yloxytris(pyrrolidino)phosphonium hexafluorophosphate
PyBrOP® bromo-tris-pyrrolidino-phosphonium hexafluorophosphate
q Quartet
R$_f$ Retention factor on TLC
s Singlet Sep-Pak® Reverse phase $C_{18}$ silica gel cartridge, Waters Corporation
t Triplet
TBDMS-Cl tert-butyldimethylchlorosilane
TFA trifluoroacetic acid
THF tetrahydrofuran
TLC Thin Layer Chromatography
TMS-Cl chlorotrimethylsilane
WSCDI 1-(3-dimethylaminopropyl)-3-ethylcarbodiimide hydrochloride
δ Chemical shift The following Examples illustrate the preparation of the compounds of the formula (I):

Preparation 1

Dimethyl 1-(2-ethoxyethyl)-4-nitro-1H-pyrazole-3,5-dicarboxylate

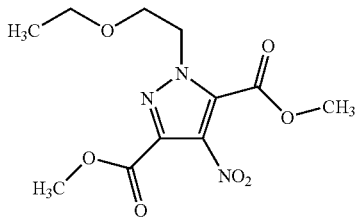

Potassium carbonate (1.32 g, 9.57 mmol) and 2-ethoxyethyl bromide (1.18 mL, 9.57 mmol) were added to a solution of dimethyl 4-nitro-1H-pyrazole-3,5-dicarboxylate (EP 1241170, pg. 50, preparation 10) (2 g, 9.57 mmol) in N,N-dimethylformamide (35 mL) and the reaction mixture was stirred at room temperature for 18 hours. The reaction mixture was concentrated in vacuo and the residue was partitioned between ethyl acetate (200 mL) and water (100 mL). The organic phase was dried over magnesium sulphate and concentrated in vacuo. The crude product was purified by column chromatography on silica gel eluting with pentane: ethyl acetate 100:0 to 70:30 in 10% increments to yield the title product, 1.63 g.
$^1$H NMR (CDCl$_3$, 400 MHz) δ: 1.07 (t, 3H), 3.41 (m, 2H), 3.73 (t, 2H), 3.89 (s, 3H), 3.94 (s, 3H), 4.76 (t, 2H). MS APCI+ m/z 302 [MH]$^+$ Preparation 2

1-(2-Ethoxyethyl)-4-nitro-1H-pyrazole-3,5-dicarboxylic acid 3-methyl ester

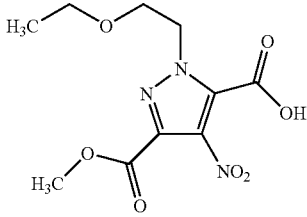

The di-ester of preparation 1 (1.63 g, 5.4 mmol) was added to a solution of potassium hydroxide (300 mg, 5.9 mmol) in methanol (20 mL) and the reaction mixture stirred at room temperature for 18 hours. The reaction mixture was concentrated in vacuo and the residue dissolved in water (100 mL) and washed with ether. The aqueous phase was acidified with 2M hydrochloric acid and extracted with dichloromethane (3×100 mL). The organic phases were combined, dried over magnesium sulphate and concentrated in vacuo to yield the title product, 1.34 g.
$^1$H NMR (CD$_3$OD, 400 MHz) δ: 1.07 (t, 3H), 3.47 (m, 2H), 3.80 (t, 2H), 3.88 (s, 3H), 4.77 (t, 2H). MS APCI+ m/z 288 [MH]$^+$ Preparation 3

Methyl 5-carbamoyl-1-(2-ethoxyethyl)-4-nitro-1H-pyrazole-3-carboxylate

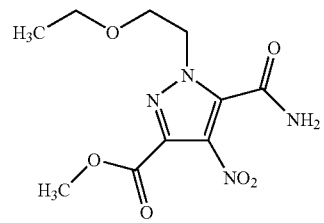

Oxalyl chloride (15.7 mL, 190 mmol) was added steadily to a solution of the carboxylic acid of preparation 2 (17.1 g, 59.5 mmol) in dichloromethane (300 mL). N,N-Dimethylformamide (46 μL, 6 mmol) was then added and the reaction mixture stirred for 2 hours. The reaction mixture was concentrated in vacuo and the residue azeotroped with dichloromethane (3×200 mL). The product was dissolved in tetrahydrofuran (300 mL), the solution cooled in ice, treated with 0.88 ammonia (200 mL) and stirred for 18 hours at room temperature. The reaction mixture was concentrated in vacuo and the residue partitioned between water (200 mL) and ethyl acetate. The organics were dried over magnesium sulphate and concentrated in vacuo to yield the crude product which was triturated from ether to yield the title product, 8.2 g.
$^1$H NMR (DMSO-D$_6$, 400 MHz) δ: 1.03 (t, 3H), 3.38 (m, 2H), 3.70 (t, 2H), 3.86 (s, 3H), 4.36 (t, 2H), 8.30 (m, 1H), 8.46 (m, 1H). MS APCI+ m/z 287 [MH]$^+$ Preparation 4

Methyl 4-amino-5-carbamoyl-1-(2-ethoxyethyl)-1H-pyrazole-3-carboxylate

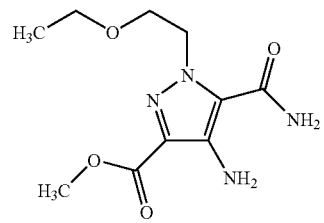

Palladium(II) hydroxide on carbon (19) was added to a solution of the nitro compound of preparation 3 (8.2 g, 28.6 mmol) in methanol (300 mL). Ammonium formate (8.8 g, 0.14 mol) was added portionwise to the reaction mixture over 20 minutes and the reaction mixture then stirred at reflux for 2 hours. The reaction was cooled to room temperature and filtered to remove catalyst. The filtrate was concentrated in vacuo and azeotroped with toluene to yield the title product, 7.3 g.

$^1$H NMR (DMSO-D$_6$, 400 MHz) δ: 1.04 (t, 3H), 3.32 (m, 2H), 3.66 (t, 2H), 3.78 (s, 3H), 4.49 (t, 2H), 5.12 (m, 2H), 7.50 (m, 2H). MS APCI+ m/z 257 [MH]$^+$

Preparation 5

Methyl 1-(2-ethoxyethyl)-5,7-dioxo-4,5,6,7-tetrahydro-1H-pyrazolo[4,3-d]pyrimidine-3-carboxylate

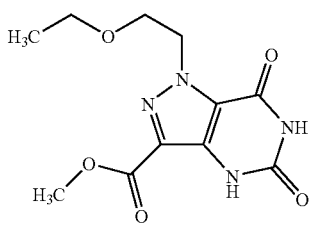

N,N'-Carbonyldiimidazole (5.54 g, 34.2 mmol) was added to a solution of the amide of preparation 4 (7.3 g, 28.5 mmol) in N,N-dimethylformamide (250 mL) and the reaction mixture stirred at room temperature for 1 hour and then at 90° C. for 18 hours. The reaction mixture was allowed to cool to room temperature and concentrated in vacuo. The residue was sonicated in acetone (200 mL), the resulting solid filtered off and dried in vacuo to yield the title product, 5.3 g.

$^1$H NMR (DMSO-D$_6$, 400 MHz) δ: 0.99 (t, 3H), 3.37 (m, 2H), 3.77 (t, 2H), 3.82 (s, 3H), 4.64 (t, 2H). MS ES− m/z 281 [M−H]$^−$

Preparation 6

Methyl 5,7-dichloro-1-(2-ethoxyethyl)-1H-pyrazolo[4,3-d]pyrimidine-3-carboxylate

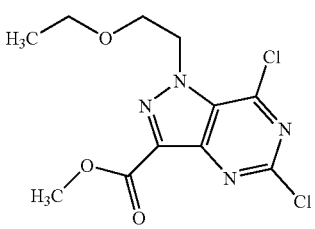

Phosphorous oxychloride (6.5 mL, 70 mmol) and tetraethylammonium chloride (3.47 g, 21 mmol) were added to a solution of the dione of preparation 5 (1.97 g, 7 mmol) in propionitrile (28 mL) and the reaction mixture heated under reflux for 4 hours. Additional phosphorous oxychloride (2.5 mL, 26.9 mmol) was added and the reaction mixture was then stirred under reflux for 18 hours. The reaction mixture was then concentrated in vacuo and the residue partitioned between dichloromethane (300 mL) and water (50 mL). The organics were separated, dried over magnesium sulphate and concentrated in vacuo. The crude product was purified by column chromatography on silica gel, eluting with ethyl acetate:pentane 0:100 to 25:75 to yield the title product, 1.98 g.

$^1$H NMR (CDCl$_3$, 400 MHz) δ: 1.03 (t, 3H), 3.40 (m, 2H), 3.87 (t, 2H), 4.06 (s, 3H), 4.98 (t, 2H). MS APCI+ m/z 319 [MH]$^+$

Preparation 7

Methyl 5-chloro-1-(2-ethoxyethyl)-7-(4-methylpyridin-2-ylamino)-1H-pyrazolo[4,3-d]pyrimidine-3-carboxylate

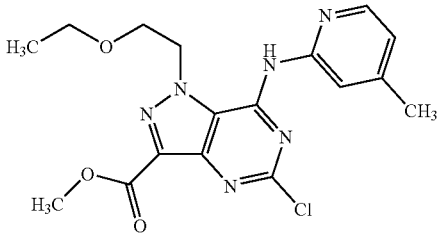

2-Amino-4-methylpyridine (1.34 g, 12.4 mmol) was added to a solution of the dichloro compound of preparation 6 (1.98 g, 6.2 mmol) in dimethyl sulphoxide (10 mL) and the reaction stirred at 35° C. for 5 hours. The reaction mixture was partitioned between dichloromethane (300 mL) and water (500 mL). The organics were separated, washed with water (3×100 mL), dried over magnesium sulphate and concentrated in vacuo. The crude product was purified by column chromatography on silica gel, eluting with dichloromethane:acetonitrile 98:2. Appropriate fractions were concentrated in vacuo, triturated with ether (50 mL), filtered and the solid dried to yield the title product, 1.2 g.

$^1$H NMR (CDCl$_3$, 400 MHz) δ: 1.06 (t, 3H), 2.49 (s, 3H), 3.62 (m, 2H), 4.00 (t, 2H), 4.06 (s, 3H), 5.05 (m, 2H), 6.98 (m, 1H), 8.16 (m, 1H), 8.50 (m, 1H).

MS APCI+ m/z 391 [MH]$^+$

Preparation 8

Methyl 5-chloro-1-(2-ethoxyethyl)-7-(5-methylpyridin-2-ylamino)-1H-pyrazolo[4,3-d]pyrimidine-3-carboxylate

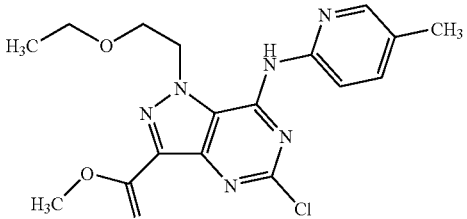

The title product was prepared by a method similar to that described for preparation 7 using the dichloro compound of preparation 6 and 2-amino-5-methylpyridine.

$^1$H NMR (DMSO-D$_6$, 400 MHz) δ: 1.01 (t, 3H), 2.26 (s, 3H), 3.52 (m, 2H), 3.88 (m, 5H), 4.96 (m, 2H), 7.76 (m, 1H), 8.03 (m, 1H), 8.20 (m, 1H).

MS APCI+ m/z 391 [MH]$^+$

Preparation 9

[5,7-Dichloro-1-(2-ethoxyethyl)-1H-pyrazolo[4,3-d]pyrimidin-3-yl]methanol

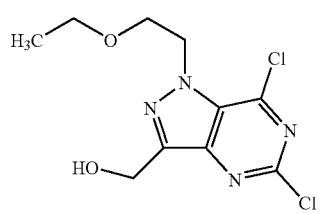

The dichloro compound of preparation 6 (2.4 g, 7.52 mmol) was dissolved in tetrahydrofuran (60 mL) and the reaction mixture cooled to −78° C. A 1 M solution of diisobutylaluminium hydride in tetrahydrofuran (37.6 mL, 37.6 mmol) was added dropwise over 10 minutes and the reaction mixture stirred at −78° C. for 10 minutes and then at −10° C. for 1 hour. The reaction mixture was cooled to −78° C., quenched with ammonium chloride solution (25 mL) and allowed to return to room temperature. The reaction mixture was diluted with dichloromethane (200 mL) and water (100 mL) and the solution filtered through Arbocel®, washing through with dichloromethane (3×100 mL). The organic phase was separated, dried over magnesium sulphate and concentrated in vacuo. The crude product was purified by column chromatography on silica gel eluting with dichloromethane:methanol 99:1 to yield the title product, 1.67 g.

$^1$H NMR (CDCl$_3$, 400 MHz) δ: 1.08 (t, 3H), 3.42 (m, 2H), 3.80 (m, 2H), 4.90 (m, 2H), 5.10 (s, 2H). MS APCI+ m/z 291 [MH]$^+$

Preparation 10

3-(tert-Butyldimethylsilyloxymethyl)-5,7-dichloro-1-(2-ethoxyethyl)-1H-pyrazolo[4,3-d]pyrimidine

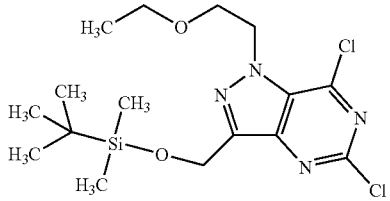

The alcohol of preparation 9 (1.32 g, 4.53 mmol) was dissolved in dichloromethane (25 mL) and the solution treated with imidazole (339 mg, 4.98 mmol) and then tert-butyldimethylsilyl chloride (750 mg, 4.98 mmol). The reaction mixture was stirred at room temperature for 18 hours, diluted with dichloromethane (200 mL) and washed with 10% potassium carbonate solution (100 mL). The organic phase was dried over sodium sulphate and concentrated in vacuo. The crude product was purified by column chromatography on silica gel eluting with dichloromethane:methanol 99:1 to yield the title product, 1.56 g.

$^1$H NMR (CDCl$_3$, 400 MHz) δ: 0.00 (s, 6H), 0.78 (s, 9H), 0.93 (t, 3H), 3.29 (q, 2H), 3.71 (t, 2H), 4.72 (m, 2H), 4.94 (s, 2H). MS APCI+ m/z 405[MH]$^+$

Preparation 11

N-[3-(tert-Butyldimethylsilyloxymethyl)-5-chloro-1-(2-ethoxyethyl)-1H-pyrazolo[4,3-d]pyrimidin-7-yl]pyrimidin-4-ylamine

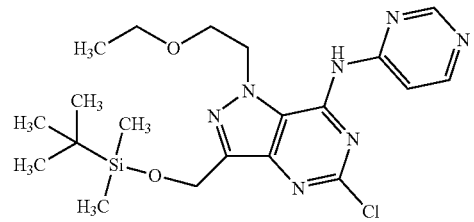

Pyrimidin-4-ylamine (1.10 g, 11.55 mmol) was dissolved in tetrahydrofuran (30 mL) and the solution treated with sodium hexamethyldisilazide (2.12 g, 11.55 mmol) and stirred at room temperature for 20 minutes. The solution was treated with a solution of the dichloro compound of preparation 10 (1.56 g, 3.85 mmol) in tetrahydrofuran (10 mL) and the reaction mixture stirred for 90 minutes at room temperature. The reaction mixture was quenched with ammonium chloride solution (100 mL) and extracted with dichloromethane (200 mL). The organic phase was separated, dried over magnesium sulphate and concentrated in vacuo. The crude product was purified by column chromatography on silica gel eluting with dichloromethane:methanol 97:3 to yield the title product, 830 mg.

$^1$H NMR (CDCl$_3$, 400 MHz) δ: 0.00 (s, 6H), 0.77 (s, 9H), 1.08 (t, 3H), 3.54 (q, 2H), 3.80 (m, 2H), 4.63 (m, 2H), 4.90 (s, 2H), 8.33 (d, 1H), 8.51 (d, 1H), 8.77 (s, 1H). MS APCI+ m/z 464 [MH]$^+$

Preparation 12

N-[3-(tert-Butyldimethylsilyloxymethyl)-5-chloro-1-(2-ethoxyethyl)-1H-pyrazolo[4,3-d]pyrimidin-7-yl]pyrazin-2-ylamine

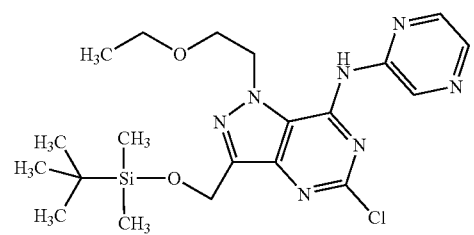

The title compound was prepared by a method similar to that described for preparation 11 using the dichloro compound of preparation 10 and aminopyrazine.

$^1$H NMR (CDCl$_3$, 400 MHz) δ: 0.18 (s, 6H), 0.93 (s, 9H), 1.21 (t, 3H), 3.65 (m, 2H), 3.97 (m, 2H), 4.80 (m, 2H), 5.06 (m, 2H), 8.30 (m, 2H), 9.77 (m, 1H), 10.17 (m, 1H)

Preparation 13

[5-Chloro-1-(2-ethoxyethyl)-7-(Pyrimidin-4-ylamino)-1H-pyrazolo[4,3-d]pyrimidin-3-yl]methanol

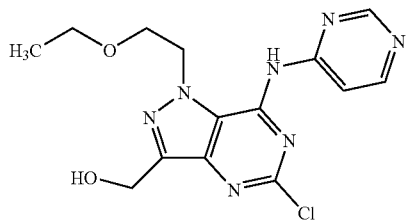

The protected alcohol of preparation 11 (2.0 g, 1.76 mmol) was dissolved in tetrahydrofuran (40 mL) and the solution treated with a 1 M solution of tetrabutylammonium fluoride in tetrahydrofuran (8.63 mL, 8.63 mmol). The reaction mixture was stirred for 90 minutes at room temperature and was then treated with additional tetrabutylammonium fluoride solution in tetrahydrofuran (4.32 mL, 4.32 mmol) and stirred for another hour. The reaction mixture was diluted with water (50 mL) and the aqueous extracted with ethyl acetate (3×50 mL). The combined organics were dried over magnesium sulphate and concentrated in vacuo. The crude product was purified by column chromatography on silica gel eluting with dichloromethane:methanol 99:1 to 95:5 to yield the title product, 1.25 g.

$^1$H NMR (CDCl$_3$, 400 MHz) δ: 1.26 (t, 3H), 3.70 (q, 2H), 3.97 (m, 2H), 4.76 (m, 2H), 5.10 (s, 2H), 8.51 (d, 1H), 8.72 (d, 1H), 8.99 (s, 1H).

MS APCI+ m/z 350 [MH]$^+$

Preparation 14

[5-Chloro-1-(2-ethoxyethyl)-7-(pyrazin-2-ylamino)-1H-pyrazolo[4,3-d]pyrimidin-3-yl]methanol

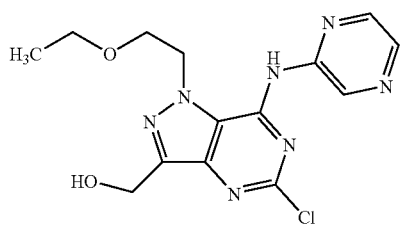

The title compound was prepared by a method similar to that described for preparation 13 using the protected alcohol of preparation 12.

$^1$H NMR (CDCl$_3$, 400 MHz) δ: 1.22 (t, 3H), 3.66 (m, 2H), 3.98 (m, 2H), 4.80 (m, 2H), 5.08 (s, 2H), 8.34 (m, 1H), 9.80 (m, 1H), 10.22 (m, 1H)

Preparation 15

[5-Chloro-1-(2-ethoxyethyl)-7-(4-methylpyridin-2-ylamino)-1H-pyrazolo[4,3-d]pyrimidin-3-yl]methanol

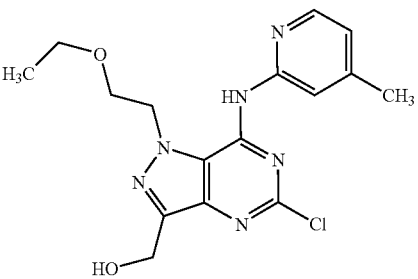

The ester of preparation 7 (1.89 g, 4.84 mmol) was suspended in tetrahydrofuran (450 mL) and the reaction mixture cooled to −78° C. Diisobutylaluminium hydride (39 mL, 1 M solution in toluene, 39 mmol) was added and the reaction mixture allowed to warm to −5° C. The reaction mixture was stirred at −5° C. for 15 minutes before being re-cooled to −78° C. and being quenched with aqueous ammonium chloride solution (10 mL). The reaction mixture was allowed to warm to room temperature and partitioned between dichloromethane (200 mL) and water (200 mL). The mixture was filtered through Arbocel® and the organic layer separated, dried over magnesium sulphate and concentrated in vacuo. The crude product was triturated with ethyl acetate and the solid filtered off to yield the title product.

$^1$H NMR (CDCl$_3$, 400 MHz) δ: 1.11 (t, 3H), 2.46 (s, 3H), 3.61 (m, 2H), 3.94 (m, 2H), 4.86 (m, 2H), 5.07 (m, 2H), 6.96 (m, 1H), 8.19 (m, 1H), 8.48 (m, 1H)

MS APCI+ m/z 363 [MH]$^+$

Preparation 16

[5-Chloro-1-(2-ethoxyethyl)-7-(5-methylpyridin-2-ylamino)-1H-pyrazolo[4,3-d]pyrimidin-3-yl]methanol

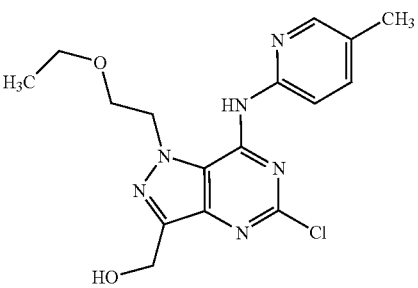

The title compound was prepared by a method similar to that described for preparation 15 using the ester of preparation 8.

$^1$H NMR (CD$_3$OD, 400 MHz) δ: 1.12 (t, 3H), 2.34 (s, 3H), 3.61 (q, 2H), 3.89 (m, 2H), 4.69 (m, 2H), 4.77 (s, 2H), 7.63 (d, 1H), 8.15 (s, 1H), 8.36 (d, 1H)

Preparation 17

5-Chloro-1-(2-ethoxyethyl)-7-(4-methylpyridin-2-ylamino)-1H-pyrazolo[4,3-d]pyrimidine-3-carbaldehyde

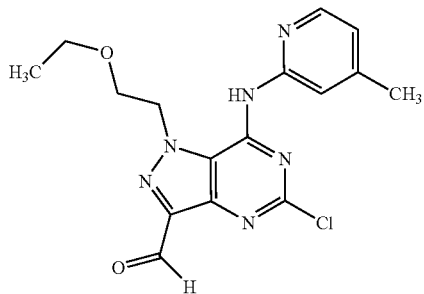

The alcohol of preparation 15 (90 mg, 0.25 mmol) was dissolved in dichloromethane (15.5 mL) and the solution cooled to 0° C. and treated with 1,1,1-triacetoxy-1,1-dihydro-1,2-benziodoxol-3(1H)-one (112 mg, 0.93 mmol). The reaction mixture was stirred at room temperature for 2 hours and was then treated with saturated sodium thiosulphate solution (13 mL), sodium hydrogencarbonate solution (13 mL) and ether (13 mL). The mixture was allowed to stand for 15 minutes before being extracted into dichloromethane (3×100 mL). The organics were combined, dried over magnesium sulphate and concentrated in vacuo. The residue was purified by column chromatography on silica gel eluting with dichloromethane:methanol 100:0 to 98:2 to yield the title product, 53 mg.

$^1$H NMR (CDCl$_3$, 400 MHz) δ: 1.10 (m, 3H), 2.40 (s, 3H), 3.62 (m, 2H), 3.99 (t, 2H), 4.85 (m, 2H), 6.90 (d, 1H), 8.20 (d, 1H), 8.40 (m, 1H), 10.35 (m, 1H)

Preparation 18

N-[5-Chloro-1-(2-ethoxyethyl)-3-methylaminomethyl-1H-pyrazolo[4,3-d]pyrimidin-7-yl]-4-methylpyridin-2-ylamine

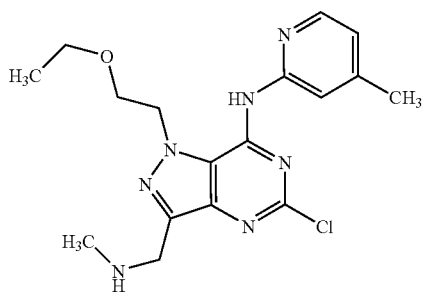

The aldehyde of preparation 17 (53 mg, 0.15 mmol) was dissolved in dichloromethane (2 mL) and the solution treated with methylamine hydrochloride (11 mg, 0.17 mmol) and triethylamine (22 μL, 0.17 mmol). The mixture was stirred at room temperature for 30 minutes and was then treated with additional methylamine hydrochloride (11 mg, 0.17 mmol) and triethylamine (22 μL, 0.17 mmol) and stirred for a further 30 minutes. Sodium triacetoxyborohydride (48 mg, 0.22 mmol) was added to the mixture and the reaction mixture stirred for 18 hours at room temperature. The reaction mixture was concentrated in vacuo and the residue partitioned between sodium hydrogencarbonate solution (100 mL) and dichloromethane (100 mL). The aqueous was extracted with dichloromethane (3×10 mL) and the organics combined, dried over magnesium sulphate and concentrated in vacuo. The residue was purified by column chromatography on silica gel eluting with dichloromethane:methanol:0.88 ammonia 95:5:0 to 90:10:1 to yield the title product, 19 mg.

$^1$H NMR (CDCl$_3$, 400 MHz) δ: 1.10 (t, 3H), 2.37 (s, 3H), 2.72 (s, 3H), 3.58 (q, 2H), 3.90 (t, 2H), 4.38 (s, 2H), 4.85 (t, 2H), 6.81 (s, 1H), 8.10 (d, 1H), 8.30 (d, 1H)

MS APCI+ m/z 376 [MH]$^+$

Preparation 19

N-[3-Bromomethyl-5-chloro-1-(2-ethoxyethyl)-1H-pyrazolo[4,3-d]pyrimidin-7-yl]-4-methylpyridin-2-ylamine

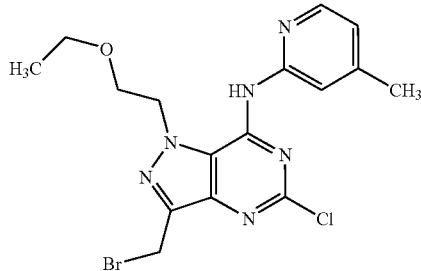

The alcohol of preparation 15 (560 mg, 1.54 mmol) was dissolved in dichloromethane (15 mL) and the solution treated with tetrabromomethane (614 mg, 1.85 mmol) and cooled to 0° C. in an ice bath. The mixture was treated dropwise with a solution of triphenylphosphine (567 mg, 2.16 mmol) in dichloromethane (5 mL) and the reaction stirred at room temperature for 18 hours. The reaction mixture was concentrated in vacuo and the residue purified by column chromatography on silica gel eluting with dichloromethane:methanol 100:0 to 98:2 to yield the title product, 457 mg.

$^1$H NMR (CDCl$_3$, 400 MHz) δ: 1.13 (t, 3H), 2.49 (s, 3H), 3.63 (q, 2H), 3.94 (t, 2H), 4.81 (s, 2H), 4.98 (t, 2H), 6.95 (s, 1H), 8.18 (d, 1H), 8.50 (d, 1H).

MS ES+ m/z 425 [MH]$^+$

Preparation 20

N-[3-Bromomethyl-5-chloro-1-(2-ethoxyethyl)-1H-pyrazolo[4,3-d]pyrimidin-7-yl]pyrazin-2-ylamine

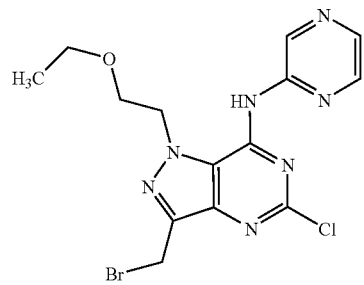

The title compound was prepared by a method similar to that described for preparation 19 using the alcohol of preparation 14.

$^1$H NMR (CDCl$_3$, 400 MHz) δ: 1.12 (t, 3H), 3.64 (q, 2H), 3.94 (t, 2H), 4.81 (s, 2H), 4.98 (t, 2H), 6.95 (s, 1H), 8.16 (d, 1H), 8.46 (d, 1H)

Preparation 21

N-[5-Chloro-3-(diethylaminomethyl)-1-(2-ethoxyethyl)-1H-pyrazolo[4,3-d]pyrimidin-7-yl]pyrimidin-4-ylamine

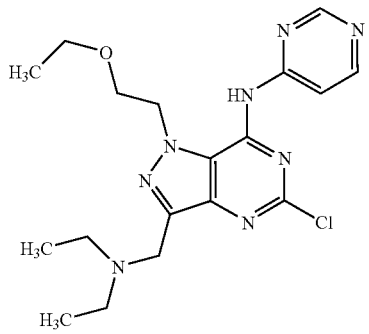

The alcohol of preparation 13 (446 mg, 1.28 mmol) was dissolved in dichloromethane (30 mL) and the solution treated with tetrabromomethane (507 mg, 1.53 mmol) and triphenylphosphine (401 mg, 1.53 mmol). The reaction mixture was stirred at room temperature for 2 hours, additional tetrabromomethane (85 mg, 0.26 mmol) and triphenylphosphine (67 mg, 0.26 mmol) were added and the reaction mixture stirred for a further 2 hours. The reaction mixture was concentrated in vacuo and the residue purified by column chromatography on silica gel eluting with pentane:ethyl acetate 80:20. The crude product was further purified by column chromatography on silica gel once more, eluting with toluene:diethylamine 95:5 to yield the title product, 196 mg.

$^1$H NMR (CDCl$_3$, 400 MHz) δ: 1.19 (t, 3H), 1.14 (t, 6H), 2.99 (m, 4H), 3.67 (q, 2H), 3.96 (t, 2H), 4.57 (s, 2H), 4.79 (t, 2H), 8.41 (d, 1H), 8.67 (d, 1H), 8.99 (s, 1H)

MS ES+ m/z 405 [MH]$^+$

Preparation 22

N-[5-Chloro-3-chloromethyl-1-(2-ethoxyethyl)-1H-pyrazolo[4,3-d]pyrimidin-7-yl]-4-methylpyridin-2-ylamine

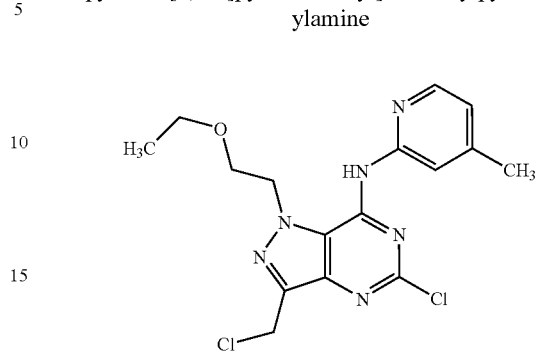

The alcohol of preparation 15 (1.80 g, 5.00 mmol) was dissolved in dichloromethane (15 mL) and the solution treated with thionyl chloride (1.50 mL, 17 mmol). The reaction mixture was stirred at room temperature for 18 hours and concentrated in vacuo, the residue was azeotroped with toluene and then dried in vacuo. The crude product was purified by column chromatography on silica gel eluting with dichloromethane:methanol 100:0 to 95:5 to yield the title product, 980 mg.

$^1$H NMR (CDCl$_3$, 400 MHz) δ: 0.92 (t, 3H), 2.63 (s, 3H), 3.58 (m, 2H), 3.91 (m, 2H), 4.81 (s, 2H), 5.20 (m, 2H), 7.14 (m, 1H), 8.16 (m, 1H), 8.97 (m, 1H)

MS APCI+ m/z 381 [MH]$^+$

Preparation 23

N-[3-Azidomethyl-5-chloro-1-(2-ethoxyethyl)-1H-pyrazolo[4,3-d]pyrimidin-7-yl]-4-methylpyridin-2-ylamine

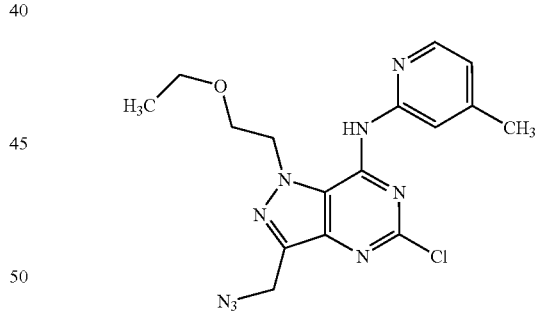

The chloro compound of preparation 22 (700 mg, 1.80 mmol) was dissolved in N,N-dimethylformamide (10 mL) and the solution treated with sodium azide (129 mg, 1.98 mmol). The reaction mixture was stirred at room temperature for 1 hour and then allowed to stand at room temperature for a further 18 hours. The reaction mixture was concentrated in vacuo and the residue taken up in water (100 mL) and washed with ether (4×20 mL). The ether washings were combined, washed with water (20 mL), dried over magnesium sulphate and concentrated in vacuo to yield the title product, 600 mg.

$^1$H NMR (CDCl$_3$, 400 MHz) δ: 1.20 (t, 3H), 2.40 (s, 3H), 3.60 (q, 2H), 3.95 (t, 2H), 4.70 (s, 2H), 4.80 (m, 2H), 6.90 (s, 1H), 8.20 (s, 1H), 8.30 (s, 1H), 10.00 (s, 1H)

MS APCI+ m/z 388 [MH]$^+$

Preparation 24

N-[3-Aminomethyl-5-chloro-1-(2-ethoxyethyl)-1H-pyrazolo[4,3-d]pyrimidin-7-yl]-4-methylpyridin-2-ylamine

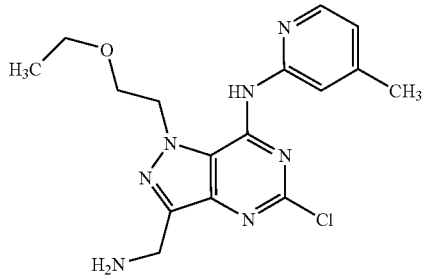

The azide of preparation 23 (130 mg, 0.34 mmol) was dissolved in tetrahydrofuran (5 mL) and the solution treated with triphenylphosphine (92 mg, 0.35 mmol). The reaction mixture was stirred at room temperature for 2 hours, diluted with water (5 mL), and stirred for a further 18 hours. The reaction mixture was concentrated in vacuo and the residue taken up in brine and extracted with dichloromethane. The dichloromethane phase was dried over magnesium sulphate and concentrated in vacuo. The residue was purified by column chromatography on silica gel eluting with dichloromethane:methanol:ammonium hydroxide 95:5:0.5 to yield the title product, 70 mg.

$^1$H NMR (CDCl$_3$, 400 MHz) δ: 1.23 (t, 3H), 2.45 (s, 3H), 3.65 (q, 2H), 3.95 (t, 2H), 4.20 (s, 2H), 4.78 (t, 2H), 6.82 (s, 1H), 8.18 (m, 1H), 8.30 (m, 1H). MS APCI+ m/z 362 [MH]$^+$

Preparation 25

N-[5-Chloro-1-(2-ethoxyethyl)-7-(4-methylpyridin-2-ylamino)-1H-pyrazolo[4,3-d]pyrimidin-3-ylmethyl]methanesulfonamide

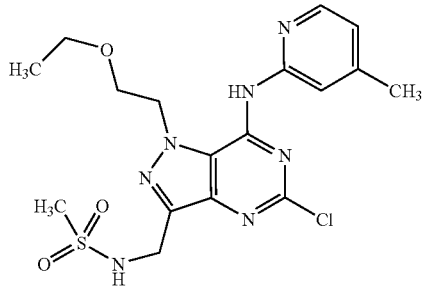

The amine of preparation 24 (150 mg, 0.40 mmol) was dissolved in dichloromethane (5 mL) and the solution treated with N-ethyldiisopropylamine (108 μL, 0.62 mmol) and methanesulfonyl chloride (34 μL, 0.44 mmol). The reaction mixture was stirred at room temperature for 18 hours before being concentrated in vacuo. The residue was purified by column chromatography on silica gel eluting with dichloromethane:methanol 100:0 to 98:2 to yield the title product, 110 mg.

$^1$H NMR (CD$_3$OD, 400 MHz) δ: 1.10 (t, 3H), 2.40 (s, 3H), 3.00 (s, 3H), 3.60 (q, 2H), 3.90 (t, 2H), 4.50 (s, 2H), 4.70 (t, 2H), 6.90 (d, 1H), 8.15 (d, 1H), 8.40 (s, 1H).

MS APCI+ m/z 438 [M−H]$^−$

Preparation 26

N-[5-chloro-1-(2-ethoxyethyl)-7-(4-methylpyridin-2-ylamino)-1H-pyrazolo[4,3-d]pyrimidin-3-ylmethyl]-2-hydroxyacetamide

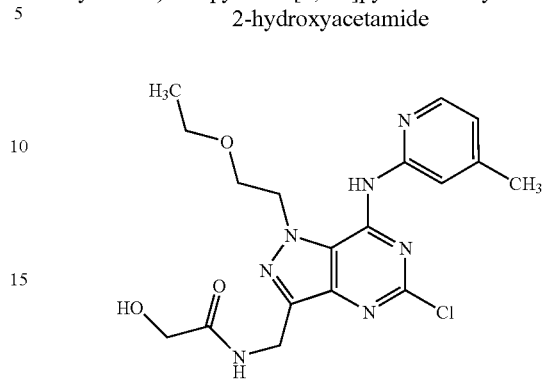

The amine of preparation 24 (50 mg, 0.14 mmol) was dissolved in dichloromethane (5 mL) and the solution treated with glycolic acid (11 mg, 0.14 mmol), N-ethyldiisopropylamine (36 μL, 0.21 mmol) and O-(7-azabenzotriazol-1-yl)-N,N,N',N'-tetramethyluronium hexafluorophosphate (57 mg, 0.15 mmol). The reaction mixture was then stirred at room temperature for 18 hours. The reaction mixture was diluted with dichloromethane (20 mL), washed with water (10 mL), dried over magnesium sulphate and concentrated in vacuo. The residue was purified by column chromatography on silica gel eluting with dichloromethane:methanol 98:2 to yield the title product, 50 mg.

$^1$H NMR (CDCl$_3$, 400 MHz) δ: 1.20 (t, 3H), 2.40 (s, 3H), 3.60 (m, 2H), 3.90 (t, 2H), 4.20 (s, 2H), 4.75 (m, 2H), 4.80 (d, 2H), 6.85 (m, 1H), 7.60 (m, 1H), 8.20 (m, 1H), 8.30 (m, 1H), 10.10 (m, 1H). MS APCI+ m/z 420 [MH]$^+$

Preparation 27

N-[5-Chloro-1-(2-ethoxyethyl)-7-(4-methylpyridin-2-ylamino)-1H-pyrazolo[4,3-d]pyrimidin-3-ylmethyl]-2-(dimethylamino)acetamide

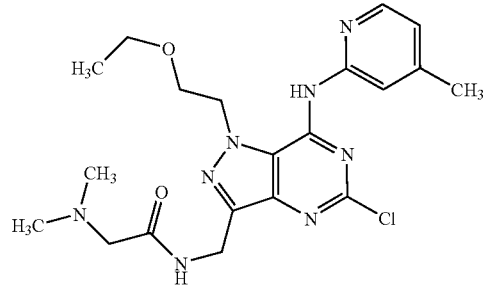

The title product was prepared by a method similar to that described for preparation 26 using N,N-dimethylaminoacetic acid and the amine of preparation 24. The crude product was purified by column chromatography on silica gel eluting with dichloromethane:methanol:ammonium hydroxide 98:2:0.5.

$^1$H NMR (CDCl$_3$, 400 MHz) δ: 1.20 (t, 3H), 2.39 (s, 6H), 2.40 (s, 3H), 3.10 (s, 2H), 3.60 (q, 2H), 3.90 (t, 2H), 4.75 (m, 2H), 4.80 (d, 2H), 6.85 (m, 1H), 7.90 (m, 1H), 8.20 (m, 1H), 8.35 (m, 1H), 10.00 (m, 1H).

MS APCI+ m/z 447 [MH]$^+$

Preparation 28

N-[5-Chloro-1-(2-ethoxyethyl)-7-(4-methylpyridin-2-ylamino)-1H-pyrazolo[4,3-d]pyrimidin-3-ylmethyl]acetamide

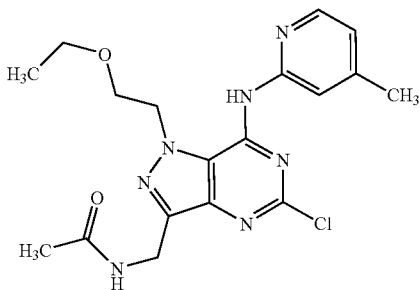

The amine of preparation 24 (70 mg, 0.19 mmol) was dissolved in dichloromethane (5 mL) and the solution treated with acetyl chloride (16 μL, 0.23 mmol) and N-ethyldiisopropylamine (40 μL, 0.23 mmol). The reaction mixture was stirred at room temperature for 1 hour and then concentrated in vacuo. The residue was taken up in methanol and treated dropwise with dichloromethane until all solid was in solution. The solution was treated with 2M sodium hydroxide solution (500 μL) and then stirred at room temperature for 30 minutes. The solution was concentrated in vacuo and the residue taken up in water (5 mL) and washed with dichloromethane (3×10 mL). The organics were combined, dried over magnesium sulphate and concentrated in vacuo. The residue was purified by column chromatography on silica gel eluting with dichloromethane:methanol 98:2 to yield the title product, 50 mg.

$^1$H NMR (CDCl$_3$, 400 MHz) δ: 1.18 (t, 3H), 2.20 (s, 3H), 2.40 (s, 3H), 3.65 (q, 2H), 3.95 (t, 2H), 4.75 (m, 2H), 4.80 (t, 2H), 6.50 (m, 1H), 6.85 (m, 1H), 8.20 (m, 1H), 8.30 (s, 1H), 10.00 (s, 1H). MS APCI+ m/z 404 [MH]$^+$

Preparation 29

N-[5-Chloro-1-(2-ethoxyethyl)-7-(4-methylpyridin-2-ylamino)-1H-pyrazolo[4,3-d]pyrimidin-3-ylmethyl]propionamide

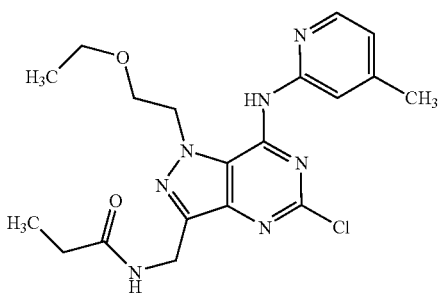

The title product was prepared by a method similar to that described for preparation 28 using propionyl chloride and the amine of preparation 24.

$^1$H NMR (CDCl$_3$, 400 MHz) δ: 1.20 (t, 6H), 2.30 (m, 2H), 2.40 (s, 3H), 3.60 (q, 2H), 3.90 (t, 2H), 4.75 (t, 2H), 4.80 (d, 2H), 6.60 (m, 1H), 6.90 (d, 1H), 8.20 (d, 1H), 8.30 (s, 1H), 10.10 (s, 1H). MS ES+ m/z 418 [MH]$^+$

Preparation 30

N-[5-Chloro-1-(2-ethoxyethyl)-7-(4-methylpyridin-2-ylamino)-1H-pyrazolo[4,3-d]pyrimidin-3-ylmethyl]-N-methylacetamide

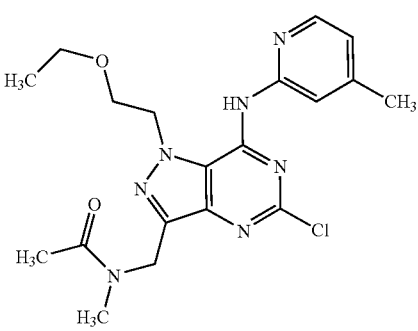

The title product was prepared by a method similar to that described for preparation 28 using the amine of preparation 18 and acetyl chloride.

$^1$H NMR (CDCl$_3$, 400 MHz) δ: Rotamers 1.20 (t, 3H), 2.15 (m, 1H), 2.40 (s, 2H), 2.45 (s, 3H), 3.05, 3.15 (2×s, 3H), 3.65 (q, 2H), 4.70 (t, 2H), 4.80 (m, 3H), 4.90 (s, 1H), 6.85 (t, 1H), 8.20 (m, 1H), 8.30 (s, 1H), 10.00 (s, 1H).

MS ES+ m/z 418 [MH]$^+$

Preparation 31

N-[5-Chloro-3-chloromethyl-1-(2-ethoxyethyl)-1H-pyrazolo[4,3-d]pyrimidin-7-yl]pyrimidin-4-ylamine

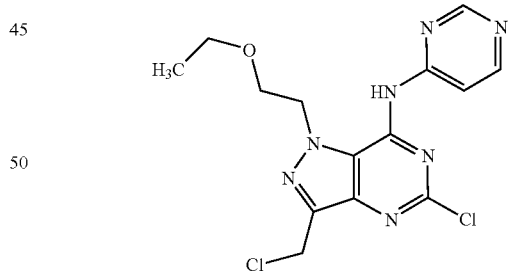

The alcohol of preparation 13 (1.35 g, 3.86 mmol) was dissolved in dichloromethane (10 mL) and the solution treated dropwise with thionyl chloride (1.13 mL, 15.44 mmol). The reaction mixture was stirred at room temperature for 18 hours and then concentrated in vacuo. The residue was azeotroped with toluene to yield the title product, 1.44 g.

$^1$H NMR (CD$_3$OD, 400 MHz) δ: 1.24 (t, 3H), 3.72 (q, 2H), 4.00 (t, 2H), 4.90 (t, 2H), 4.99 (s, 2H), 8.68 (m, 1H), 8.86 (m, 1H), 9.22 (m, 1H). MS APCI+ m/z 368 [MH]$^+$

Preparation 32

N-[5-Chloro-1-(2-ethoxyethyl)-3-methylaminomethyl-1H-pyrazolo[4,3-d]pyrimidin-7-yl]pyrimidin-4-ylamine

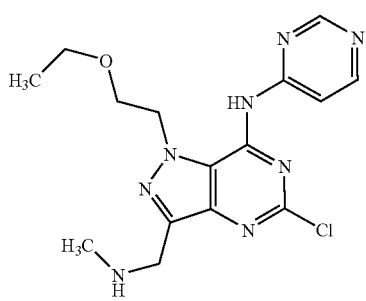

The chloro compound of preparation 31 (770 mg, 2.09 mmol) and N-ethyldiisopropylamine (400 μL, 2.30 mmol) were dissolved in N,N-dimethylformamide (10 mL) and the solution treated with a 33% solution of methylamine in ethanol (6 mL, 42.0 mmol). The reaction mixture was stirred at room temperature for 3 hours and then concentrated in vacuo. The residue was purified by column chromatography on silica gel eluting with dichloromethane:methanol:0.88 ammonia 95:5:0 to 95:5:0.5 to 90:10:1 to yield the title product, 560 mg.

$^1$H NMR (CD$_3$OD, 400 MHz) δ: 1.17 (t, 3H), 2.52 (s, 3H), 3.65 (q, 2H), 3.95 (t, 2H), 4.13 (s, 2H), 4.87 (m, 2H), 8.36 (dd, 1H), 8.65 (d, 1H), 8.84 (s, 1H)

MS APCI+ m/z 363 [MH]$^+$

Preparation 33

N-[5-Chloro-1-(2-ethoxyethyl)-3-methylaminomethyl-1H-pyrazolo[4,3-d]pyrimidin-7-yl]pyrazin-2-ylamine

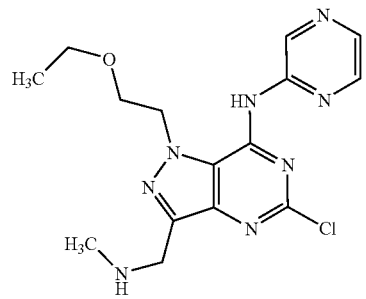

The bromo compound of preparation 20 (109 mg, 0.26 mmol) and a 33% solution of methylamine in ethanol (490 μL, 5.2 mmol) were added to 1-methyl-2-pyrrolidinone (1 mL) and the reaction mixture heated to 35° C. for 1 hour. The reaction mixture was concentrated in vacuo to yield the title product.

MS APCI+ m/z 363 [MH]$^+$

Preparation 34

N-[5-Chloro-1-(2-ethoxyethyl)-7-(Pyrimidin-4-ylamino)-1H-pyrazolo[4,3-d]pyrimidin-3-ylmethyl]-N-methylacetamide

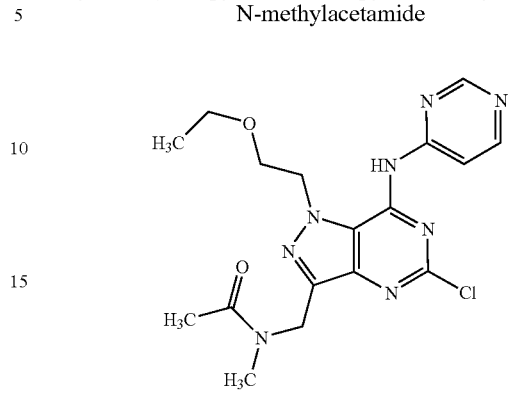

The amine of preparation 32 (530 mg, 1.45 mmol) and N-ethyldiisopropylamine (280 μL, 1.59 mmol) were dissolved in dichloromethane (15 mL) and the solution treated with acetyl chloride (114 μL, 1.59 mmol). The reaction mixture was stirred at room temperature for 45 minutes and then concentrated in vacuo. The residue was dissolved in methanol (15 mL), treated with 2M sodium hydroxide solution (5 mL) and allowed to stand at room temperature for 1 hour. The mixture was concentrated in vacuo and the residue purified by column chromatography on silica gel eluting with dichloromethane:methanol 100:0 to 96:4 to yield the title product, 495 mg.

$^1$H NMR (CD$_3$OD, 400 MHz) δ: Rotamers 1.20 (t, 3H), 2.16, 2.38 (2×s, 3H), 2.99, 3.18 (2×s, 3H), 3.67 (m, 2H), 3.95 (q, 2H), 4.75-4.91 (m, 4H), 8.43 (d, 1H), 8.67 (dd, 1H), 8.86 (s, 1H). MS APCI+ m/z 405 [MH]$^+$

Preparation 35 tert-Butyl N-[5-chloro-1-(2-ethoxyethyl)-7-(4-methylpyridin-2-ylamino)-1H-pyrazolo[4,3-d]pyrimidin-3-ylmethyl]-N-methylcarbamate

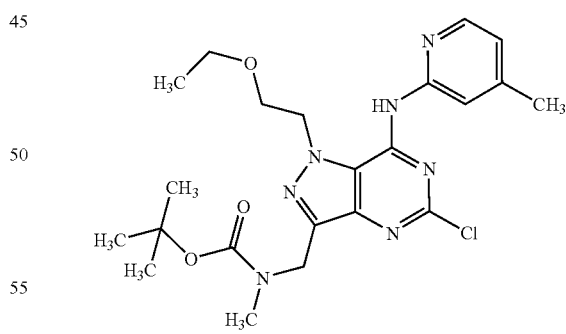

The amine of preparation 18 (157 mg, 0.42 mmol) was dissolved in dichloromethane (10 mL) and the solution treated with di-tert-butyldicarbonate (129 mg, 0.59 mmol). The reaction mixture stirred at room temperature for 1 hour and concentrated in vacuo to yield the title product, 200 mg.

$^1$H NMR (CD$_3$OD, 400 MHz) δ: 1.10 (t, 3H), 1.52 (s, 9H), 2.42 (s, 3H), 2.96 (s, 3H), 3.60 (q, 2H), 3.94 (t, 2H), 4.75 (s, 2H), 4.82 (t, 2H), 7.00 (d, 1H), 8.18 (m, 1H), 8.36 (m, 1H). MS APCI+ m/z 476 [MH]$^+$

Preparation 36

[5-Dimethylamino-1-(2-ethoxyethyl)-7-(4-methylpyridin-2-ylamino)-1H-pyrazolo[4,3-d]pyrimidin-3-yl]methanol

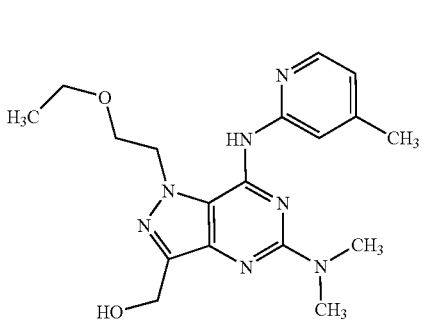

The chloro compound of preparation 15 (780 mg, 2.15 mmol) and N-ethyldiisopropylamine (1.125 mL, 6.46 mmol) were dissolved in dimethyl sulphoxide (6 mL) and the mixture treated with a 5.6M solution of dimethylamine in ethanol (1.15 mL, 6.46 mmol) and heated to 120° C. for 18 hours in a sealed vessel. The reaction mixture was partitioned between dichloromethane (100 mL) and water (100 mL) and the organic phase separated and washed with water (3×200 mL). The organic phase was dried over magnesium sulphate and concentrated in vacuo. The residue was purified by column chromatography on silica gel eluting with dichloromethane:methanol 100:0 to 98:2. The product was triturated with ether to yield the title product, 230 mg.

$^1$H NMR (CD$_3$OD, 400 MHz) δ: 1.07 (t, 3H), 2.38 (s, 3H), 3.20 (s, 6H), 3.60 (q, 2H), 3.85 (t, 2H), 4.65 (t, 2H), 4.80 (s, 2H), 6.90 (d, 1H), 8.12 (d, 1H), 8.39 (s, 1H)

MS APCI+ m/z 372 [MH]$^+$

Preparation 37

[5-Dimethylamino-1-(2-ethoxyethyl)-7-(5-methylpyridin-2-ylamino)-1H-pyrazolo[4,3-d]pyrimidin-3-yl]methanol

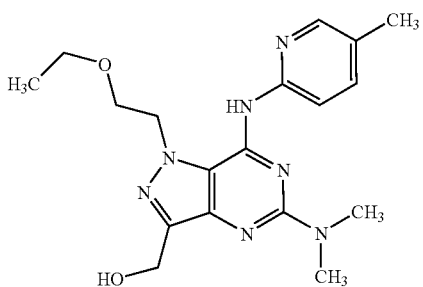

The title product was prepared by a method similar to that described for preparation 36 using the chloro compound of preparation 16.

$^1$H NMR (CD$_3$OD, 400 MHz) δ: 1.12 (t, 3H), 2.33 (s, 3H), 3.20 (s, 6H), 3.59 (q, 2H), 3.85 (m, 2H), 4.71 (m, 2H), 4.81 (s, 2H), 7.62 (d, 1H), 8.13 (s, 1H), 8.38 (d, 1H)

MS APCI+ m/z 372 [MH]$^+$

Preparation 38

[5-Dimethylamino-1-(2-ethoxyethyl)-7-(pyrimidin-4-ylamino)-1H-pyrazolo[4,3-d]pyrimidin-3-yl]methanol

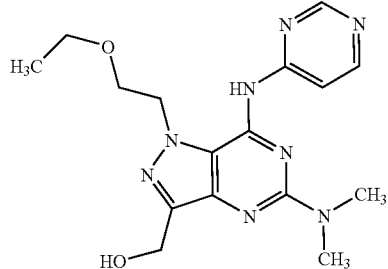

The title product was prepared by a method similar to that described for preparation 36 using the chloro compound of preparation 1.

$^1$H NMR (CD$_3$OD, 400 MHz) δ: 1.21 (t, 3H), 3.30 (s, 6H), 3.66 (q, 2H), 3.92 (t, 2H), 4.69 (t, 2H), 4.83 (s, 2H), 8.39 (d, 1H), 8.58 (d, 1H), 8.79 (s, 1H)

MS APCI+ m/z 359 [MH]$^+$

Preparation 39

5-Dimethylamino-1-(2-ethoxyethyl)-7-(4-methylpyridin-2-ylamino)-1H-pyrazolo[4,3-d]pyrimidine-3-carbaldehyde

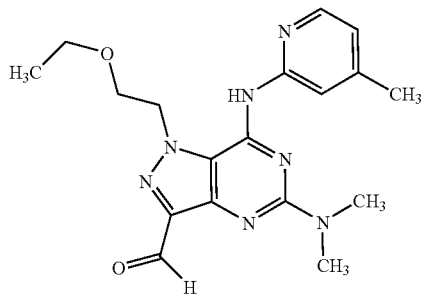

The alcohol of preparation 36 (330 mg, 0.89 mmol) was dissolved in dichloromethane (15.5 mL) and the solution cooled to 0° C. and treated with 1,1,1-triacetoxy-1,1-dihydro-1,2-benziodoxol-3(1H)-one (394 mg, 0.93 mmol). The reaction mixture was stirred at room temperature for 2 hours and was then treated with saturated sodium thiosulphate solution (13 mL), sodium hydrogencarbonate solution (13 mL) and ether (13 mL). The mixture was allowed to stand for 15 minutes before being extracted into dichloromethane (3×100 mL). The organics were combined, dried over magnesium sulphate and concentrated in vacuo. The residue was purified by column chromatography on silica gel eluting with dichloromethane:methanol 100:0 to 98:2 to yield the title product, 300 mg.

$^1$H NMR (CDCl$_3$, 400 MHz) δ: 1.10 (m, 3H), 2.40 (s, 3H), 3.30 (s, 6H), 3.62 (m, 2H), 3.99 (t, 2H), 4.85 (m, 2H), 6.90 (d, 1H), 8.20 (d, 1H), 8.40 (m, 1H), 10.35 (s, 1H). MS APCI+ m/z 370 [MH]$^+$

Preparation 40

5-Dimethylamino-1-(2-ethoxyethyl)-7-(5-methylpyridin-2-ylamino)-1H-pyrazolo[4,3-d]pyrimidine-3-carbaldehyde

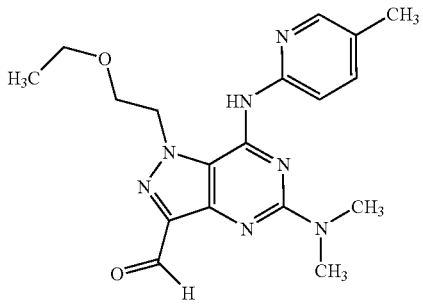

The title product was prepared by a method similar to that described for preparation 39 using the alcohol of preparation 37.

$^1$H NMR (CD$_3$OD, 400 MHz) δ: 1.11 (t, 3H), 2.34 (s, 3H), 3.24 (s, 6H), 3.61 (q, 2H), 3.97 (m, 2H), 4.80 (m, 2H), 7.63 (d, 1H), 8.13 (s, 1H), 8.31 (d, 1H), 10.10 (s, 1H).
MS APCI+ m/z 370 [MH]$^+$

Preparation 41

5-Dimethylamino-1-(2-ethoxyethyl)-7-(pyrimidin-4-ylamino)-1H-pyrazolo[4,3-d]pyrimidine-3-carbaldehyde

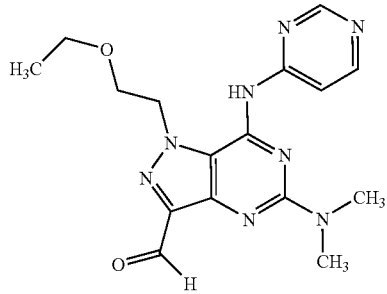

The title product was prepared by a method similar to that described for preparation 39 using the alcohol of preparation 38.

$^1$H NMR (CD$_3$OD, 400 MHz) δ: 1.21 (t, 3H), 3.25 (s, 6H), 3.62 (q, 2H), 4.00 (t, 2H), 4.83 (t, 2H), 8.35 (d, 1H), 8.59 (d, 1H), 8.82 (s, 1H). MS APCI+ m/z 357 [MH]$^+$

Preparation 42 tert-Butyl 4-[5-dimethylamino-1-(2-ethoxyethyl)-7-(4-methylpyridin-2-ylamino)-1H-pyrazolo[4,3-d]pyrimidin-3-ylmethyl]piperazine-1-carboxylate

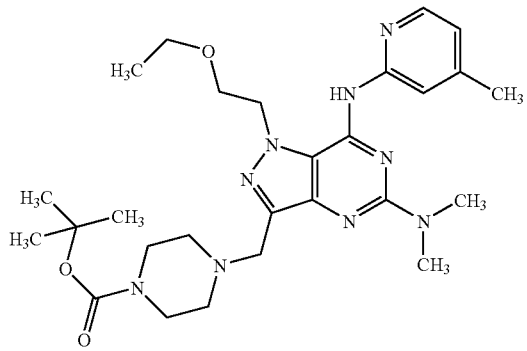

The aldehyde of preparation 39 (75 mg, 0.20 mmol) was dissolved in dichloromethane (5 mL) and the solution treated with sodium triacetoxyborohydride (52 mg, 0.24 mmol) and piperazine-1-carboxylic acid tert-butyl ester (45 mg, 0.24 mmol) The reaction mixture was shaken in a ReactiVial™ for 2 hours at room temperature and then treated with saturated sodium bicarbonate solution (8 mL). The mixture was extracted into dichloromethane (3×15 mL) and the organics combined and concentrated in vacuo. The residue was purified by column chromatography on silica gel eluting with dichloromethane:methanol 100:0 to 97.5:2.5 to yield the title product, 80 mg.

$^1$H NMR (CD$_3$OD, 400 MHz) δ: 1.10 (t, 3H), 1.42 (s, 9H), 2.38 (s, 3H), 2.59 (m, 4H), 3.20 (s, 6H), 3.40 (m, 4H), 3.58 (q, 2H), 3.80 (s, 2H), 3.81 (t, 2H), 4.65 (m, 2H), 4.85 (d, 1H), 6.88 (d, 1H), 8.10 (d, 1H), 8.40 (s, 1H).
MS APCI+ m/z 538 [MH]$^+$

Preparation 43 tert-Butyl (3R)-3-methoxypyrrolidine-1-carboxylate

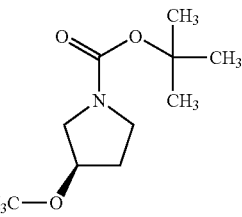

(3R)-3-Hydroxy-pyrrolidine-1-carboxylic acid tert-butyl ester (12.59, 66.70 mmol) was dissolved in tetrahydrofuran (334 mL) and the reaction mixture cooled to 0° C. in an ice bath. The reaction mixture was treated with 80% sodium hydride in mineral oil (2.20 g, 73.3 mmol) and stirred until back at room temperature. The reaction mixture was then treated with methyl iodide (14.5 g, 100.0 mmol) and stirred at room temperature for 18 hours. The reaction mixture was diluted with water (100 mL) and concentrated in vacuo until just the aqueous remained. The aqueous solution was extracted with ethyl acetate (750 mL), the organic layer separated, dried over magnesium sulphate and concentrated in vacuo to yield the title product as a brown oil, 12.48 g.

$^1$H NMR (CDCl$_3$, 400 MHz) δ: 1.41 (s, 9H), 1.95 (m, 2H), 3.30 (s, 3H), 3.40 (m, 4H), 3.86 (m, 1H)

Preparation 44 tert-Butyl (3S)-3-methoxypyrrolidine-1-carboxylate

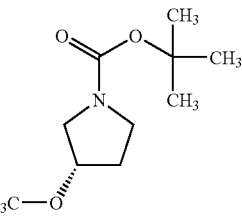

The title product was prepared by a method similar to that described for preparation 43 using (3S)-3-hydroxy-pyrrolidine-1-carboxylic acid tert-butyl ester.

$^1$H NMR (CDCl$_3$, 400 MHz) δ: 1.41 (s, 9H), 1.95 (m, 2H), 3.30 (s, 3H), 3.40 (m, 4H), 3.86 (m, 1H)

Preparation 45

(3R)-3-Methoxypyrrolidine hydrochloride

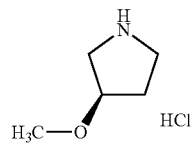

Hydrogen chloride gas was bubbled through an ice-cooled solution of the compound from preparation 43 (6.02 g, 30.0 mmol) in dichloromethane (30 mL), and the reaction then allowed to warm to room temperature and stirred for 48 hours. The solution was concentrated under reduced pressure and the residue triturated with ether. The resulting crystals were filtered off and dried in vacuo to afford the title compound.

$^1$H NMR (CD$_3$OD, 400 MHz) δ: 2.06 (m, 1H), 2.20 (m, 1H), 3.26-3.42 (m, 7H), 4.17 (m, 1H).

Preparation 46

(3S)-3-Methoxypyrrolidine hydrochloride

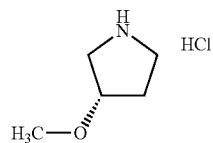

The title compound was obtained from the compound from preparation 44, following a similar method to that described in preparation 45.

$^1$H NMR (CD$_3$OD, 400 MHz) δ: 2.14 (m, 1H), 2.20 (m, 1H), 3.24-3.44 (m, 7H), 4.18 (m, 1H).

EXAMPLE 1

2-Dimethylamino-N-[5-dimethylamino-1-(2-ethoxyethyl)-7-(4-methylpyridin-2-ylamino)-1H-pyrazolo[4,3-d]pyrimidin-3-ylmethyl]acetamide

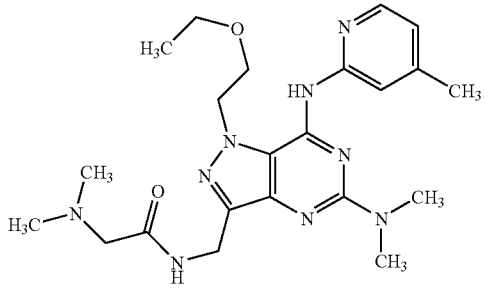

The chloro compound of preparation 27 (50 mg, 0.11 mmol) was dissolved in dimethyl sulphoxide (2 mL) and the solution treated with N-ethyldiisopropylamine (22 μL, 0.12 mmol) and a 33% solution of dimethylamine in ethanol (160 μL, 1.10 mmol). The reaction mixture was heated to 100° C. in a ReactiVial™ for 18 hours and then partitioned between water (20 mL) and ethyl acetate (20 mL) and the aqueous washed with ethyl acetate (2×20 mL). The organics were combined, washed with water (10 mL), dried over magnesium sulphate and concentrated in vacuo. The residue was purified by column chromatography on silica gel eluting with dichloromethane:methanol:ammonium hydroxide 98:2:0.5 to yield the title product 32 mg.

$^1$H NMR (CD$_3$OD, 400 MHz) δ: 1.10 (t, 3H), 2.30 (s, 6H), 2.40 (s, 3H), 3.00 (s, 2H), 3.25 (s, 6H), 3.60 (q, 2H), 3.90 (t, 2H), 4.70 (m, 4H), 6.90 (d, 1H), 8.10 (d, 1H), 8.40 (s, 1H). MS APCl+ m/z 456 [MH]$^+$

EXAMPLES 2-15

The following compounds, of the general formula shown below, were prepared by a method similar to that described for example 1 using the appropriate chloro compound of preparations 18, 25, 26, 28, 29 and 30, and the appropriate HNR$^3$R$^4$ amine.

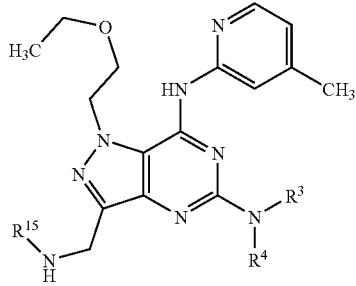

| No. | —NR$^3$R$^4$ | R$^{15}$ | Data |
|---|---|---|---|
| 2 | —N(CH$_3$)$_2$ | CH$_3$SO$_2$— | $^1$H NMR (CD$_3$OD, 400 MHz) δ: 1.10 (t, 3H), 2.40 (s, 3H), 3.00 (s, 3H), 3.20 (s, 6H), 3.60 (q, 2H), 3.90 (t, 2H), 4.50 (s, 2H), 4.70 (t, 2H), 6.90 (d, 1H), 8.15 (d, 1H), 8.40 (s, 1H). MS APCl+ m/z 449 [MH]$^+$ |

-continued

| No. | —NR³R⁴ | | Data |
|---|---|---|---|
| 3 | —NHCH₂CH₃ | CH₃SO₂— | ¹H NMR (CD₃OD, 400 MHz) δ: 1.10 (1, 3H), 1.30 (t, 3H), 2.40 (s, 3H), 2.90 (s, 3H), 3.50 (q, 2H), 3.60 (q, 2H), 3.90 (t, 2H), 4.50 (s, 2H), 4.70 (m, 1H), 4.85 (m, 2H), 6.90 (d, 1H), 8.10 (d, 1H). MS APCl+ m/z 449 [MH]⁺ |
| 4 | —N(CH₃)₂ | lHOCH₂C(O)— | ¹H NMR (CD₃OD, 400 MHz) δ: 1.10 (t, 3H), 2.40 (s, 3H), 3.20 (s, 6H), 3.60 (q, 2H), 3.90 (t, 2H), 4.05 (s, 2H), 4.70 (m, 4H), 6.90 (m, 1H), 8.15 (d, 1H), 8.40 (s, 1H). MS APCl+ m/z 429 [MH]⁺ |
| 5 | —NHCH₂CH₃ | HOCH₂C(O)— | ¹H NMR (CD₃OD, 400 MHz) δ: 1.10 (t, 3H), 1.30 (t, 3H), 2.40 (s, 3H), 3.50 (q, 2H), 3.60 (q, 2H), 3.85 (t, 2H), 4.00 (s, 2H), 4.60 (s, 4H), 6.90 (s, 1H), 8.15 (d, 1H), 8.45 (s, 1H). MS ES+ m/z 429 [MH]⁺ |
| 6 | —N(CH₃)₂ | CH₃C(O)— | ¹H NMR (CD₃OD, 400 MHz) δ: 1.20 (t, 3H), 2.10 (s, 3H), 2.40 (s, 3H), 3.20 (s, 6H), 3.60 (q, 2H), 3.90 (t, 2H) 4.60 (t, 2H), 4.80 (d, 2H), 6.80 (d, 1H), 7.50 (m, 1H), 8.20 (s, 1H), 8.35 (s, 1H), 9.70 (s, 1H). MS ES+ m/z 413 [MH]⁺ |
| 7 | —NHCH₃ | CH₃C(O)— | ¹H NMR (CD₃OD, 400 MHz) δ: 1.20 (t, 3H), 2.10 (s, 3H), 2.40 (s, 3H), 3.10 (s, 3H), 3.60 (q, 2H), 3.90 (t, 2H), 4.60 (t, 2H), 4.70 (d, 2H), 4.90 (m, 1H), 6.80 (d, 1H), 7.30 (m, 1H), 8.18 (d, 1H), 8.30 (s, 1H), 9.75 (s, 1H). MS ES+ m/z 399.8 [MH]⁺ |
| 8 | —NHCH₂CH₃ | CH₃C(O)— | ¹H NMR (CD₃OD, 400 MHz) δ: 1.20 (t, 3H), 1.30 (t, 3H), 2.10 (s, 3H), 2.40 (s, 3H), 3.50 (q, 2H), 3.60 (q, 2H), 3.90 (t, 2H), 4.60 (t, 2H), 4.75 (d, 2H), 4.80 (m, 1H), 6.80 (d, 1H), 8.20 (d, 1H), 8.30 (s, 1H), 9.75 (s, 1H). MS ES+ m/z 413 [MH]⁺ |
| 9 | —N(CH₃)₂ | CH₃CH₂C(O)— | ¹H NMR (CD₃OD, 400 MHz) δ: 1.19 (t, 3H), 1.20 (t, 3H), 2.30 (q, 2H), 2.40 (s, 3H), 3.20 (s, 6H), 3.60 (q, 2H), 3.90 (t, 2H), 4.60 (t, 2H), 4.80 (d, 2H), 6.80 (d, 1H), 7.60 (m, 1H), 8.20 (d, 1H), 8.40 (s, 1H), 9.70 (m, 1H). MS ES+ m/z 427 [MH]⁺ |
| 10 | —NHCH₃ | CH₃CH₂C(O)— | ¹H NMR (CDCl₃, 400 MHz) δ: 1.95 (t, 3H), 2.20 (t, 3H), 2.30 (q, 2H), 2.40 (s, 3H), 3.10 (d, 3H), 3.60 (q, 2H), 3.90 (t, 2H), 4.60 (t, 2H), 4.75 (d, 2H), 4.80 (m, 1H), 6.80 (d, 1H), 7.30 (m, 1H), 8.20 (d, 1H), 8.30 (s, 1H), 9.75 (s, 1H). MS ES+ m/z 413 [MH]⁺ |
| 11 | —NHCH₂CH₃ | CH₃CH₂C(O)— | ¹H NMR (CDCl₃, 400 MHz) δ: 1.03 (t, 3H), 1.20 (t, 3H), 1.30 (t, 3H), 2.30 (q, 2H), 2.40 (s, 3H), 3.50 (q, 2H), 3.60 (q, 2H), 3.90 (t, 2H), 4.60 (t, 2H), 4.75 (d, 2H), 4.80 (t, 1H), 6.80 (d, 1H), 8.15 (d, 1H), 8.25 (s, 1H), 9.70 (s, 1H). MS ES+ m/z 427 [MH]⁺ |
| 12 | —N(CH₃)₂ | CH₃— | ¹H NMR (CDCl₃, 400 MHz) δ: 1.20 (t, 3H), 2.38 (s, 3H), 2.72 (s, 3H), 3.22 (s, 6H), 3.63 (m, 2H), 3.91 (m, 2H), 4.43 (s, 2H), 4.68 (m, 2H), 6.83 (m, 1H), 8.18 (m, 1H). MS APCl+ m/z 385 [MH]⁺ |

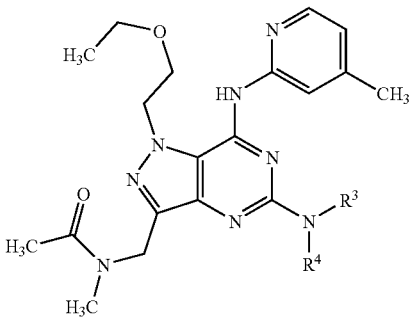

| No. | —NR³R⁴ | Data |
|---|---|---|
| 13 | —N(CH₃)₂ | ¹H NMR (CDCl₃, 400 MHz) δ: Rotamers 1.20 (t, 3H), 2.15 (s, 0.5H), 2.40 (s, 3H), 2.50 (s, 2.5H), 3.00 (s, 2.5H), 3.10 (s, 0.5H), 3.20 (s, 6H), 3.60 (q, 2H), 3.90 (t, 2H), 4.60 (s, 1.5H, t, 2H), 4.80 (s, 0.5H), 6.80 (t, 1H), 8.20 (d, 1H), 8.35 (s, 1H), 9.60 (s, 1H). MS ES+ m/z 427 [MH]⁺ |
| 14 | —NHCH₃ | ¹H NMR (CDCl₃, 400 MHz) δ: Rotamers 1.20 (t, 3H), 2.15 (s, 4H), 2.40 (s, 3H), 2.50 (s, 2H), 3.10 (s, 6H), 3.60 (q, 2H), 3.90 (t, 2H), 4.65 (t, 2H), 4.75, 4.85 (2xs, 2H), 4.90 (q, 1H), 6.80 (d, 1H), 8.15 (d, 1H), 8.25, 8.30 (2xs, 1H), 9.65, 9.70 (2xs, 1H). MS ES+ m/z 413 [MH]⁺ |
| 15 | —NHCH₂CH₃ | ¹H NMR (CDCl₃, 400 MHz) δ: Rotamers 1.20 (t, 3H), 1.25 (t, 3H), 2.10, 2.45 (2xs, 3H), 2.40 (s, 3H), 3.00, 3.10 (2xs, 3H), 3.50 (q, 2H), 3.60 (q, 2H), 3.90 (t, 2H), 4.60, 4.85 (2xs, 4H), 4.80 (m, 1H), 6.80 (s, 1H), 8.20 (d, 1H), 8.25, 8.30 (2xs 1H), 9.60, 9.65 (2xs, 1H). MS ES+ m/z 427 [MH]⁺ |

Examples 3, 5, 8, 11 and 15 used a 2M solution of ethylamine in methanol as the source of the $HNR^3R^4$ amine Examples 2, 4, 6, 9, 12 and 13 used 33% solutions of dimethylamine in ethanol as the source of the $HNR^3R^4$ amine Examples 7, 10 and 14 used 2M solutions of methylamine in methanol as the source of the $HNR^3R^4$ amine

EXAMPLE 16

N-[5-Dimethylamino-1-(2-ethoxyethyl)-7-(pyrimidin-4-ylamino)-1H-pyrazolo[4,3-d]pyrimidin-3-ylmethyl]-N-methylacetamide

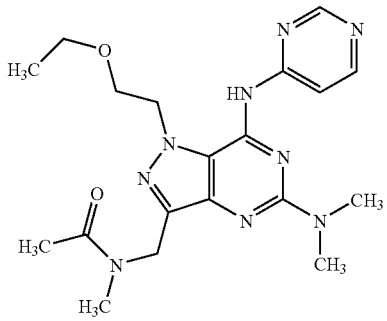

The title product was prepared by a method similar to that described for example 1 using the chloro compound of preparation 34 and a 33% solution of dimethylamine in ethanol.

$^1$H NMR (CD$_3$OD, 400 MHz) δ: Rotamers 1.22 (t, 3H), 2.15, 2.47 (2×s, 3H), 2.97, 3.16 (2×s, 3H), 3.21 (s, 3H), 3.22 (s, 3H), 3.65 (q, 2H), 3.90 (m, 2H), 4.68 (m, 2H), 4.77, 4.84 (2×s, 2H), 8.37 (d, 1H), 8.56 (d, 1H), 8.78 (d, 1H).

MS APCI+ m/z 414 [MH]$^+$

EXAMPLE 17

1-(2-ethoxyethyl)-N$^5$,N$^5$-dimethyl-3-(methylaminomethyl)-N$^7$-(pyrazin-2-yl)-1H-pyrazolo[4,3-d]pyrimidine-5,7-diamine hydrochloride

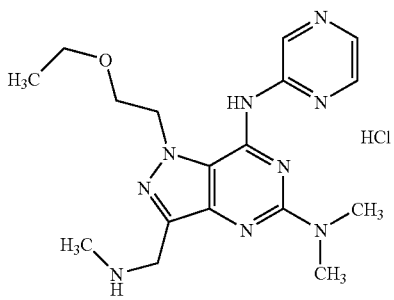

A mixture of the chloride from preparation 33 (109 mg, 0.3 mmol), dimethylamine (33% in ethanol, 0.27 ml, 1.5 mmol) and N,N-diisopropylethylamine (0.26 ml, 1.5 mmol) in 1-methyl-2-pyrrolidinone (1 mL) was heated at 120° C. for 18 hours in a ReactiVial™. The cooled mixture was evaporated in vacuo and the residue purified by column chromatography on silica gel using dichloromethane:methanol:ammonium hydroxide (98:2:0.2) as eluant. The product was dissolved in dichloromethane, 2M hydrogen chloride in ether (0.037 mL, 0.074 mmol) added and the solution evaporated in vacuo to afford the title compound, 23 mg.

$^1$H NMR (CD$_3$OD, 400 MHz) δ: 1.20 (t, 3H), 2.62 (s, 3H), 3.23 (s, 6H), 3.66 (q, 2H), 3.92 (t, 2H), 4.19 (s, 2H), 4.73 (t, 2H), 7.04 (s, 1H), 8.24 (d, 1H), 8.38 (d, 1H)

MS APCI+ m/z 372 [MH]$^+$

EXAMPLE 18

1-(2-Ethoxyethyl)-N$^5$,N$^5$-dimethyl-3-[(4-methylpiperazin-1-yl)methyl]-N$^7$-(4-methylpyridin-2-yl)-1H-pyrazolo[4,3-d]pyrimidine-5,7-diamine hydrochloride

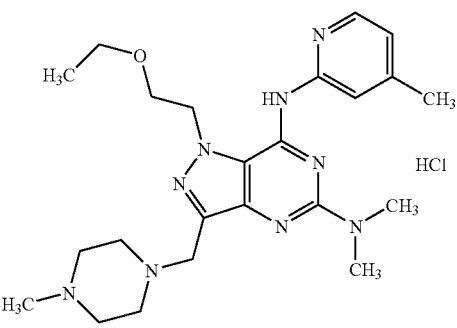

The aldehyde of preparation 39 (75 mg, 0.2 mmol), sodium triacetoxyborohydride (52 mg, 0.24 mmol) and 1-methylpiperazine (73 mg, 0.73 mmol) were dissolved in dichloromethane (15 mL). The reaction mixture was stirred at room temperature for 2 hours and was then treated with sodium bicarbonate solution (8 mL) and extracted with dichloromethane (3×15 mL). The organics were combined, concentrated in vacuo and the residue purified by column chromatography on silica gel eluting with dichloromethane:methanol 100:0 to 90:10. The product was treated with 2M hydrogen chloride in ether (0.1 mL), the mixture concentrated and the product dried in vacuo, to afford the title compound as a yellow crystalline solid, 29.6 mg.

$^1$H NMR (D$_2$O, 400 MHz) δ: 0.80 (t, 3H), 2.30 (s, 3H), 2.50 (br m, 2H), 2.72 (s, 3H), 3.00 (br m, 4H), 3.06 (s, 6H), 3.38 (m, 4H), 3.80 (m, 4H), 4.75 (t, 2H), 7.00 (d, 1H), 7.55 (s, 1H), 7.84 (d, 1H).

MS APCI+ m/z 454 [MH]$^+$

EXAMPLES 19-27

The following compounds, of the general formula shown below, were prepared by a method similar to that described for example 18 using the appropriate HNR$^{15}$R$^{16}$ amine and the appropriate aldehyde of preparations 39 and 40.

| No. | NR¹⁵R¹⁶ | Data |
|---|---|---|
| | (structure: pyrazolopyrimidine with ethoxyethyl, methylpyridylamino, dimethylamino, CH₂NR¹⁵R¹⁶, · HCl) | |
| 19 | (S)-2-(methoxymethyl)pyrrolidinyl | ¹H NMR (D₂O, 400 MHz) δ: 0.65 (t, 3H), 1.72 (m, 1H), 1.85 (m, 2H), 2.08 (m, 1H), 2.15 (s, 3H), 2.94 (s, 6H), 3.08 (s, 3H), 3.24 (m, 1H), 3.35 (m, 2H), 3.40 (m, 3H), 3.75 (m, 3H), 4.45 (m, 2H), 4.58 (m, 2H), 6.82 (d, 1H), 7.70 (m, 1H), 7.90 (d, 1H). MS APCl+ m/z 469 [MH]⁺ |
| 20 | (R)-2-(methoxymethyl)pyrrolidinyl | ¹H NMR (D₂O, 400 MHz) δ: 0.75 (t, 3H), 1.70-2.08 (m, 3H), 2.18 (s, 3H), 2.59 (s, 6H), 3.10 (s, 3H), 3.20-3.47 (m, 6H), 3.77 (m, 3H), 4.40-4.70 (m, 5H), 6.62 (d, 1H), 7.70 (m, 1H), 7.90 (d, 1H). MS APCl+ m/z 469 [MH]⁺ |
| 21 | (S)-3-methoxypyrrolidinyl | ¹H NMR (D₂O, 400 MHz) δ: 0.82 (t, 3H), 2.10 (m, 2H), 2.35 (s, 3H), 3.10 (s, 6H), 3.18 (s, 3H), 3.40-3.50 (m, 6H), 3.85 (t, 2H), 4.15 (m, 1H), 4.60 (m, 2H), 4.80 (m, 2H), 7.05 (d, 1H), 7.59 (s, 1H), 7.99 (d, 1H). MS APCl+ m/z 455 [MH]⁺ |
| 22 | (R)-3-methoxypyrrolidinyl | ¹H NMR (D₂O, 400 MHz) δ: 0.82 (t, 3H), 2.35 (s, 3H), 3.10 (s, 6H), 3.18 (s, 3H), 3.40-3.50 (m, 6H), 3.80 (t, 2H), 4.15 (m, 1H), 4.61 (m, 2H), 4.82 (m, 2H), 7.10 (d, 1H), 7.59 (s, 1H), 7.99 (d, 1H). MS APCl+ m/z 455 [MH]⁺ |
| 23 | (CH₃)₂CHNH— | ¹H NMR (D₂O, 400 MHz) δ: 0.83 (t, 3H), 1.27 (d, 6H), 2.26 (s, 3H), 3.06 (s, 6H), 3.41 (m, 3H), 3.80 (t, 2H), 4.36 (s, 2H), 4.69 (m, 2H), 6.94 (d, 1H), 7.61 (m, 1H), 7.93 (d, 1H). MS APCl+ m/z 427 [MH]⁺ |
| 24 | CH₃(CH₂)₂NH— | ¹H NMR (D₂O, 400 MHz) δ: 0.83 (m, 6H), 1.60 (m, 2H), 2.26 (s, 3H), 2.97 (t, 2H), 3.06 (s, 6H), 3.40 (q, 2H), 3.80 (t, 2H), 4.35 (s, 2H), 4.70 (m, 2H), 6.94 (d, 1H), 7.62 (m, 1H), 7.93 (d, 1H). MS APCl+ m/z 413 [MH]⁺ |
| 25 | pyrrolidinyl | ¹H NMR (D₂O, 400 MHz) δ: 0.86 (t, 3H), 2.02 (m, 4H), 2.35 (s, 3H), 3.15 (s, 6H), 3.18 (m, 2H), 3.40 (q, 2H), 3.45 (m, 2H), 3.84 (t, 2H), 4.55 (s, 2H), 4.81 (t, 2H), 7.03 (d, 1H), 7.57 (s, 1H), 7.96 (d, 1H). MS APCl+ m/z 425 [MH]⁺ |

-continued

| No. | NR¹⁵R¹⁶ | Data |
|---|---|---|
| | (structure: pyrazolopyrimidine with ethoxyethyl, 5-methylpyridylamino, dimethylamino, CH₂NR¹⁵R¹⁶) | |
| 26 | CH₃CH₂NH— | ¹H NMR (CD₃OD, 400 MHz) δ: 1.11 (t, 3H), 1.21 (t, 3H), 2.32 (s, 3H), 2.84 (q, 2H), 3.21 (s, 6H), 3.60 (q, 2H), 3.86 (m, 2H), 4.09 (s, 2H), 4.71 (m, 2H), 7.63 (d, 1H), 8.16 (m, 1H), 8.37 (m, 1H). MS APCl+ m/z 399 [MH]⁺ |
| 27 | morpholinyl | ¹H NMR (CD₃OD, 400 MHz) δ: 1.08 (t, 3H), 2.28 (s, 3H), 2.64 (m, 4H), 3.21 (s, 6H), 3.59 (q, 2H), 3.68 (m, 4H), 3.86 (s, 2H), 3.89 (m, 2H), 4.69 (m, 2H), 7.63 (d, 1H), 8.16 (s, 1H), 8.37 (d, 1H). MS APCl+ m/z 441 [MH]⁺ |

Example 21—The product of preparation 46 was used as the HNR¹⁵R¹⁶ amine

Example 22—The product of preparation 45 was used as the HNR¹⁵R¹⁶ amine

EXAMPLES 28-31

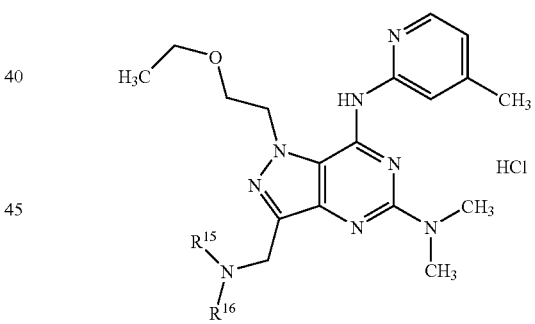

The bromo compound of preparation 19 (76 mg, 0.18 mmol) was dissolved in 1-methyl-2-pyrrolidinone (150 μL) and the solution treated with the appropriate HNR¹⁵R¹⁶ amine (1.78 mmol). The reaction mixture was stirred at 60° C. for 2 hours and then concentrated to low volume in vacuo. A 33% solution of dimethylamine (0.18 mmol) in ethanol was added and the reaction mixture sealed in a ReactiVial™ and heated to 120° C. for 18 hours. The reaction mixture was concentrated in vacuo and the residue partitioned between dichloromethane (1 mL) and saturated sodium bicarbonate solution (1 mL). The organic layer was separated and purified by column chromatography on silica gel eluting with dichloromethane:methanol:0.88 ammonia 100:0:0 to 90:10:1. The residues were treated with 2M hydrogen chloride in ether (30 μL), and the mixtures evaporated in vacuo to afford the title compounds.

| No | NR¹⁵R¹⁶ | Data |
|---|---|---|
| 28 | (CH₃)₂N— | ¹H NMR (D₂O, 400 MHz) δ: 0.80 (t, 3H), 2.22 (s, 3H), 2.80 (s, 6H), 3.04 (s, 6H), 3.40 (q, 2H), 3.81 (t, 2H), 4.43 (s, 2H), 4.75 (m, 2H), 6.93 (d, 1H), 7.70 (m, 1H), 7.96 (d, 1H). MS APCI+ m/z 399 [MH]⁺ |
| 29 | CH₃O(CH₂)₂NH— | ¹H NMR (D₂O, 400 MHz) δ: 0.85 (t, 3H), 2.32 (s, 3H), 3.11 (m, 6H), 3.23 (t, 2H), 3.27 (s, 3H), 3.43 (q, 2H), 3.63 (t, 2H), 3.85 (t, 2H), 4.43 (s, 2H), 4.79 (m, 2H), 7.02 (d, 1H), 7.59 (s, 1H), 7.96 (d, 1H). MS APCl+ m/z 429 [MH]⁺ |
| 30 | morpholino | ¹H NMR (D₂O, 400 MHz) δ: 0.82 (t, 3H), 2.31 (s, 3H), 3.08 (m, 6H), 3.14 (m, 4H), 3.41 (q, 2H), 3.80 (m, 6H), 4.37 (m, 2H), 4.75 (m, 2H), 6.98 (d, 1H), 7.65 (s, 1H), 7.96 (d, 1H). MS APCl+ m/z 441 [MH]⁺ |
| 31 | CH₃CH₂NH— | ¹H NMR (CD₃OD, 400 MHz) δ: 1.10 (t, 3H), 1.37 (t, 3H), 2.40 (s, 3H), 3.23 (q, 2H), 3.26 (s, 6H), 3.60 (q, 2H), 3.91 (t, 2H), 4.45 (s, 2H), 4.78 (m, 2H), 6.96 (d, 1H), 8.17 (d, 1H), 8.38 (s, 1H). MS APCl+ m/z 399 [MH]⁺ |

Example 28—Used a 33% solution of dimethylamine in ethanol as the source of the HNR¹⁵R¹⁶amine Example 31—Used a 2M solution of ethylamine in methanol as the source of the HNR¹⁵R¹⁶amine

EXAMPLE 32

1-(2-ethoxyethyl)-3-(ethylaminomethyl)-N⁵,N⁵-dimethyl-N⁷-(pyrimidin-4-yl)-1H-pyrazolo[4,3-d]pyrimidine-5,7-diamine

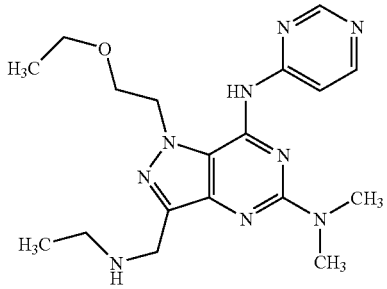

The aldehyde of preparation 41 (50 mg, 0.14 mmol) was dissolved in dichloromethane (2 mL) and the solution treated with ethylamine hydrochloride (13 mg, 0.15 mmol), sodium triacetoxyborohydride (45 mg, 0.21 mmol) and triethylamine (20 μL, 0.15 mmol). The mixture was stirred at room temperature for 30 minutes and was then treated with additional ethylamine hydrochloride (13 mg, 0.15 mmol) and triethylamine (20 μL, 0.15 mmol) and stirred for a further 30 minutes. The mixture was then treated with a 2M solution of ethylamine in ethanol (160 μL) and tetrahydrofuran (1 mL) and stirred at room temperature for 1 hour. The reaction mixture was partitioned between saturated sodium hydrogencarbonate solution (20 mL) and dichloromethane (20 mL) and the aqueous was extracted with dichloromethane (20 mL). The organics were combined, dried over magnesium sulphate and concentrated in vacuo. The residue was purified by column chromatography on silica gel eluting with dichloromethane:methanol:0.88 ammonia 90:10:1 to yield the title product, 29 mg.

1H NMR (CD₃OD, 400 MHz) δ: 1.18 (m, 6H), 2.78 (q, 2H), 3.23 (s, 6H), 3.63 (q, 2H), 3.90 (m, 2H), 4.69 (m, 2H), 4.85 (s, 2H), 8.40 (m, 1H), 8.56 (d, 1H), 8.79 (s, 1H). MS APCI+ m/z 386 [MH]⁺

EXAMPLE 33

1-(2-ethoxyethyl)-3-[(2-methoxyethylamino)methyl]-N⁵,N⁵-dimethyl-N⁷-pyrimidin-4-yl-1H-pyrazolo[4,3-d]pyrimidine-5,7-diamine

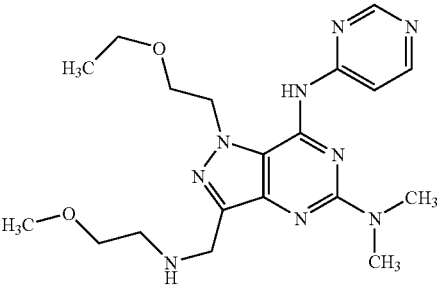

The title product was prepared by a method similar to that described in example 32 using 2-methoxyethylamine and the aldehyde of preparation 41.

¹H NMR (CD₃OD, 400 MHz) δ: 1.20 (t, 3H), 2.90 (t, 2H), 3.23 (s, 6H), 3.34 (s, 3H), 3.55 (m, 2H), 3.63 (q, 2H), 3.91 (m, 2H), 4.09 (s, 2H), 4.68 (m, 2H), 8.38 (m, 1H), 8.58 (d, 1H), 8.79 (s, 1H). MS APCI+ m/z 416 [MH]⁺

EXAMPLE 34

3-(Diethylaminomethyl)-1-(2-ethoxyethyl)-N⁵,N⁵-dimethyl-N⁷-(pyrimidin-4-yl)-1H-pyrazolo[4,3-d]pyrimidine-5,7-diamine

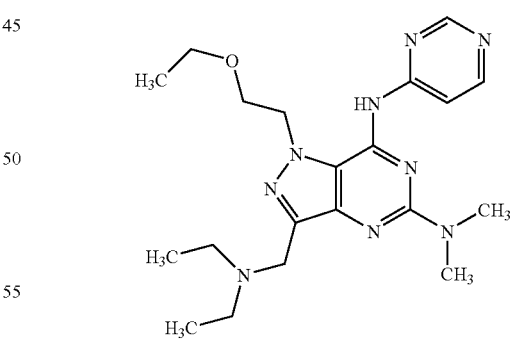

The chloro compound of preparation 21 (60 mg, 0.15 mmol) was dissolved in dimethyl sulphoxide (2 mL) and the solution treated with N-ethyldiisopropylamine (129 μL, 0.74 mmol) and a 33% solution of dimethylamine in ethanol (133 μL, 0.74 mmol). The reaction mixture was sealed in a ReactiVial™ and heated to 120° C. for 18 hours. The reaction mixture was partitioned between ethyl acetate and water and the aqueous extracted with ethyl acetate (×3). The organics were combined and washed with water and brine, dried over magnesium sulphate and concentrated in vacuo. The residue was purified by column chromatography on silica gel eluting with dichloromethane:methanol 95:5 to 90:10 to yield the title product, 29 mg.

$^1$H NMR (CDCl$_3$, 400 MHz) δ: 1.24 (t, 6H), 1.42 (t, 3H), 2.86 (q, 2H), 3.22 (s, 6H), 3.65 (q, 2H), 3.92 (t, 2H), 4.25 (s, 4H), 4.68 (t, 2H), 8.32 (d, 1H), 8.58 (d, 1H), 8.86 (s, 1H). MS ES+ m/z 414 [MH]$^+$

EXAMPLE 35

1-(2-ethoxyethyl)-N$^5$,N$^5$-dimethyl-3-(methylaminomethyl)-N$^7$-pyrimidin-4-yl-1H-pyrazolo[4,3-d]pyrimidine-5,7-diamine hydrochloride

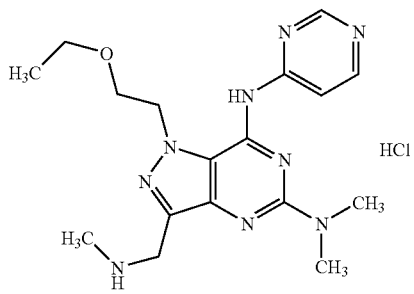

The chloro compound of preparation 32 (32 mg, 0.09 mmol) was added to a mixture of a 33% solution of dimethylamine in ethanol (60 μL, 0.45 mmol) and N-ethyldiisopropylamine (80 μL, 0.45 mmol) in 1-methyl-2-pyrrolidinone (1 mL). The reaction mixture was heated to 120° C. for 18 hours in a ReactiVial™ and was then concentrated in vacuo. The residue was purified by column chromatography on silica gel eluting with dichloromethane:methanol:0.88 ammonia 90:10:1. The crude product was dissolved in dichloromethane and treated with ethereal 2M hydrogen chloride and then concentrated in vacuo to yield the title product, 9 mg.

$^1$H NMR (CD$_3$OD, 400 MHz) δ: 1.21 (t, 3H), 2.63 (s, 3H), 3.24 (s, 6H), 3.64 (q, 2H), 3.92 (m, 2H), 4.21 (s, 2H), 4.73 (m, 2H), 8.36 (s, 1H), 8.58 (d, 1H), 8.81 (s, 1H)

MS APCI+ m/z 372 [MH]$^+$

EXAMPLE 36

2-{[1-(2-ethoxyethyl)-3-(methylaminomethyl)-7-(4-methylpyridin-2-ylamino)-1H-pyrazolo[4,3-d]pyrimidin-5-yl]methylamino}ethanol hydrochloride

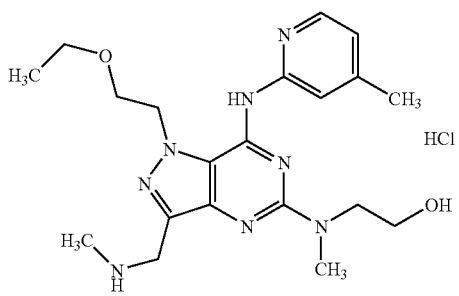

The BOC protected amine of preparation 35 (66.5 mg, 0.14 mmol) was dissolved in dimethyl sulphoxide (1.5 mL) and the solution treated with 2-(methylamino)ethanol (56 μL, 0.70 mmol) and N-ethyldiisopropylamine (120 μL, 0.70 mmol). The reaction mixture was sealed in a ReactiVial™ and heated to 120° C. for 18 hours and then concentrated in vacuo. The residue was dissolved in dichloromethane (5 mL) and the solution treated with trifluoroacetic acid (1 mL) and stirred for 1 hour at room temperature. The mixture was concentrated in vacuo and the residue partitioned between dichloromethane (10 mL) and saturated sodium bicarbonate solution (10 mL). The organic layer was separated and purified by column chromatography on silica gel eluting with dichloromethane:methanol 100:0 to 97:3. The crude product was dissolved in dichloromethane, treated with 2M ethereal hydrogen chloride (100 μL) and concentrated in vacuo to yield the title product, 30 mg.

$^1$H NMR (D$_2$O, 400 MHz) δ: 0.85 (t, 3H), 2.37 (s, 3H), 2.65 (s, 3H), 3.14 (s, 3H), 3.42 (q, 2H), 3.72 (m, 2H), 3.78 (m, 2H), 3.85 (t, 2H), 4.40 (s, 2H), 4.80 (t, 2H), 7.08 (d, 1H), 7.48 (s, 1H), 7.95 (d, 1H). MS APCI+ m/z 415 [MH]$^+$

EXAMPLE 37

1-(2-ethoxyethyl)-N$^5$-(2-methoxyethyl)-N$^5$-methyl-3-(methylaminomethyl)-N$^7$-(4-methylpyridin-2-yl)-1H-pyrazolo[4,3-d]pyrimidine-5,7-diamine hydrochloride

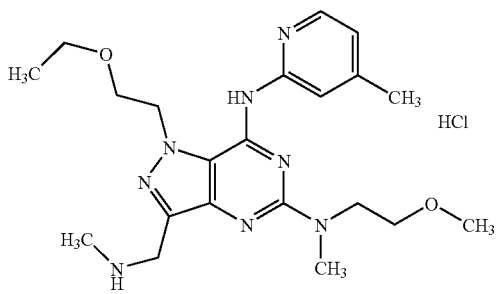

The title product was prepared by a method similar to that described for example 36 using N-(2-methoxyethyl)methylamine and the BOC protected amine of preparation 35.

$^1$H NMR (D$_2$O, 400 MHz) δ: 0.85 (t, 3H), 2.37 (s, 3H), 2.65 (s, 3H), 3.14 (s, 3H), 3.22 (s, 3H), 3.44 (q, 2H), 3.65 (t, 2H), 3.78 (t, 2H), 3.87 (t, 2H), 4.40 (s, 2H), 4.82 (t, 2H), 7.10 (d, 1H), 7.49 (s, 1H), 7.95 (d, 1H). MS APCI+ m/z 429 [MH]$^+$

EXAMPLE 38

2-[1-(2-ethoxyethyl)-3-(methylaminomethyl)-7-(4-methylpyridin-2-ylamino)-1H-pyrazolo[4,3-d]pyrimidin-5-ylamino]ethanol

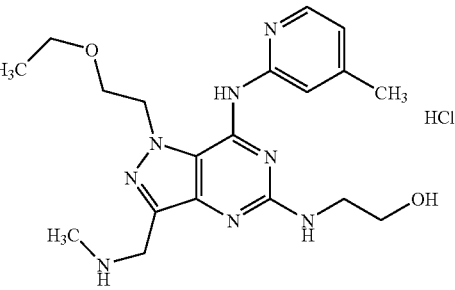

The title product was prepared by a method similar to that described for example 36 using ethanolamine and the protected amine of preparation 35.

$^1$H NMR (D$_2$O, 400 MHz) δ: 0.80 (t, 3H), 2.35 (s, 3H), 2.62 (s, 3H), 3.40 (m, 4H), 3.65 (m, 2H), 3.82 (t, 2H), 4.33 (s, 2H), 4.78 (t, 2H), 7.05 (d, 1H), 7.42 (s, 1H), 7.95 (d, 1H). MS APCI+ m/z 402 [MH]$^+$

EXAMPLE 39

N-[5-Dimethylamino-1-(2-ethoxyethyl)-7-(4-methylpyridin-2-ylamino)-1H-pyrazolo[4,3-d]pyrimidin-3-ylmethyl]-N-propylacetamide

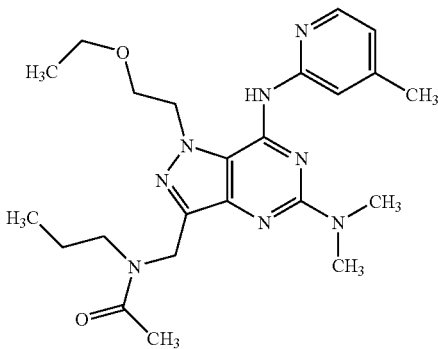

The product of example 24 (30 mg, 0.07 mmol) was added to a solution of triethylamine (10 L, 0.09 mmol) in dichloromethane (1 mL) and the mixture treated with acetyl chloride (8 μL, 0.09 mmol). The reaction mixture was stirred at room temperature for 18 hours and then concentrated in vacuo. The residue was dissolved in methanol (2 mL) and washed with 2M sodium hydroxide solution (10 mL) and water (10 mL). The solution was concentrated in vacuo and the residue partitioned between ethyl acetate and water, the organic phase was dried over magnesium sulphate and purified by column chromatography on silica gel eluting with dichloromethane:methanol:ammonium hydroxide 98:2:0.2 to yield the title product, 10 mg.

$^1$H NMR (CDCl$_3$, 400 MHz) δ: 0.90 (t, 3H), 1.15 (t, 3H), 1.65 (m, 2H), 2.19 (s, 3H), 2.42 (s, 3H), 3.32 (s, 6H), 3.59 (q, 2H), 3.85 (t, 2H), 4.59 (s, 2H), 4.79 (s, 2H), 4.82 (t, 2H), 6.95 (d, 1H), 7.75 (s, 1H), 8.27 (d, 1H), 10.60 (s, 1H). MS APCI+ m/z 455 [MH]$^+$

EXAMPLE 40

1-(2-ethoxyethyl)-N$^5$,N$^5$-dimethyl-N$^7$-(4-methylpyridin-2-yl)-3-(piperazin-1-ylmethyl)-1H-pyrazolo[4,3-d]pyrimidine-5,7-diamine hydrochloride

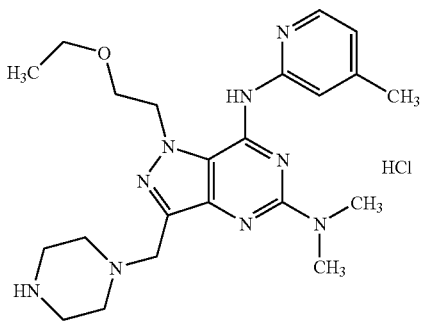

The protected amine of preparation 42 (80 mg, 0.15 mmol) was dissolved in 10% solution of trifluoroacetic acid in dichloromethane (5 mL) and the reaction mixture stirred at room temperature for 1 hour. The reaction mixture was concentrated in vacuo and the residue purified by column chromatography on silica gel eluting with dichloromethane:methanol 100:0 to 90:10. The crude product was treated with 2M hydrogen chloride in ether (100 μL) and concentrated in vacuo to yield the title product, 33 mg.

$^1$H NMR (D$_2$O, 400 MHz) δ: 0.70 (t, 3H), 1.80 (s, 3H), 2.50 (m, 4H), 2.70 (m, 6H), 2.80 (m, 4H), 3.30 (q, 2H), 3.55 (s, 2H), 3.65 (m, 2H), 4.30 (m, 2H), 6.65 (m, 1H), 7.80 (m, 2H). MS APCI+ m/z 440 [MH]$^+$

EXAMPLE 41

5-Piperazin-1-yl-3-(piperazin-1-ylmethyl)-N-pyrimidin-4-yl-1-[2-(2,2,2-trifluoroethoxy)ethyl]-1H-pyrazolo[4,3-d]pyrimidin-7-amine trifluoroacetate

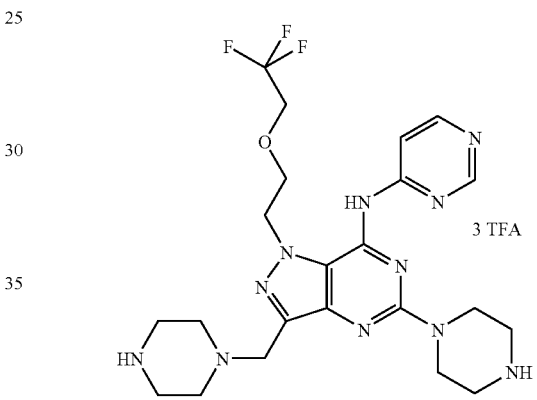

5-Chloro-3-(chloromethyl)-N-pyrimidin-4-yl-1-[2-(2,2,2-trifluoroethoxy)ethyl]-1H-pyrazolo[4,3-d]pyrimidin-7-amine (100 mg, 0.24 mmol), 1-boc-piperazine (220 mg, 1.18 mmol) and N,N-diisopropylethylamine (150 mg, 1.18 mmol) were mixed in methyl sulfoxide (1 ml) in a reaction vial. The reaction mixture was stirred 1.5 hours at room temperature then heated at 110° C. for 18 hours. The reaction mixture was purified on reverse phase HPLC to give Boc protected compound (160 mg). The Boc protected compound was treated with trifluoroacetic acid (6 ml) at room temperature for 30 minutes. The reaction mixture was purified by reverse phase HPLC and lyophilized to give 5-piperazin-1-yl-3-(piperazin-1-ylmethyl)-N-pyrimidin-4-yl-1-[2-(2,2,2-trifluoroethoxy)ethyl]-1H-pyrazolo[4,3-d]pyrimidin-7-amine trifluoroacetate (58 mg).

$^1$H NMR (400 MHz, (CD$_3$)$_2$SO) δ: 9.13 (bs, 1H), 8.90 (m, 1H), 8.71 (m, 2H), 8.69 (m, 1H), 7.90 (m, 1H), 4.80 (t, 2H, J=5.0 Hz), 4.66 (s, 2H), 3.89 (m, 8H), 3.47 (m, 4H), 3.36 (m, 4H), 3.16 (m, 4H). $^{19}$F NMR (400 MHz, (CD$_3$)$_2$SO) δ: −73.55 (t, 3F, J=9.2 Hz). Calculated Exact Mass: M+H 522.2660, found: 522.2635.

EXAMPLE 42

5-[(3R)-3-Methylpiperazin-1-yl]-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate

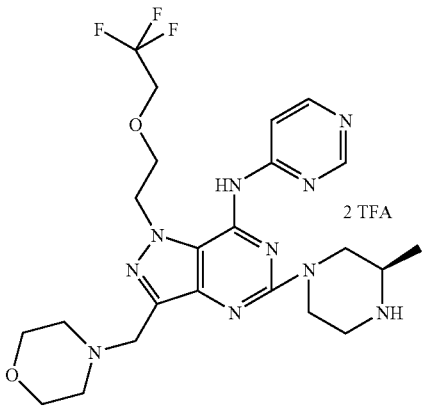

Step 1: Preparation of 5-chloro-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate

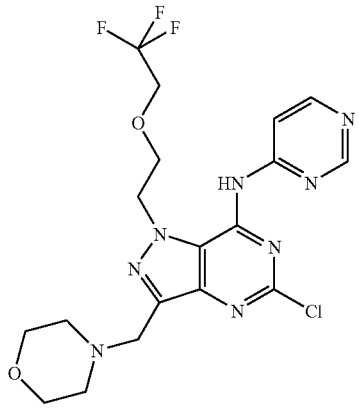

5-Chloro-3-(chloromethyl)-N-pyrimidin-4-yl-1-[2-(2,2,2-trifluoroethoxy)ethyl]-1H-pyrazolo[4,3-d]pyrimidin-7-amine (300 mg, 0.7 mmol), morpholine (185 mg, 2.1 mmol) and N,N-diisopropylethylamine (270 mg, 2.1 mmol) were mixed in methyl sulfoxide (2 ml) in a reaction vial. The reaction mixture was stirred 18 hours at room temperature and then purified on reverse phase HPLC and lyophilized to give 5-chloro-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate (350 mg).

$^1$H NMR (400 MHz, (CD$_3$)$_2$SO) δ: 9.15 (m, 1H), 8.77 (m, 1H), 8.06 (m, 1H), 4.91 (t, 2H, J=4.8 Hz), 4.70 (s, 2H), 3.80 (m, 6H), 3.60 (m, 2H), 3.42 (m, 2H), 3.18 (m, 2H). $^{19}$F NMR (400 MHz, (CD$_3$)$_2$SO) δ: −73.69 (t, 3F, J=9.78 Hz). Calculated Exact Mass: M+H 473.1423, found: 473.1437.

Step 2: Preparation of 5-[(3R)-3-methylpiperazin-1-yl]-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate

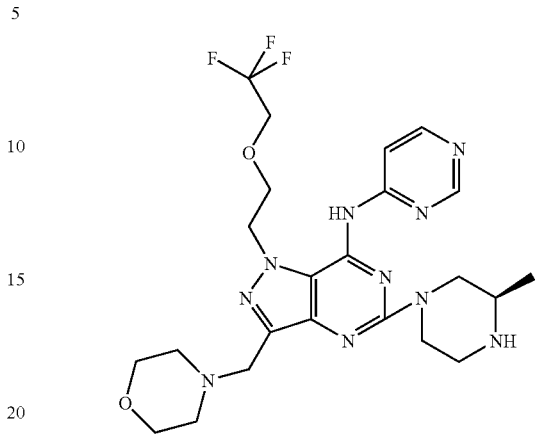

5-Chloro-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate (150 mg, 0.2 mmol), (R)(−)-2-methylpiperazine (86 mg, 0.85 mmol) and N,N-diisopropylethylamine (140 mg, 1.0 mmol) were mixed in methyl sulfoxide (1.0 ml) in a reaction vial. The reaction mixture was heated at 110° C. for 18 hours. The reaction was cooled to room temperature and brought to acidic condition by adding trifluoroacetic acid. The crude reaction mixture was purified on reverse phase HPLC (5-95% acetonitrile in water with 0.05% trifluoroacetic acid) and lyophilized to give 5-[(3R)-3-methylpiperazin-1-yl]-3-(morpholin-4-ylmethyl)-N-pyrimidin-4-yl-1-[2-(2,2,2-trifluoroethoxy)ethyl]-1H-pyrazolo[4,3-d]pyrimidin-7-amine trifluoroacetate (143 mg).

$^1$H NMR (400 MHz, (CD$_3$)$_2$SO) δ: 9.16 (s, 1H), 9.03 (m, 1H), 8.71 (m, 2H), 7.91 (m, 1H), 4.80 (t, 2H, J=5.2 Hz), 4.59 (s, 2H), 4.53 (m, 2H), 3.87 (m, 6H), 3.62 (m, 2H), 3.28 (m, 9H), 1.23 (d, 3H, J=6.6 Hz).

$^{19}$F NMR (400 MHz, (CD$_3$)$_2$SO) δ: −73.53 (t, 3F, J=9.6 Hz). Calculated Exact Mass: M+H 537.2656, found: 537.2647.

EXAMPLE 43

3-(Morpholin-4-ylmethyl)-5-piperazin-1-yl-N-pyrimidin-4-yl-1-[2-(2,2,2-trifluoroethoxy)ethyl]-1H-Pyrazolo[4,3-d]pyrimidin-7-amine trifluoroacetate

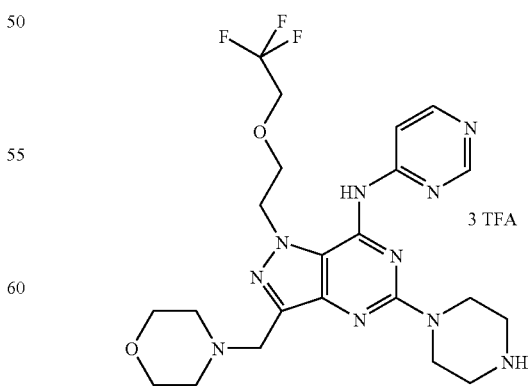

Example 43 was prepared by a method similar to that described in Example 42, using piperazine in place of (R)(−)-2-methylpiperazine in Step 2.

¹H NMR (400 MHz, (CD₃)₂SO) δ: 8.84 (bs, 3H), 8.60 (m, 1H), 7.86 (m, 1H), 4.82 (t, 2H, J=4.9 Hz), 4.53 (s, 2H), 4.03-3.88 (m, 10H), 3.6 (m, 2H), 3.4 (m, 2H), 3.17 (m, 6H). ¹⁹F NMR (400 MHz, (CD₃)₂SO) δ: −73.56 (t, 3F, J=9.0 Hz). Calculated Exact Mass: M+H 523.2500, found: 523.2475.

EXAMPLE 44

N⁵-Ethyl-N⁵-methyl-N⁷-pyrimidin-4-yl-3-(thiomorpholin-4-ylmethyl)-1-[2-(2,2,2-trifluoroethoxy)ethyl]-1H-pyrazolo[4,3-d]pyrimidine-5,7-diamine trifluoroacetate

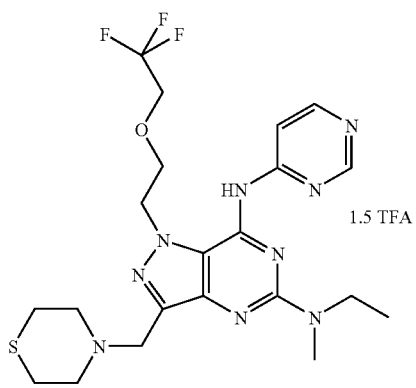

1.5 TFA

Example 44 was prepared by a method similar to that described in Example 42, using thiomorpholine in place of morpholine in Step 1 and N-ethyl-N-methylamine in place of (R)(−)-2-methylpiperazine in Step 2.

¹H NMR (400 MHz, (CD₃)₂SO) δ: 8.83 (bs, 1H), 8.61 (m, 1H), 7.99 (m, 1H), 4.79 (m, 2H), 4.52 (s, 2H), 4.04-3.94 (m, 4H), 3.64 (m, 2H), 3.47 (m, 4H), 3.10 (s, 3H), 2.89 (m, 4H), 1.10 (t, 3H, J=6.98 Hz). ¹⁹F NMR (400 MHz, (CD₃)₂SO) δ: −73.53 (t, 3F, J=9.0 Hz). Calculated Exact Mass: M+H 512.2162, found: 512.2154.

EXAMPLE 45

5-[(3R)-3-Methylpiperazin-1-yl]-3-(piperidin-1-ylmethyl)-N-pyrimidin-4-yl-1-[2-(2,2,2-trifluoroethoxy)ethyl]-1H-pyrazolo[4,3-d]pyrimidin-7-amine trifluoroacetate

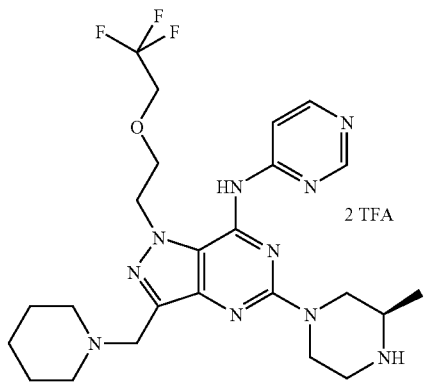

2 TFA

Example 45 was prepared by a method similar to that described in Example 42, using piperidine in place of morpholine.

¹H NMR (400 MHz, (CD₃)₂SO) δ: 9.90 (bs, 1H), 9.13 (m, 1H), 8.83 (m, 2H), 8.63 (m, 1H), 7.86 (m, 1H), 4.84 (t, 2H, J=4.9 Hz), 4.51 (m, 4H), 4.05-3.94 (m, 4H), 3.48-3.24 (m, 5H), 3.09-3.03 (m, 2H), 2.93-2.91 (m, 2H), 1.80-1.77 (m, 2H), 1.64-1.62 (m, 3H), 1.30-1.25 (m, 4H). ¹⁹F NMR (400 MHz, (CD₃)₂SO) δ: −73.57 (t, 3F, J=9.2 Hz). Calculated Exact Mass: M+H 535.2864, found: 535.2827.

EXAMPLE 46

5-[(3R)-3-methylpiperazin-1-yl]-N-pyrimidin-4-yl-3-(thiomorpholin-4-ylmethyl)-1-[2-(2,2,2-trifluoroethoxy)ethyl]-1H-pyrazolo[4,3-d]pyrimidin-7-amine trifluoroacetate

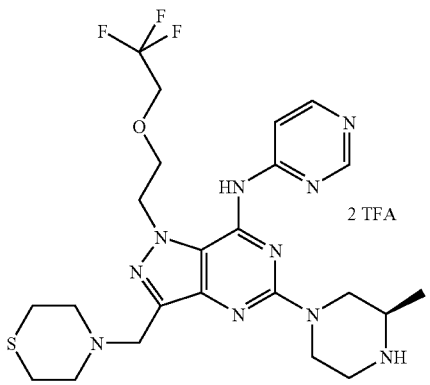

2 TFA

Example 46 was prepared by a method similar to that described in Example 42, using thiomorpholine in place of morpholine in Step 1.

¹H NMR (400 MHz, (CD₃)₂SO) δ: 9.10 (m, 1H), 8.86 (m, 1H), 8.79 (m, 1H), 8.63 (m, 1H), 7.86 (m, 1H), 4.84 (m, 2H), 4.53 (m, 4H), 4.05-3.94 (m, 4H), 3.75 (m, 2H), 3.40-2.9 (m, 11H), 1.26 (d, 3H, J=6.45 Hz). ¹⁹F NMR (400 MHz, (CD₃)₂SO) δ: −73.53 (t, 3F, J=9.2 Hz). Calculated Exact Mass: M+H 553.2428, found: 553.2410.

EXAMPLE 47

5-[(3R)-3-Methylpiperazin-1-yl]-3-[(4-methylpiperazin-1-yl)methyl]-N-pyrimidin-4-yl-1-[2-(2,2,2-trifluoroethoxy)ethyl]-1H-pyrazolo[4,3-d]pyrimidin-7-amine trifluoroacetate

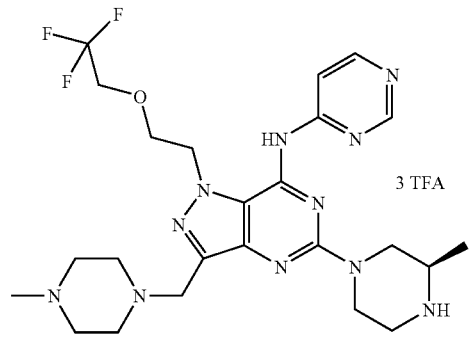

3 TFA

Example 47 was prepared by method similar to that described in Example 42, using 1-methylpiperazine in place of morpholine in Step 1.

$^1$H NMR (400 MHz, (CD$_3$)$_2$SO) δ: 9.06 (m, 1H), 8.85 (m, 1H), 8.76 (m, 1H), 8.61 (m, 1H), 7.86 (m, 1H), 4.76 (t, 2H, J=4.8 Hz), 4.50 (m, 2H), 4.03-3.91 (m, 6H), 3.40-2.99 (m, 10H), 2.73 (s, 3H), 2.48-2.50 (m, 3H), 1.25 (d, 3H, J=6.4 Hz). $^{19}$F NMR (400 MHz, (CD$_3$)$_2$SO) δ: −73.53 (t, 3F, J=9.2 Hz). Calculated Exact Mass: M+H 550.2973, found: 550.2976.

EXAMPLE 48

3-[(Diethylamino)methyl]-N$^5$,N$^5$-diethyl-N$^7$-pyrimidin-4-yl-1-[2-(2,2,2-trifluoroethoxy)ethyl]-1H-pyrazolo[4,3-d]pyrimidine-5,7-diamine trifluoroacetate

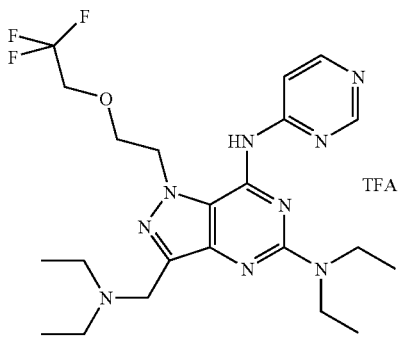

Example 48 was prepared by a method similar to that described in Example 41, using N,N-diethylamine in place of 1-Boc-piperazine in Step 1 and N,N-diethylamine in place of (R)-methylpiperazine in Step 2.

$^1$H NMR (400 MHz, (CD$_3$)$_2$SO) δ: 9.66 (m, 1H), 9.10 (m, 1H), 8.71 (m, 1H), 7.90 (m, 1H), 4.76 (t, 2H, J=5.0 Hz), 4.51 (m, 2H), 3.94-3.87 (m, 4H), 3.60-3.55 (m, 4H), 3.10-3.08 (m, 4H), 1.30 (t, 6H), 1.12 (t, 6H, J=7.0 Hz). $^{19}$F NMR (400 MHz, (CD$_3$)$_2$SO) δ: −73.53 (t, 3F, J=9.6 Hz). Calculated Exact Mass: M+H 496.2755, found: 496.2750.

EXAMPLE 49

3-[(1,1-Dioxidothiomorpholin-4-yl)methyl]-5-[(3R)-3-methylpiperazin-1-yl]-N-pyrimidin-4-yl-1-[2-(2,2,2-trifluoroethoxy)ethyl]-1H-pyrazolo[4,3-d]pyrimidin-7-amine trifluoroacetate

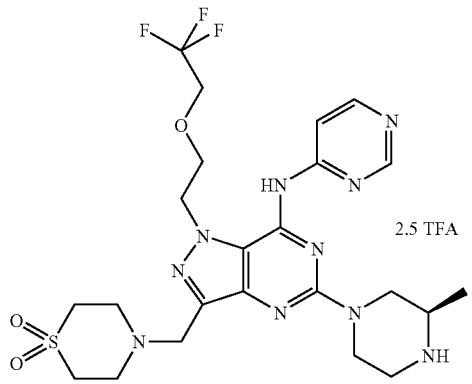

Example 49 was prepared by a method similar to that described in Example 42, using thiomorpholine 1,1-dioxide in place of morpholine in Step 1.

$^1$H NMR (400 MHz, (CD$_3$)$_2$SO) δ: 9.00 (m, 1H), 8.85 (bs, 1H), 8.68 (m, 1H), 8.61 (m, 1H), 7.86 (m, 1H), 4.77 (t, 2H, J=4.8 Hz), 4.51 (m, 2H), 4.09 (s, 2H), 4.0 (q, 2H, J=9.3 Hz), 3.92 (t, 2H, J=4.8 Hz), 3.40-3.00 (m, 13H), 1.25 (d, 3H, J=6.8 Hz). $^{19}$F NMR (400 MHz, (CD$_3$)$_2$SO) δ: −73.53 (t, 3F, J=9.0 Hz). Calculated Exact Mass: M+H 585.2326, found: 585.2322.

EXAMPLE 50

1-(2-(2,2,2-trifluoroethoxy)ethyl)-3-((2,2,2-trifluoroethylamino)methyl)-5-(piperazin-1-yl)-N-(pyrimidin-4-yl)-1H-pyrazolo[4,3-d]pyrimidin-7-amine trifluoroacetate

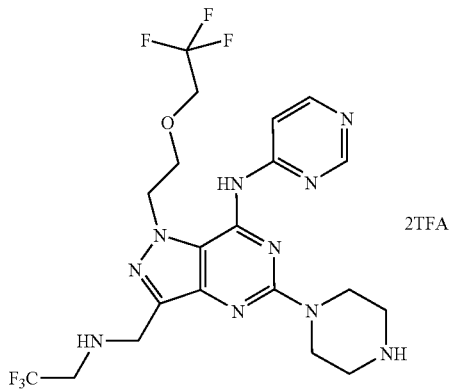

Step 1. Preparation of 1-(2-(2,2,2-trifluoroethoxy)ethyl)-3-((2,2,2-trifluoroethylamino)methyl)-5-chloro-N-(pyrimidin-4-yl)-1H-pyrazolo[4,3-d]pyrimidin-7-amine

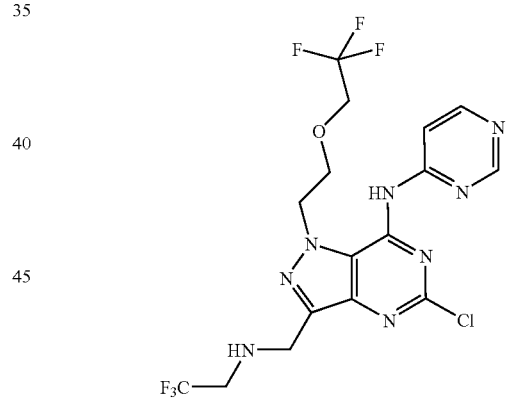

5-Chloro-3-(chloromethyl)-N-pyrimidin-4-yl-1-[2-(2,2,2-trifluoroethoxy)ethyl]-1H-pyrazolo[4,3-d]pyrimidin-7-amine (610 mg, 1.5 mmol), trifluoroethylamine hydrochloride (390 mg, 2.9 mmol) and N,N-diisopropylethylamine (410 mg, 3.2 mmol) along with tetraethylammonium bromide (1 mg) and tetraethylammonium iodide were mixed in dimethyl sulfoxide (10 ml) in a reaction vial. The reaction mixture was stirred for two days at room temperature and a second quantity of trifluoroethylamine hydrochloride (390 mg, 2.9 mmol) and N,N-diisopropyl-ethylamine (410 mg, 3.2 mmol) were added and the reaction allowed to proceed for another two days. The reaction mixture was partitioned between ethyl acetate (70 mLs) and water (2×25 mLs) and the organic layer dried (Na$_2$SO$_4$) and concentrated to an oil that solidified on standing. This intermediate was used without further purification. MS ES+ [MH]$^+$ m/z (relative intensity): 485.1 (100), 486.1 (10), 487.1 (20).

Step 2. 1-(2-(2,2,2-trifluoroethoxy)ethyl)-3-((2,2,2-trifluoroethylamino)methyl)-5-chloro-N-(pyrimidin-4-yl)-1H-pyrazolo[4,3-d]pyrimidin-7-amine (213 mg, 0.41 mmol) prepared in Step 1 and piperazine (152 mg, 1.8 mmol) were mixed in dimethyl sulfoxide (3.0 ml) in a reaction vial. The reaction mixture was heated at 120° C. for 10 hours. The reaction was cooled to room temperature and brought to acidic condition by adding trifluoroacetic acid. The crude reaction mixture was purified by reverse phase HPLC (5-95% acetonitrile in water with 0.05% trifluoroacetic acid) and lyophilized to give the title compound as a dark yellow solid (70 mg).

$^1$H NMR (400 MHz, (CD$_3$)$_2$SO): 10.4 (bs, 1H), 8.87 (s,s 2H), 8.61 (m, 1H), 7.88 (m, 1H), 4.77 (t, 2H, J=4.9 Hz), 4.19 (s, 2H), 3.99 (m, 2H), 3.90 (m, 6H), 3.6 (m, 2H), 3.19 (bs, 4H). $^{19}$F NMR (400 MHz, (CD$_3$)$_2$SO) δ: −73.57 (t, 3F, J=9.64 Hz), −74.88 (s). MS ES+ [MH]$^+$ m/z (relative intensity): 535.2 (100), 536.2 (25).

Examples 51-107 can be prepared by selecting suitable reagents and following the guidance of Schemes 1-41 and Examples 1-50.

EXAMPLE 51

N$^5$-Ethyl-N$^5$-methyl-3-(piperazin-1-ylmethyl)-N$^7$-pyrimidin-4-yl-1-[2-(2,2,2-trifluoroethoxy)ethyl]-1H-pyrazolo[4,3-d]pyrimidine-5,7-diamine

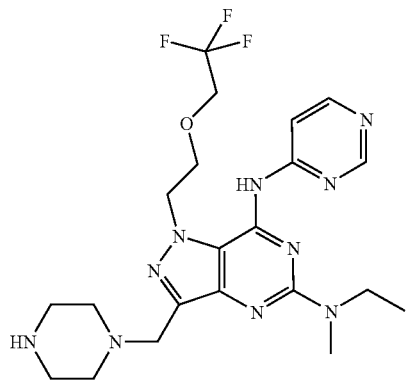

EXAMPLE 52

5-[(3R)-3-Methylpiperazin-1-yl]-3-(piperazin-1-ylmethyl)-N-pyrimidin-4-yl-1-[2-(2.2.2-trifluoroethoxy)ethyl]-1H-pyrazolo[4,3-d]pyrimidin-7-amine

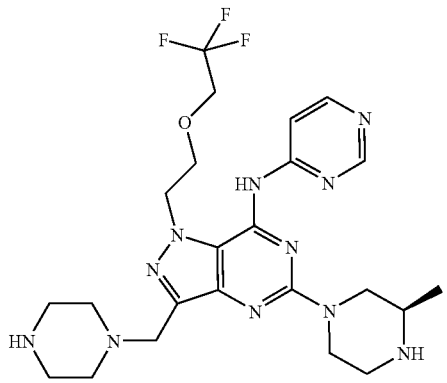

EXAMPLE 53

5-[(3S)-3-Methylpiperazin-1-yl]-3-(piperazin-1-ylmethyl)-N-pyrimidin-4-yl-1-[2-(2.2.2-trifluoroethoxy)ethyl]-1H-pyrazolo[4,3-d]pyrimidin-7-amine

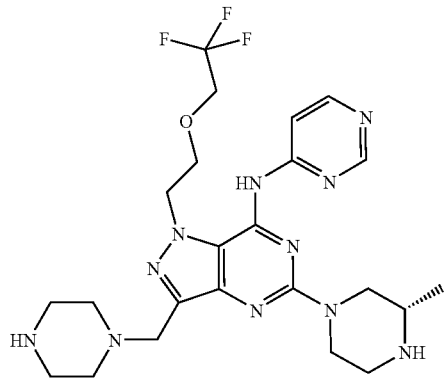

EXAMPLE 54

N-(4-Fluorophenyl)-5-piperazin-1-yl-3-(piperazin-1-ylmethyl)-1-[2-(2,2,2-trifluoroethoxy)ethyl]-1H-pyrazolo[4,3-d]pyrimidin-7-amine

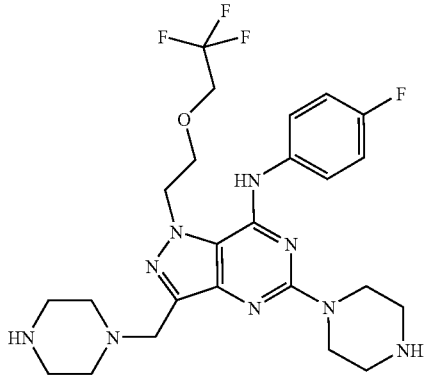

EXAMPLE 55

1-(2-Ethoxyethyl)-5-piperazin-1-yl-3-(piperazin-1-ylmethyl)-N-pyrimidin-4-yl-1H-pyrazolo[4,3-d]pyrimidin-7-amine

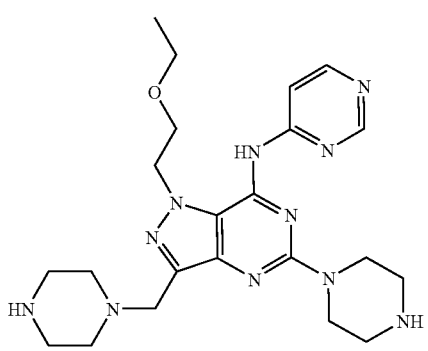

EXAMPLE 56

1-(2-Ethoxyethyl)-N~5~-ethyl-N~5~—methyl-3-(morpholin-4-ylmethyl)-N~7~-pyrimidin-4-yl-1H-pyrazolo[4,3-d]pyrimidine-5,7-diamine

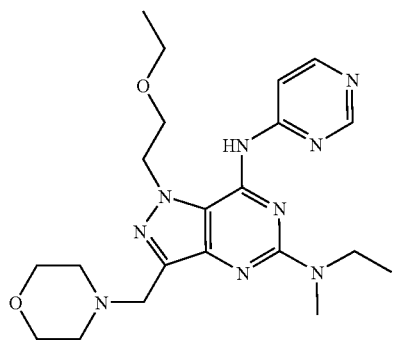

EXAMPLE 57

N~5~-Ethyl-N~5~-methyl-3-(piperidin-1-ylmethyl)-N~7~-pyrimidin-4-yl-1-[2-(2,2,2-trifluoroethoxy)ethyl]-1H-pyrazolo[4,3-d]pyrimidine-5,7-diamine

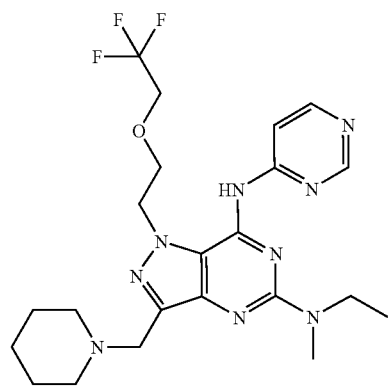

EXAMPLE 58

5-Piperazin-1-yl-3-(piperidin-1-ylmethyl)-N-pyrimidin-4-yl-1-[2-(2,2,2-trifluoroethoxy)ethyl]-1H-pyrazolo[4,3-d]pyrimidin-7-amine

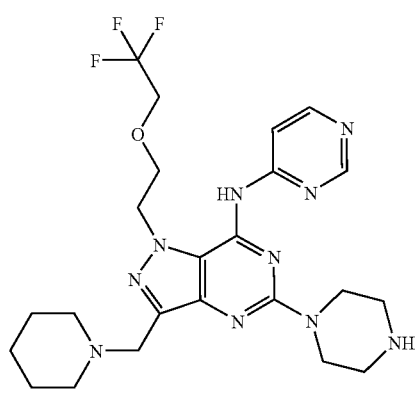

EXAMPLE 59

N-(4-Methylpyridin-2-yl)-5-piperazin-1-yl-3-(piperidin-1-ylmethyl)-1-[2-(2,2,2-trifluoroethoxy)ethyl]-1H-pyrazolo[4,3-d]pyrimidin-7-amine

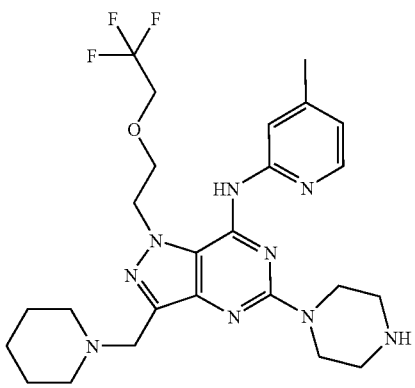

EXAMPLE 60

1-(2-Ethoxyethyl)-5-piperazin-1-yl-3-(piperidin-1-ylmethyl)-N-pyrimidin-4-yl-1H-pyrazolo[4,3-d]pyrimidin-7-amine

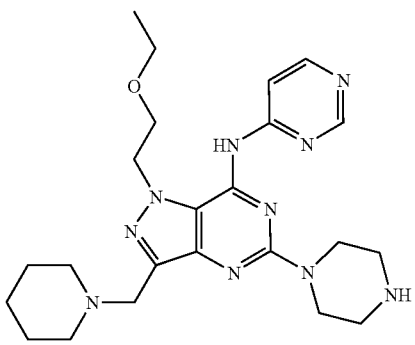

EXAMPLE 61

5-Piperazin-1-yl-N-pyrimidin-4-yl-3-(pyrrolidin-1-ylmethyl)-1-[2-(2.22-trifluoroethoxy)ethyl]-1H-pyrazolo[4,3-d]pyrimidin-7-amine

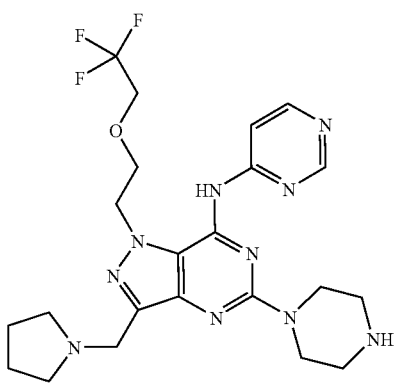

EXAMPLE 62

1-({5-Piperazin-1-yl-7-(pyrimidin-4-ylamino)-1-[2-(2,2,2-trifluoroethoxy)ethyl]-1H-Pyrazolo[4,3-d]pyrimidin-3-yl}methyl)piperidin-4-ol

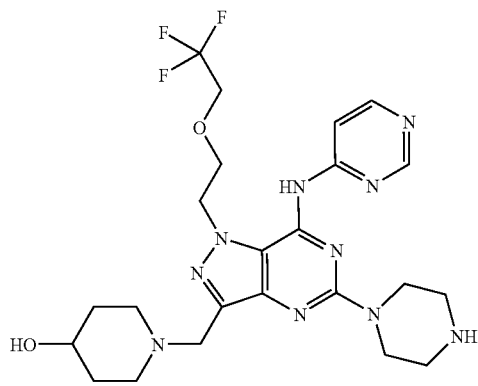

EXAMPLE 63

3-{[Ethyl(methyl)amino]methyl}-5-piperazin-1-yl-N-pyrimidin-4-yl-1-[2-(2,2,2-trifluoroethoxy)ethyl]-1H-pyrazolo[4,3-d]pyrimidin-7-amine

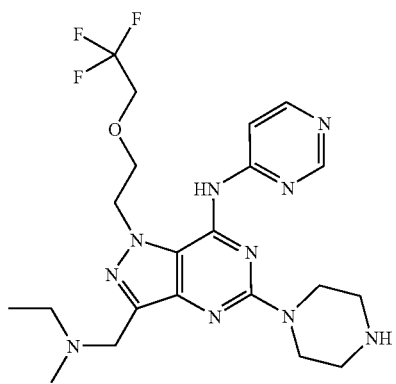

EXAMPLE 64

3-{[(3S)-3-Methylpiperazin-1-yl]methyl}-5-piperazin-1-yl-N-pyrimidin-4-yl-1-[2-(2,2,2-trifluoroethoxy)ethyl]-1H-pyrazolo[4,3-d]pyrimidin-7-amine

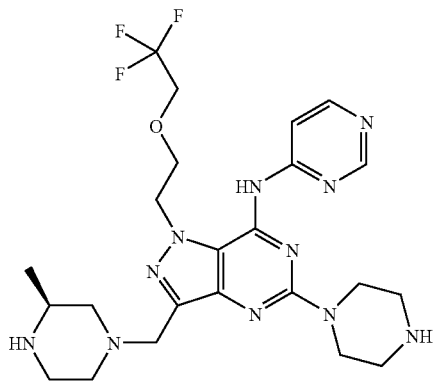

EXAMPLE 65

3-{[(3R)-3-methylpiperazin-1-yl]methyl}-5-piperazin-1-yl-N-pyrimidin-4-yl-1-[2-(2,2,2-trifluoroethoxy)ethyl]-1H-pyrazolo[4,3-d]pyrimidin-7-amine

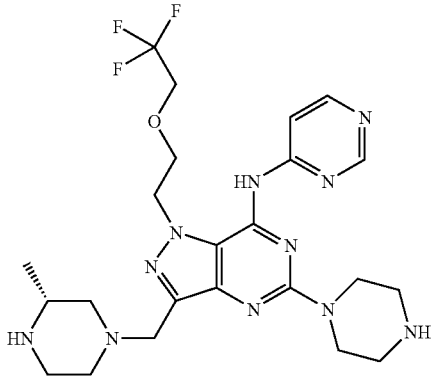

EXAMPLE 66

3-[(1,1-Dioxidothiomorpholin-4-yl)methyl]-1-(2-ethoxyethyl)-5-piperazin-1-yl-N-pyrimidin-4-yl-1H-pyrazolo[4,3-d]pyrimidin-7-amine

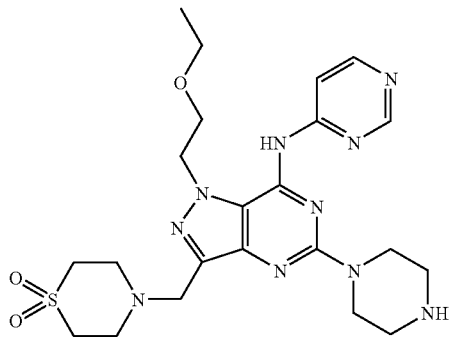

EXAMPLE 67

3-[(3,5-Dimethylpiperazin-1-yl)methyl]-5-piperazin-1-yl-N-pyrimidin-4-yl-1-[2-(2,2,2-trifluoroethoxy)ethyl]-1H-pyrazolo[4,3-d]pyrimidin-7-amine

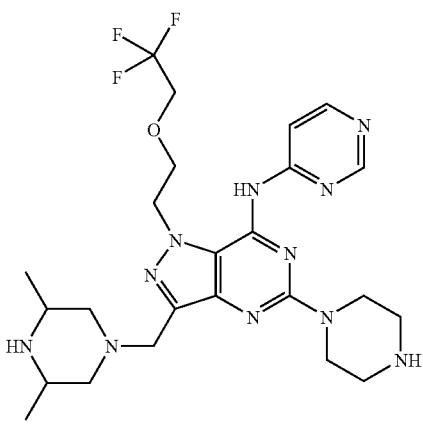

EXAMPLE 68

1-(2-(2,2-trifluoroethoxy)ethyl)-3-((2-methylpiperidin-1-yl)methyl)-5-(Piperazin-1-yl)-N-(pyrimidin-4-yl)-1H-pyrazolo[4,3-d]pyrimidin-7-amine

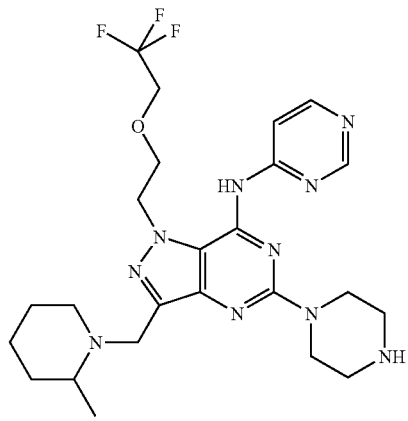

EXAMPLE 69

3-((2,2,2-trifluoroethylamino)methyl)-1-(2-ethoxyethyl)-5-(Piperazin-1-yl)-N-(pyrimidin-4-yl)-1H-pyrazolo[4,3-d]pyrimidin-7-amine

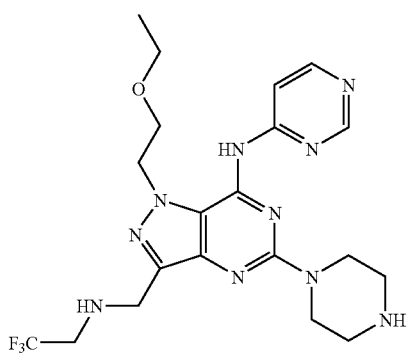

EXAMPLE 70

1-(2-ethoxyethyl)-3-((3,3-dimethylpiperazin-1-yl)methyl)-5-(piperazin-1-yl)-N-(pyrimidin-4-yl)-1H-pyrazolo[4,3-d]pyrimidin-7-amine

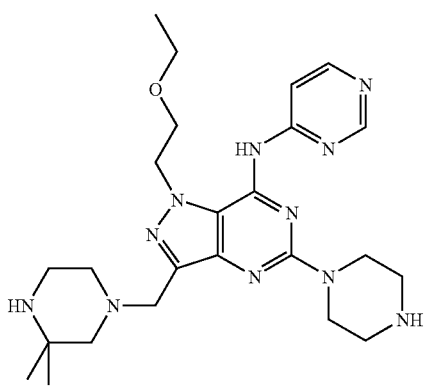

EXAMPLE 71

5-[(3S)-3-methylpiperazin-1-yl]-3-(piperidin-1-ylmethyl)-N-pyrimidin-4-yl-1-[2-(2,2,2-trifluoroethoxy)ethyl]-1H-pyrazolo[4,3-d]pyrimidin-7-amine

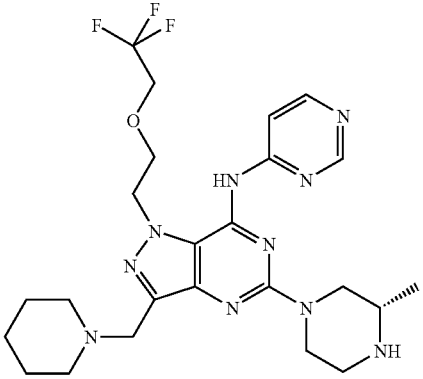

EXAMPLE 72

5-(3,3-dimethylpiperazin-1-yl)-3-(Piperidin-1-ylmethyl)-N-pyrimidin-4-yl-1-[2-(2,2,2-trifluoroethoxy)ethyl]-1H-pyrazolo[4,3-d]pyrimidin-7-amine

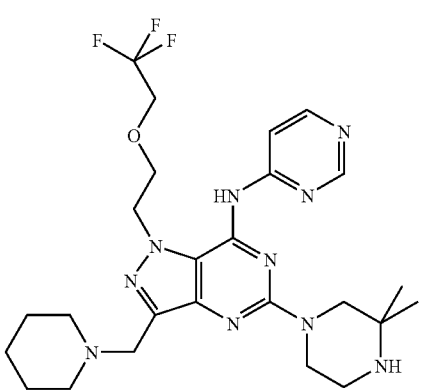

EXAMPLE 73

1-(2-ethoxyethyl)-5-[(3R)-3-methylpiperazin-1-yl]-3-(piperidin-1-ylmethyl)-N-pyrimidin-4-yl-1H-pyrazolo[4,3-d]pyrimidin-7-amine

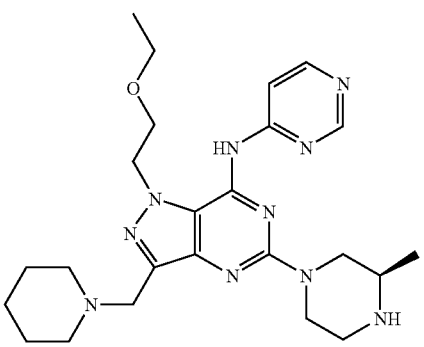

EXAMPLE 74

1-(2-ethoxyethyl)-5-[(3S)-3-methylpiperazin-1-yl]-3-(piperidin-1-ylmethyl)-N-pyrimidin-4-yl-1H-pyrazolo[4,3-d]pyrimidin-7-amine

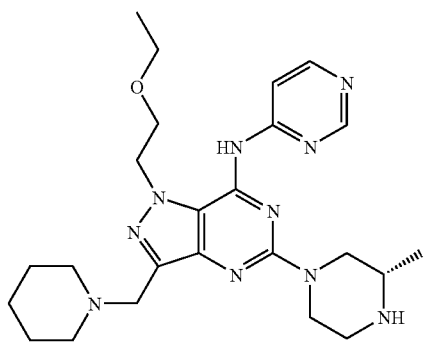

EXAMPLE 75

5-(3,3-dimethylpiperazin-1-yl)-1-(2-ethoxyethyl)-3-(piperidin-1-ylmethyl)-N-pyrimidin-4-yl-1H-pyrazolo[4,3-d]pyrimidin-7-amine

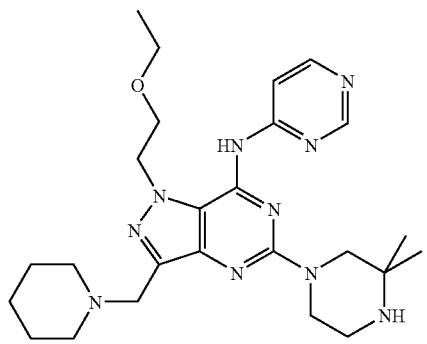

EXAMPLE 76

5-[(3R)-3-methylpiperazin-1-yl]-N-(4-methylpyridin-2-yl)-3-(piperidin-1-ylmethyl)-1-[2-(2,2,2-trifluoroethoxy)ethyl]-1H-Pyrazolo[4,3-d]pyrimidin-7-amine

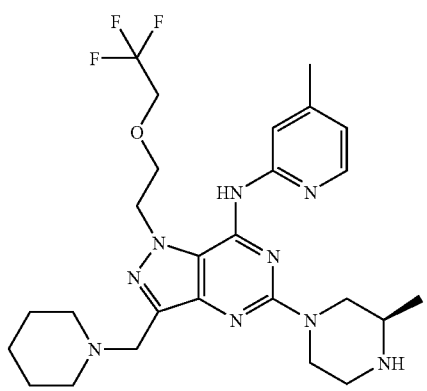

EXAMPLE 77

5-[(3S)-3-methylpiperazin-1-yl]-N-(4-methylpyridin-2-yl)-3-(piperidin-1-ylmethyl)-1-[2-(2,2,2-trifluoroethoxy)ethyl]-1H-pyrazolo[4,3-d]pyrimidin-7-amine

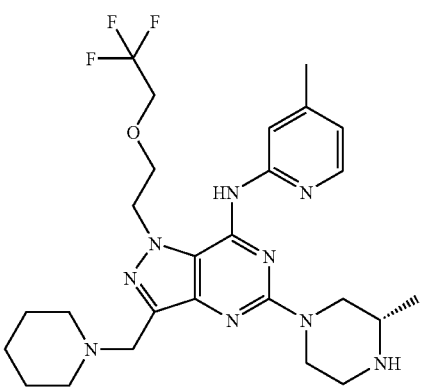

EXAMPLE 78

1-(2-ethoxyethyl)-5-[(3R)-3-methylpiperazin-1-yl]-N-(4-methylpyridin-2-yl)-3-(piperidin-1-ylmethyl)-1H-pyrazolo[4,3-d]pyrimidin-7-amine

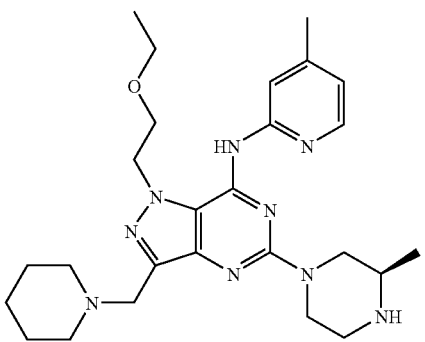

EXAMPLE 79

1-(2-ethoxyethyl)-5-[(3S)-3-methyl piperazin-1-yl]-N-(4-methylpyridin-2-yl)-3-(piperidin-1-ylmethyl)-1H-pyrazolo[4,3-d]pyrimidin-7-amine

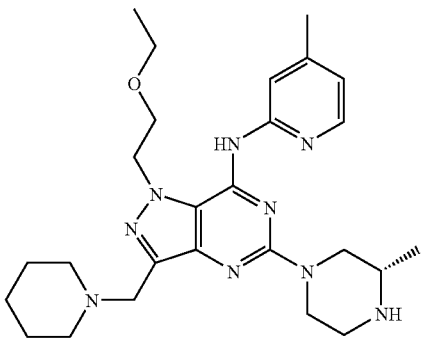

EXAMPLE 80

1-(2-ethoxyethyl)-N-(4-methylpyridin-2-yl)-5-piperazin-1-yl-3-(piperidin-1-ylmethyl)-1H-pyrazolo[4,3-d]pyrimidin-7-amine

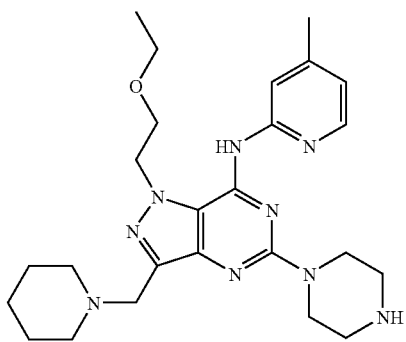

EXAMPLE 81

1-(2-ethoxyethyl)-N~5~-ethyl-N~5~-methyl-N~7~-(4-methylpyridin-2-yl)-3-(piperidin-1-ylmethyl)-1H-pyrazolo[4,3-d]pyrimidine-5,7-diamine

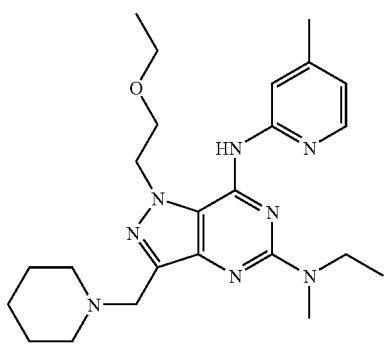

EXAMPLE 82

N-(4-fluorophenyl)-5-[(3R)-3-methylpiperazin-1-yl]-3-(piperidin-1-ylmethyl)-1-[2-(2,2,2-trifluoroethoxy)ethyl]-1H-pyrazolo[4,3-d]pyrimidin-7-amine

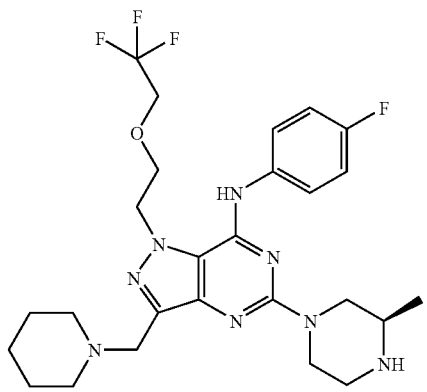

EXAMPLE 83

N-(4-fluorophenyl)-5-piperazin-1-yl-3-(piperidin-1-ylmethyl)-1-[2-(2,2,2-trifluoroethoxy)ethyl]-1H-pyrazolo[4,3-d]pyrimidin-7-amine

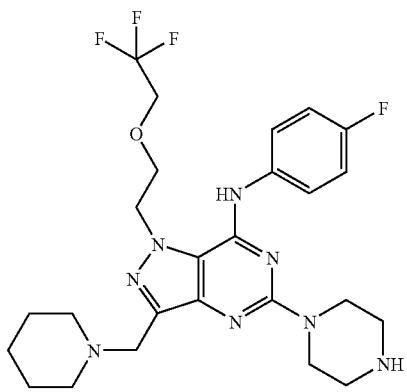

EXAMPLE 84

N-(4-fluorophenyl)-5-[(3S)-3-methylpiperazin-1-yl]-3-(piperidin-1-ylmethyl)-1-[2-(2,2,2-trifluoroethoxy)ethyl]-1H-pyrazolo[4,3-d]pyrimidin-7-amine

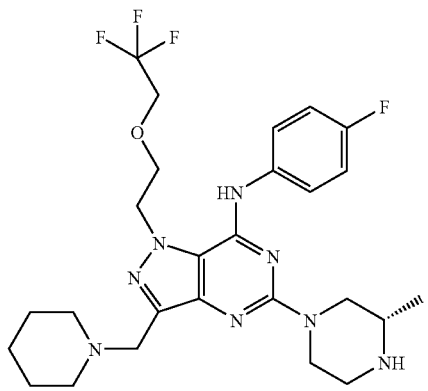

EXAMPLE 85

1-(2-ethoxyethyl)-N-(4-fluorophenyl)-5-[(3R)-3-methylpiperazin-1-yl]-3-(piperidin-1-ylmethyl)-1H-pyrazolo[4,3-d]pyrimidin-7-amine

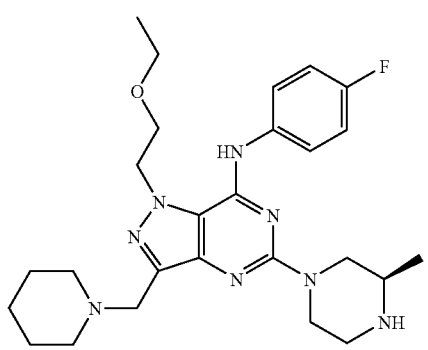

EXAMPLE 86

1-(2-ethoxyethyl)-N-(4-fluorophenyl)-5-piperazin-1-yl-3-(piperidin-1-ylmethyl)-1H-pyrazolo[4,3-d]pyrimidin-7-amine

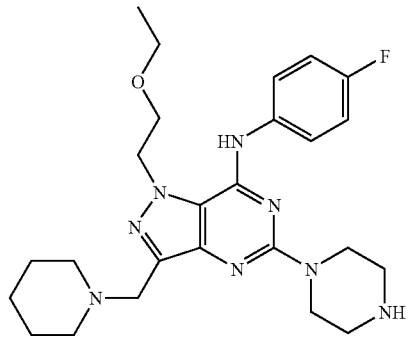

EXAMPLE 87

1-(2-ethoxyethyl)-N-(4-fluorophenyl)-5-[(3S)-3-methylpiperazin-1-yl]-3-(piperidin-1-ylmethyl)-1H-pyrazolo[4,3-d]pyrimidin-7-amine

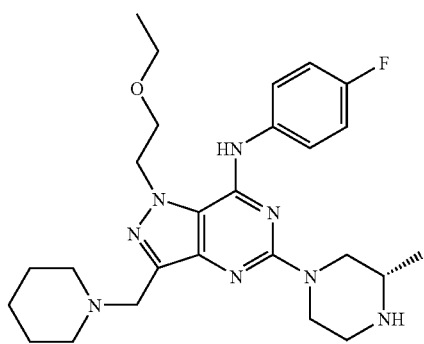

EXAMPLE 88

1-(2-ethoxyethyl)-N-(4-fluorophenyl)-5-[(3S)-3-methylpiperazin-1-yl]-3-(piperidin-1-ylmethyl)-1H-pyrazolo[4,3-d]pyrimidin-7-amine

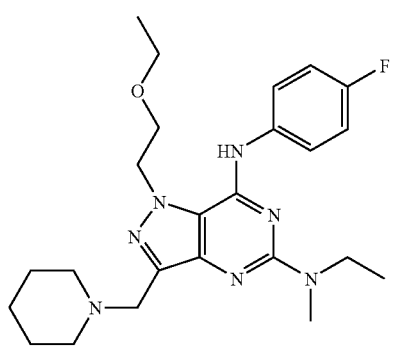

EXAMPLE 89

3-(azepan-1-ylmethyl)-1-(2-ethoxyethyl)-5-piperazin-1-yl-N-pyrimidin-4-yl-1H-pyrazolo[4,3-d]pyrimidin-7-amine

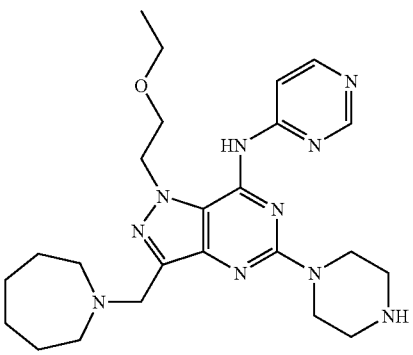

EXAMPLE 90

3-[(2,6-dimethylpiperidin-1-yl)methyl]-1-(2-ethoxyethyl)-5-piperazin-1-yl-N-pyrimidin-4-yl-1H-pyrazolo[4,3-d]pyrimidin-7-amine

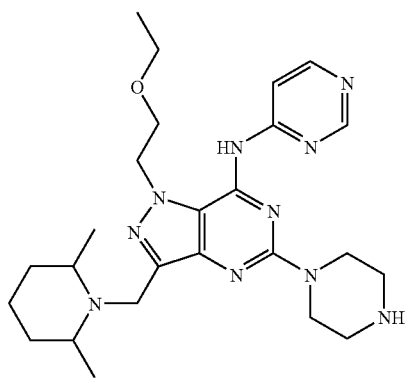

EXAMPLE 91

3-[(3,3-dimethylpiperidin-1-yl)methyl]-1-(2-ethoxyethyl)-5-piperazin-1-yl-N-pyrimidin-4-yl-1H-pyrazolo[4,3-d]pyrimidin-7-amine

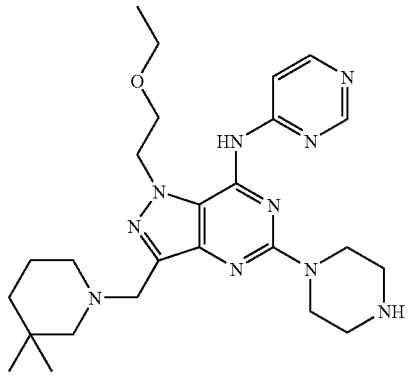

EXAMPLE 92

3-((cyclohexylamino)methyl)-1-(2-ethoxyethyl)-5-(piperazin-1-yl)-N-(pyrimidin-4-yl)-1H-pyrazolo[4,3-d]pyrimidin-7-amine

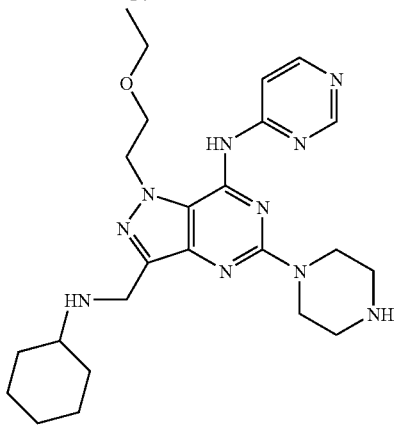

EXAMPLE 93

4-((1-(2-ethoxyethyl)-5-(piperazin-1-yl)-7-(pyrimidin-4-ylamino)-1H-pyrazolo[4,3-d]pyrimidin-3-yl)methylamino)cyclohexanol

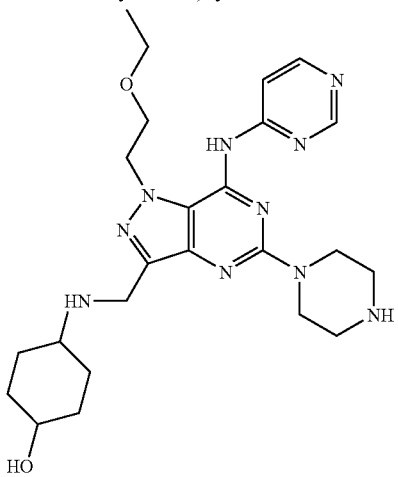

EXAMPLE 94

(1r,4r)-4-((1-(2-ethoxyethyl)-5-(piperazin-1-yl)-7-(pyrimidin-4-ylamino)-1H-pyrazolo[4,3-d]pyrimidin-3-yl)methylamino)cyclohexanol

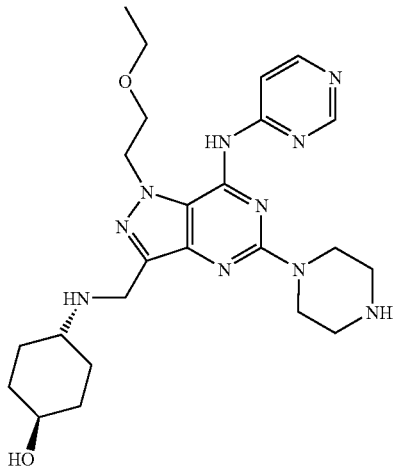

EXAMPLE 95

3-((cyclopentylamino)methyl)-1-(2-ethoxyethyl)-5-(piperazin-1-yl)-N-(pyrimidin-4-yl)-1H-pyrazolo[4,3-d]pyrimidin-7-amine

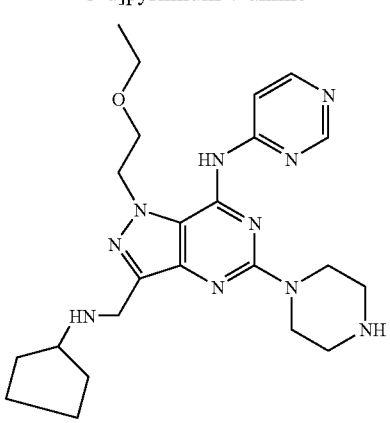

EXAMPLE 96

3-((cyclopropylamino)methyl)-1-(2-ethoxyethyl)-5-(piperazin-1-yl)-N-(pyrimidin-4-yl)-1H-pyrazolo[4,3-d]pyrimidin-7-amine

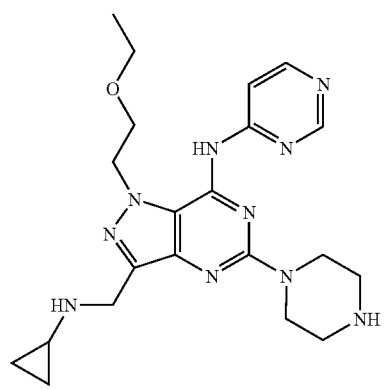

EXAMPLE 97

3-((tert-butylaminomethyl)-1-(2-ethoxyethyl)-5-(piperazin-1-yl)-N-(pyrimidin-4-yl)-1H-pyrazolo[4,3-d]pyrimidin-7-amine

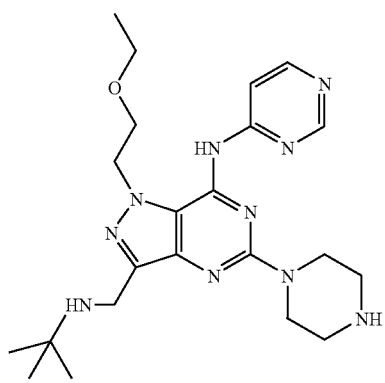

EXAMPLE 98

1-(2-ethoxyethyl)-5-(piperazin-1-yl)-3-((piperidin-1-yl)methyl)-N-(pyridin-2-yl)-1H-pyrazolo[4,3-d]pyrimidin-7-amine

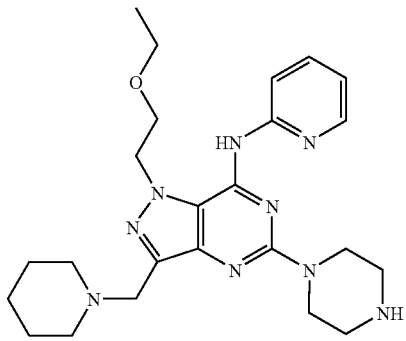

EXAMPLE 99

1-(2-ethoxyethyl)-N-phenyl-5-(piperazin-1-yl)-3-((piperidin-1-yl)methyl)-1H-pyrazolo[4,3-d]pyrimidin-7-amine

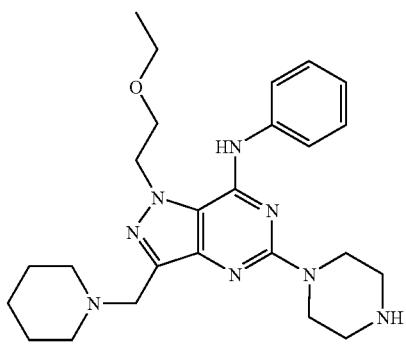

EXAMPLE 100

1-(2-ethoxyethyl)-N-(6-methylpyridin-2-yl)-5-(piperazin-1-yl)-3-((piperidin-1-yl)methyl)-1H-pyrazolo[4,3-d]pyrimidin-7-amine

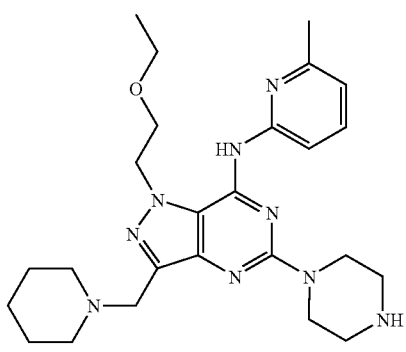

EXAMPLE 101

5-[(3R)-3-methylpiperazin-1-yl]-N-(4-methylpyridin-2-yl)-3-(morpholin-4-ylmethyl)-1-[2-(2,2,2-trifluoroethoxy)ethyl]-1H-pyrazolo[4,3-d]pyrimidin-7-amine

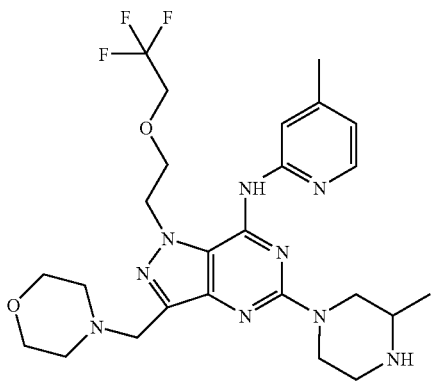

EXAMPLE 102

$N^5$-ethyl-$N^5$-methyl-3-(morpholin-4-ylmethyl)-$N^7$-pyrimidin-4-yl-1-[2-(2,2,2-trifluoroethoxy)ethyl]-1H-pyrazolo[4,3-d]pyrimidine-5,7-diamine

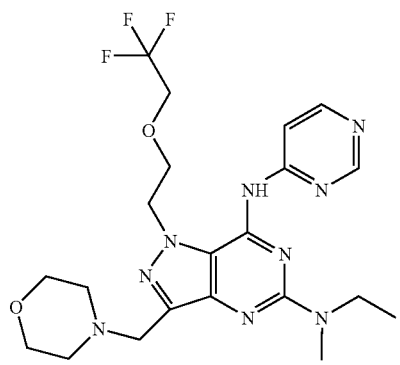

EXAMPLE 103

$N^5$-ethyl-$N^5$-methyl-$N^7$-(4-methylpyridin-2-yl)-3-(morpholin-4-ylmethyl)-1-[2-(2,2,2-trifluoroethoxy)ethyl]-1H-pyrazolo[4,3-d]pyrimidine-5,7-diamine

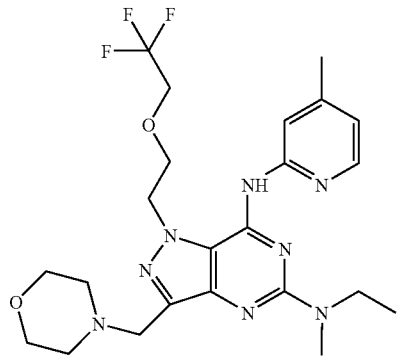

EXAMPLE 104

$N^5$-ethyl-$N^7$-(4-fluorophenyl)-$N^5$-methyl-3-(morpholin-4-ylmethyl)-1-[2-(2,2,2-trifluoroethoxy)ethyl]-1H-pyrazolo[4,3-d]pyrimidine-5,7-diamine

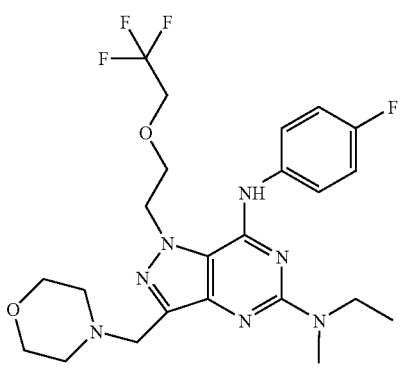

EXAMPLE 105

1-(2-ethoxyethyl)-5-[(3R)-3-methylpiperazin-1-yl]-3-(morpholin-4-ylmethyl)-N-pyrimidin-4-yl-1H-pyrazolo[4,3-d]pyrimidin-7-amine

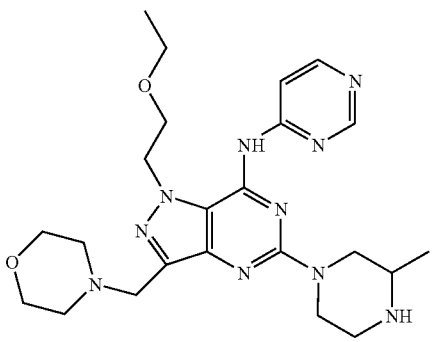

EXAMPLE 106

1-(2-ethoxyethyl)-5-[(3R)-3-methylpiperazin-1-yl]-N-(4-methylpyridin-2-yl)-3-(morpholin-4-ylmethyl)-1H-pyrazolo[4,3-d]pyrimidin-7-amine

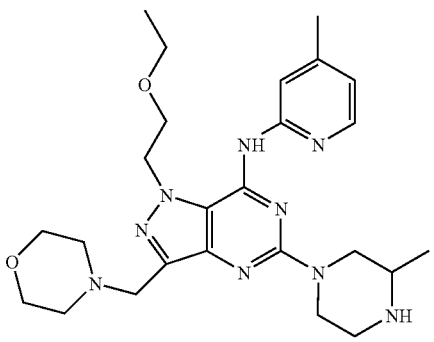

EXAMPLE 107

1-(2-ethoxyethyl)-N-(4-fluorophenyl)-5-[(3R)-3-methylpiperazin-1-yl]-3-(morpholin-4-ylmethyl)-1H-pyrazolo[4,3-d]pyrimidin-7-amine

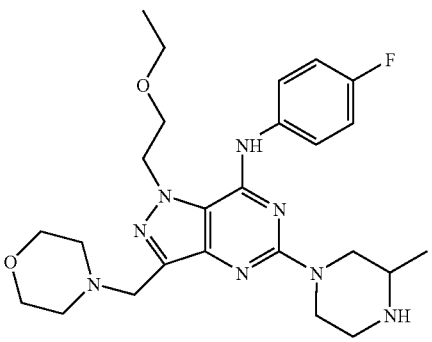

Assay

The compounds of the invention are inhibitors of cyclic guanylate monophosphate (cGMP)-specific phosphodiesterase type 5 (PDE-5 inhibitors). Preferred compounds suitable for use in accordance with the present invention are potent and selective PDE5 inhibitors. In vitro PDE inhibitory activities against cyclic guanosine 3',5'-monophosphate (CGMP) and cyclic adenosine 3',5'-monophosphate (cAMP) phosphodiesterases can be determined by measurement of their $IC_{50}$ values (the concentration of compound required for 50% inhibition of enzyme activity).

The required PDE enzymes can be isolated from a variety of sources, including human corpus cavernosum, human and rabbit platelets, human cardiac ventricle, human skeletal muscle and bovine retina, essentially by a modification of the method of Thompson, W J et al.; Biochemistry 18(23), 5228-5237, 1979, as described by Ballard S A et al.; J. Urology 159(6), 2164-2171, 1998. In particular, cGMP-specific PDE5 and cGMP-inhibited cAMP PDE3 can be obtained from human corpus cavernosum tissue, human platelets or rabbit platelets; cGMP-stimulated PDE2 was obtained from human corpus cavernosum; calcium/calmodulin (Ca/CAM)-dependent PDE1 from human cardiac ventricle; cAMP-specific PDE4 from human skeletal muscle; and photoreceptor PDE6 from bovine retina. Phosphodiesterases 7-11 can be generated from full length human recombinant clones transfected into SF9 cells.

Assays can be performed either using a modification of the "batch" method of Thompson W J and Appleman M M; Biochemistry 10(2), 311-316, 1971, essentially as described by Ballard S A et al.; J. Urology 159(6), 2164-2171, 1998, or using a scintillation proximity assay for the direct detection of [$^3$H]-labelled AMP/GMP using a modification of the protocol described by Amersham plc under product code TRKQ7090/7100. In summary, for the scintillation proximity assay the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a concentration of ~⅓ $K_m$ or less) such that $IC_{50}≅K_i$. The final assay volume was made up to 100 μl with assay buffer [20 mM Tris-HCl pH 7.4, 5 mM $MgCl_2$, 1 mg/ml bovine serum albumin]. Reactions were initiated with enzyme, incubated for 30-60 min at 30° C. to give <30% substrate turnover and terminated with 50 μl yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension.

In Vitro Assays

Method A: PDE-5 Inhibition Scintillation Proximity Assay (SPA)—Human Platelet

The assay measures the inhibition of human platelet PDE5 enzyme activity by a test compound in an in vitro assay that utilizes PDE5 isolated from human platelets. The PDE5 enzyme can be isolated from platelets essentially by a modification of the method of Thompson, W J et al.; Biochemistry 18(23), 5228-5237, 1979, as described by Ballard S A et al.; J. Urology 159(6), 2164-2171, 1998. PDE5 catalyzes the hydrolysis of $[^3H]$cGMP to the 5' nucleotide $[^3H]$GMP. $[^3H]$GMP binds to yttrium silicate SPA beads and is detected by scintillation counting. In summary, for the scintillation proximity assay the effect of a test compound was investigated by assaying a fixed amount of enzyme in the presence of varying test compound concentrations and low substrate, (cGMP or cAMP in a 3:1 ratio unlabelled to $[^3H]$-labeled at a concentration of $\sim\frac{1}{3} K_m$ or less) such that $IC_{50} \cong K_i$. The inhibition of enzyme activity is calculated relative to total PDE5 activity of uninhibited controls.

PDE5 $IC_{50}$ Assay: 96-Well Microtiter Plate Format

Reagents

Buffer A: 20 mM Tris-HCl, 5 mM $MgCl_2$, pH 7.4

Buffer B: 2 mg/ml BSA in Buffer A (enzyme buffer)

cGMP substrate: Final concentration of 500 nM in assay

The amount of $^3H$-labeled substrate added depends upon the specific activity of $[^3H]$cGMP, and it is diluted with a 10 mM stock of cold cGMP in Buffer A for a final substrate concentration of 500 nM in the assay.

PDE enzyme: Prepared in Buffer B. The dilution factor is determined by enzyme activity.

SPA beads: 20 mg/ml suspension prepared in dH2O.

| Positive Control | Negative Control | Standard/Test compound |
|---|---|---|
| 2 μl 100% DMSO | 2 μl 100% DMSO | 2 μl Standard/Test compound |
| 25 μl Buffer A | 25 μl Buffer A | 25 μl Buffer A |
| 25 μl Enzyme | 25 μl Buffer B | 25 μl Enzyme |
| 50 μl Substrate | 50 μl Substrate | 50 μl Substrate |
| 50 μl SPA to stop | 50 μl SPA to stop | 50 μl SPA to stop |

Stocks of standard and test compounds are prepared at 5 mM in 100% DMSO. Compounds are serially diluted in separate dilution plates using a 10-point ½ log dilution format. 2 μl of the compound dilutions are added in duplicate to the wells of the assay plate; 2 μl of 100% DMSO are added to designated control wells. 25 μl of Buffer A are added to all wells. 25 μl of Buffer B are added to the negative control wells, and 25 μl of enzyme are added to the remaining wells. 50 μl of substrate are added to each well. Plates are sealed and incubated for 60 minutes on a plate shaker at 30 C. 50 μl of SPA beads are added to stop the reaction. The plates are again sealed and shaken for 15 minutes to allow the beads to bind the GMP product. The beads are allowed to settle for 30 minutes and then read on a NXT TopCount. Data is analyzed with the ECADA application. In this analysis, % inhibition is calculated: (mean maximum−compound value/(mean maximum−mean minimum)×100. $IC_{50}$s are determined from sigmoid dose-response curves of enzyme activity vs compound concentration.

Method B: PDE-5 Inhibition Scintillation Proximity Assay (SPA)—Human Platelet

This method is a modified protocol of Method A.

The assay measures the inhibition of human platelet PDE5 enzyme activity by a test compound in an in vitro assay that utilizes PDE5 isolated from human platelets. PDE5 catalyzes the hydrolysis of $[^3H]$cGMP to the 5' nucleotide $[^3H]$GMP. $[^3H]$GMP binds to yttrium silicate SPA beads and is detected by scintillation counting. The inhibition of enzyme activity is calculated relative to total PDE5 activity of uninhibited controls.

PDE5 $IC_{50}$ Assay: 96-Well Microtiter Plate Format

Reagents

Buffer A: 20 mM Tris-HCl, 5 mM $MgCl_2$, pH 7.4

Buffer B: 2 mg/ml BSA in Buffer A (enzyme buffer)

cGMP substrate: Final concentration of 50 nM in assay

The amount of $^3H$-labeled substrate added depends upon the specific activity of $[^3H]$cGMP, and it is diluted in Buffer A.

PDE enzyme: Prepared in Buffer B. The dilution factor is determined by enzyme activity.

SPA beads: 4 mg/ml suspension prepared in $dH_2O$.

| Positive Control | Negative Control | Standard/Test compound |
|---|---|---|
| 3 μl 100% DMSO | 3 μl 100% DMSO | 3 μl Standard/Test compound |
| 27 μl Buffer A | 27 μl Buffer A | 27 μl Buffer A |
| 30 μl Enzyme | 30 μl Buffer B | 30 μl Enzyme |
| 30 μl Substrate | 30 μl Substrate | 30 μl Substrate |
| 30 μl SPA to stop | 30 μl SPA to stop | 30 μl SPA to stop |

Stocks of standard and test compounds are prepared at 2 mM in 100% DMSO. Compounds are serially diluted in separate dilution plates using an 8-point ⅓ log dilution format such that the starting concentration in the assay is 2 μM for an initial $IC_{50}$ screen. 27 μl of Buffer A are added to the wells of the assay plates. From the dilution plates, 3 μl of diluted compounds are delivered in duplicate or 3 μl of 100% DMSO (for positive and negative controls) are added. 30 μl of enzyme are added. For the negative control wells, Buffer B is substituted in place of the enzyme. 30 μl of labeled substrate are added to all wells.

After incubating for 60 minutes at room temperature, the reaction is stopped with the addition of 30 μl of the yttrium silicate beads. These beads are dense and require constant agitation while being added to the plate. The plates are sealed and shaken on a plate shaker for fifteen minutes to allow the beads to bind the GMP product.

After allowing the beads to settle for 30 minutes, plates are read on a NXT TopCount and data is analyzed in the Bioassay Solver application. Percent inhibition values are calculated using the means of the 0% and 100% controls on each plate. The estimates of the 4-parameters of the logistic, sigmoid dose-response model are then calculated using the well-level percent inhibition values for each compound. These estimates are used to calculate the concentration that corresponds to 50% inhibition.

Ex Vivo Assays

Method C: Aortic Ring Assay

This protocol describes the procedure for measuring the direct relaxation of rat aortic rings exposed to test compounds. In this assay, PDE5 inhibiting compounds elicit a relaxation of aortic rings by enhancing the cGMP signal evoked by a stable exogenous NO-donor, DETA-NO. An $EC_{50}$, with 95% confidence intervals, for compound-evoked relaxation is calculated as an index of potency.

Male Sprague-Dawley rats (250-350 g) are asphyxiated by $CO_2$ gas and their thoracic aorta carefully excised and placed in Krebs buffer. The aortas are then carefully dissected free of connective tissue and divided into 8 sections, each 3-4 mm in length.

Aortic rings are suspended between parallel stainless steel wires in a water jacketed (37° C.), 15 mL tissue bath under a resting tension of 1 gram. Tension is measured using isometric tension transducers and recorded using Ponemah tissue platform system. Each preparation is allowed to equilibrate for at least 60 minutes prior to drug testing. During this time, the tissues are also incubated with 200 uM L-NMMA, and the incubation media changed every 15-20 minutes (L-NMMA is added after each wash to maintain the final concentration at 200 uM in each tissue bath).

Following the equilibration period, baseline tensions are recorded for each tissue. The vasoconstrictor response to phenylepherine (1 uM) is assessed and when the response to phenylepherine reached a maximum, vascular reactivity was subsequently assessed by a challenge of acetylcholine (1 uM). Following another washout period, a second baseline value is recorded, the vasoconstrictor noradrenaline (25 nM) is added to each bath and the tissues incubated for a time period (~15 minutes) to achieve a stable tone. An exogenous NO drive is supplied using the stable NO-donor, DETA-NO. The concentration of DETA-NO is titrated (cumulatively in half-log increments) to achieve approximately 5-15% relaxation of the noradrenaline-evoked preconstriction. Cumulative concentration-response curves are constructed in a single ring, typically using 5 doses/ring and allowing 15 minutes between each addition.

Method D: Aortic Ring Assay

The protocol of Method C can be modified to provide an alternative protocol to generate aortic ring data. For the modified protocol, the endothelium is first removed by gently rubbing the lumen of the vessel together between the fingers prior to preparing the rings (denuded rings). The resting tension is set at 2 grams and the vasoconstrictor response to a maximal concentration of phenylepherine (1 μM) is assessed, followed (after a washout period) by two further exposures to 300 nM of pheylephrine. The concentration-response relationship to noradrenaline is constructed in each tissue over concentration range 0.1 to 300 nM. After another washout period, the tissues are constricted with an $EC_{90}$ concentration of noradrenaline for compound testing.

In Vivo Assays

Method E: CuleX™ Assay

A conscious pre-cannulated spontaneously hypertensive rat (SHR) model is used for evaluating the efficacy of test compounds and other anti-hypertensive agents in lowering systemic arterial blood pressure. An automated blood sampler (ABS) system is incorporated into this model. The Culex™ ABS system is comprised of a laptop computer, four control units and metabolic cages. This system allows for the collection of multiple blood samples from a single rat without causing undue stress to the animal. In addition, the system allows for the collection of urine samples that can be potentially used for biomarker identifications. Through this approach, efficacy and standard PK studies are conducted in the conscious unrestrained SHR rats simultaneously to accelerate the speed of compound screenings, and to define the relationship between plasma free drug concentration or potential biomarker(s) and pharmacological effect (reduction of mean arterial blood pressure).

SHR rats at age of 14 week old, weighing about 300 g, undergo surgeries of bilateral jugular veins and right carotid artery cannulations. After surgical recovery, animals are placed on the Culex™ cages and tethered to a movement-responsive arm with a sensor that controls cage movement when animal moves to prevent the catheters from being twisted. Connections are made between right jugular catheter and the Culex™ sterile tubing set for blood sampling, or left jugular catheter and the extend tubing for drug administration, or catheter in the right carotid artery and the extend tubing that is connected to a pressure transducer for monitoring blood pressure. To keep the patency of the catheters, right jugular cannula is maintained by the "tend" function of the Culex™ that flushes catheter with 20 μL heparin saline (10 units/mL) every 12 minutes or between sampling events, and left jugular cannula is filled with heparin saline (20 units/mL). The patency of the right carotid cannula is maintained by slow infusion of heparin saline either directly into the extend tubing when blood pressure is not recorded or through the pressure transducer during the blood pressure monitoring. Animals are allowed to acclimate for at least 2 hours before being used for evaluating any compounds. Animals receive three testing compounds over a 5 days study period with 30-40 hours washout period between two consecutive testing compounds. All testing compound may be administered via iv or oral gavage. Blood sampling protocols (sampling time and volume) are programmed using the Culex™ software. The total amount of blood withdrawn from each animal will not exceed 750 μL/24 hrs and 10 mL/kg within two weeks. Systemic arterial blood pressure is recorded by a pressure transducer through a data acquisition system (PONEMAH) for 6-24 hrs based on experimental protocol. Mean arterial blood pressure (primary endpoint) is analyzed for assessing the efficacy of the compounds. Blood samples will be analyzed for measuring plasma drug concentration and for evaluating potential biomarkers.

Method F.: Implantation of Radio Transmitters and Subsequent Blood

Pressure Screening by Telemetry in Spontaneously Hypertensive Rats

Spontaneously Hypertensive Rats (SHR) are anesthetized with isoflurane gas via an isoflurane anesthesia machine that is calibrated to deliver isoflurane over a range of percentages as oxygen passes through the machine's inner chambers. The animals are placed in an induction chamber and administered isoflurane at 4-5% to reach a surgical plane of anesthesia. They are then maintained at 1-2% during the surgical procedure via a nose cone, with isoflurane delivered via a smaller isoflurane anesthesia device on the surgical table.

Following administration of anesthesia, the rats are implanted with transmitters using aseptic procedures with commercially available sterile radio-telemetry units (Data Sciences, International, Roseville, Minn. 55113-1136). Prior to surgery the surgical field is shaved, scrubbed with Dial™ brand antimicrobial solution (containing 4% chlorhexidine gluconate and 4% isopropyl alcohol) followed by an application of iodine (10%) spray solution. A 2.5 to 3.0 cm laparotomy is preformed and the radio-telemetry units implanted into the abdomen, with the catheter tip inserted into the abdominal aorta. Baby Weitlaner retractors are used to retain soft tissue. A 1 cm section of the abdominal aorta is partially dissected and that section cross-clamped briefly, punctured with a 21-gauge needle and the transmitter catheter tip introduced into the vessel and secured by a single 4.0 silk suture anchored to the adjacent psoas muscle. The transmitter body is then inserted into the abdominal cavity and simultaneously secured to the abdominal muscle wall while closing with running 4.0 silk suture. The skin layer is closed with subdermal continuous 4.0 absorbable suture. A subcutaneous (s.c.) administration of marcaine followed by a topical application of iodine is administered into and around the suture line, respectively, upon closing. All rats receive a postoperative injection of buprenorphine @0.05 mg/kg, s.c. before regaining consciousness. A typical dose volume for a 0.300 kg rat will be 0.050 ml. The rats must be fully recovered from their operative anesthesia before the administration of buprenorphine. They then receive the same dose once daily for 2 consecutive days, unless the animal demonstrates that it is in compromising postoperative pain.

Following surgery, the rats are returned to their cages and housed individually on solid bottom caging with paper bedding. A period of no less than 7 days is allowed for recovery before experimental procedures are initiated. It has been observed that the rats are typically hypertensive for several days following surgery and return to "normotensive" levels by approximately the $7^{th}$ day post-surgery. They are fed standard rat chow and water ad libitum throughout the experimental time line.

Test compounds are administered intragastrically (i.g.) via gavage, using of a stainless steel, 2½ inch, 18 gauge gavage needle with a balled end. For single daily dosing, the target volume is 3.33 ml/kg, i.g. The vehicles in which the test compounds are administered will vary depending on solubility of the compound, however, methylcellulose (0.5%) in water will be the primary choice.

Blood pressure data will be obtained using Data Sciences International's data acquisition program. Blood pressure samples are recorded at 1.5-3 minute intervals for a 5 second duration 24 hours per day for the entire study. This data is processed by Data Science's data analysis software into averages of a desired time inervals. All other data reduction is performed in Microsoft Excel™ spreadsheets.

Method G: SHR Rat

This experimental protocol is designed to screen for blood pressure lowering by test compounds. The spontaneously hyperentsive rat (SHR) is cannulated in the jugular vein and carotid artery; one for compound administration and one for direct blood pressure measurement, respectively. The animals are fully conscious following surgery and all experimentation takes place within one working day. Blood pressure lowering is the primary parameter to be evaluated. However, systolic and diastolic pressure and heart rate data is collected as well. Rats will be dosed in an escalating, or cumulative manner to observe the responses following this regimen. This particular method will also permit screening of more than one compound or multiple doses of a compound in one day using the same animals.

Methods:

Anesthesia: Rats are anesthetized with 5% isoflurane to effect. Incision sites are shaved and aseptically prepared for surgery. Rats are then transferred to the surgical field with a heating pad, supplemental isoflurane and maintained at 37° C., and isoflurane to effect throughout the surgical procedure.

Surgery: Arterial and venous cannula are implanted in the jugular vein and carotid artery, respectively. Cannulas are tunneled subcutaneously to the back of the neck where they exit percutaneously. Stainless steel staples are used to close each incision site. The cannulae are then run through a spring-tether to a swivel apparatus by which protects the cannulae from the animals chewing throughout the experiment.

Recovery: Rats are placed into an opaque polycarbonate cage instrumented with a counter balance arm that supports the weight of the tether and swivel apparatus. A paper bedding material is used to cover the bottom of the cage. The rats are allowed to recover from surgery at this point and receive 2 mL of volume early during their recovery stage. No food is provided to the animals. The timeline shown in FIG. 1 shows the experimental time course used for the test period.

All compounds of the invention have an activity against PDE-5 of less than 10,000 nM. $IC_{50}$ values found using Method A for compounds 1-40 are listed in the table below. $IC_{50}$ values found using Method B for compounds 41-50 are also listed in the table below.

| Example | $IC_{50}$ (nM) |
|---|---|
| 1 | 1.12 |
| 2 | 1.25 |
| 3 | 1.1 |
| 4 | 0.77 |
| 5 | 0.58 |
| 6 | 0.39 |
| 7 | 9.0 |
| 8 | 0.59 |
| 9 | 0.33 |
| 10 | 2.5 |
| 11 | 0.53 |
| 12 | 4.5 |
| 13 | 0.4 |
| 14 | 5.5 |
| 15 | 0.48 |
| 16 | 5.9 |
| 17 | >100 |
| 18 | 2.30 |
| 19 | 4.3 |
| 20 | 2.1 |
| 21 | 2.0 |
| 22 | 3.2 |
| 23 | 9.5 |
| 24 | 5.8 |
| 25 | 5.2 |
| 26 | 3.4 |
| 27 | N/A |
| 28 | 6.9 |
| 29 | 3.3 |
| 30 | 1.06 |
| 31 | 3.40 |
| 32 | >100 |
| 33 | >100 |
| 34 | 23.6 |
| 35 | >100 |
| 36 | 188 |
| 37 | 4.4 |
| 38 | N/A |
| 39 | 1.53 |
| 40 | 5.8 |
| 41 | 1.8 |
| 42 | 0.32 |
| 43 | 0.21 |
| 44 | 0.79 |
| 45 | 1.25 |
| 46 | 0.14 |
| 47 | 0.47 |
| 48 | 7.39 |
| 49 | 0.58 |
| 50 | 1.06 |

The invention claimed is:
1. A compound of formula (I)

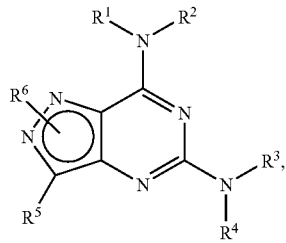

or a tautomer thereof or a pharmaceutically acceptable salt of said compound or tautomer,
wherein
- $R^1$ is a cyclic group selected from $R^A$, $R^B$, $R^C$ and $R^D$, each of which is optionally substituted with one or more $R^7$ groups;
- $R^2$ is hydrogen or $C_1$-$C_2$ alkyl;
- $R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ or $R^E$, which is optionally substituted with one or more $R^9$ groups, or hydrogen;
- or —$NR^3R^4$ forms $R^F$, which is optionally substituted with one or more $R^{10}$ groups;
- $R^5$ is —Y—$NR^{15}R^{16}$;
- $R^6$, which may be attached at $N^1$ or $N^2$, is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, ($C_3$-$C_6$ cycloalkyl)methoxy, $C_1$-$C_6$ haloalkoxy or a cyclic group selected from $R^J$, $R^K$, $R^L$ and $R^M$, or $R^6$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy, or $R^6$ is hydrogen;
- $R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;
- $R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $C_3$-$C_6$ cycloalkyl, $R^G$ or $R^H$, the last two of which are optionally substituted with one or more $R^9$ group;
- $R^9$ is $C_1$-$C_6$ alkyl, $C_1$-$C_6$ haloalkyl or $CO_2R^{12}$;
- $R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, oxo, $C_1$-$C_6$ alkyl or $C_1$-$C_6$ haloalkyl, the last two of which are optionally substituted by $R^{11}$;
- $R^{11}$ is phenyl, $NR^{12}R^{13}$ or $NR^{12}CO_2R^{14}$;
- $R^{12}$ and $R^{13}$ are each independently hydrogen, $C_1$-$C_6$alkyl or $C_1$-$C_6$ haloalkyl;
- $R^{14}$ is $C_1$-$C_6$ alkyl or $C_1$-$C_6$ haloalkyl;
- $R^{15}$ is selected from $R^{17}$, $R^{17}C(O)$ and $R^{18}SO_2$, and
- $R^{16}$ is selected from hydrogen, $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups,
- or —$NR^{15}R^{16}$ constitutes a 3- to 8-membered saturated ring optionally containing one or more heteroatoms in addition to said nitrogen selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl;
- $R^{17}$ is hydrogen or $R^{18}$;
- $R^{18}$ is selected from $C_1$-$C_6$ alkyl optionally substituted with one or more $R^{19}$ groups, $C_1$-$C_6$ haloalkyl and $C_3$-$C_{10}$ cycloalkyl optionally substituted with one or more $R^{20}$ groups;
- $R^{19}$ is selected from $R^{21}$, —$NR^{23}R^{24}$, —$CO_2R^{25}$, —$CONR^{26}R^{27}$, $R^{28}$ and phenyl optionally substituted by $R^{29}$;
- $R^{20}$ is selected from $R^{21}$, $R^{22}$ and oxo;
- $R^{21}$ is oxo, hydroxy, $C_1$-$C_6$ alkoxy, $C_1$-$C_6$ (haloalkyl)oxy or $C_3$-$C_7$ cycloalkyloxy;
- $R^{22}$ is $C_1$-$C_6$ alkyl or $C_1$-$C_6$ haloalkyl;
- $R^{23}$ and $R^{24}$ are each independently selected from hydrogen and $C_1$-$C_6$ alkyl;
- or —$NR^{23}R^{24}$ constitutes an azetidine, pyrrolidine, piperidine or morpholine ring;
- $R^{25}$ is hydrogen or $C_1$-$C_6$ alkyl;
- $R^{26}$ and $R^{27}$ are each independently selected from hydrogen and $C_1$-$C_6$ alkyl;
- or —$NR^{26}R^{27}$ constitutes an azetidine, pyrrolidine, piperidine or morpholine ring;
- $R^{28}$ is a saturated, unsaturated or aromatic heterocycle with up to 10 ring atoms, at least one of which is selected from nitrogen, oxygen and sulphur;
- $R^{29}$ is selected from halo, $R^{21}$ and $R^{22}$,
- $R^A$ and $R^J$ are each independently a $C_3$-$C_{10}$ cycloalkyl or $C_3$-$C_{10}$ cycloalkenyl group, each of which may be either monocyclic or, when there are an appropriate number of ring atoms, polycyclic and which may be fused to either
  - (a) a monocyclic aromatic ring selected from a benzene ring and a 5- or 6-membered heteroaromatic ring containing up to three heteroatoms selected from nitrogen, oxygen and sulphur, or
  - (b) a 5-, 6- or 7-membered heteroalicyclic ring containing up to three heteroatoms selected from nitrogen, oxygen and sulphur;
- $R^B$ and $R^K$ are each independently a phenyl or naphthyl group, each of which may be fused to
  - (a) a $C_5$-$C_7$ cycloalkyl or $C_5$-$C_7$ cycloalkenyl ring,
  - (b) a 5-, 6- or 7-membered heteroalicyclic ring containing up to three heteroatoms selected from nitrogen, oxygen and sulphur, or
  - (c) a 5- or 6-membered heteroaromatic ring containing up to three heteroatoms selected from nitrogen, oxygen and sulphur;
- $R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;
- $R^D$ and $R^M$ are each independently a 5- or 6-membered heteroaromatic ring containing up to three heteroatoms independently selected from nitrogen, oxygen and sulphur, which ring may further be fused to
  - (a) a second 5- or 6-membered heteroaromatic ring containing up to three heteroatoms selected from nitrogen, oxygen and sulphur;

(b) $C_5$-$C_7$ cycloalkyl or $C_5$-$C_7$ cycloalkenyl ring;
(c) a 5-, 6- or 7-membered heteroalicyclic ring containing up to three heteroatoms selected from nitrogen, oxygen and sulphur; or
(d) a benzene ring;

$R^E$, $R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur; and Y is a covalent bond, $C_1$-$C_6$ alkylenyl or $C_3$-$C_7$ cycloalkylenyl.

2. A compound according to claim 1 wherein $R^1$ is $R^B$, which is optionally substituted with one or more $R^7$ groups.

3. A compound according to claim 1 wherein $R^1$ is $R^D$, which is optionally substituted with one or more $R^7$ groups.

4. A compound according to claim 1 wherein $R^7$ is halo, $C_1$-$C_6$ alkyl, $C_1$-$C_6$ haloalkyl, $OR^{12}$ or $CONR^{12}R^{13}$.

5. A compound according to claim 1 wherein $R^2$ is hydrogen.

6. A compound according to claim 1 wherein $R^3$ is hydrogen, $C_1$-$C_6$ alkyl, which is optionally substituted with one or more $R^8$ groups, or $R^E$, which is optionally substituted with one or more $R^9$ groups; and wherein $R^E$ is a monocyclic or, when there are an appropriate number of ring atoms, polycyclic saturated ring system containing between 3 and 7 ring atoms, of which at least one is a heteroatom selected from nitrogen, oxygen and sulphur.

7. A compound according to claim 1 wherein $R^4$ is hydrogen, $C_1$-$C_6$ alkyl, $C_1$-$C_6$ haloalkyl, $C_2$-$C_6$ alkenyl or $C_2$-$C_6$ alkynyl.

8. A compound according to claim 1 wherein —$NR^3R^4$ forms $R^F$, which is optionally substituted with one or more $R^{10}$ groups and wherein $R^F$ is a monocyclic or, when there are an appropriate number of ring atoms, polycyclic saturated ring system containing between 3 and 10 ring atoms containing at least one nitrogen atom and optionally one other atom selected from oxygen and sulphur.

9. A compound according to claim 1 wherein Y is $C_1$-$C_6$ alkylenyl.

10. A compound according to claim 1 wherein $R^{15}$ is $R^{17}C(O)$ or $R^{18}SO_2$ and $R^{16}$ is hydrogen or $C_1$-$C_6$ alkyl.

11. A compound according to claim 1 wherein $R^{15}$ is $R^{17}$ and $R^{16}$ is hydrogen or $C_1$-$C_6$ alkyl.

12. A compound according to claim 1 wherein —$NR^{15}R^{16}$ constitutes a 3- to 8-membered saturated ring optionally containing one or more heteroatoms in addition to said nitrogen selected from nitrogen, oxygen and sulphur, and which may optionally be substituted with one or more groups selected from $R^{21}$, $R^{22}$ and ($C_1$-$C_6$ alkoxy)$C_1$-$C_6$ alkyl.

13. A compound according to claim 1 wherein $R^6$ is positioned on $N^1$.

14. A compound according to claim 1 wherein
$R^6$ is $C_1$-$C_6$ alkyl or $C_1$-$C_6$ haloalkyl, each of which is optionally substituted by $C_1$-$C_6$ alkoxy, $C_1$-$C_6$ haloalkoxy or a cyclic group selected from $R^J$, $R^L$ and $R^M$, or $R^6$ is $R^N$ or hydrogen;
$R^J$ is a $C_3$-$C_7$ monocyclic cycloalkyl group;

$R^L$ and $R^N$ are each independently a monocyclic, saturated or partly unsaturated ring system containing between 4 and 7 ring atoms, of which at least one is a heteroatom selected from nitrogen, oxygen and sulphur; and
$R^M$ is a 5- or 6-membered heteroaromatic ring containing up to three heteroatoms independently selected from nitrogen, oxygen and sulphur.

15. A compound according to claim 1 wherein
$R^3$ is hydrogen, $C_1$-$C_4$ alkyl, which is optionally substituted with one or more $R^8$ groups, or $R^E$, which is optionally substituted with one or more $R^9$ groups;
$R^4$ is hydrogen, $C_1$-$C_6$ alkyl or $C_1$-$C_6$ haloalkyl;
or —$NR^3R^4$ forms $R^F$, which is optionally substituted with one or more $R^{10}$ groups;
$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;
$R^A$ is a monocyclic $C_3$-$C_8$ cycloalkyl group;
$R^B$ is phenyl;
$R^C$ is a monocyclic saturated or partly unsaturated ring system containing between 3 and 8 ring atoms, of which at least one is a heteroatom selected from nitrogen, oxygen and sulphur;
$R^D$ is a 5- or 6-membered heteroaromatic ring containing up to three heteroatoms independently selected from nitrogen, oxygen and sulphur;
$R^E$ is a monocyclic saturated ring system containing between 3 and 7 ring atoms, of which at least one is a heteroatom selected from nitrogen, oxygen and sulphur;
$R^F$ is a monocyclic or, when there are an appropriate number of ring atoms, polycyclic saturated ring system containing between 3 and 10 ring atoms, of which at least one is a heteroatom selected from nitrogen, oxygen and sulphur;
$R^J$ is cyclopropyl or cyclobutyl;
$R^L$ and $R^N$ are each independently a monocyclic saturated ring system containing either 5 or 6 ring atoms, of which at least one is a heteroatom selected from nitrogen, oxygen and sulphur;
$R^M$ is a 5- or 6-membered heteroaromatic ring containing a heteroatom selected from nitrogen, oxygen and sulphur; and
Y is $C_1$-$C_6$ alkylenyl.

16. A compound according to claim 15 wherein $R^1$ is a cyclic group selected from $R^A$, $R^B$, $R^C$ and $R^D$, each of which is optionally substituted with one or more $R^7$ groups;
$R^7$ is halo, $C_1$-$C_6$ alkyl, $C_1$-$C_6$ haloalkyl, $OR^{12}$ or $CONR^{12}R^{13}$;
$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;
$R^A$ is a monocyclic $C_5$-$C_7$ cycloalkyl group;
$R^B$ is phenyl;
$R^C$ is a monocyclic saturated ring system containing between 5 and 7 ring atoms, of which at least one is a heteroatom selected from nitrogen, oxygen and sulphur;
$R^D$ is a 5-membered heteroaromatic ring containing a heteroatom selected from nitrogen, oxygen and sulphur and optionally up to two further nitrogen atoms in the ring, or a 6-membered heteroaromatic ring containing 1, 2 or 3 nitrogen atoms;
$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms; and Y is —$CH_2$—.

17. A pharmaceutical composition comprising a compound of claim 1, or a pharmaceutically acceptable salt thereof, and a pharmaceutically acceptable diluent or carrier.

18. A method of treating a disorder or condition in a mammal, which method comprises administering to said mammal a compound of claim 1 or a pharmaceutically acceptable salt thereof, or a pharmaceutical composition comprising a compound of claim 1 or a pharmaceutically acceptable salt thereof and a pharmaceutically acceptable diluent or carrier, wherein the disorder or condition is hypertension.

* * * * *